US011248000B2

(12) United States Patent
Wiles et al.

(10) Patent No.: US 11,248,000 B2
(45) Date of Patent: *Feb. 15, 2022

(54) QUINAZOLINE AND INDOLE COMPOUNDS TO TREAT MEDICAL DISORDERS

(71) Applicant: Achillion Pharmaceuticals, Inc., Blue Bell, PA (US)

(72) Inventors: Jason Allan Wiles, Madison, CT (US); Avinash Phadke, Branford, CT (US)

(73) Assignee: Achillion Pharmaceuticals, Inc., Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/774,117

(22) Filed: Jan. 28, 2020

(65) Prior Publication Data
US 2020/0165262 A1 May 28, 2020

Related U.S. Application Data

(63) Continuation of application No. 16/226,378, filed on Dec. 19, 2018, now Pat. No. 10,961,252, which is a continuation of application No. PCT/US2017/039587, filed on Jun. 27, 2017.

(60) Provisional application No. 62/471,799, filed on Mar. 15, 2017, provisional application No. 62/355,273, filed on Jun. 27, 2016.

(51) Int. Cl.
C07D 491/056 (2006.01)
C07D 401/14 (2006.01)
C07D 401/04 (2006.01)
C07D 401/06 (2006.01)
C07D 239/94 (2006.01)
C07D 417/12 (2006.01)
A61K 31/454 (2006.01)
A61K 45/06 (2006.01)
C07D 403/12 (2006.01)
C07D 487/08 (2006.01)
A61K 31/662 (2006.01)
C07F 9/38 (2006.01)
C07D 403/04 (2006.01)
A61K 31/517 (2006.01)
C07D 403/14 (2006.01)
C07D 417/14 (2006.01)
C07D 451/02 (2006.01)
C07D 471/02 (2006.01)

(52) U.S. Cl.
CPC ........ C07D 491/056 (2013.01); A61K 31/454 (2013.01); A61K 31/517 (2013.01); A61K 31/662 (2013.01); A61K 45/06 (2013.01); C07D 239/94 (2013.01); C07D 401/04 (2013.01); C07D 401/06 (2013.01); C07D 401/14 (2013.01); C07D 403/04 (2013.01); C07D 403/12 (2013.01); C07D 403/14 (2013.01); C07D 417/12 (2013.01); C07D 417/14 (2013.01); C07D 451/02 (2013.01); C07D 471/02 (2013.01); C07D 487/08 (2013.01); C07F 9/3834 (2013.01)

(58) Field of Classification Search
CPC .................................................. C07D 491/056
See application file for complete search history.

(56) References Cited

U.S. PATENT DOCUMENTS

| 5,110,927 A | 5/1992 | Pitha et al. |
| 5,747,490 A | 5/1998 | Bock et al. |
| 9,452,990 B2 | 9/2016 | Dechantsreiter et al. |
| 9,475,806 B2 | 10/2016 | Adams et al. |
| 9,676,728 B2 | 6/2017 | Adams et al. |
| 9,682,968 B2 * | 6/2017 | Adams ............... A61K 31/438 |
| 10,961,252 B2 * | 3/2021 | Wiles .................. A61P 13/02 |
| 2015/0175994 A1 | 6/2015 | Turner |
| 2016/0024079 A1 | 1/2016 | Adams et al. |
| 2016/0152605 A1 | 6/2016 | Adams et al. |
| 2016/0311779 A1 | 10/2016 | Adams et al. |

FOREIGN PATENT DOCUMENTS

| JP | 2000/281660 A | 10/2000 |
| JP | 2015-515976 A | 6/2015 |
| JP | 2015-521624 A | 7/2015 |
| WO | WO 1996/002524 A1 | 2/1996 |
| WO | WO 1997/011698 A1 | 4/1997 |
| WO | WO 1997/020820 A1 | 6/1997 |
| WO | WO 1997/023462 A1 | 7/1997 |
| WO | WO 2000/021559 A2 | 4/2000 |
| WO | WO 2000/067735 A2 | 11/2000 |
| WO | WO 2001/068615 A1 | 9/2001 |
| WO | WO 2005/112938 A1 | 12/2005 |
| WO | WO 2005/123697 A1 | 12/2005 |
| WO | WO 2007/071055 A1 | 9/2007 |
| WO | WO 2008/003702 A2 | 1/2008 |
| WO | WO 2008/106644 | 9/2008 |
| WO | WO 2010/093727 A1 | 8/2010 |
| WO | WO 2012/151468 A1 | 11/2012 |
| WO | WO-2013/164802 A1 | 11/2013 |

(Continued)

OTHER PUBLICATIONS

US, 2019/0135825, A1, U.S. Appl. No. 16/226,378, Wiles, et al., May 9, 2019.
Office Action for Japanese Application No. 2018-567716, dated Jun. 8, 2021 (4 pages).
SID 234491011 (PubChem).
International Search Report and Written Opinion of International Application No. PCT/US17/39587.

Primary Examiner — Paul V Ward
(74) Attorney, Agent, or Firm — Clark & Elbing LLP

(57) ABSTRACT

Compounds, methods of use, and processes for making inhibitors of Complement Factor B are provided.

16 Claims, No Drawings

(56) References Cited

FOREIGN PATENT DOCUMENTS

| WO | WO 2013/192345 A1 | 12/2013 |
| WO | WO 2014/035876 A1 | 3/2014 |
| WO | WO 2014/143638 A1 | 9/2014 |
| WO | WO 2015/009616 A1 | 1/2015 |
| WO | WO 2015/038939 A2 | 3/2015 |
| WO | WO 2015/066241 A1 | 5/2015 |

* cited by examiner

US 11,248,000 B2

QUINAZOLINE AND INDOLE COMPOUNDS TO TREAT MEDICAL DISORDERS

CROSS-REFERENCE TO RELATED APPLICATIONS

This application is a continuation of U.S. patent application Ser. No. 16/226,378, filed Dec. 19, 2018, which is a continuation of International Application No. PCT/US2017/039587, filed with the Patent Cooperation Treaty, U.S. Receiving Office on Jun. 27, 2017, which claims the benefit of priority to U.S. Application No. 62/355,273, filed Jun. 27, 2016, and U.S. Application No. 62/471,799 filed Mar. 15, 2017, each of which is incorporated by reference herein for all purposes.

BACKGROUND

The Complement system is a part of the innate immune system that does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the Complement system. These proteins act through opsonization (enhancing phagocytosis of antigens), chemotaxis (attracting macrophages and neutrophils), cell lysis (rupturing membranes of foreign cells) and agglutination (clustering and binding of pathogens together).

The Complement system has three pathways: classical, alternative and lectin. Complement Factor B plays an early and central role in activation of the alternative pathway of the Complement cascade. Activation of the alternative Complement pathway is initiated by spontaneous hydrolysis of a thioester bond within C3 to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined Complement pathways, leading ultimately to the recruitment and assembly of additional factors in the Complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction or excessive activation of Complement has been linked to certain autoimmune, inflammatory, and neurodegenerative diseases, as well as ischemia-reperfusion injury and cancer. For example, activation of the alternative pathway of the Complement cascade contributes to the production of C3a and C5a, both potent anaphylatoxins that also have roles in a number of inflammatory disorders. Therefore, in some instances, it is desirable to decrease the response of the Complement pathway, including the alternative Complement pathway. Some examples of disorders mediated by the Complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the Complement cascade and macular degeneration. Individuals with mutations in the gene encoding Complement Factor H have a fivefold increased risk of macular degeneration and individuals with mutations in other Complement factor genes, including Factor B, also have an increased risk of AMD. Individuals with mutant Factor H also have increased levels of C-reactive protein, a marker of inflammation. Without adequate functioning Factor H, the alternative pathway of the Complement cascade is overly activated leading to cellular damage. Inhibition of the alternative pathway is thus desired.

Paroxysmal nocturnal hemoglobinuria (PNH) is a non-malignant, hematological disorder characterized by the expansion of hematopoietic stem cells and progeny mature blood cells which are deficient in some surface proteins. PNH erythrocytes are not capable of modulating their surface Complement activation, which leads to the typical hallmark of PNH—the chronic activation of Complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections. Thus, there is an unmet need to develop novel inhibitors of the Complement pathway.

Other disorders that have been linked to the Complement cascade include atypical hemolytic uremic syndrome (aHUS), hemolytic uremic syndrome (HUS), abdominal aortic aneurysm, hemodialysis complications, hemolytic anemia, or hemodialysis, neuromyelitis (NMO), myasthenia gravis (MG), fatty liver disease, nonalcoholic steatohepatitis (NASH), liver inflammation, cirrhosis, liver failure, dermatomyositis, and amyotrophic lateral sclerosis.

While initial attempts have been made to develop inhibitors of Factor B, there are currently no small molecule Factor B inhibitors in clinical trials. Examples of Factor B inhibitors are described in the following disclosures: Advanced Vision Therapies Inc. patent publication WO2008/106644 titled "Treatment of diseases characterized by inflammation"; Wellstate Immunotherapeutics 11c patent publication WO2012/151468 titled "Complement Factor B analogs and their uses"; William Marsh Rice University patent publication WO2014/035876 titled "Heat-inactivated Complement Factor B compositions and methods"; Musc. Foundation for Research Development patent publication US1999/023485 titled "Blocking factor b to treat complement-mediated immune disease"; and Novartis patent publication WO2013/192345 and US2015/126592 titled "Complement pathway modulators and uses thereof". Additional Factor B inhibitors are described in Novartis patent publications WO2015/066241, US2016/311779, WO2015/009616, US2016/152605, WO2014/143638, and US2016/024079. Another example of Factor B inhibitors is the IONIS Pharmaceuticals Inc. patent publication WO2015/038939 titled "Modulators of Complement Factor B". Examples of granted patents covering Factor B inhibitors include U.S. Pat. Nos. 9,452,990; 9,676,728; 9,682,968; and 9,475,806.

Given the wide variety of medical disorders that are caused by detrimental immune or inflammatory responses, new uses and compounds are needed for medical treatment.

It is an object of the present invention to provide compounds which act as Complement Factor B inhibitors for the treatment of disorders in a host, including a human, associated with misregulation of the Complement cascade, or with the undesired result of the Complement cascade performing its normal function.

SUMMARY

This invention includes an active compound of Formula I, Formula II, Formula III, or Formula IV or a pharmaceutically acceptable salt or composition thereof, wherein Formula I and Formula II contain a substituted quinazoline and Formula III and Formula IV contain a substituted indole. In one embodiment, an active compound or its salt or composition, as described herein is used to treat a medical disorder which is an inflammatory or immune condition, a disorder mediated by the Complement cascade (including a dysfunctional cascade), a disorder or abnormality of a cell that adversely affects the ability of the cell to engage in or respond to normal Complement activity, or an undesired complement-mediated response to a medical treatment, such as surgery or other medical procedure or a pharmaceutical or biopharmaceutical drug administration, a blood transfusion, or other allogeneic tissue or fluid administration.

These compounds can be used to treat such condition in a host in need thereof, typically a human. In one embodiment, the active compound acts as an inhibitor of the Complement Factor B cascade. In another embodiment, a method for the treatment of such a disorder is provided that includes the administration of an effective amount of a compound of Formula I, Formula II, Formula III, or Formula IV or a pharmaceutically acceptable salt thereof, optionally in a pharmaceutically acceptable carrier, as described in more detail below.

Formula I is:

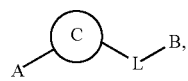

(I)

or a pharmaceutically acceptable salt, isotopic analog, prodrug, or isolated isomer thereof optionally in pharmaceutically acceptable carrier;
wherein:
A is selected from: A1 and A2;
B is selected from: B1 and B2;
C is selected from: C1 and C2;
L is selected from: L1 and L2;
at least one of A, B, C, or L is selected from: A2, B2, C2, or L2 respectively;
A1 is

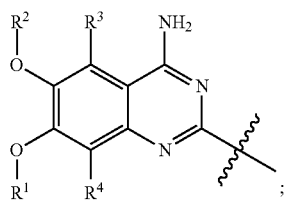

$R^1$ and $R^2$ are independently selected from: hydrogen, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, alkenyl, alkynyl, cycloalkyl, cycloalkylalkyl, heterocyclyl, and heterocycloalkyl;

$R^3$ and $R^4$ are independently selected from: hydrogen, halogen, amino, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, hydroxyl, cyano, mercapto, thioalkyl, nitro, alkoxy, haloalkoxy, alkenyl, alkynyl, cycloalkyl, cycloalkylalkyl, heterocyclyl, heterocycloalkyl, aryloxy, —S(O)$_2$R$^1$, —S(O)$_2$OH, —S(O)$_2$NH$_2$, —S(O)R$^1$, —S(O)OH, —S(O)NH$_2$, —P(O)(OR$^1$)$_2$, —P(O)(OH)$_2$, B(OH)$_2$, —Si(R$^1$)$_3$, —COOH, —COOalkyl, —C(O)alkyl, —C(S)alkyl, —COOR$^1$, —C(O)R$^1$, —C(S)R$^1$, —C(O)NH$_2$, —C(S)NH$_2$, —NR$^1$C(O)alkyl, —NR$^1$C(O)R$^2$, —NR$^1$C(S)alkyl, —NR$^1$C(S)R$^2$, —NHC(O)NH$_2$, —NHC(S)NH$_2$, —NHC(O)OR$^1$, and —OC(O)R$^1$ each of which except halogen, nitro, cyano, and hydrogen may be optionally substituted, for example with halogen, alkyl, aryl, heterocycle or heteroaryl;

Non-limiting examples of A1 include:

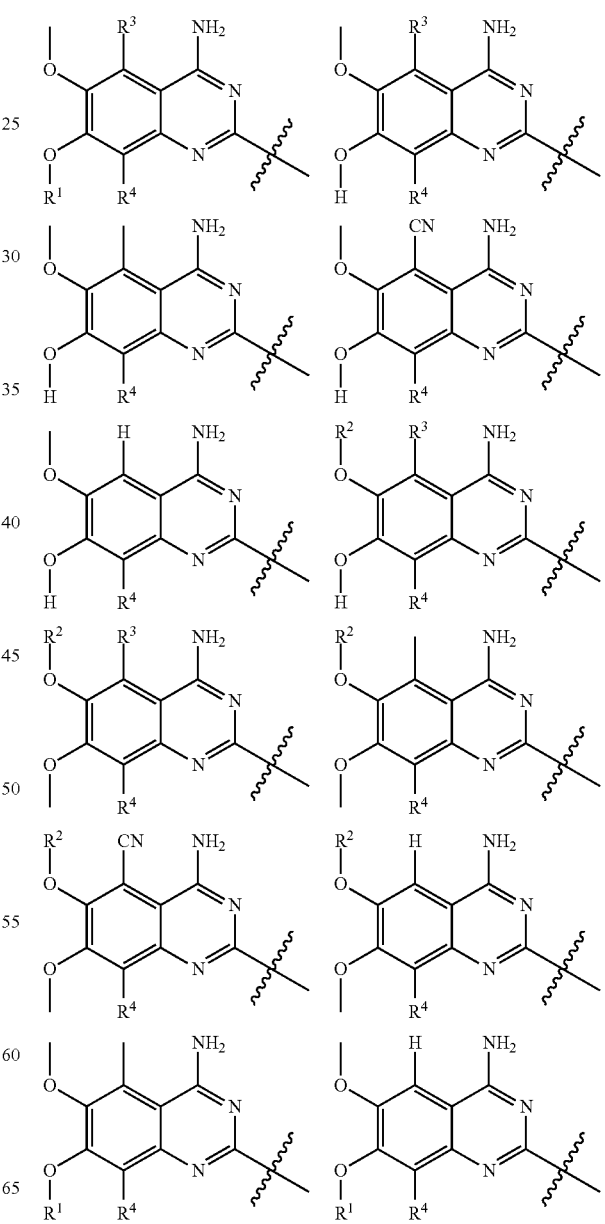

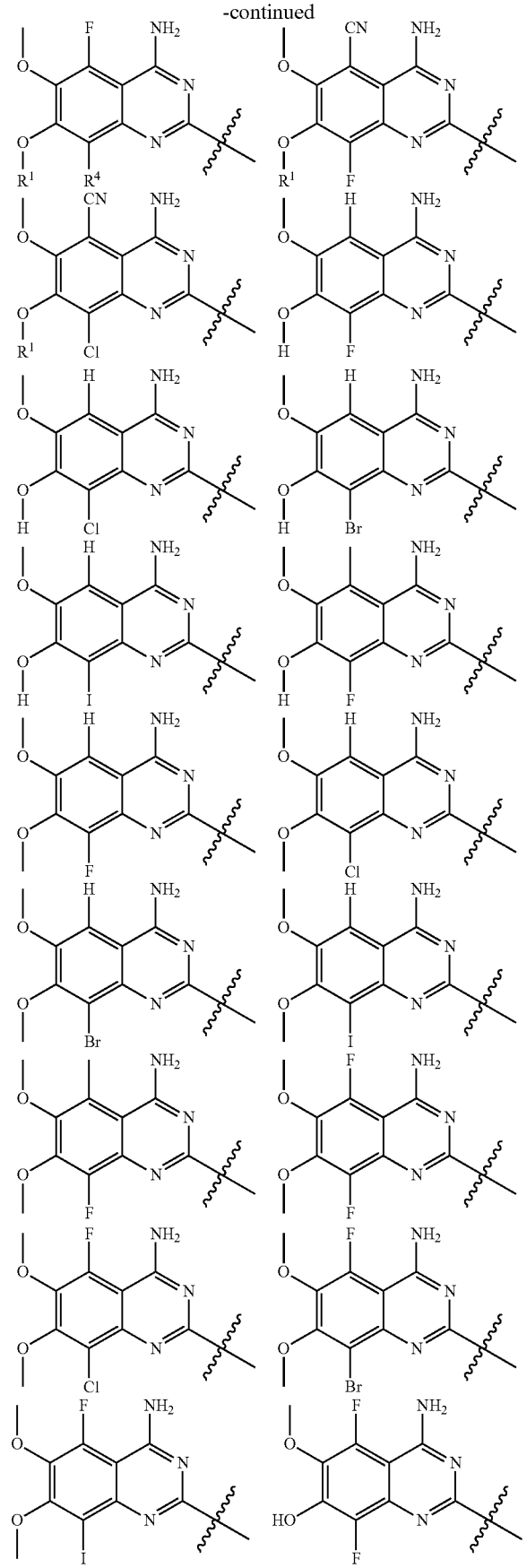
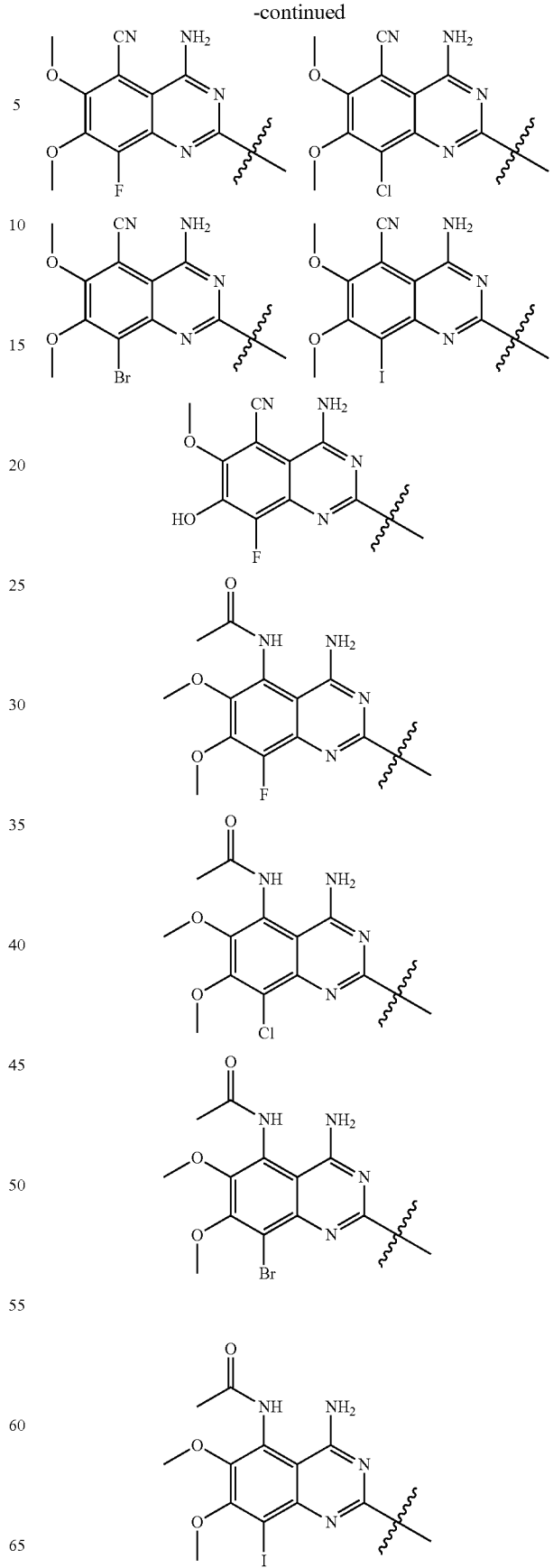

-continued
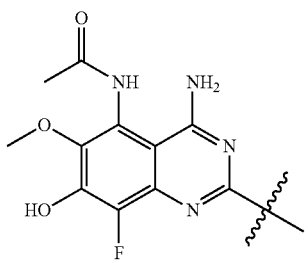
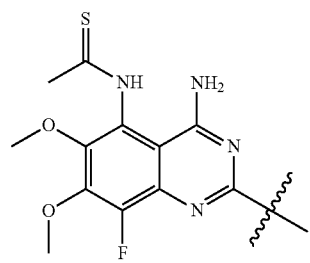
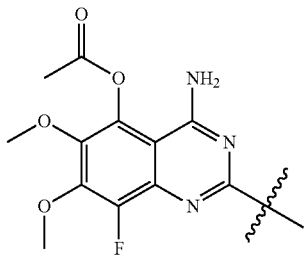
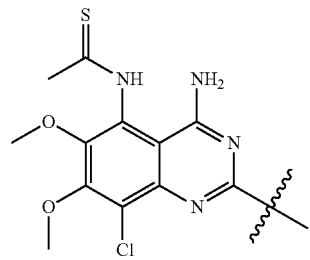
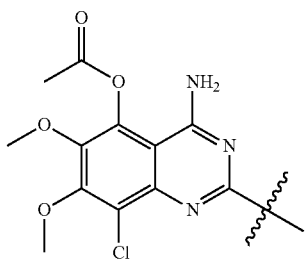
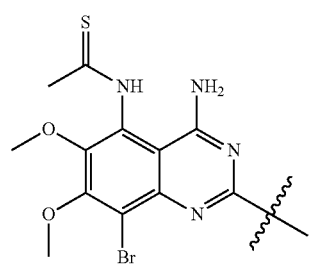
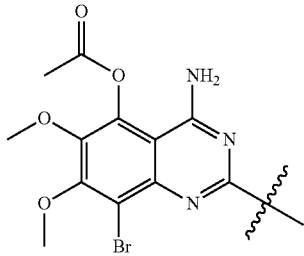
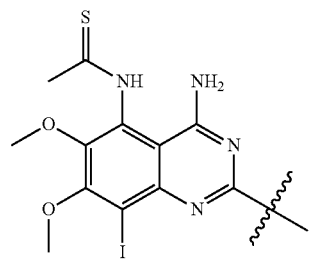
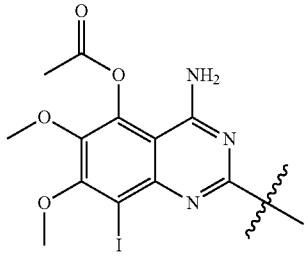
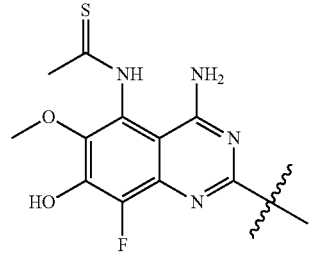
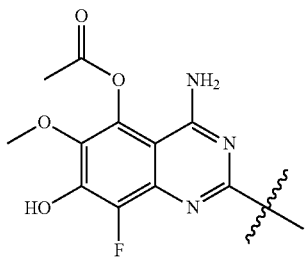
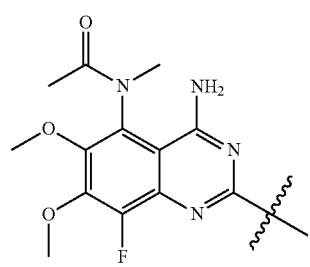

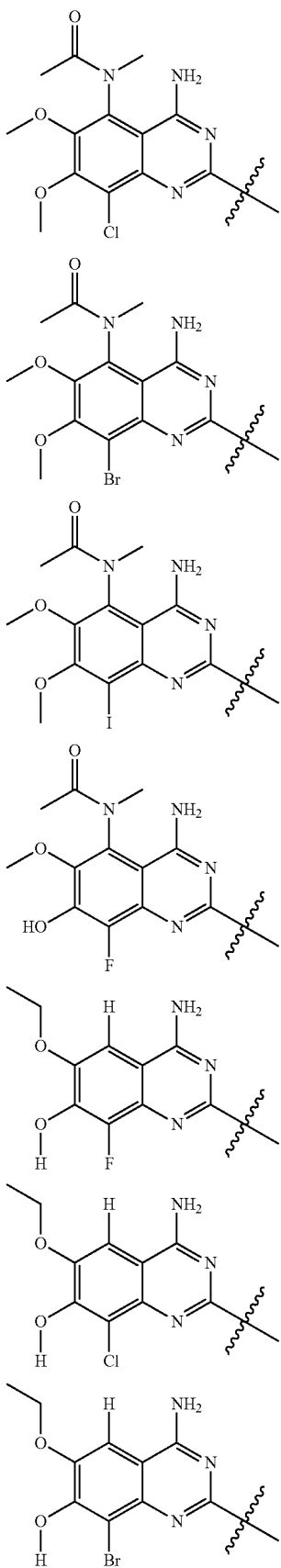
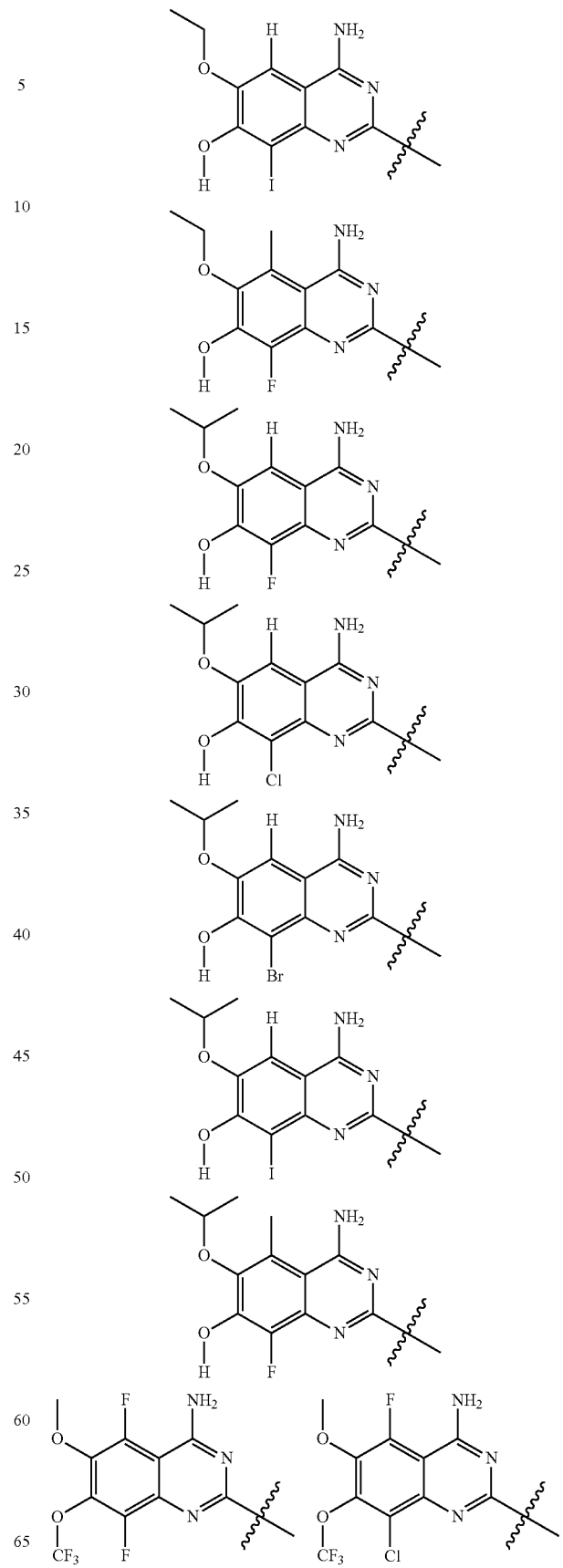

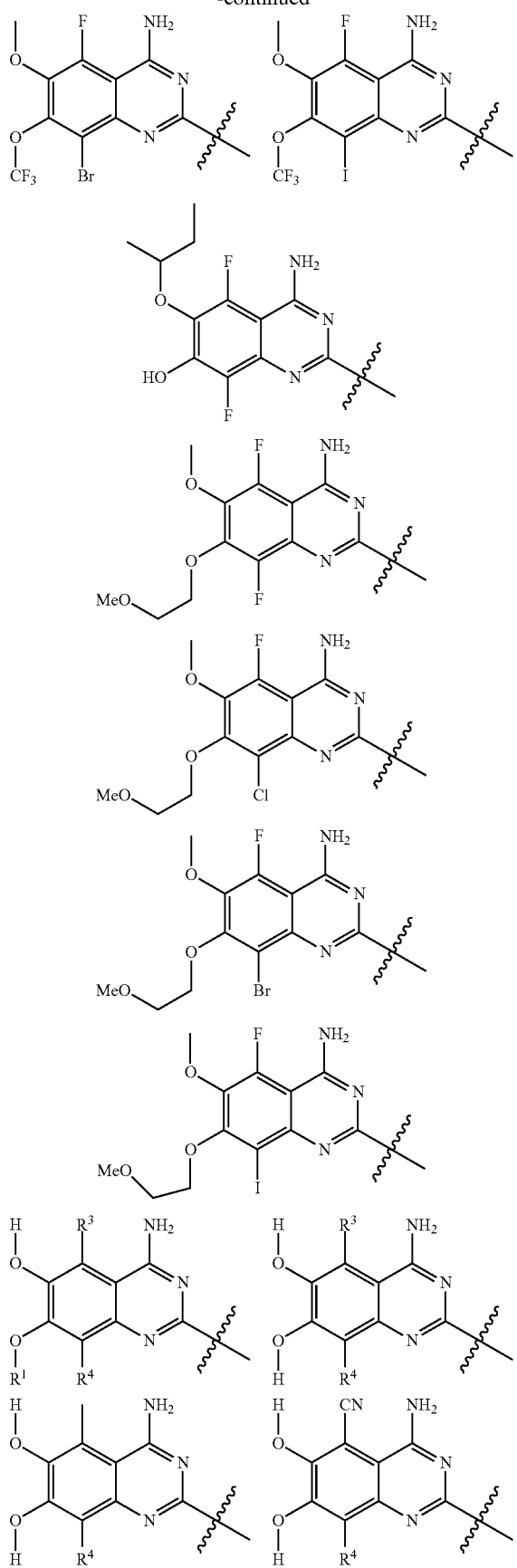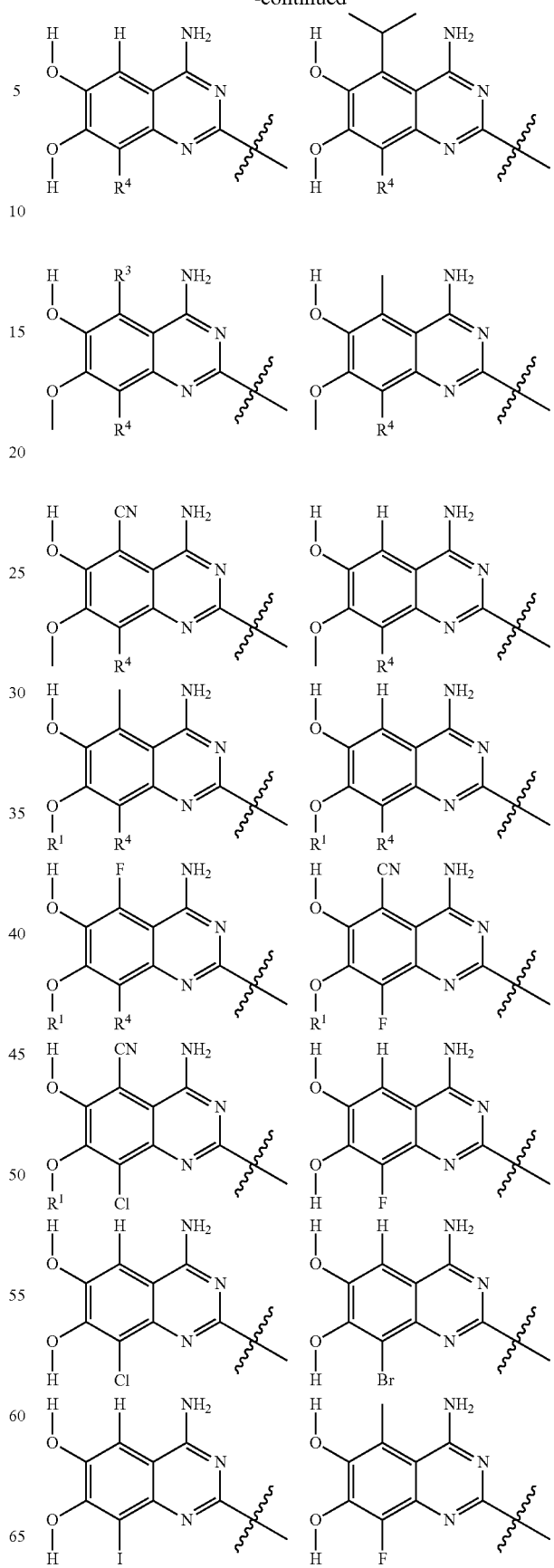

-continued

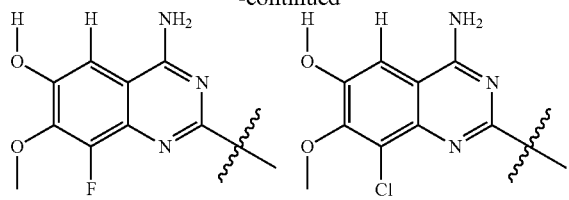

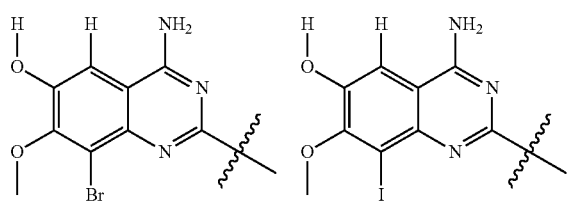

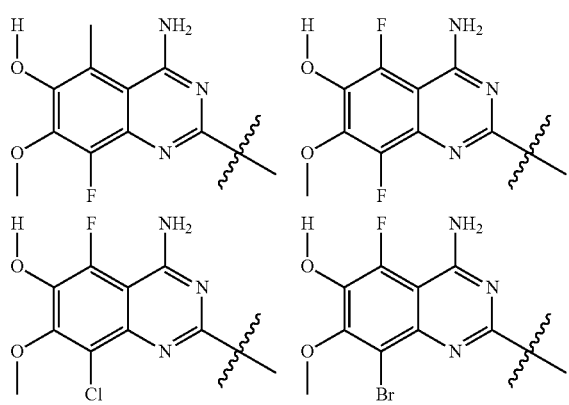

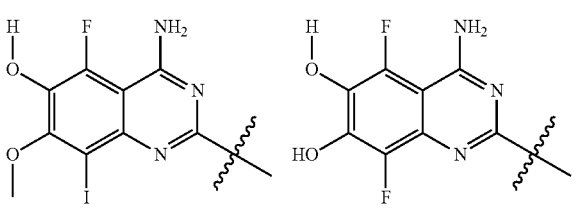

A2 is selected from:

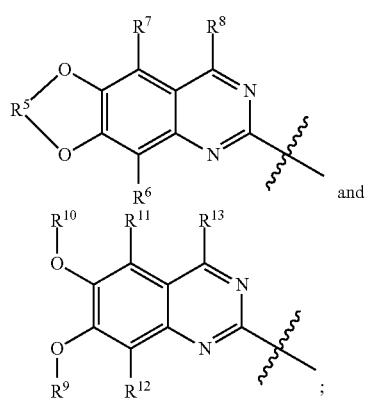

and

R⁵ is selected from:

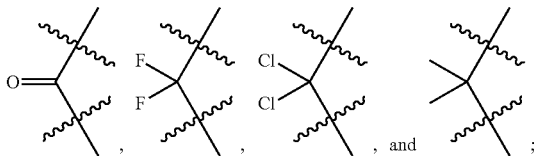

, , , and ;

or R⁵ is selected from

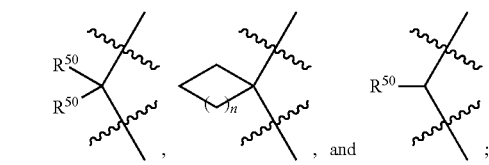

, , and ;

R⁵⁰ is independently selected from halogen and alkyl;
n is 0, 1, 2, 3, or 4;
R⁶, R⁷, and R⁸ are independently selected from: hydrogen, halogen, amino, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, hydroxyl, cyano, mercapto, thioalkyl, nitro, alkoxy, haloalkoxy, alkenyl, alkynyl, cycloalkyl, cycloalkylalkyl, heterocyclyl, heterocycloalkyl, aryloxy, —S(O)₂R¹, —S(O)₂ OH, —S(O)₂NH₂, —S(O)R¹, —S(O)OH, —S(O)NH₂—P(O)(OR¹)₂, —P(O)(OH)₂, B(OH)₂, —Si(R¹)₃, —COOH, —COOalkyl, —C(O)alkyl, —C(S)alkyl, —COOR¹, —C(O)R¹, —C(S)R¹, —C(O)NH₂, —C(S)NH₂, —NR¹C(O)alkyl, —NR¹C(O)R², —NR¹C(S)alkyl, —NR¹C(S)R², —NHC(O)NH₂, —NHC(S)NH₂, —NHC(O)OR¹, —OC(O)R¹, and —SF₅ each of which except halogen, nitro, cyano, —SF₅ and hydrogen may be optionally substituted, for example with halogen, alkyl, aryl, heterocycle or heteroaryl;
R⁹ and R¹⁰ are independently selected from: hydrogen, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, alkenyl, alkynyl, cycloalkyl, cycloalkylalkyl, heterocyclyl, and heterocycloalkyl;
R¹¹, R¹², and R¹³ are independently selected from: hydrogen, halogen, amino, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, hydroxyl, cyano, mercapto, thioalkyl, nitro, alkoxy, haloalkoxy, alkenyl, alkynyl, cycloalkyl, cycloalkylalkyl, heterocyclyl, heterocycloalkyl, aryloxy, —S(O)₂R¹, —S(O)₂ OH, —S(O)₂NH₂, —S(O)R¹, —S(O)OH, —S(O)NH₂—P(O)(OR¹)₂, —P(O)(OH)₂, B(OH)₂, —Si(R¹)₃, —COOH, —COOalkyl, —C(O)alkyl, —C(S)alkyl, —COOR¹, —C(O)R¹, —C(S)R¹, —C(O)NH₂, —C(S)NH₂, —NR¹C(O)alkyl, —NR¹C(O)R², —NR¹C(S)alkyl, —NR'C(S)R², —NHC(O)NH₂, —NHC(S)NH₂, —NHC(O)OR¹, —OC(O)R¹, and —SF₅ each of which except halogen, nitro, cyano, —SF₅ and hydrogen may be optionally substituted, for example with halogen, alkyl, aryl, heterocycle or heteroaryl;
wherein at least one of R¹¹, R¹², and R¹³ is —SF₅;
or wherein at least one of R¹¹, R¹², and R¹³ is selected from

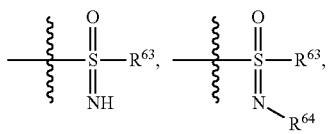

P(O)R$^{65}$R$^{65}$, and SF$_5$;

R$^{63}$ and R$^{64}$ are independently selected at each occurrence from hydrogen, hydroxyl, cyano, amino, alkyl, haloalkyl, alkoxy, cycloalkylalkyl, (phenyl)C$_0$-C$_4$alkyl, —C$_1$-C$_4$alkylOC(O)OC$_1$-C$_6$alkyl, —C$_1$-C$_4$alkylOC(O)C$_1$-C$_6$alkyl, —C$_1$-C$_4$alkylC(O)OC$_1$-C$_6$alkyl, aryl, heteroaryl, heterocycle, arylalkyl, heteroarylalkyl, heterocycloalkyl; and R$^{65}$ is independently selected at each occurrence from hydroxy, alkoxy, haloalkoxy, alkyl, cycloalkylalkyl-, aryl, arylalkyl, —O-arylalkyl, —O-aryl, heterocycle, heterocycloalkyl, heteroaryl, heteroarylalkyl, O-heteroaryl, O-heterocycle, —N(R$^{25}$)$_2$;

Non-limiting examples of A2 include:

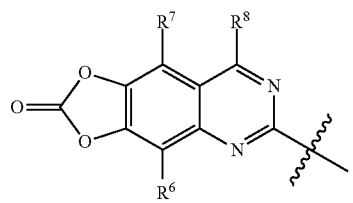

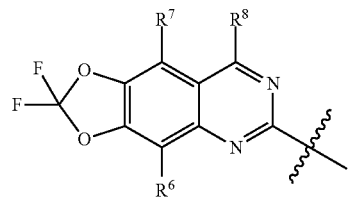

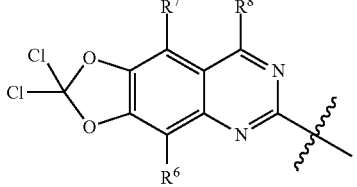

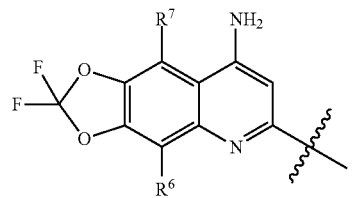

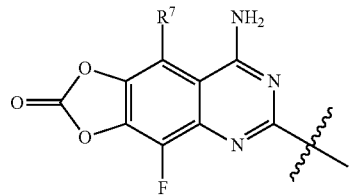

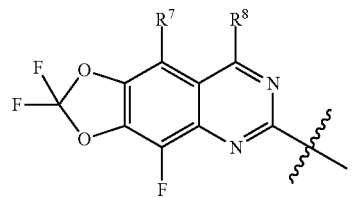

-continued

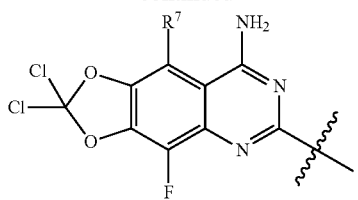

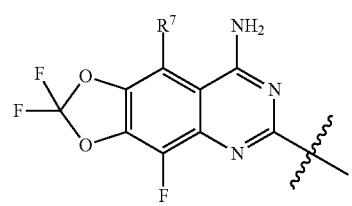

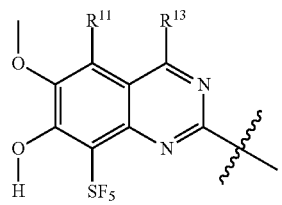

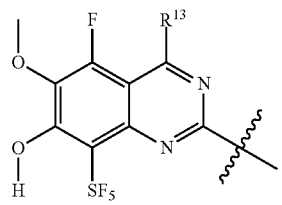

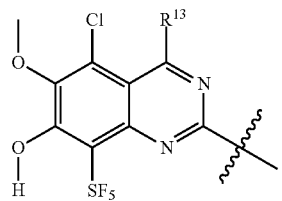

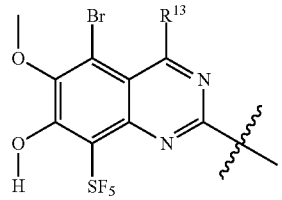

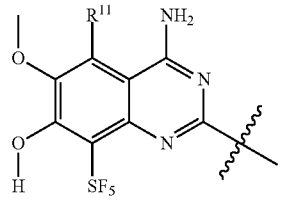

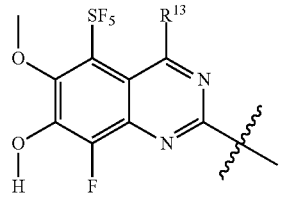

-continued
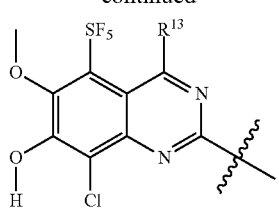
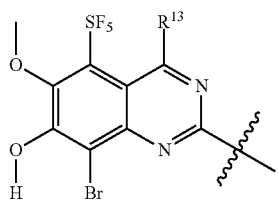
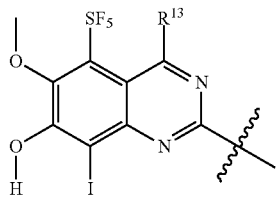
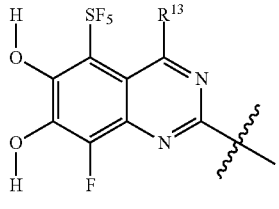
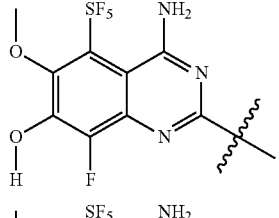
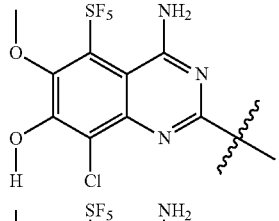
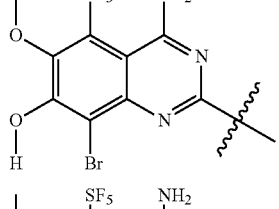
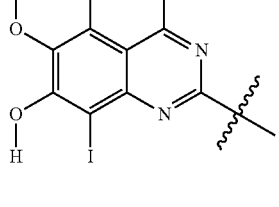
-continued
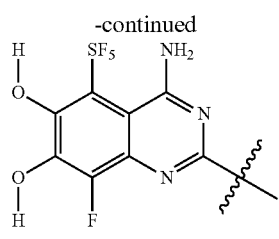
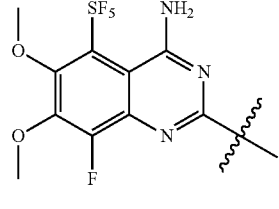
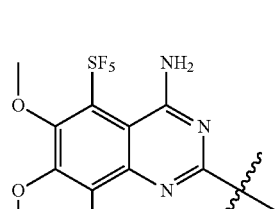
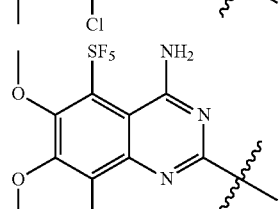
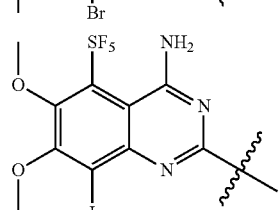
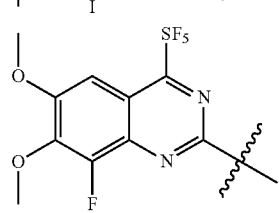
Cl is
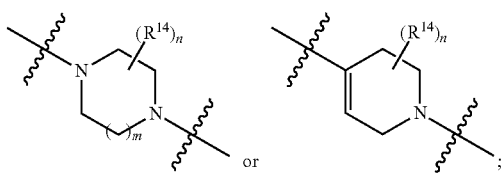
$R^{14}$ is independently selected at each occurrence from: hydrogen, $C_1$-$C_6$alkyl, $C_1$-$C_4$alkoxy$C_1$-$C_4$alkyl, and aryl;
m is 0, 1, or 2;

Non-limiting examples of C1 include:
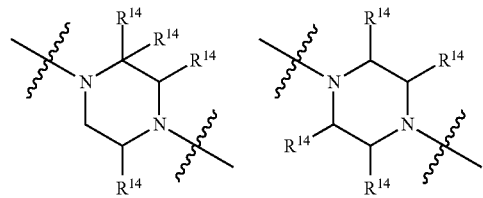
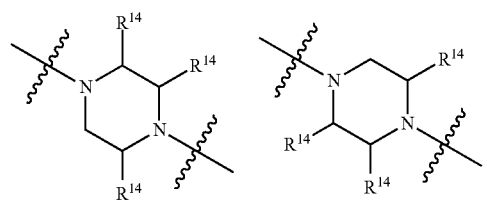
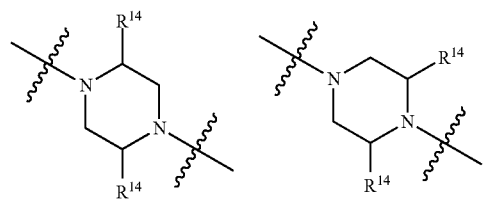
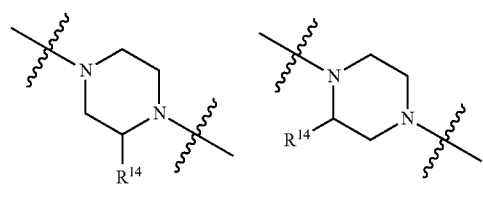
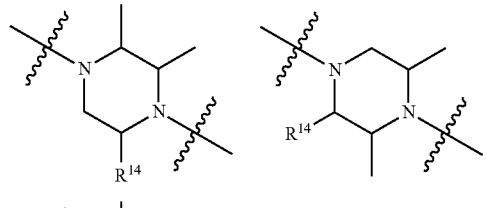
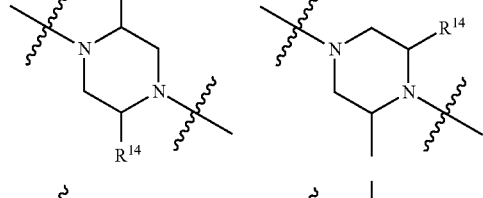
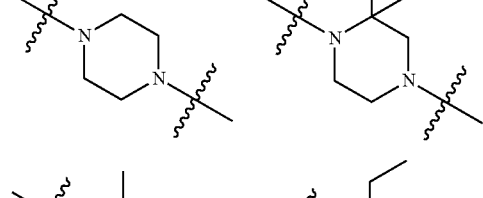
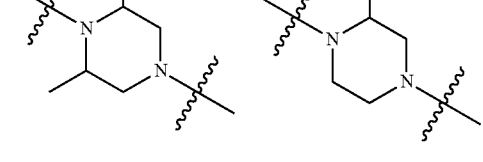
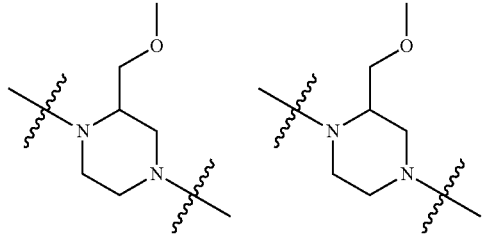
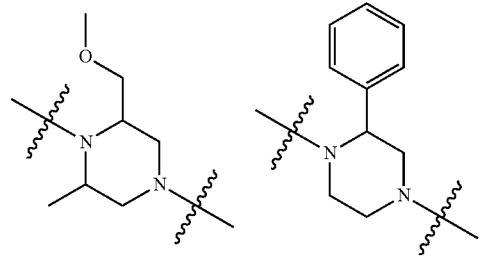
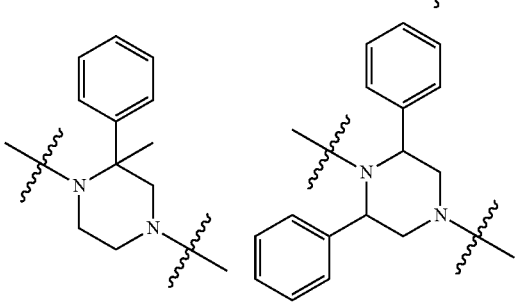
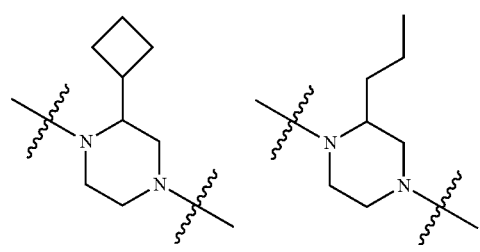
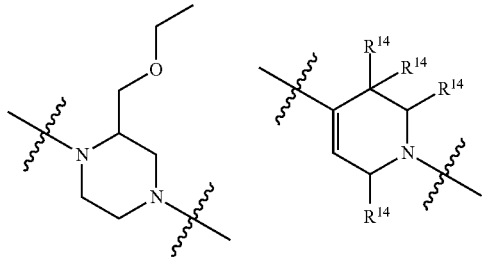
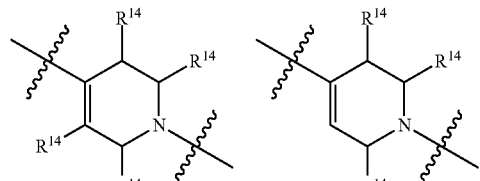
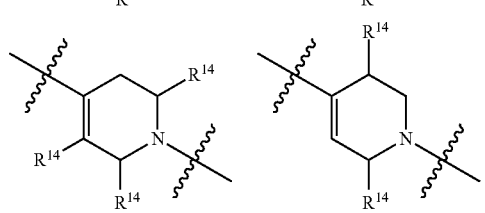

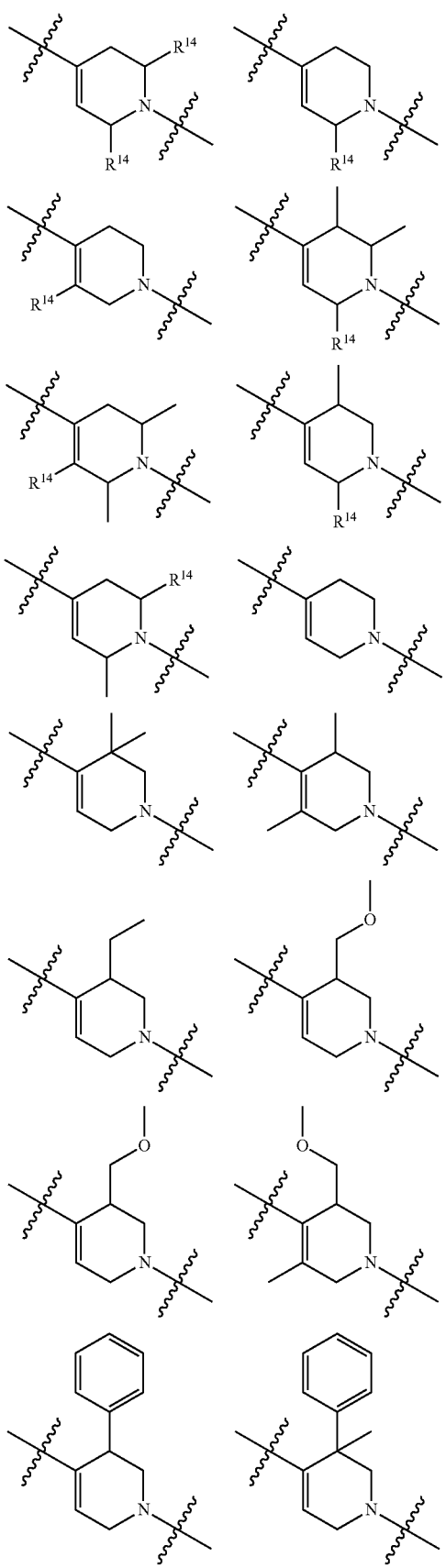
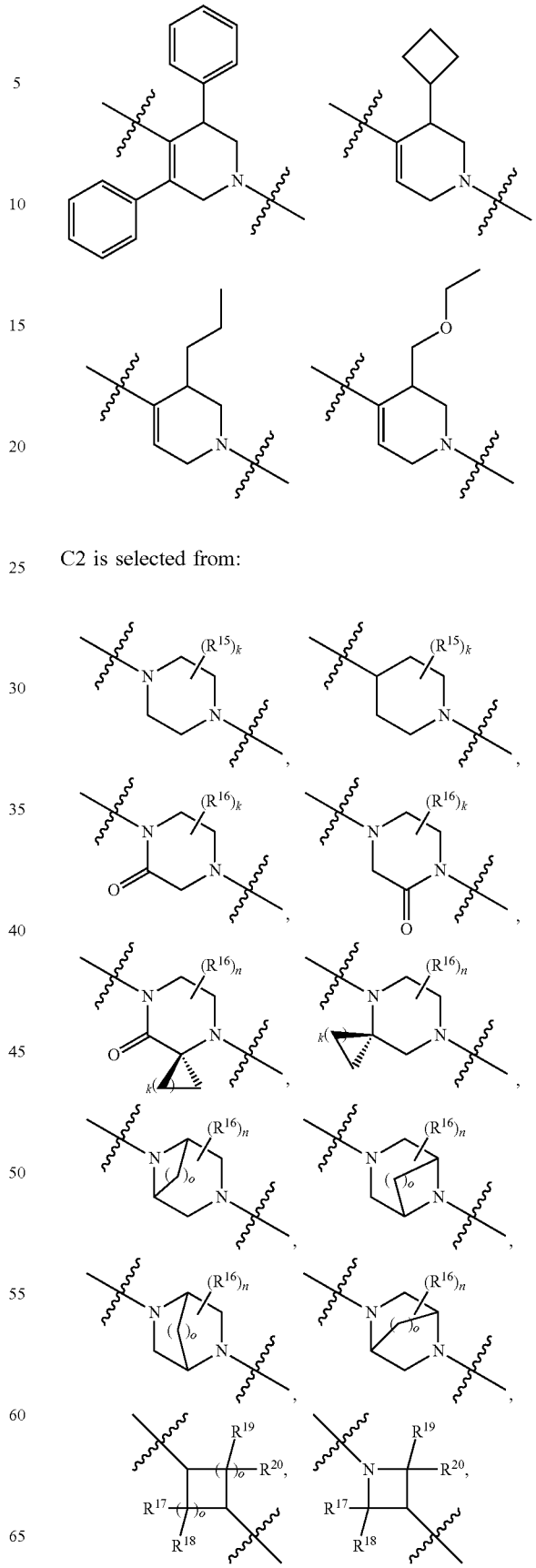
C2 is selected from:

-continued

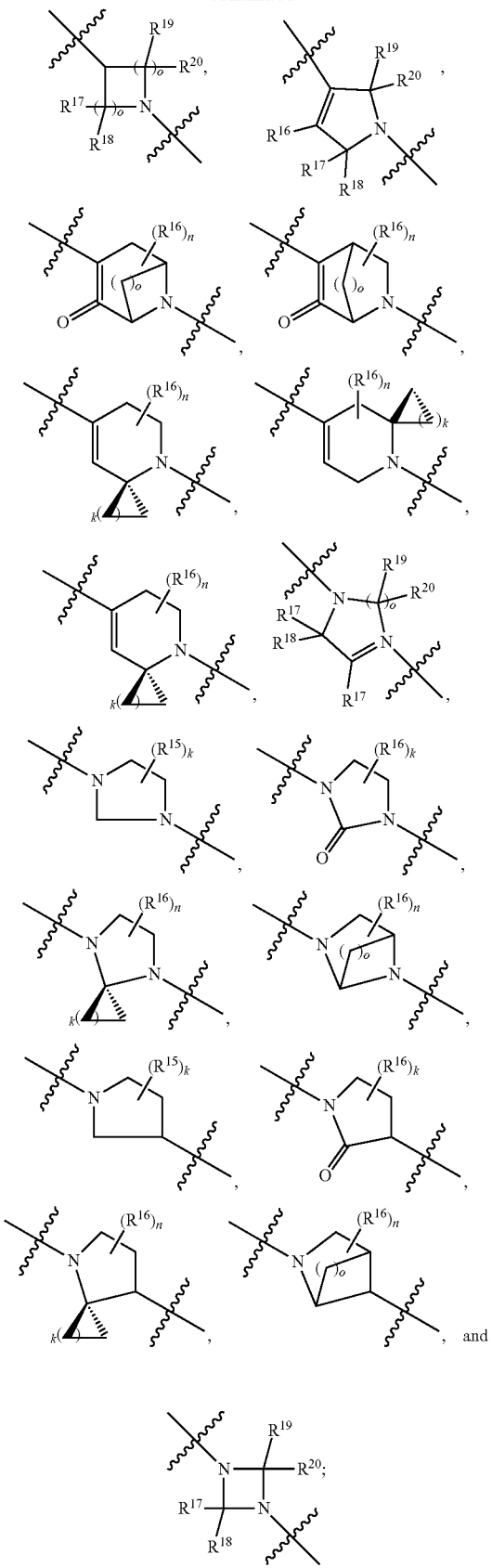

or C2 is selected from:

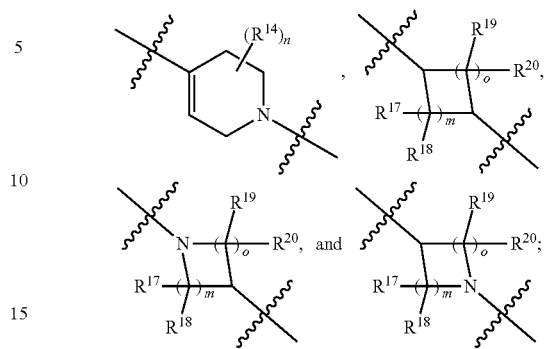

m is 0, 1, or 2;
o is independently 1 or 2;
k is 1, 2, 3, or 4;
n is 0, 1, 2, 3, or 4;
$R^{15}$ is independently selected at each occurrence from: hydrogen, $C_1$-$C_6$alkyl, $C_1$-$C_4$alkoxy$C_0$-$C_4$alkyl, aryl, and heteroaryl wherein at least one $R^{15}$ is heteroaryl;
$R^{16}$, $R^{17}$, $R^{18}$, $R^{19}$, and $R^{20}$ are independently selected at each occurrence from: hydrogen, $C_1$-$C_6$alkyl, $C_1$-$C_4$alkoxy$C_0$-$C_4$alkyl, aryl, and heteroaryl;
or, $R^{17}$ and $R^{18}$ or $R^{19}$ and $R^{20}$ may be taken together to form a 3- to 6-membered carbocyclic spiro ring or a 3- to 6-membered heterocyclic spiro ring containing 1 or 2 heteroatoms independently selected from nitrogen, oxygen, and sulfur;
or, $R^{17}$ and $R^{18}$ or $R^{19}$ and $R^{20}$ may be taken together to form a 3- to 6-membered carbocyclic fused ring or a 3- to 6-membered heterocyclic fused ring containing 1 or 2 heteroatoms independently selected from nitrogen, oxygen, and sulfur;
or, $R^{17}$ and $R^{18}$ or $R^{19}$ and $R^{20}$ may be taken together to form a carbonyl;
or, $R^{17}$ and $R^{19}$ or $R^{18}$ and $R^{20}$ can be taken together to form a bridged ring wherein the bridge can have 1 or 2 carbon atoms;

Non-limiting examples of C2 include:

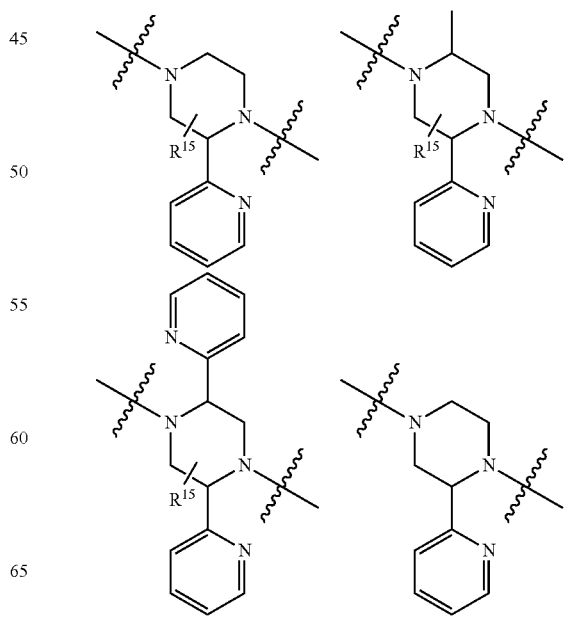

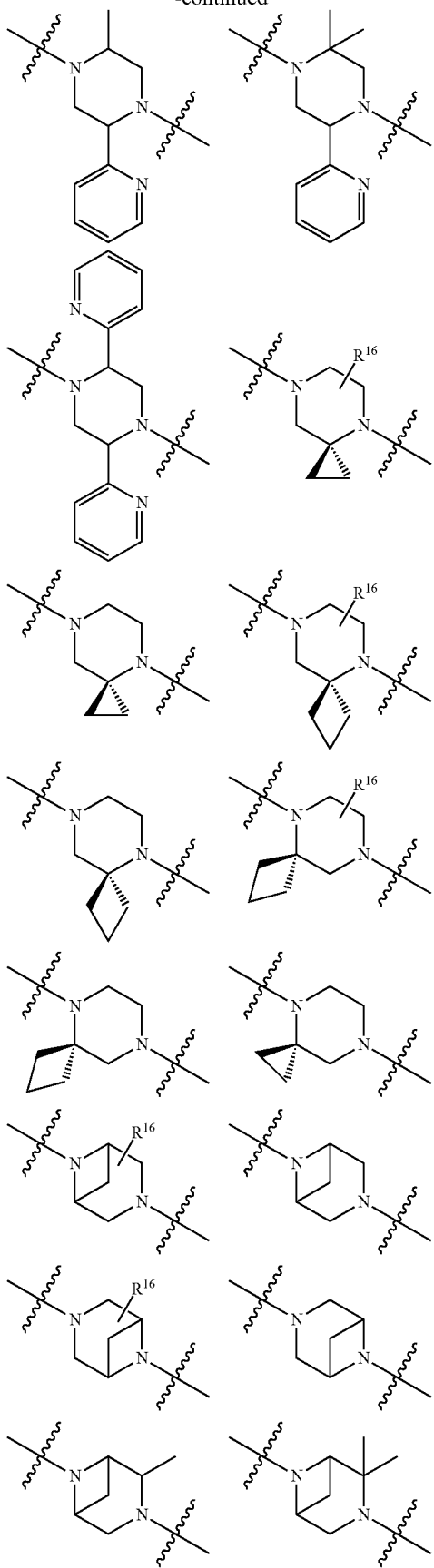
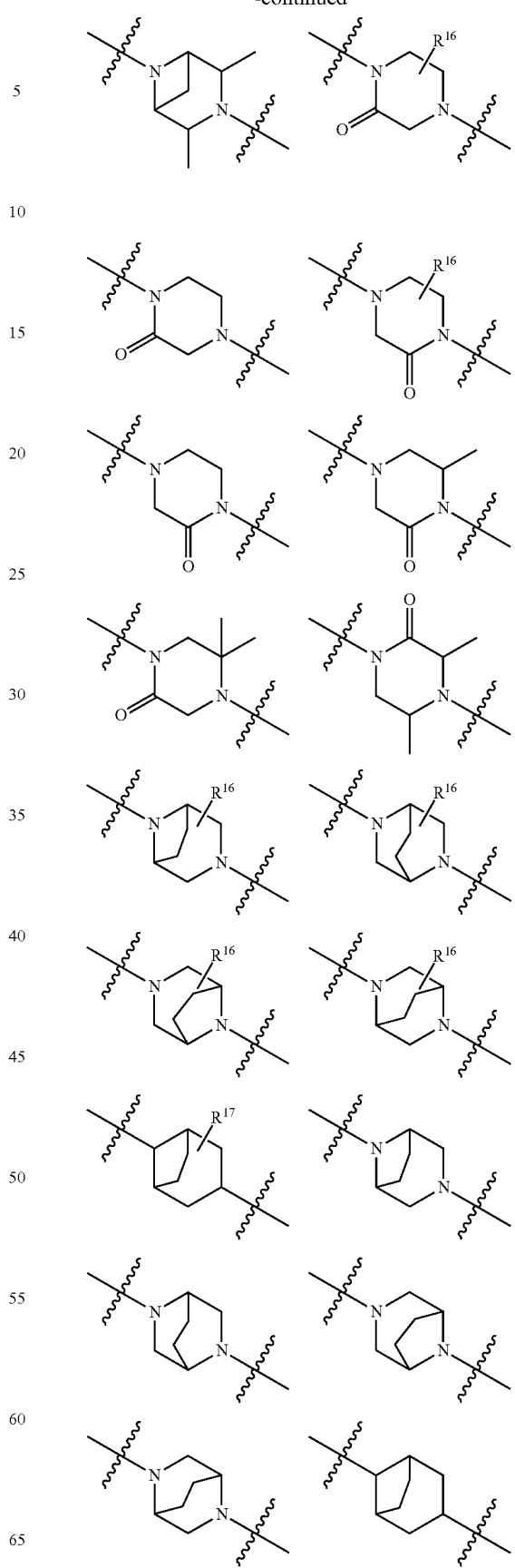

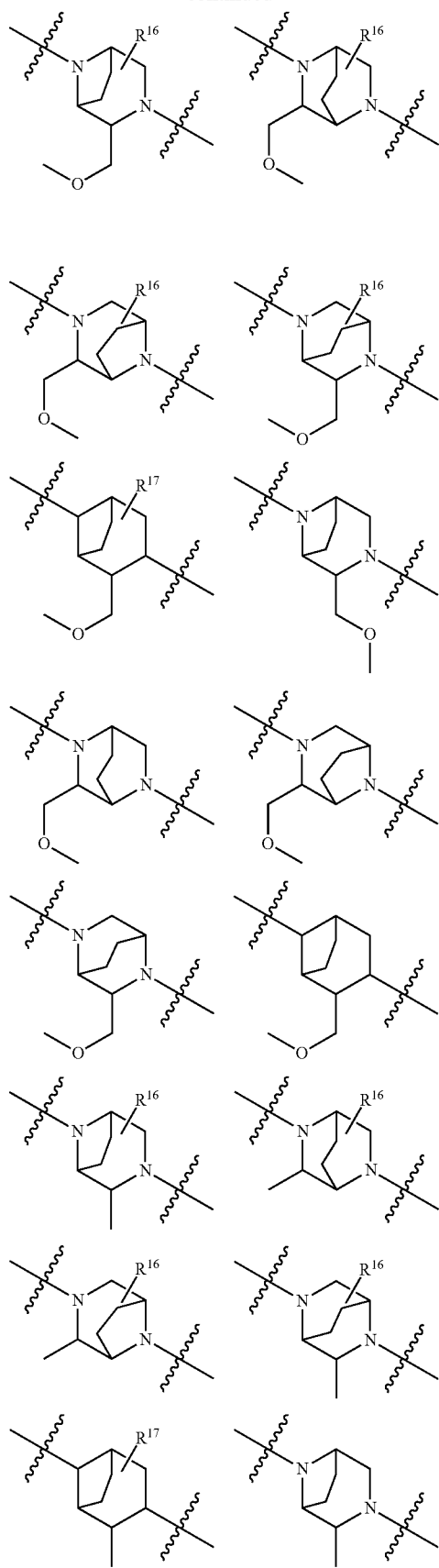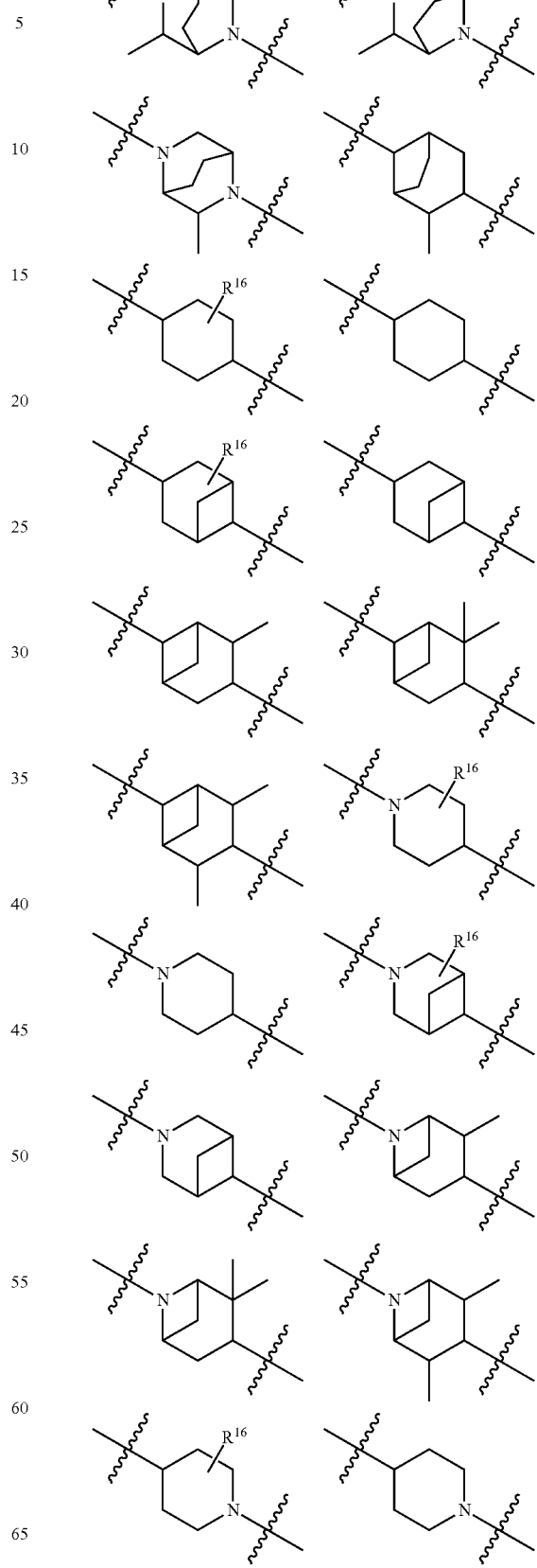

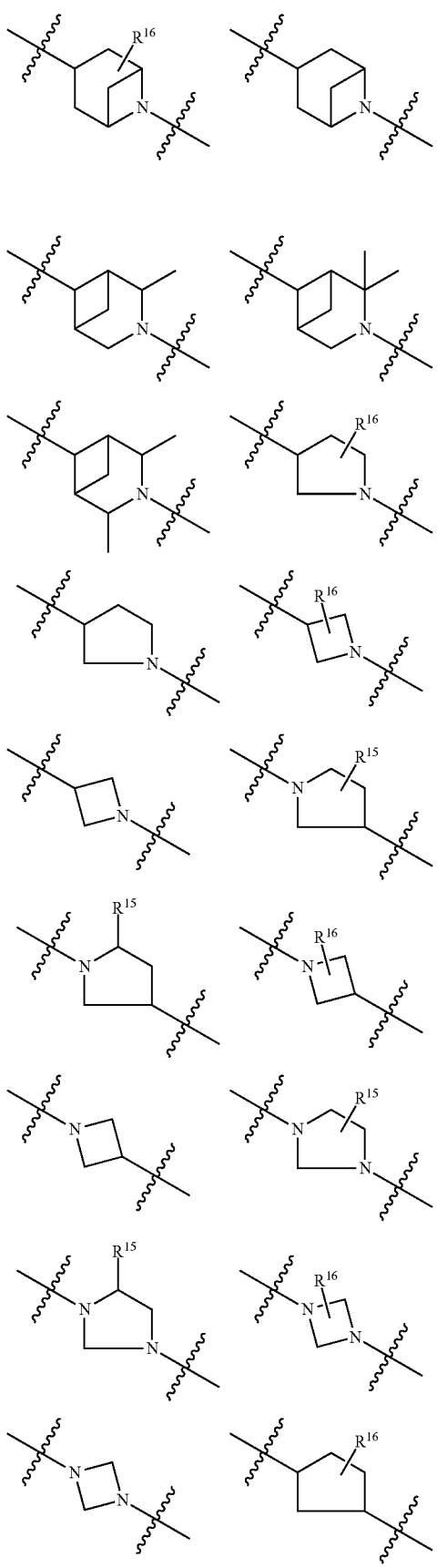
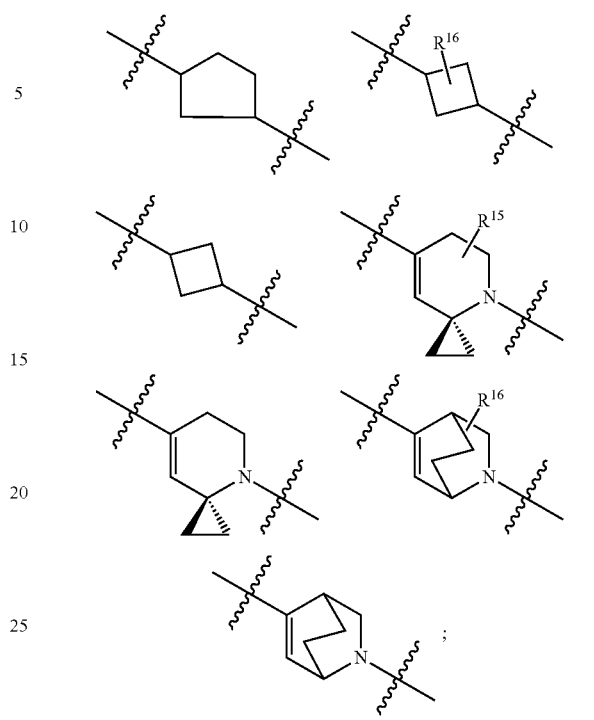
L1 is selected from:
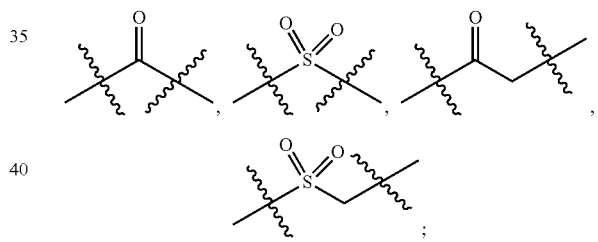
L2 is selected from:
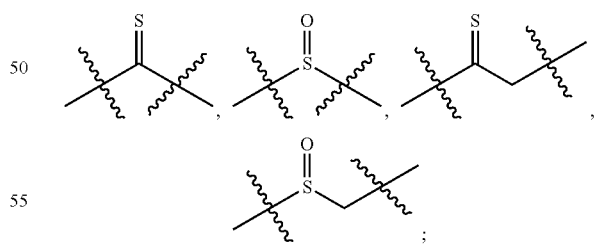
B1 is selected from:
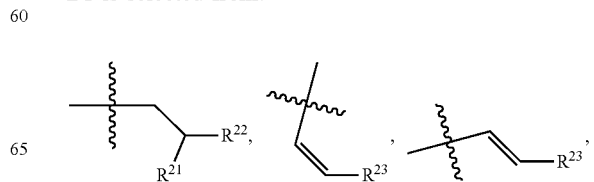

-continued

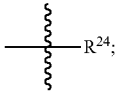

R²¹ is $(CH_2)_p NR^{25}R^{26}$ or $C(O)N(R^{27})_2$;
p is 0 or 1;
R²² is $C_1$-$C_6$alkyl or aryl optionally substituted with 0, 1, 2, or 3 R²⁸ groups;
R²³ is $C_3$-$C_6$cycloalkyl or aryl optionally substituted with 0, 1, 2, or 3 groups independently selected from halogen, $C_1$-$C_4$alkyl, $C_1$-$C_4$alkoxy, haloalkoxy, halo$C_1$-$C_4$alkyl, cyano, and hydroxyl;
R²⁴ is selected from: R²⁹ and R³⁰;
R²⁵ is hydrogen or $C_1$-$C_4$alkyl;
R²⁶ is selected from: hydrogen, optionally substituted $C_1$-$C_6$alkyl, and optionally substituted $C_1$-$C_6$haloalkyl, wherein the optional substituents are selected from $C_1$-$C_4$alkoxy, $C_3$-$C_6$cycloalkyl, and 4-6 membered heterocycle having 1-2 ring heteroatoms selected from nitrogen, oxygen, and sulfur;
or NR²⁵R²⁶ can be taken in combination to form a 4 to 7 membered saturated azacycle optionally substituted with 0, 1, or 2 $C_1$-$C_4$ alkyl groups;
R²⁷ is independently selected at each occurrence from: hydrogen and $C_1$-$C_4$alkyl;
or $N(R^{27})_2$ can be taken in combination can form a 4-6 member azacycle;
R²⁸ is independently selected at each occurrence from: hydrogen, cyano, hydroxyl, halogen, $C_1$-$C_4$alkyl, $C_2$-$C_4$alkenyl, $C_2$-$C_4$alkynyl, $C_1$-$C_4$haloalkyl, haloalkoxy, and $C_1$-$C_4$alkoxy;
R²⁹ is CH₂heterocycle having 4 to 6 ring atoms and 1 or 2 ring heteroatoms independently selected from nitrogen, oxygen, and sulfur, which is optionally substituted with 0, 1, or 2 substituents independently selected from phenyl, halogen, and $C_1$-$C_6$alkyl, or two substituents, taken in combination form a benzo ring optionally substituted with halogen or cyano;
R³⁰ is a bicyclic heteroaryl group having 1 or 2 ring heteroatoms independently selected from nitrogen, oxygen, and sulfur, partially unsaturated carbocycle or partially unsaturated heterocycle having 1 or 2 ring heteroatoms independently selected from nitrogen, oxygen, and sulfur, each of which is optionally substituted with 0, 1, 2, or 3 substituents independently selected from amino, halogen, cyano, hydroxy, $C_1$-$C_4$alkyl, haloalkoxy, and $C_1$-$C_4$alkoxy;
Non-limiting examples of B1 include:

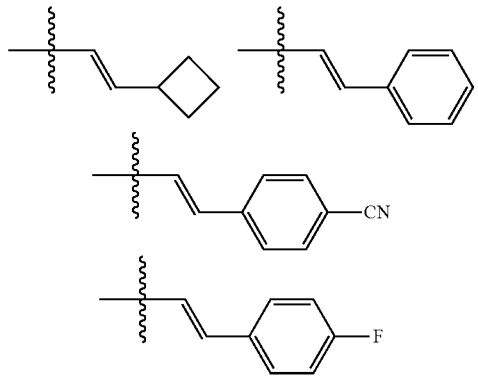

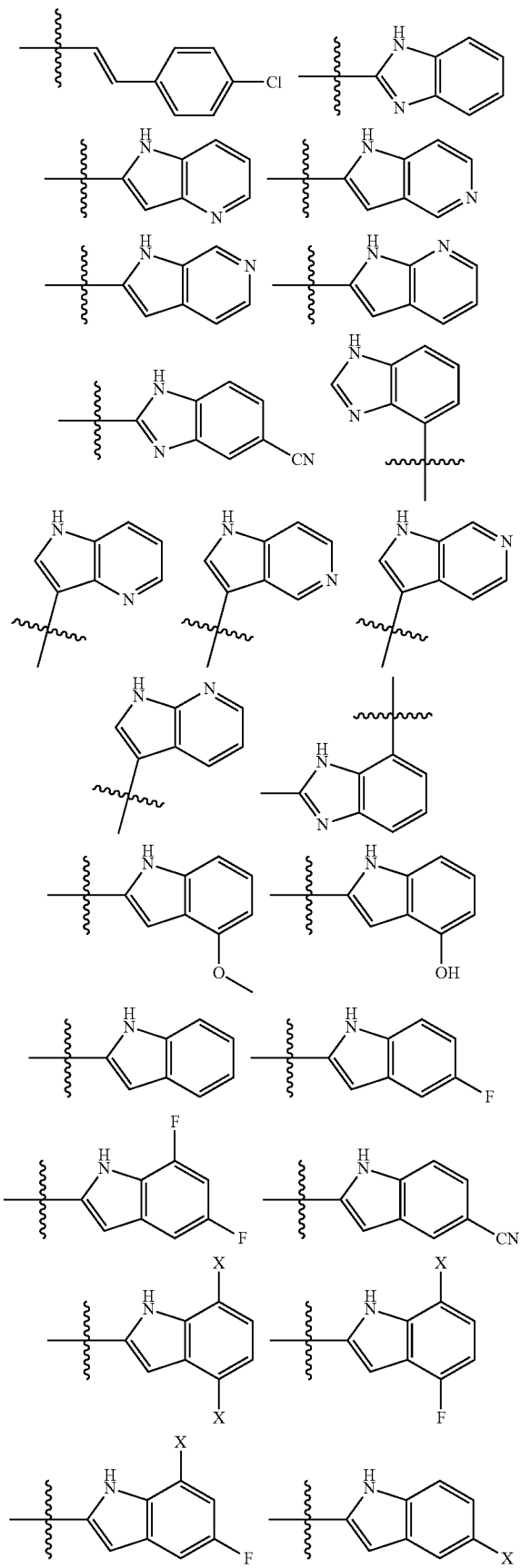

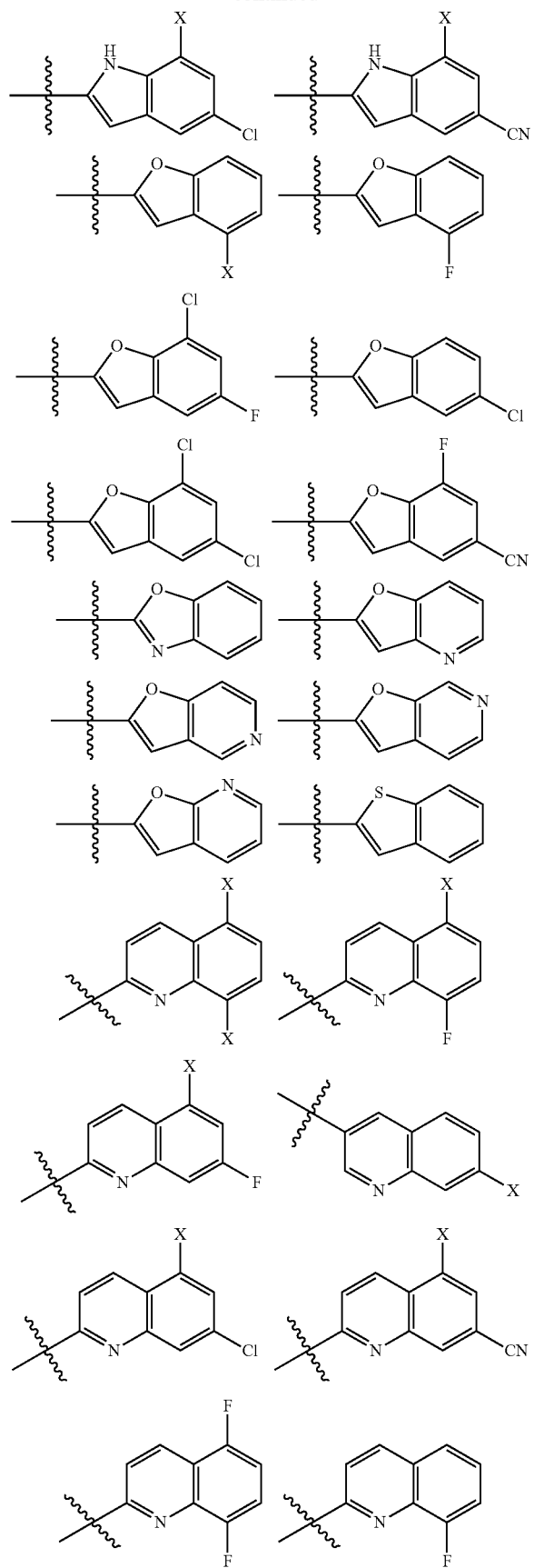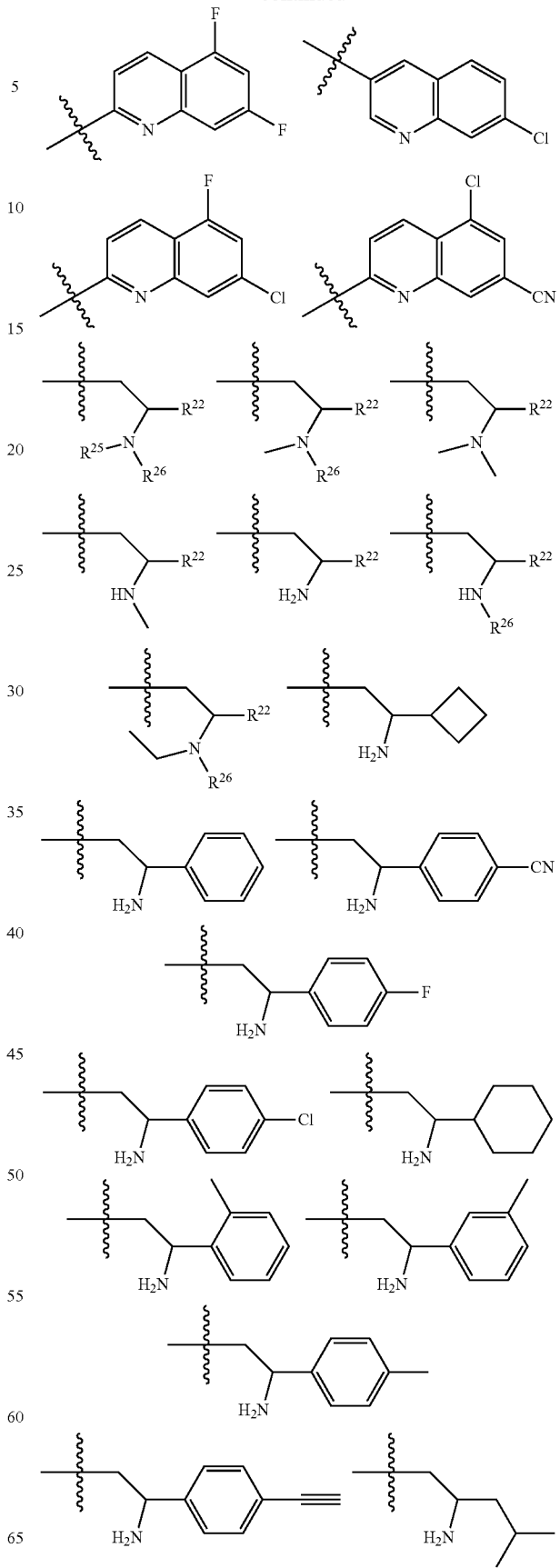

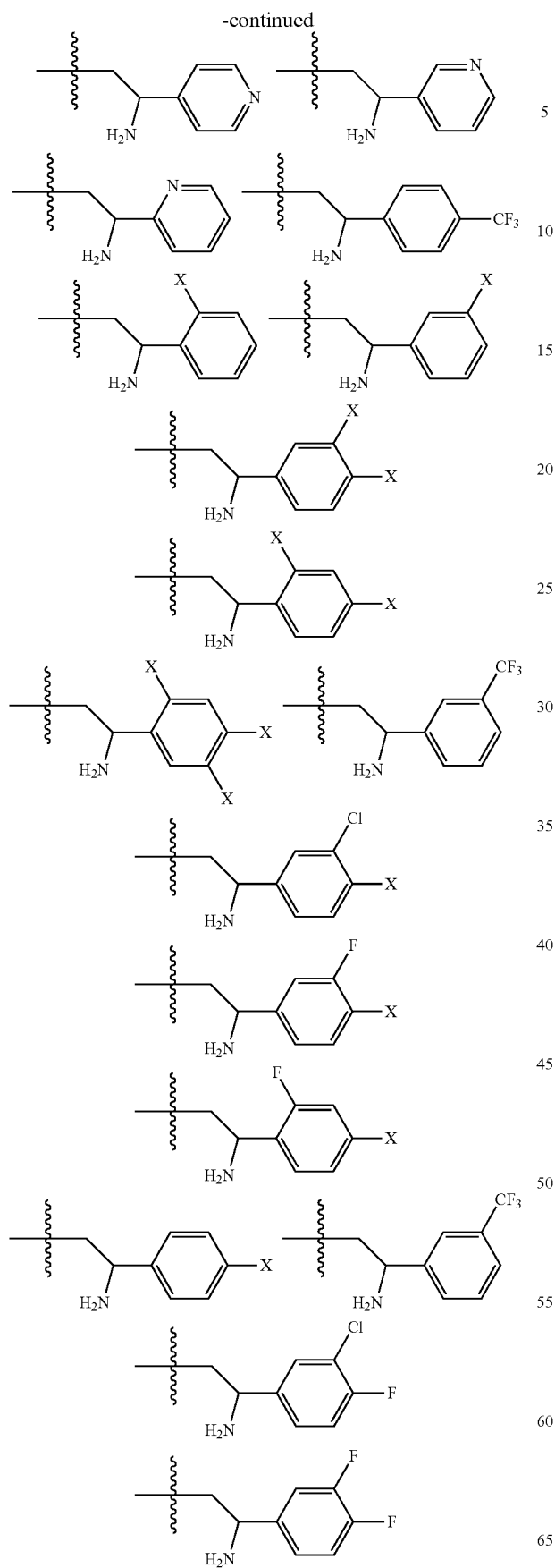
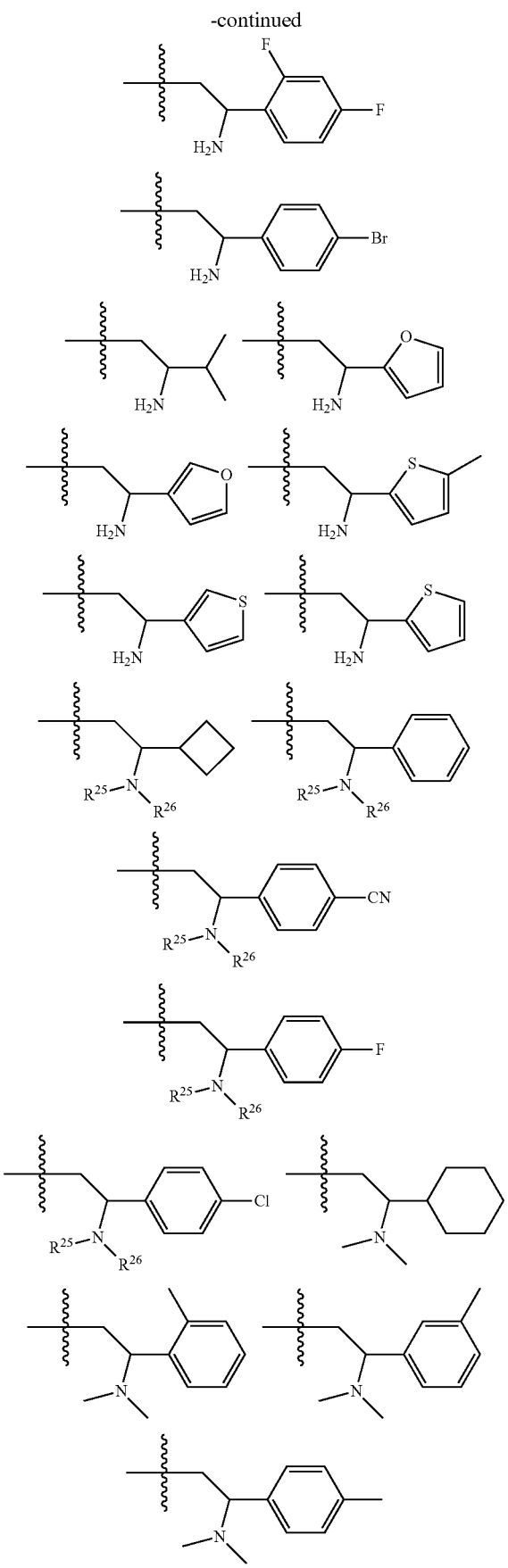

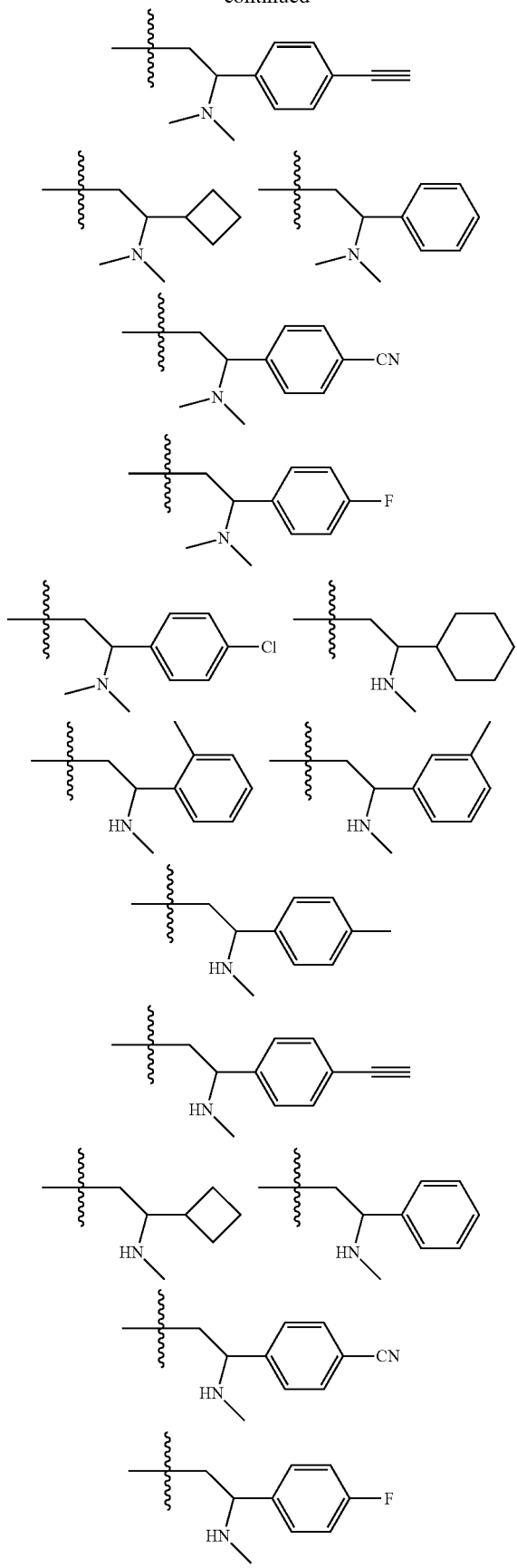
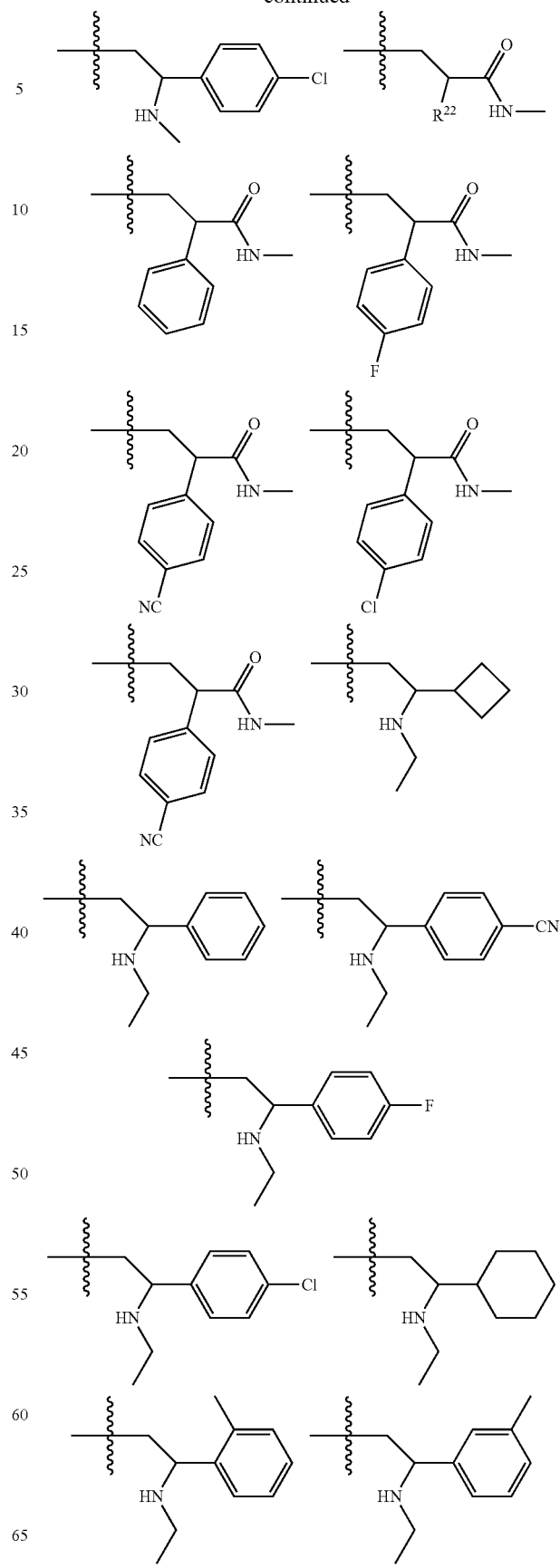

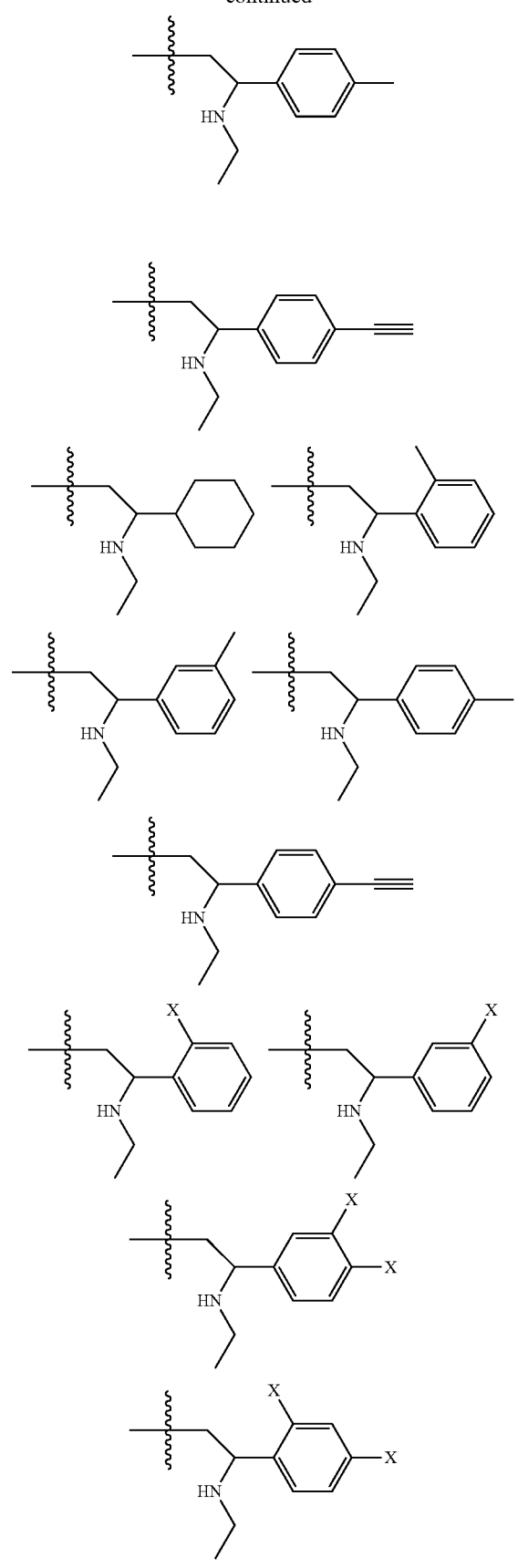
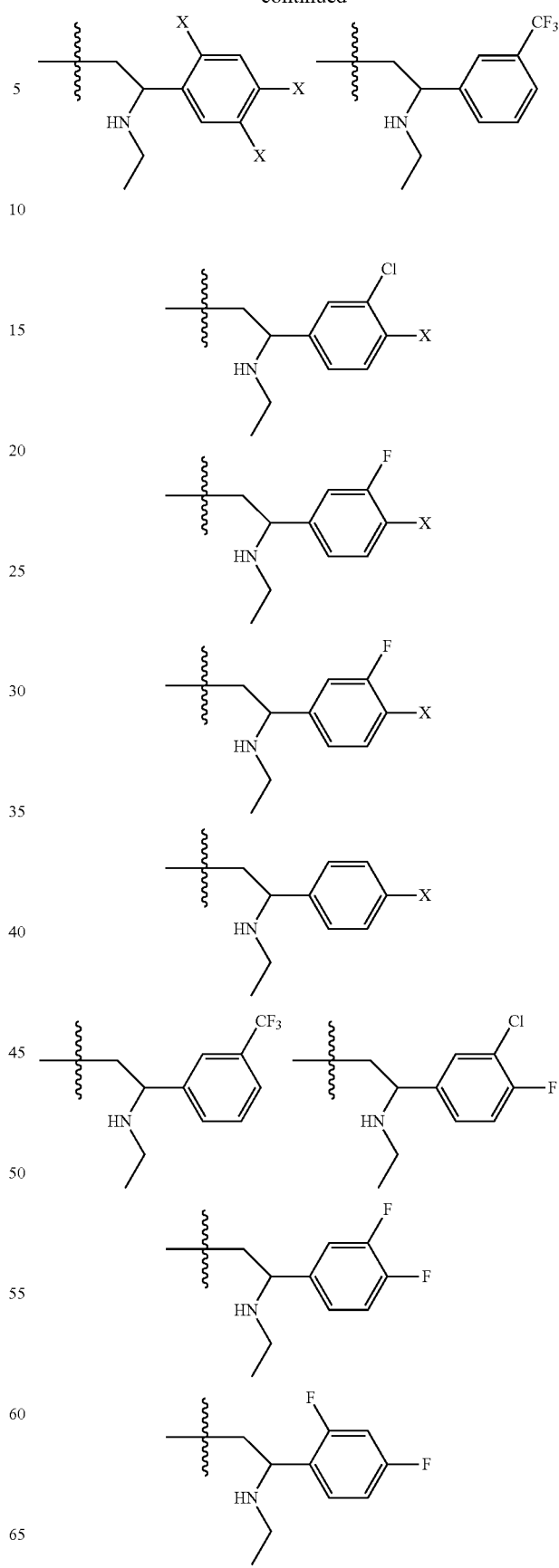

-continued
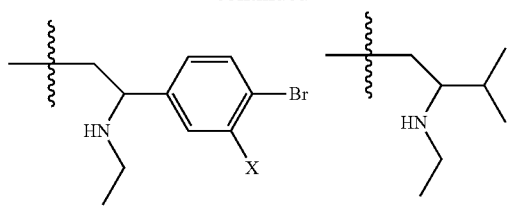
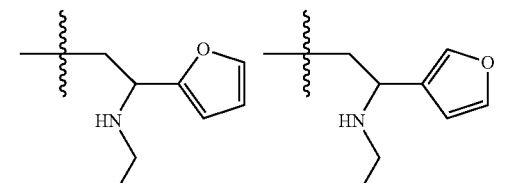
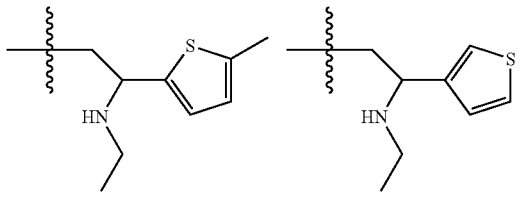
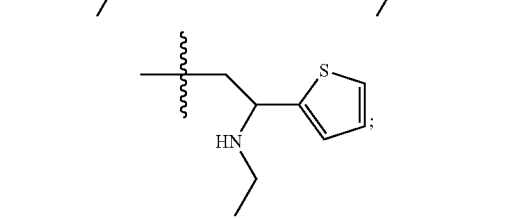

X is a halogen; and
B2 is a CH$_2$ linked bicyclic heterocycle with 7 to 12 ring atoms and 1, 2, or 3 ring heteroatoms selected from nitrogen, oxygen, and sulfur, which is optionally substituted with 0, 1, or 2 groups independently selected from aryl, heteroaryl, halogen, and C$_1$-C$_6$alkyl.
Non-limiting examples of B2 include:
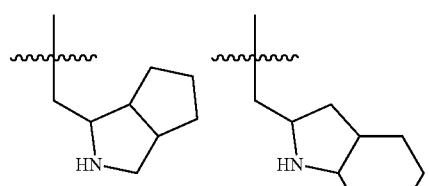
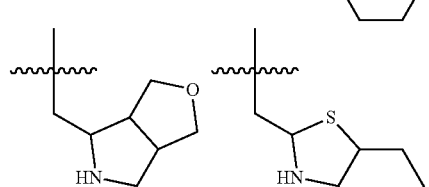
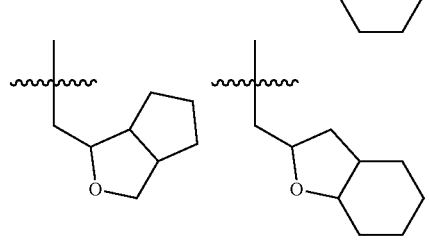
-continued
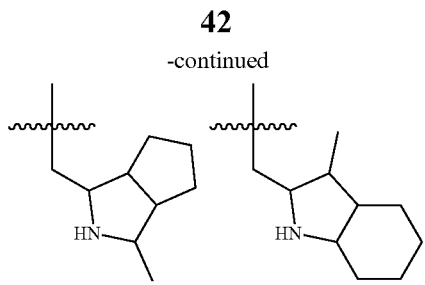
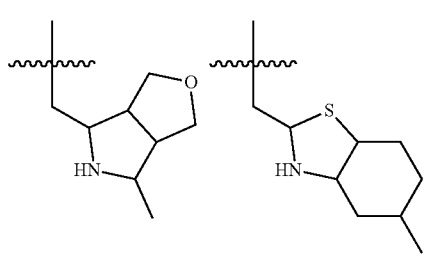
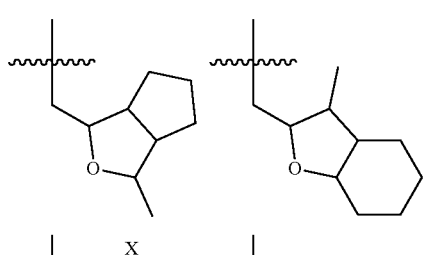
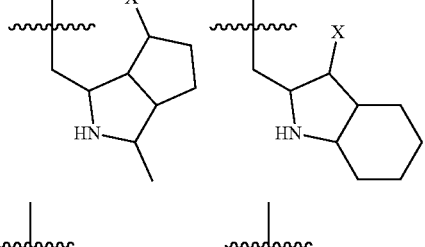
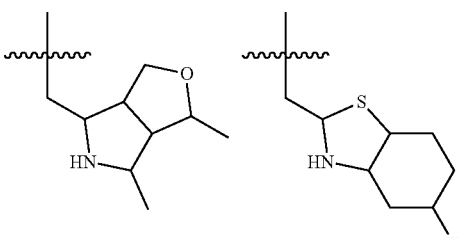
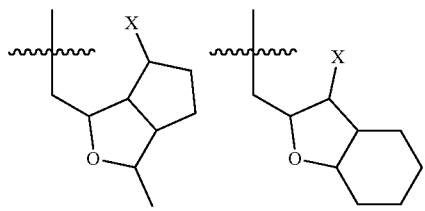
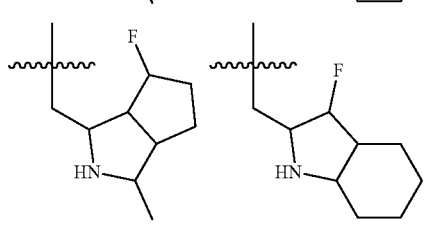

-continued
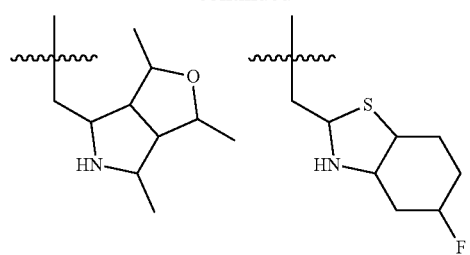
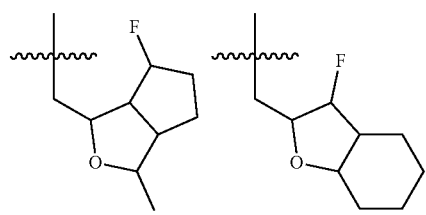
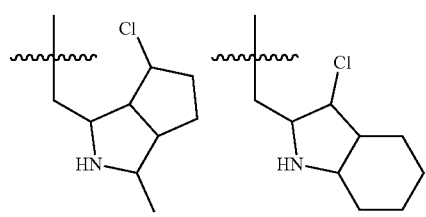
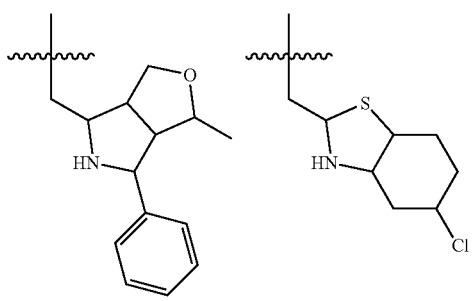
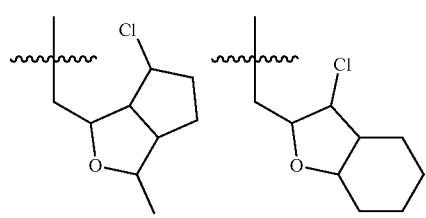
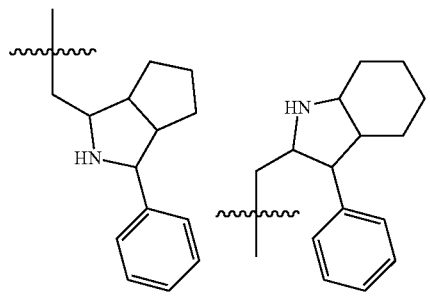
-continued
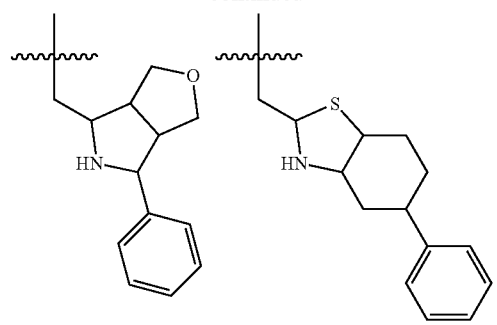
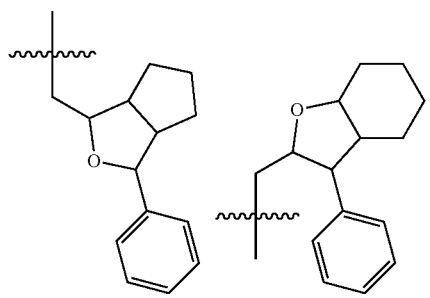
In the above illustrations X represents F, Cl, Br, or I.
One skilled in the art will appreciate that there are species of A, B, and C that comprise chiral centers and that all stereoisomers are included in the present invention except where shown otherwise or excluded by context.
Non-limiting examples of compounds of Formula I include:
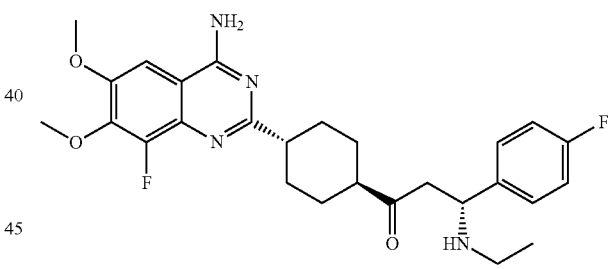
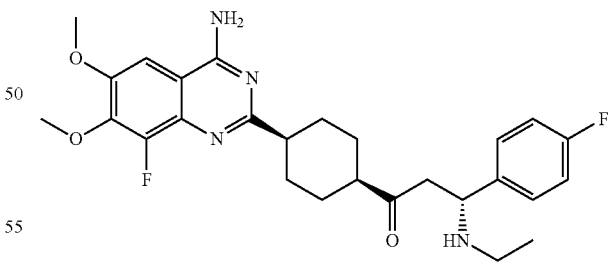
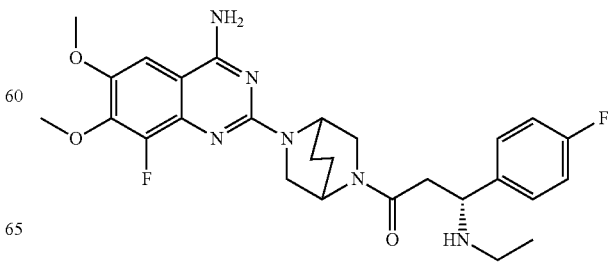

45
-continued
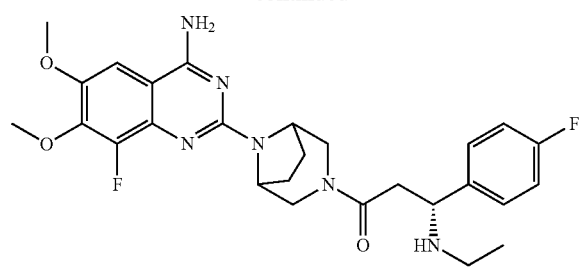
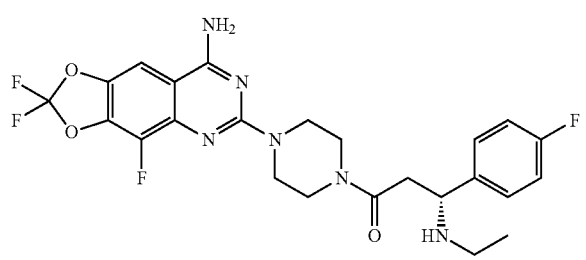
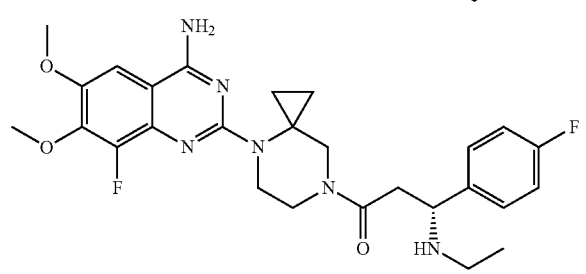
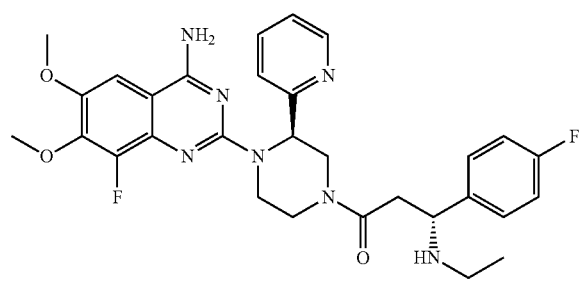
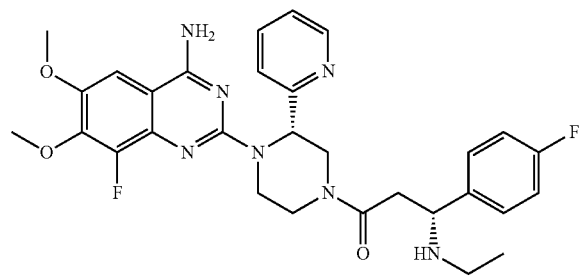
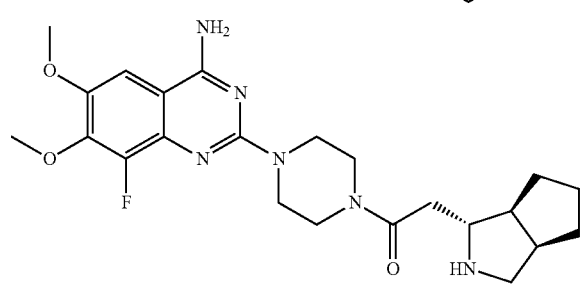
46
-continued
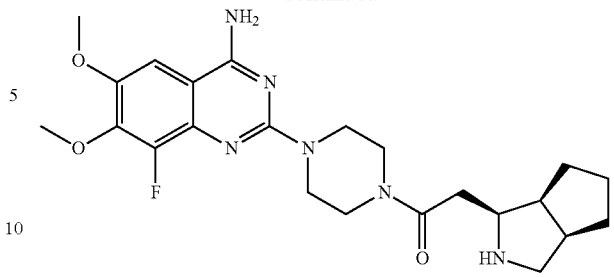
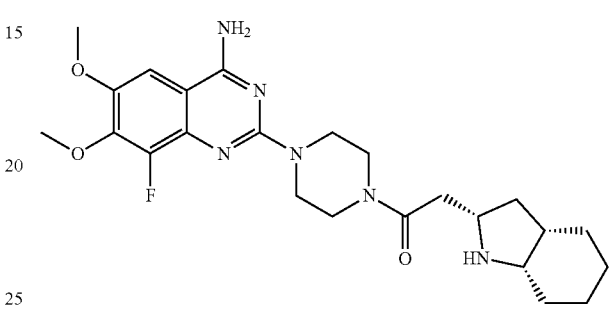
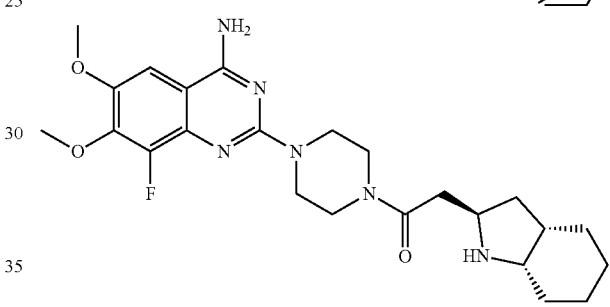
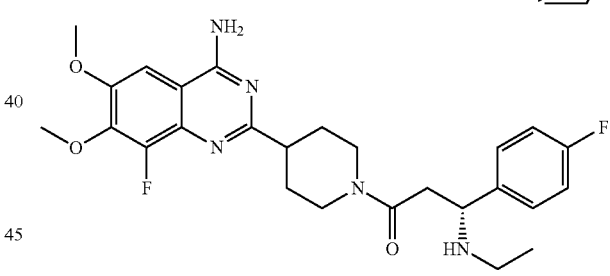
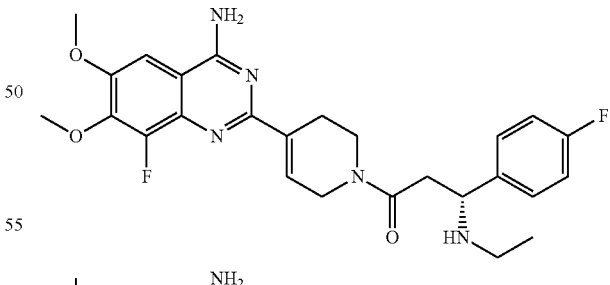
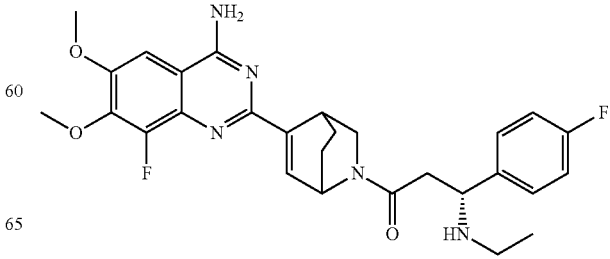

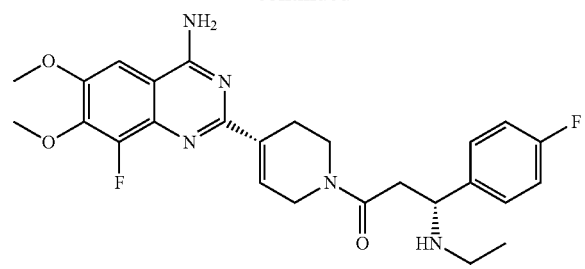
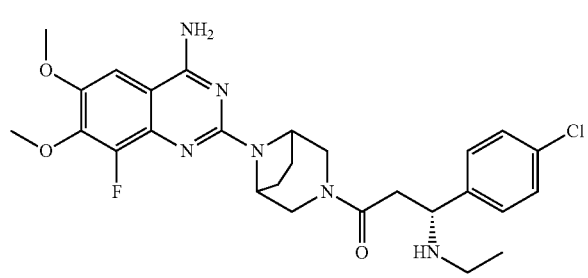
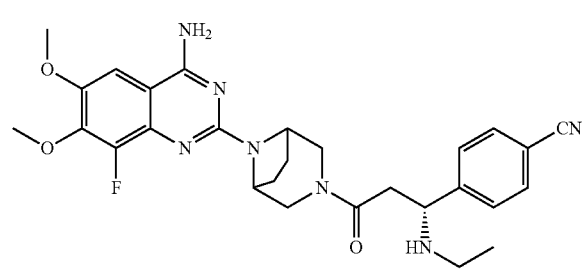
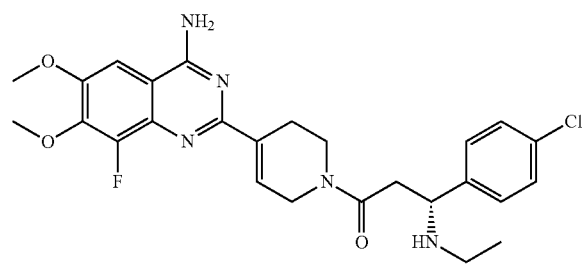
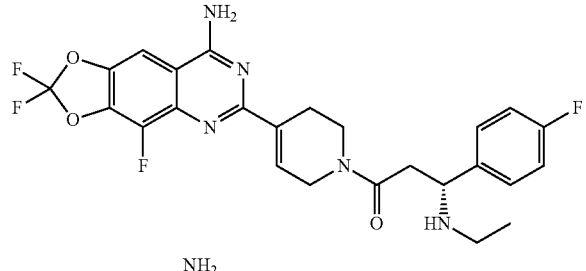
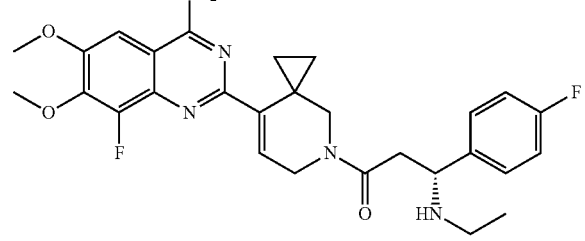
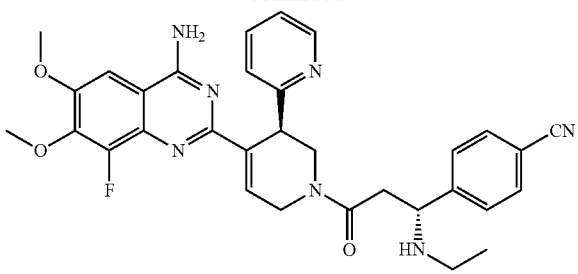
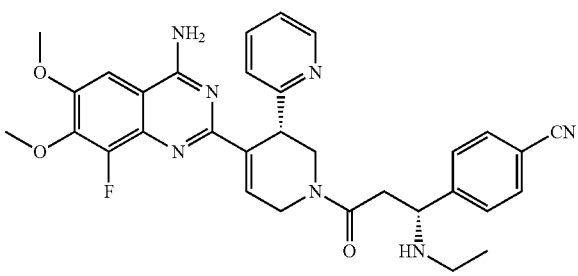
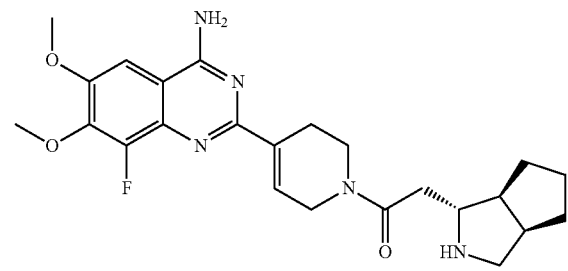
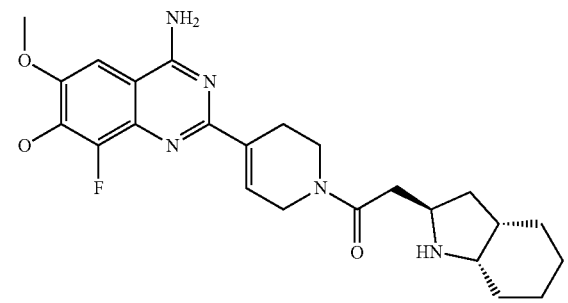
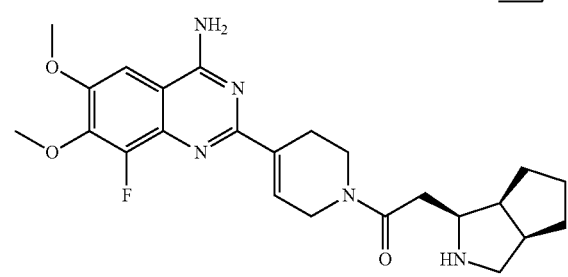
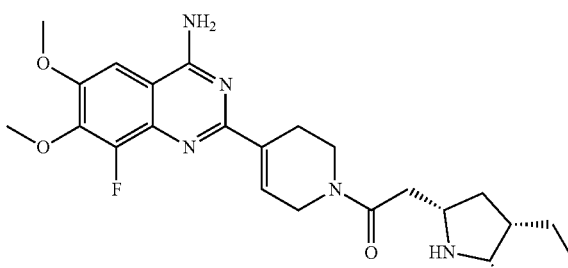

Formula II is:

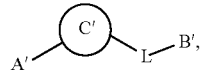

or a pharmaceutically acceptable salt, isotopic analog, prodrug, or isolated isomer thereof optionally in pharmaceutically acceptable carrier;

wherein:
A' is selected from: A1, A2, and A3;
B' is selected from: B1, B2, and B3;
C' is selected from: C1, C2 and C3;
L is selected from: L1 and L2;
wherein at least one of A', B', or C' is selected from: A3, B3, or C3 respectively;

A1 is

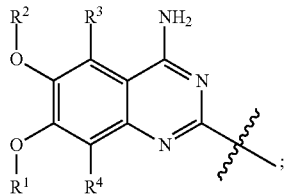

$R^1$ and $R^2$ are independently selected from: hydrogen, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, alkenyl, alkynyl, cycloalkyl, cycloalkylalkyl, heterocyclyl, and heterocycloalkyl;

$R^3$ and $R^4$ are independently selected from: hydrogen, halogen, amino, $C_1$-$C_6$alkyl, C1-C4alkoxy$C_1$-$C_4$alkyl, halo$C_1$-$C_4$alkyl, aryl, heteroaryl, arylalkyl, heteroarylalkyl, hydroxyl, cyano, mercapto, thioalkyl, nitro, alkoxy, haloalkoxy, alkenyl, alkynyl, cycloalkyl, cycloalkylalkyl, heterocyclyl, heterocycloalkyl, aryloxy, —S(O)$_2$R$^1$, —S(O)$_2$ OH, —S(O)$_2$NH$_2$, —S(O)R$^1$, —S(O)OH, —S(O)NH$_2$—P(O)(OR$^1$)$_2$, —P(O)(OH)$_2$, B(OH)$_2$, —Si(R$^1$)$_3$, —COOH, —COOalkyl, —C(O)alkyl, —C(S)alkyl, —COOR$^1$, —C(O)R$^1$, —C(S)R$^1$, —C(O)NH$_2$, —C(S)NH$_2$, —NR$^1$C(O)alkyl, —NR$^1$C(O)R$^2$, —NR$^1$C(S)alkyl, —NR$^1$C(S)R$^2$, —NHC(O)NH$_2$, —NHC(S)NH$_2$, —NHC(O)OR$^1$, and —OC(O)R$^1$ each of which except halogen, nitro, cyano, and hydrogen may be optionally substituted, for example with halogen, alkyl, aryl, heterocycle or heteroaryl;

A2 is selected from:

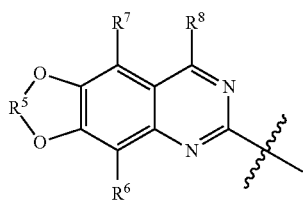

and

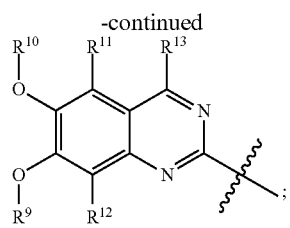

$R^5$ is selected from:

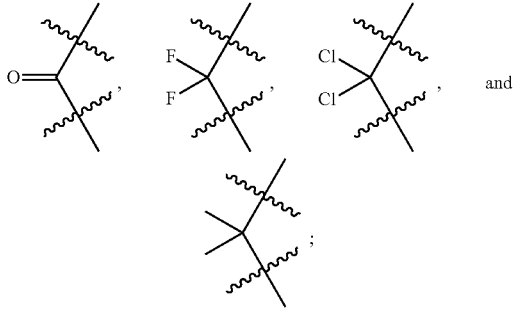

or $R^5$ is selected from

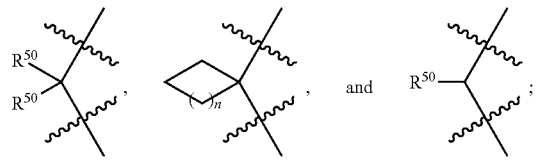

$R^{50}$ is independently selected from halogen and alkyl;
n is 0, 1, 2, 3, or 4;

$R^6$, $R^7$, and $R^8$ are independently selected from: hydrogen, halogen, amino, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, hydroxyl, cyano, mercapto, thioalkyl, nitro, alkoxy, haloalkoxy, alkenyl, alkynyl, cycloalkyl, cycloalkylalkyl, heterocyclyl, heterocycloalkyl, aryloxy, —S(O)$_2$R$^1$, —S(O)$_2$ OH, —S(O)$_2$NH$_2$, —S(O)R$^1$, —S(O)OH, —S(O)NH$_2$—P(O)(OR$^1$)$_2$, —P(O)(OH)$_2$, B(OH)$_2$, —Si(R$^1$)$_3$, —COOH, —COOalkyl, —C(O)alkyl, —C(S)alkyl, —COOR$^1$, —C(O)R$^1$, —C(S)R$^1$, —C(O)NH$_2$, —C(S)NH$_2$, —NR$^1$C(O)alkyl, —NR$^1$C(O)R$^2$, —NR$^1$C(S)alkyl, —NR$^1$C(S)R$^2$, —NHC(O)NH$_2$, —NHC(S)NH$_2$, —NHC(O)OR$^1$, —OC(O)R$^1$, and —SF$_5$ each of which except halogen, nitro, cyano, —SF$_5$ and hydrogen may be optionally substituted, for example with halogen, alkyl, aryl, heterocycle or heteroaryl;

$R^9$ and $R^{10}$ are independently selected from: hydrogen, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, alkenyl, alkynyl, cycloalkyl, cycloalkylalkyl, heterocyclyl, and heterocycloalkyl;

$R^{11}$, $R^{12}$, and $R^{13}$ are independently selected from: hydrogen, halogen, amino, $C_1$-$C_6$alkyl, $C_1$-$C_4$alkoxy$C_1$-$C_4$alkyl, halo$C_1$-$C_4$alkyl, aryl, heteroaryl, arylalkyl, heteroarylalkyl, hydroxyl, cyano, mercapto, thioalkyl, nitro, alkoxy, haloalkoxy, alkenyl, alkynyl, cycloalkyl, cycloalkylalkyl, heterocyclyl, heterocycloalkyl, aryloxy, —S(O)$_2$R$^1$, —S(O)$_2$ OH, —S(O)$_2$NH$_2$, —S(O)R$^1$, —S(O)OH, —S(O)NH$_2$—P(O)(OR$^1$)$_2$, —P(O)(OH)$_2$, B(OH)$_2$, —Si(R$^1$)$_3$, —COOH, —COOalkyl, —C(O)alkyl, —C(S)alkyl, —COOR$^1$, —C(O)R$^1$, —C(S)R$^1$, —C(O)NH$_2$, —C(S)NH$_2$, —NR$^1$C(O)alkyl, —NR$^1$C(O)R$^2$, —NR$^1$C(S)alkyl, —NR$^1$C(S)R$^2$, —NHC(O)NH$_2$, —NHC(S)NH$_2$, —NHC(O)OR$^1$, —OC(O)R$^1$, and —SF$_5$ each of which except halogen, nitro, cyano, —SF$_5$ and hydrogen may be optionally substituted, for example with halogen, alkyl, aryl, heterocycle or heteroaryl;

wherein at least one of R$^{11}$, R$^{12}$, and R$^{13}$ is —SF$_5$;
or wherein at least one of R$^{11}$, R$^{12}$, and R$^{13}$ is selected from

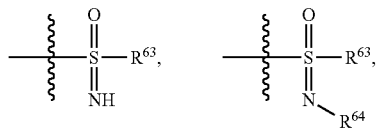

P(O)R$^{65}$R$^{65}$, and SF$_5$;

R$^{63}$ and R$^{64}$ are independently selected at each occurrence from hydrogen, hydroxyl, cyano, amino, alkyl, haloalkyl, alkoxy, cycloalkylalkyl, (phenyl)C$_0$-C$_4$alkyl, —C$_1$-C$_4$alkylOC(O)OC$_1$-C$_6$alkyl, —C$_1$-C$_4$alkylOC(O)C$_1$-C$_6$alkyl, —C$_1$-C$_4$alkylC(O)OC$_1$-C$_6$alkyl, aryl, heteroaryl, heterocycle, arylalkyl, heteroarylalkyl, heterocycloalkyl; and R$^{65}$ is independently selected at each occurrence from hydroxy, alkoxy, haloalkoxy, alkyl, cycloalkylalkyl-, aryl, arylalkyl, —O-arylalkyl, —O-aryl, heterocycle, heterocycloalkyl, heteroaryl, heteroarylalkyl, O-heteroaryl, O-heterocycle, —N(R$^{25}$)$_2$;

A3 is

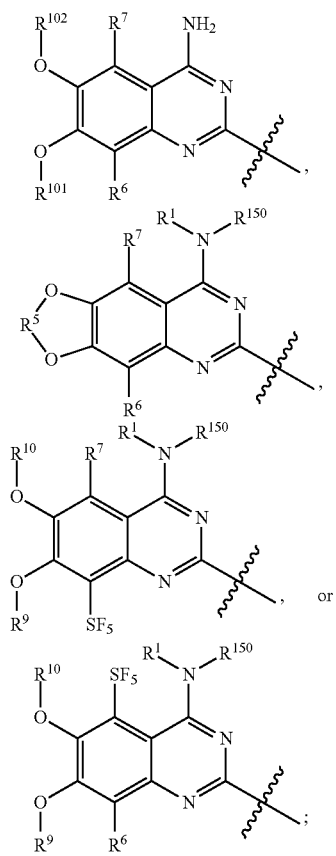

R$^{101}$ and R$^{102}$ are independently selected from: hydrogen, C$_1$-C$_6$alkyl, C$_1$-C$_4$alkoxyC$_1$-C$_4$alkyl, haloC$_1$-C$_4$alkyl, aryl, heteroaryl, arylalkyl, heteroarylalkyl, alkenyl, alkynyl, cycloalkyl, cycloalkylalkyl, heterocyclyl, R$^{150}$, and heterocycloalkyl;

wherein at least one of R$^{101}$ or R$^{102}$ is R$^{150}$;

R$^{150}$ is selected from the following:

i. The residue of a fatty acid. Examples are short chain fatty acids with 3, 4, or 5 aliphatic carbons, medium-chain fatty acids with aliphatic tails of 6, 7, 8, 9, 10, 11 or 12 carbons, long chain fatty acids, which have aliphatic tails of 13, 14, 15, 16, 17, 18, 19, 20, 21 or 22 carbons, or a very long fatty acid, which has 22, 23, 24, 25, 26 27, or 28 or more aliphatic carbons. The aliphatic chain can be saturated, mono-unsaturated, di-unsaturated, tri-unsaturated, polyunsaturated, or alkynyl. Unsaturated fatty acids can be used in a cis or trans configuration, and include, but are not limited to oleic acid, ω6 fatty acid such as linoleic acid, ω3 fatty acid such as α-linolenic acid, docosahexaenoic acid, stearidonic acid, eicosapentaenoic acid, docosapentaenoic acid, eicosatetraenoic acid, myristoleic acid, palmitoleic acid, sapienic acid, elaidic acid, vaccenic acid, gadoleic acid, eicosenoic acid, nervonic acid, eicosadienoic acid, docasadienoic acid, linolenic acid, t-linolenic acid, pinolenic acid, eleosteric acid, β-eleostearic acid, mead acid, eicosatrienoic acid, linoleic acid, linoelaidic acid, α-linolenic acid, arachidonic acid, erucic acid and docosahexaenoic acid. Nonlimiting examples of saturated fatty acids that can be used to provide the prodrugs of the present invention are caprylic acid, capric acid, lauric acid, myristic acid, palmitic, stearic acid, arachidic acid, behenic acid, lignoceric acid and cerotic acid.

ii. The residue of an amino acid that is naturally occurring or synthetic, and includes for example, α, β γ or δ amino acids. Naturally occurring amino acids include those found in proteins, e.g., glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In some embodiments, the amino acid is in the L-configuration. Alternatively, the amino acid can be used in the D-configuration or in a mixture of L- and D-. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-argininyl or β-histidinyl. Additional amino acids include selenocysteine, pyrrolysine, N-formylmethionine, γ-aminobutyric acid (GABA), δ-aminolevulinic acid, aminobenzoic acid (including 4-aminobenzoic acid), aminoisobutyric acid, dehydroalanine, cystathionine, lanthionine, djenkolic acid, diaminopimelic acid, norvaline, alloisoleucine, t-leucine, α-amino-heptanoic acid, pipecolic acid, α, β-diaminopropionic acid, α,γ-diaminobutyric acid, ornithine, glutamic acid, allothreonine, homocysteine, β-aminobutyric acid, α-aminoisobutyric acid, isovaline, sarcosine, N-ethylglycine, N-propylglycine, N-isopropyl glycine, N-methyl alanine, N-ethyl alanine, N-methyl-β-alanine, isoserine, norleucine, homoserine, O-methyl-homoserine, O-ethyl-homoserine, homonorleucine, carboxyglutamic acid, hydroxyproline, hypusine, pyroglutamic acid, and α-hydroxy-γ-aminobutyric acid.

iii. The residue of a non-naturally occurring amino acid with an extended length between the amino group and the carboxylic acid, which can be used either alone or as a linker to another prodrug moiety. Examples include amino acids wherein the amino and carboxylic acid are separated by an aliphatic or heteroaliphatic moiety (nonlimiting example is 8-amino-3,6-dioxaoctanoic acid), for example an alkyl, alkenyl, alkynyl, ethylene glycol, propylene glycol, alkylene glycol, or the like, moiety, e.g., with 3, 4, 5, 6, 7, 8, 9, 10, 11 or 12 or more straight, branched or cyclic atoms or moieties (e.g., alkylene glycol moieties), as appropriate to provide the desired properties. In some embodiments, the amino acid has one or more internal amine, carbonyl, carboxy, oxo, thio, phosphate or phosphonate moieties in the heteroaliphatic chain.

iv. The residue of one or a series of amino acids linked to a terminal fatty acid or to an endcap like hydrogen or alkyl. In one non-limiting example, 8-amino-3,6-dioxaoctanoic acid (one or several in sequence) is covalently bound to the selected Complement D inhibitor of the present invention through a functional group such as a carboxylic acid, sulfonyl, hydroxyl or amino group. See generally Lau, et al., "Discovery of the Once-Weekly Glucagon-Like Peptide-1 (GLP-1) Analogue Semiglutide", *J. Med. Chem.*, 2015, 58, 7370-7380. The 8-amino-3,6-dioxaoctanoic acid is covalently linked to an aliphatic acid, including but not limited to a C16, C18, C20 aliphatic acid, or a dicarboxylic acid, including but not limited to a C8, C10, C12, C14, C16, C18 or C20 diacid. One or more amino acids can also be used in the selected configuration to add length or functionality;

Non-limiting examples of A3 include:

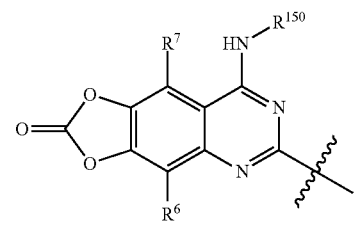

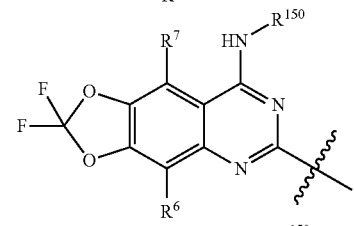

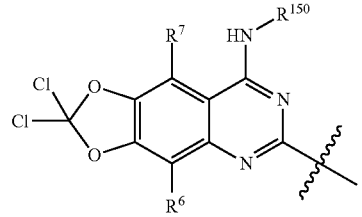

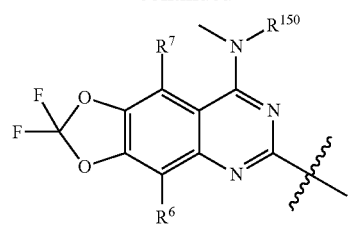

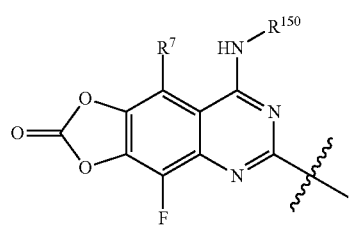

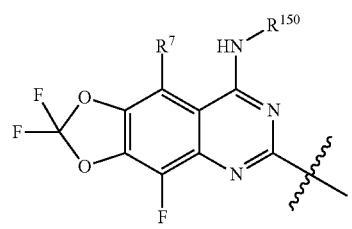

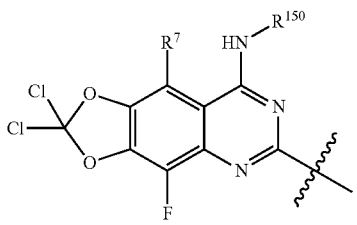

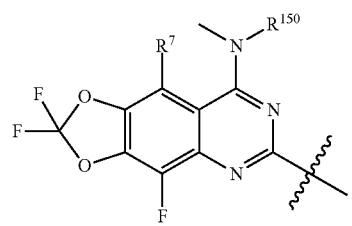

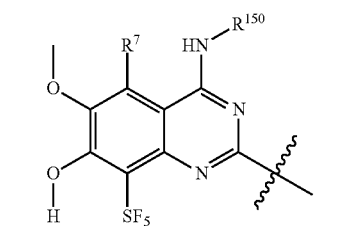

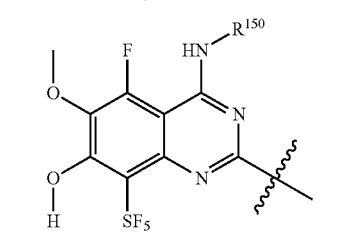

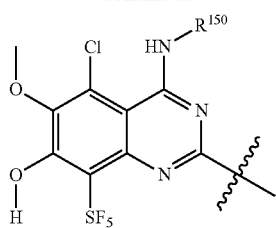
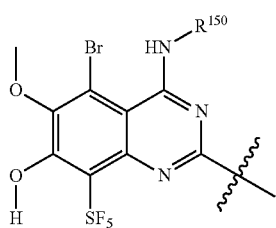
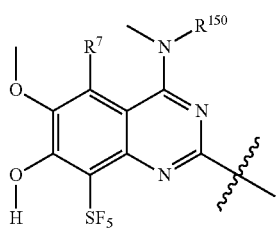
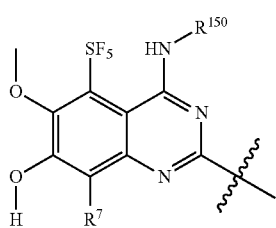
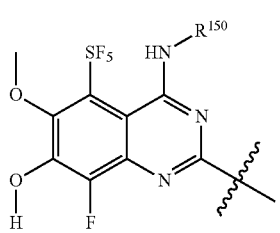
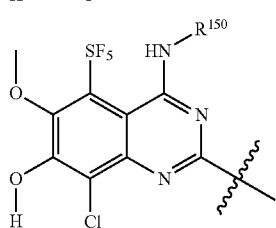
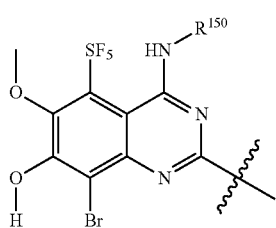
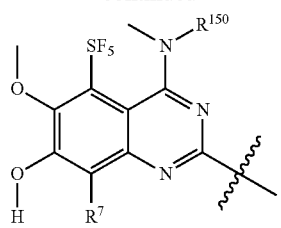
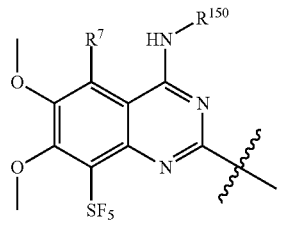
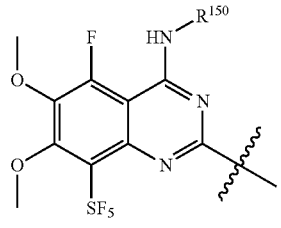
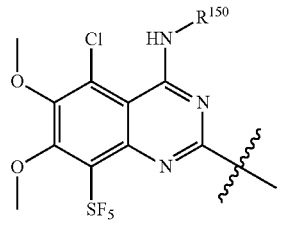
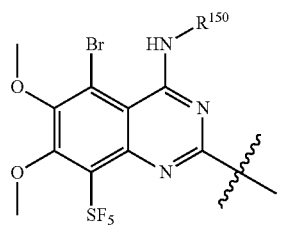
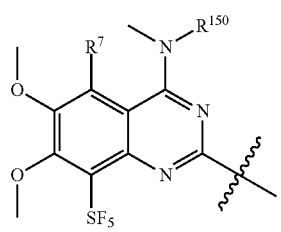

-continued
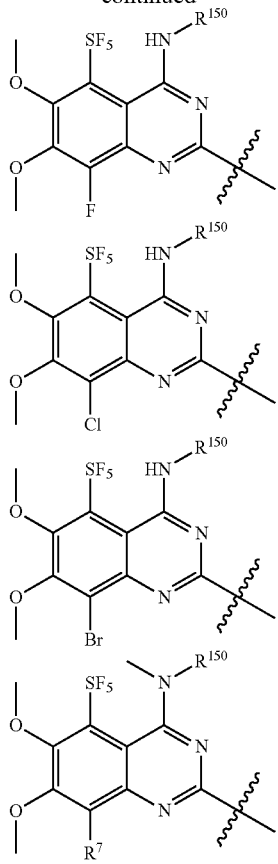
C1 is
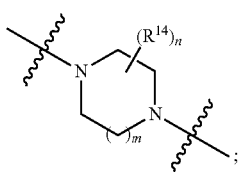
$R^{14}$ is independently selected at each occurrence from: hydrogen, $C_1$-$C_6$alkyl, $C_1$-$C_4$alkoxyC$_1$-$C_4$alkyl, and aryl;
m is 0, 1, or 2;
n is 0, 1, 2, 3, or 4;
C2 is selected from:
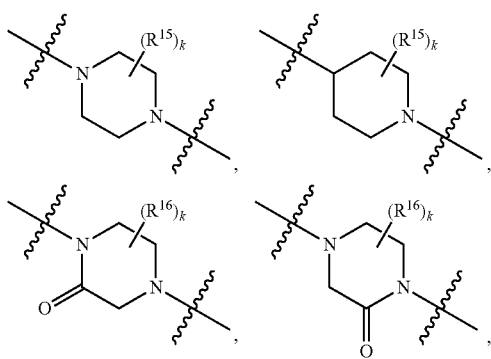
-continued
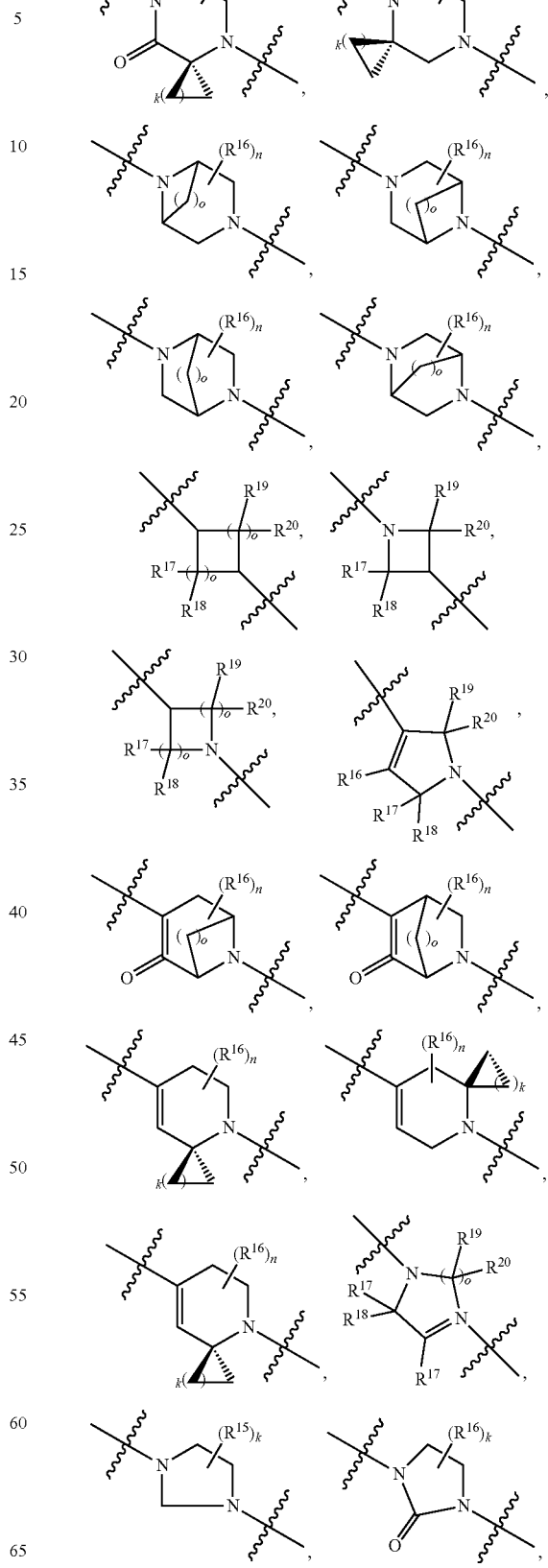

-continued

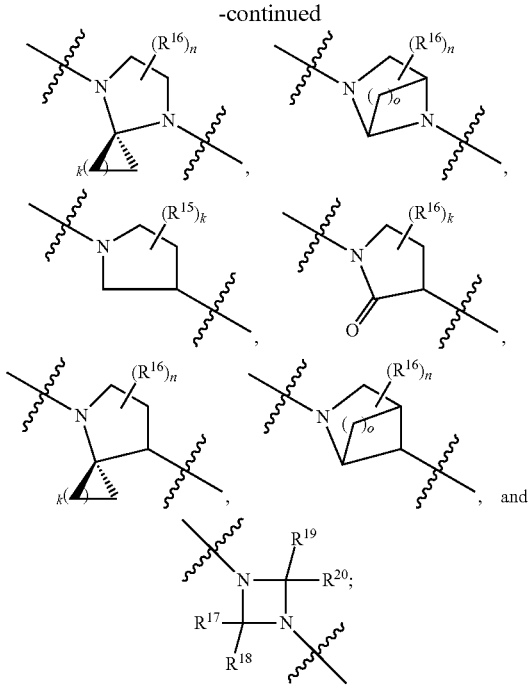

or
C2 is selected from:

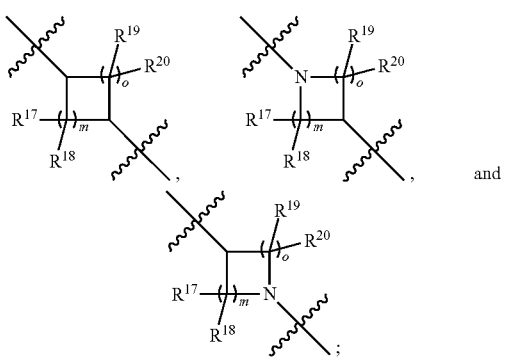

o is independently 1 or 2;
k is 1, 2, 3, or 4;
$R^{15}$ is independently selected at each occurrence from: hydrogen, $C_1$-$C_6$alkyl, $C_1$-$C_4$alkoxy$C_0$-$C_4$alkyl, aryl, and heteroaryl wherein at least one $R^{15}$ is heteroaryl;
$R^{16}$, $R^{17}$, $R^{18}$, $R^{19}$, and $R^{20}$ are independently selected at each occurrence from: hydrogen, $C_1$-$C_6$alkyl, $C_1$-$C_4$alkoxy$C_0$-$C_4$alkyl, aryl, and heteroaryl;
or, $R^{17}$ and $R^{18}$ or $R^{19}$ and $R^{20}$ may be taken together to form a 3- to 6-membered carbocyclic spiro ring or a 3- to 6-membered heterocyclic spiro ring containing 1 or 2 heteroatoms independently selected from nitrogen, oxygen, and sulfur;
or, $R^{17}$ and $R^{18}$ or $R^{19}$ and $R^{20}$ may be taken together to form a 3- to 6-membered carbocyclic fused ring or a 3- to 6-membered heterocyclic fused ring containing 1 or 2 heteroatoms independently selected from nitrogen, oxygen, and sulfur;
or, $R^{17}$ and $R^{18}$ or $R^{19}$ and $R^{20}$ may be taken together to form a carbonyl;

or, $R^{17}$ and $R^{19}$ or $R^{18}$ and $R^{20}$ can be taken together to form a bridged ring wherein the bridge can have 1 or 2 carbon atoms;
C3 is selected from:

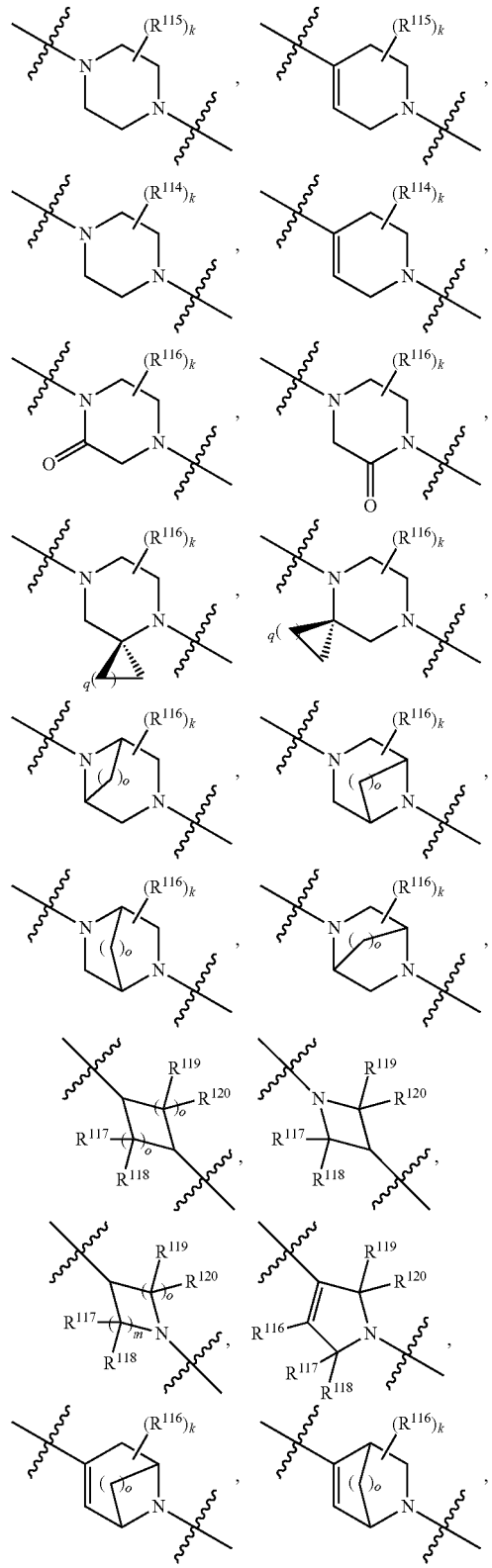

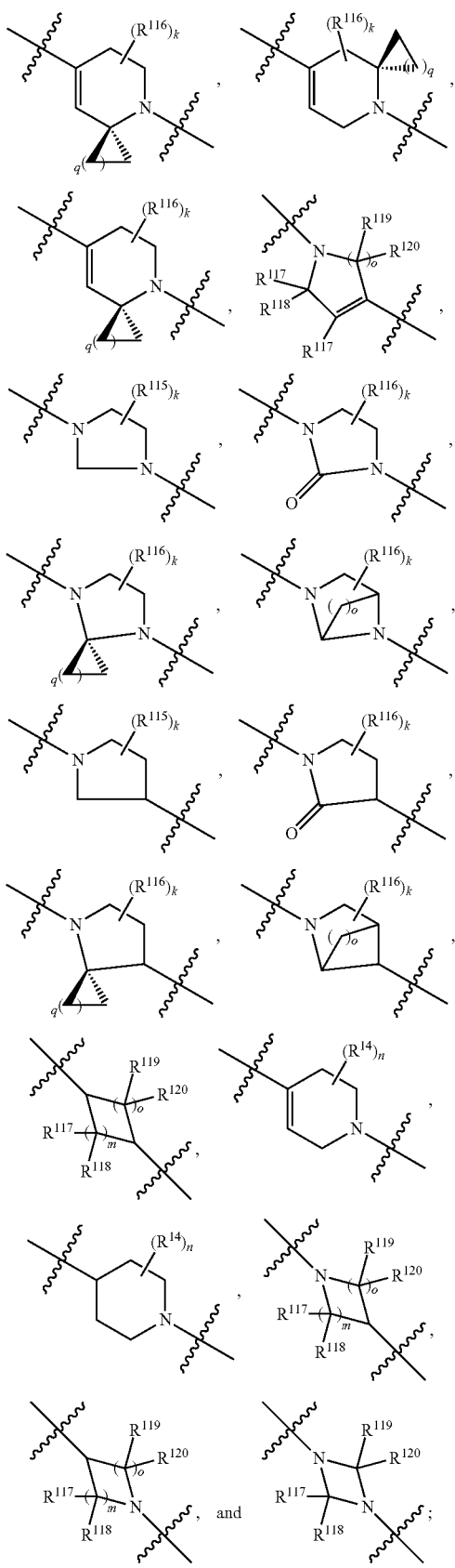

q is 1, 2, 3, or 4;

$R^{114}$ is independently selected at each occurrence from: hydrogen, $C_1$-$C_6$alkyl, $C_1$-$C_4$alkoxy$C_0$-$C_4$alkyl, aryl, $C(O)R^1$, $NR^1R^2$, and heteroaryl wherein at least one $R^{114}$ is $C(O)R^1$ or $NR^1R^2$;

$R^{115}$ is independently selected at each occurrence from: hydrogen, $C_1$-$C_6$alkyl, $C_1$-$C_4$alkoxy$C_0$-$C_4$alkyl, aryl, $R^{152}$, and heteroaryl wherein at least one $R^{115}$ is $R^{152}$;

$R^{152}$ is —$C(O)R^{150}$, —$NR^1R^{150}$, —$OR^{150}$, or $R^{150}$;

$R^{116}$, $R^{117}$, $R^{118}$, $R^{119}$, and $R^{120}$ are independently selected at each occurrence from: hydrogen, $R^{152}$, $C_1$-$C_6$alkyl, $C(O)R^1$, $NR^1R^2$, $C_1$-$C_4$alkoxy$C_0$-$C_4$alkyl, aryl, and heteroaryl;

or, $R^{117}$ and $R^{118}$ or $R^{119}$ and $R^{120}$ may be taken together to form a 3- to 6-membered carbocyclic spiro ring or a 3- to 6-membered heterocyclic spiro ring containing 1 or 2 heteroatoms independently selected from nitrogen, oxygen, and sulfur;

or, $R^{117}$ and $R^{118}$ or $R^{119}$ and $R^{120}$ may be taken together to form a 3- to 6-membered carbocyclic fused ring or a 3- to 6-membered heterocyclic fused ring containing 1 or 2 heteroatoms independently selected from nitrogen, oxygen, and sulfur;

or, $R^{117}$ and $R^{118}$ or $R^{119}$ and $R^{120}$ may be taken together to form a carbonyl;

or, $R^{117}$ and $R^{119}$ or $R^{118}$ and $R^{120}$ can be taken together to form a bridged ring wherein the bridge can have 1 or 2 carbon atoms;

wherein at least one of $R^{116}$, $R^{117}$, $R^{118}$, $R^{119}$, and $R^{120}$ is $C(O)R^1$, $NR^1R^2$, or $R^{152}$;

Non-limiting examples of C3 include:

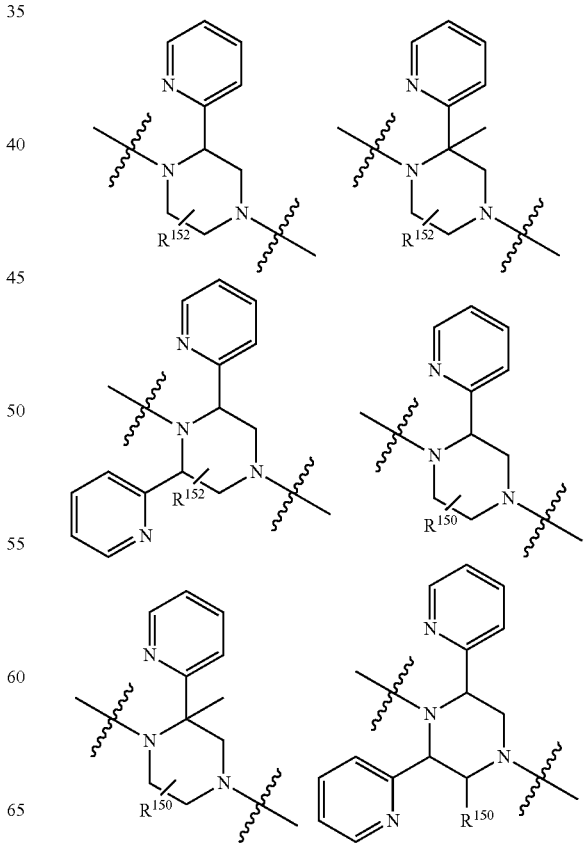

-continued

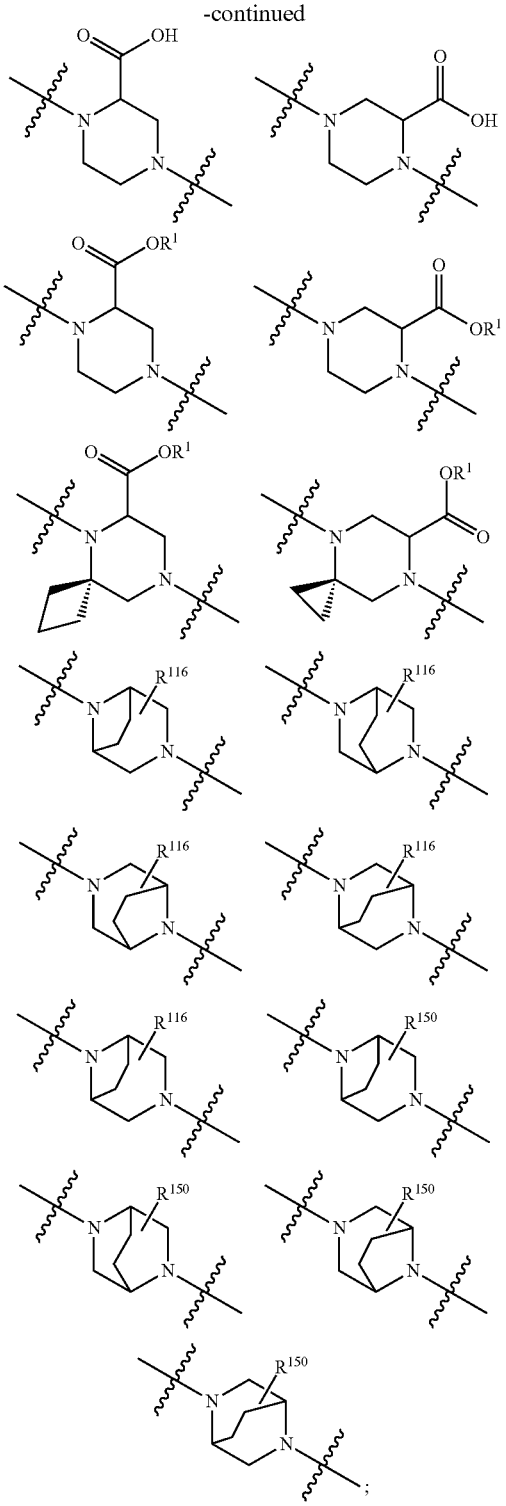

L1 is selected from:

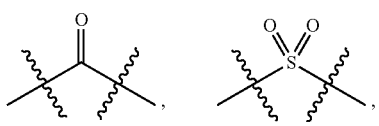

-continued

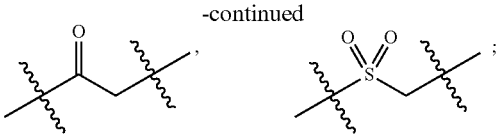

L2 is selected from:

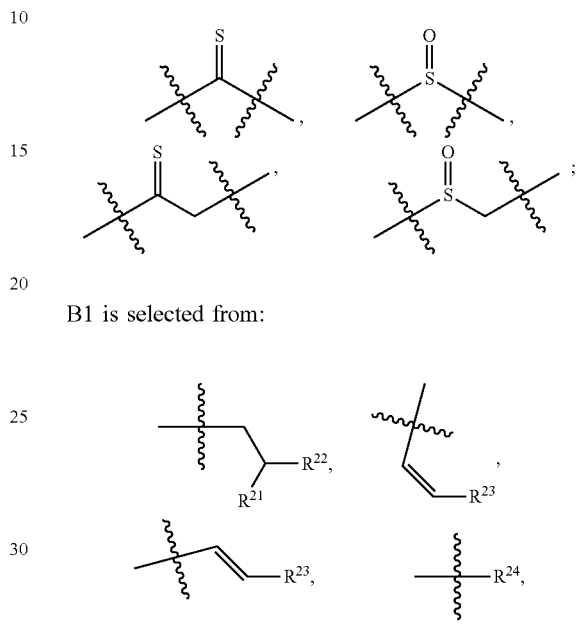

B1 is selected from:

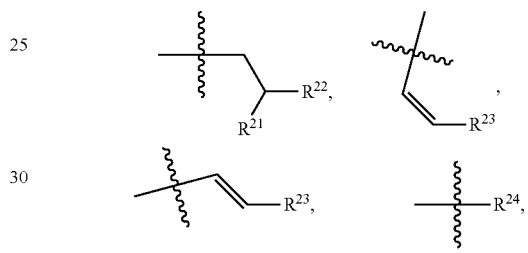

$R^{21}$ is $(CH_2)_p NR^{25}R^{26}$ or $C(O)N(R^{27})_2$;

p is 0 or 1;

$R^{22}$ is $C_1$-$C_6$alkyl or aryl optionally substituted with 0, 1, 2, or 3 $R^{28}$ groups;

$R^{23}$ is $C_3$-$C_6$cycloalkyl or aryl optionally substituted with 0, 1, 2, or 3 groups independently selected from halogen, $C_1$-$C_4$alkyl, $C_1$-$C_4$alkoxy, haloalkoxy, halo$C_1$-$C_4$alkyl, cyano, and hydroxyl;

$R^{24}$ is selected from: $R^{29}$ and $R^{30}$;

$R^{25}$ is hydrogen or $C_1$-$C_4$alkyl;

$R^{26}$ is selected from: hydrogen, optionally substituted $C_1$-$C_6$alkyl or $C_1$-$C_6$haloalkyl, wherein the optional substituents are selected from $C_1$-$C_4$alkoxy, $C_3$-$C_6$cycloalkyl, and 4-6 membered heterocycle having 1-2 ring heteroatoms selected from nitrogen, oxygen, and sulfur;

or $NR^{25}R^{26}$ can be taken in combination to form a 4 to 7 membered saturated azacycle optionally substituted with 0, 1, or 2 $C_1$-$C_4$ alkyl groups;

$R^{27}$ is independently selected at each occurrence from: hydrogen and $C_1$-$C_4$alkyl;

or $N(R^{27})_2$ can be taken in combination can form a 4-6 member azacycle;

$R^{28}$ is independently selected at each occurrence from: hydrogen, cyano, hydroxyl, halogen, $C_1$-$C_4$alkyl, $C_2$-$C_4$alkenyl, $C_2$-$C_4$alkynyl, $C_1$-$C_4$haloalkyl, haloalkoxy, and $C_1$-$C_4$alkoxy;

$R^{29}$ is $CH_2$heterocycle having 4 to 6 ring atoms and 1 or 2 ring heteroatoms independently selected from nitrogen, oxygen, and sulfur, which is optionally substituted with 0, 1, or 2 substituents independently selected from phenyl, halogen, and $C_1$-$C_6$alkyl, or two substituents, taken in combination form a benzo ring optionally substituted with halogen or cyano;

$R^{30}$ is a bicyclic heteroaryl group having 1 or 2 ring heteroatoms independently selected from nitrogen, oxygen, and sulfur, partially unsaturated carbocycle or partially unsaturated heterocycle having 1 or 2 ring heteroatoms independently selected from nitrogen, oxygen, and sulfur, each of which is optionally substituted with 0, 1, 2, or 3 substituents independently selected from amino, halogen, cyano, hydroxy, $C_1$-$C_4$alkyl, haloalkoxy, and $C_1$-$C_4$alkoxy;

B2 is a $CH_2$ linked bicyclic heterocycle with 7 to 12 ring atoms and 1, 2, or 3 ring heteroatoms selected from nitrogen, oxygen, and sulfur, which is optionally substituted with 0, 1, or 2 groups independently selected from aryl, heteroaryl, halogen, and $C_1$-$C_6$alkyl; and B3 is a $CH_2$ linked bicyclic heterocycle with 7 to 12 ring atoms and 1, 2, or 3 ring heteroatoms selected from nitrogen, oxygen, and sulfur, which is optionally substituted with 1, 2, 3, or 4 groups independently selected from $R^{150}$, $NR^{150}R^1$, $OR^{150}$, aryl, heteroaryl, halogen, and $C_1$-$C_6$alkyl, wherein each B3 is substituted with at least one $R^{150}$, $NR^{150}R^1$, or $OR^{150}$.

Non-limiting examples of B3 include:

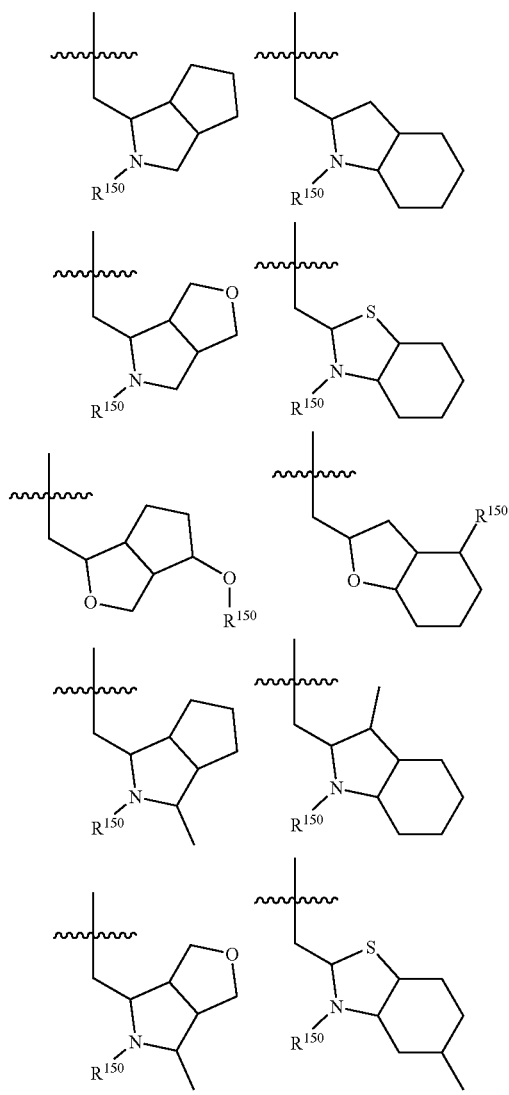

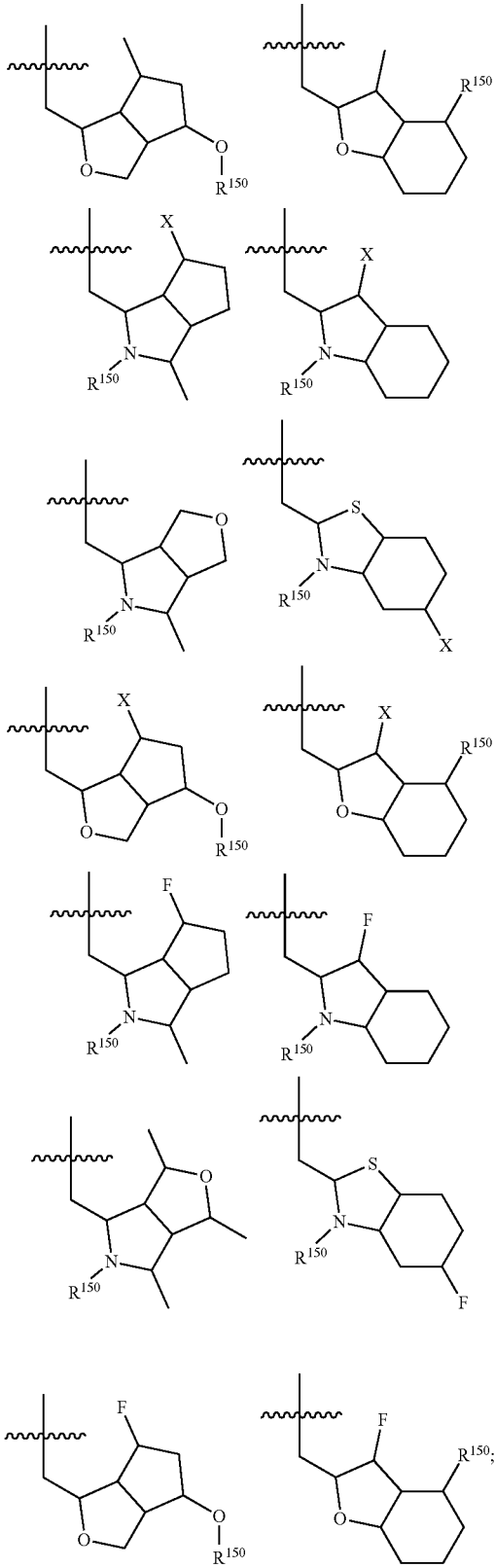

wherein X is halogen.

In an additional embodiment a compound of Formula III is provided:

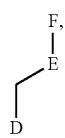
(III)

or a pharmaceutically acceptable salt, isotopic analog, prodrug, or isolated isomer thereof optionally in pharmaceutically acceptable carrier;
wherein:
D is selected from: D1 and D2;
E is selected from: E1 and E2;
F is selected from: F1 and F2;
wherein at least one of D, E, or F is selected from: D2, E2, or F2 respectively;
D1 is

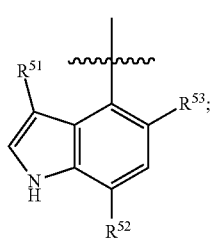

D2 is selected from

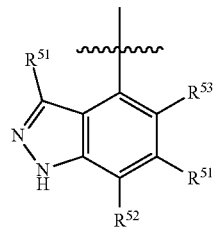 and 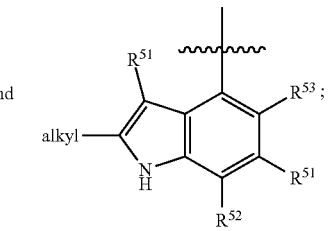

wherein each hydrogen of D2 is optionally replaced by a substituent selected from $R^{55}$ and $R^{62}$;
$R^{51}$ is independently selected from hydrogen, halogen, cyano, alkyl, alkenyl, cycloalkyl, alkoxy, haloalkyl, hydroxyalkyl, aminoalkyl, alkoxyalkyl, alkoxyalkoxy, haloalkoxy, —Salkyl, —S(O)alkyl, —S(O)$_2$alkyl, —CH$_2$NHC(O)alkyl, and —OCH$_2$C(O)R$^{57}$;
$R^{52}$ is selected from alkyl, alkoxy, hydroxyalkyl, or halogen;
$R^{53}$ is selected from hydrogen, halogen, cyano, alkyl, haloalkyl, —CH$_2$C(O)R$^{57}$, aryl, heteroaryl, wherein the aryl and heteroaryl group is optionally substituted with alkyl groups, and wherein the alkyl and haloalkyl groups are optionally substituted with hydroxy;
E1 is

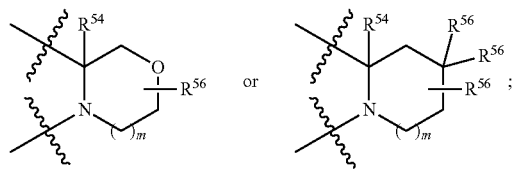

E2 is

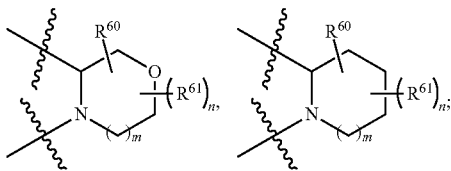

F1 is phenyl, napthyl, or heteroaryl, wherein F1 is optionally substituted by $R^{55}$ and further substituted by 0 or 1 substituents selected from halogen, alkyl, alkoxy, hydroxy, and cyanomethyl;

F2 is selected from

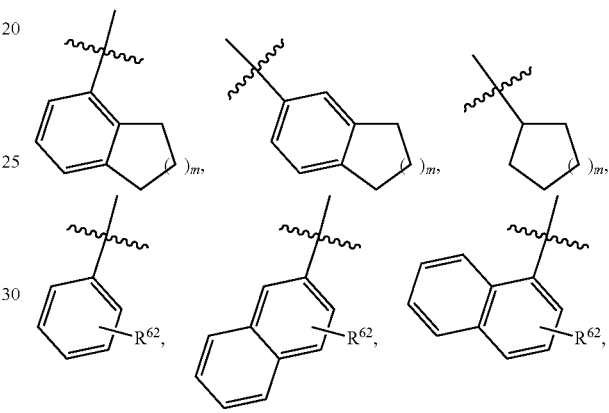

and a heteroaryl group with a $R^{62}$ substituent;

wherein each F2 is optionally substituted with 1, 2, 3, or 4 substituents independently selected from $R^{55}$ and $R^{62}$;

$R^{54}$ is hydrogen, alkyl, or hydroxyalkyl;

$R^{55}$ is —C(O)R$^{58}$, —CH$_2$C(O)R$^{58}$, R$^{59}$, —C(O)NHSO$_2$alkyl, —SO$_2$NR$^{25}$C(O)alkyl, —SO$_2$N(R$^{25}$)$_2$, —SO$_2$alkyl, cyano, halogen, hydroxyalkyl, and heteroaryl;

m is independently 0, 1, or 2;

n is 0, 1, 2, 3, or 4;

$R^{25}$ is independently selected from hydrogen and C$_1$-C$_4$alkyl;

$R^{56}$ is independently selected at each occurrence from hydrogen, hydroxy, —N(R$^{25}$)$_2$, alkyl, hydroxyalkyl, cyanoalkyl, or alkyoxy;

or C(R$^{56}$)$_2$, taken in combination, forms a spirocyclic carbocycle having 3, 4, 5, or 6 ring atoms;

$R^{57}$ is hydroxy, alkoxy, or —N(R$^{25}$)$_2$;

$R^{58}$ is hydroxy, alkoxy, —N(R$^{25}$)$_2$, or heterocycle, wherein each R$^{58}$ other than hydroxy is optionally substituted with halogen, hydroxy, or alkyl;

$R^{59}$ is heteroaryl optionally substituted with one or more alkyl groups;

$R^{60}$ is halogen;

$R^{61}$ is independently selected at each occurrence from hydrogen, halogen, hydroxy, —N(R$^{25}$)$_2$, alkyl, hydroxyalkyl, cyanoalkyl, or alkyoxy;

$R^{62}$ is selected from

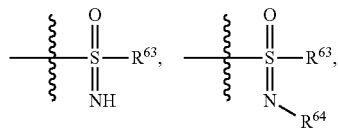

$P(O)R^{65}R^{65}$, and $SF_5$;

in an alternative embodiment $R^{62}$ is —$C(O)NR^{25}OR^{25}$;

$R^{63}$ and $R^{64}$ are independently selected at each occurrence from hydrogen, hydroxyl, cyano, amino, alkyl, haloalkyl, alkoxy, cycloalkylalkyl, (phenyl)$C_0$-$C_4$alkyl, —$C_1$-$C_4$alkylOC(O)OC$_1$-$C_6$alkyl, —$C_1$-$C_4$alkylOC(O)C$_1$-$C_6$alkyl, —$C_1$-$C_4$alkylC(O)OC$_1$-$C_6$alkyl, aryl, heteroaryl, heterocycle, arylalkyl, heteroarylalkyl, heterocycloalkyl; and $R^{65}$ is independently selected at each occurrence from hydroxy, alkoxy, haloalkoxy, alkyl, cycloalkylalkyl-, aryl, arylalkyl, —O-arylalkyl, —O-aryl, heterocycle, heterocycloalkyl, heteroaryl, heteroarylalkyl, O-heteroaryl, O-heterocycle, —$N(R^{25})_2$.

In an additional embodiment the compound of Formula III is substituted with a $R^{150}$ substituent.

In an additional embodiment the compound of Formula III is:

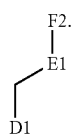

In an additional embodiment the compound of Formula III is:

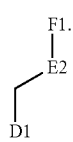

In an additional embodiment the compound of Formula III is:

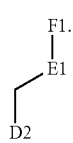

In an additional embodiment the compound of Formula III is selected from:

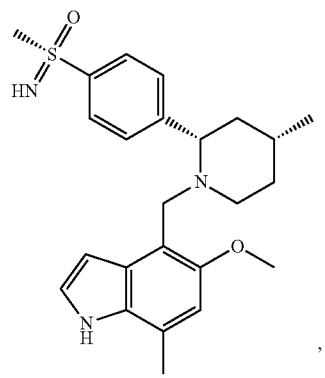

,

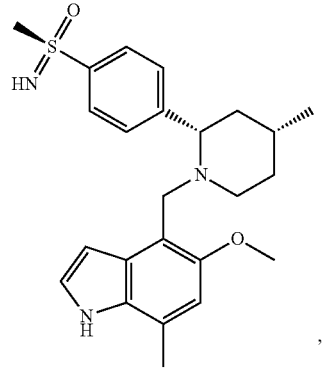

,

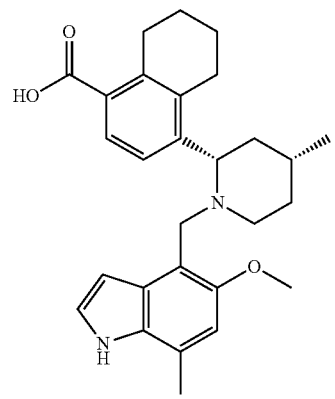

,

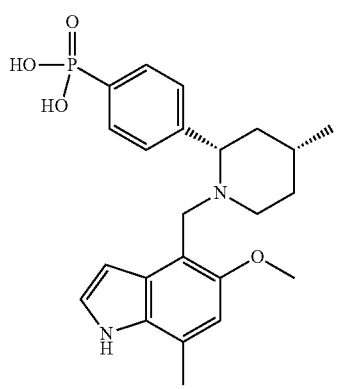

,

-continued

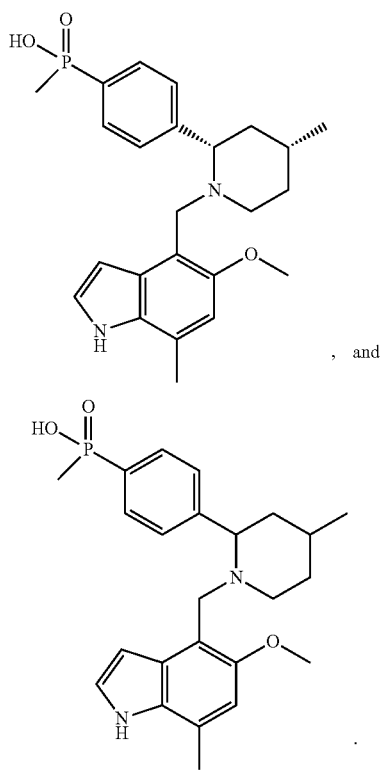
, and

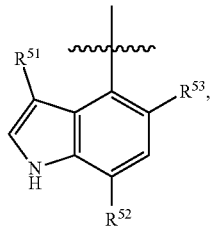

In an additional embodiment a compound of Formula IV is provided:

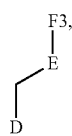
(IV)

or a pharmaceutically acceptable salt, isotopic analog, prodrug, or isolated isomer thereof optionally in pharmaceutically acceptable carrier;

wherein:
D is selected from: D1 and D2;
E is selected from: E1 and E2;
D1 is

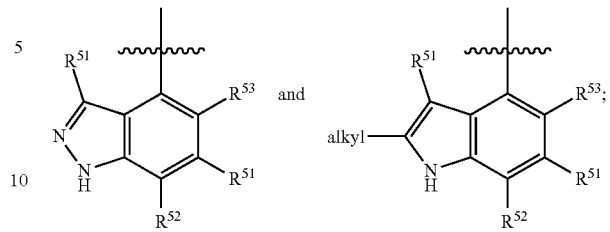

D2 is selected from

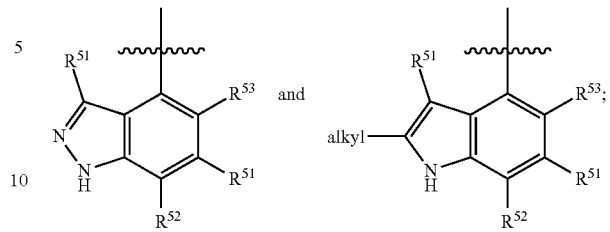

wherein each hydrogen of D2 is optionally replaced by a substituent selected from $R^{55}$ and $R^{62}$;

$R^{51}$ is independently selected from hydrogen, halogen, cyano, alkyl, alkenyl, cycloalkyl, alkoxy, haloalkyl, hydroxyalkyl, aminoalkyl, alkoxyalkyl, alkoxyalkoxy, haloalkoxy, —Salkyl, —S(O)alkyl, —S(O)$_2$alkyl, —CH$_2$NHC(O)alkyl, and —OCH$_2$C(O)$R^{57}$;

$R^{52}$ is selected from alkyl, alkoxy, hydroxyalkyl, or halogen;

$R^{53}$ is selected from hydrogen, halogen, cyano, alkyl, haloalkyl, —CH$_2$C(O)$R^{57}$, aryl, heteroaryl, wherein the aryl and heteroaryl group is optionally substituted with alkyl groups, and wherein the alkyl and haloalkyl groups are optionally substituted with hydroxy;

E1 is

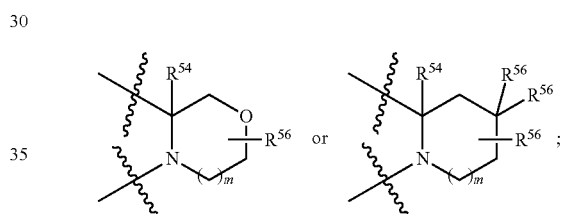

E2 is

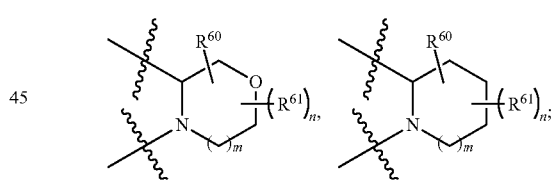

F3 is selected from

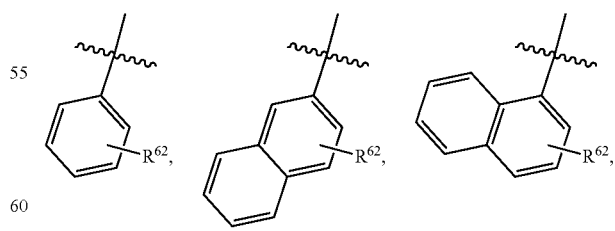

a heteroaryl group with a $R^{66}$ substituent, and an aryl group with a $R^{66}$ substituent;
wherein each F2 is optionally substituted with 1, 2, 3, or 4 substituents independently selected from $R^{66}$, $R^{62}$, and $R^{55}$;

$R^{54}$ is hydrogen, alkyl, or hydroxyalkyl;

$R^{55}$ is —C(O)$R^{58}$, —CH$_2$C(O)$R^{58}$, $R^{59}$, —C(O)NHSO$_2$alkyl, —SO$_2$NR$^{25}$C(O)alkyl, —SO$_2$N(R$^{25}$)$_2$, —SO$_2$alkyl, cyano, halogen, hydroxyalkyl, and heteroaryl;

$R^{56}$ is independently selected at each occurrence from hydrogen, hydroxy, —N(R$^{25}$)$_2$, alkyl, hydroxyalkyl, cyanoalkyl, or alkyoxy;

or C(R$^{56}$)$_2$, taken in combination, forms a spirocyclic carbocycle having 3, 4, 5, or 6 ring atoms;

$R^{66}$ is —PO(OR$^{69}$)$_2$, —P(O)OR$^{69}$R$^{69}$, —SO$_2$OR$^{69}$, C(O)CR$^{70}$SO$_2$R$^{69}$, —SO$_2$NHSO$_2$R$^{69}$, —SO$_2$NHSO$_2$C$_1$-C$_3$alkyl substituted with 1, 2, 3, 4, or 5 fluorine atoms, C(O)NHOR$^{69}$, C(O)N(OR$^{69}$)R$^{69}$, C(O)NHCN, C(O)NHR$^{71}$, —SR$^{71}$, —S(O)R$^{71}$, —SO$_2$R$^{71}$, —N(OR$^{69}$)C(O)alkyl, —NHC(O)NHSO$_2$R$^{69}$, a 5-membered or 6-membered heterocycle having 1-3 nitrogen atoms and 0 or 1 oxygen atoms substituted with 1, 2, or 3 substituents independently selected from $R^{68}$, or a 4-membered or 5-membered cycloalkyl optionally substituted with 1, 2, or 3 substituents independently selected from $R^{68}$;

m is independently 0, 1, or 2;

n is 0, 1, 2, 3, or 4;

$R^{25}$ is independently selected from hydrogen and C$_1$-C$_4$alkyl;

$R^{57}$ is hydroxy, alkoxy, or —N(R$^{25}$)$_2$;

$R^{60}$ is halogen;

$R^{61}$ is independently selected at each occurrence from hydrogen, halogen, hydroxy, —N(R$^{25}$)$_2$, alkyl, hydroxyalkyl, cyanoalkyl, and alkyoxy;

$R^{62}$ is selected from

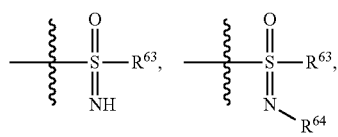

P(O)R$^{65}$R$^{65}$, and SF$_5$;

$R^{63}$ and $R^{64}$ are independently selected at each occurrence from hydrogen, hydroxy, cyano, amino, alkyl, haloalkyl, alkoxy, cycloalkylalkyl, (phenyl)C$_0$-C$_4$alkyl, —C$_1$-C$_4$alkylOC(O)OC$_1$-C$_6$alkyl, —C$_1$-C$_4$alkylOC(O)C$_1$-C$_6$alkyl, —C$_1$-C$_4$alkylC(O)OC$_1$-C$_6$alkyl, aryl, heteroaryl, heterocycle, arylalkyl, heteroarylalkyl, and heterocycloalkyl;

$R^{65}$ is independently selected at each occurrence from hydroxy, alkoxy, haloalkoxy, alkyl, cycloalkylalkyl-, aryl, arylalkyl, —O-arylalkyl, —O-aryl, heterocycle, heterocycloalkyl, heteroaryl, heteroarylalkyl, O-heteroaryl, O-heterocycle, and —N(R$^{25}$)$_2$;

$R^{68}$ is independently selected at each occurrence from hydrogen, halogen, hydroxy, —N(R$^{25}$)$_2$, alkyl, hydroxyalkyl, cyanoalkyl, and alkyoxy;

$R^{69}$ is independently selected from hydrogen, C$_1$-C$_4$alkyl, aryl, and heteroaryl;

$R^{70}$ is selected from hydrogen, cyano, alkyl, and C(O)OR$^{25}$; and $R^{71}$ is selected from cycloalkylalkyl-, aryl, arylalkyl, heterocycle, heterocycloalkyl, heteroaryl, and heteroarylalkyl.

Non-limiting examples of $R^{66}$ include

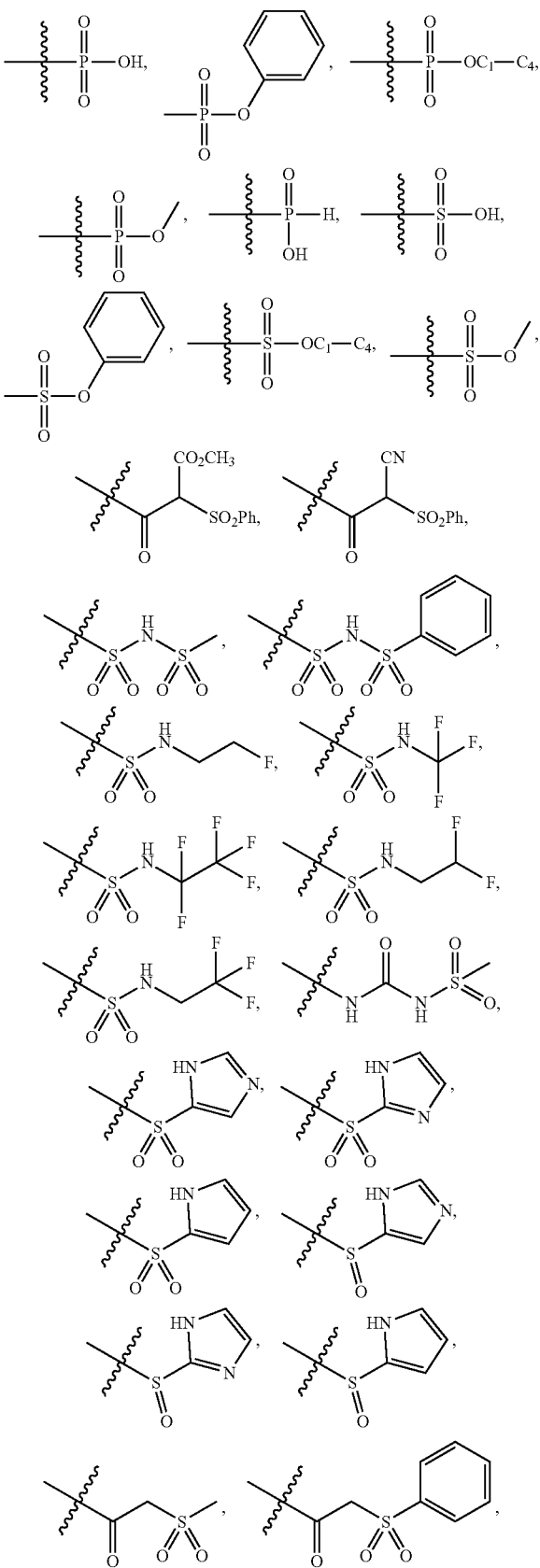

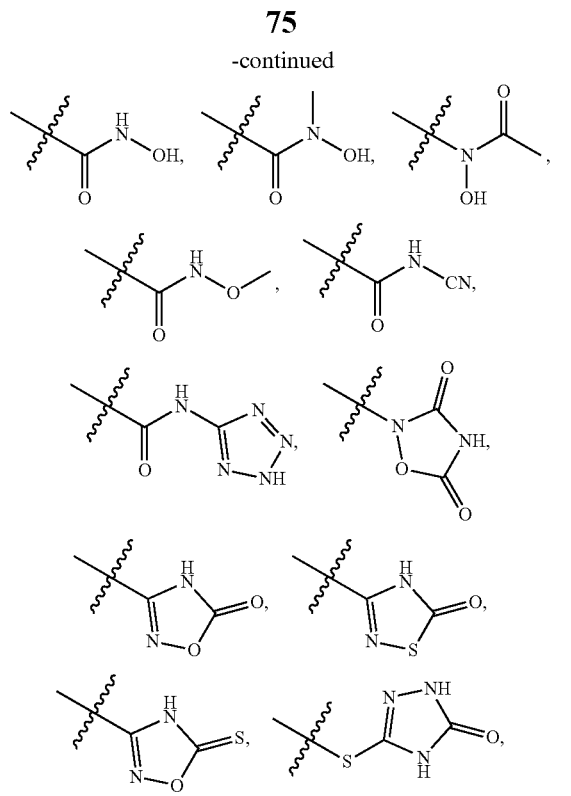

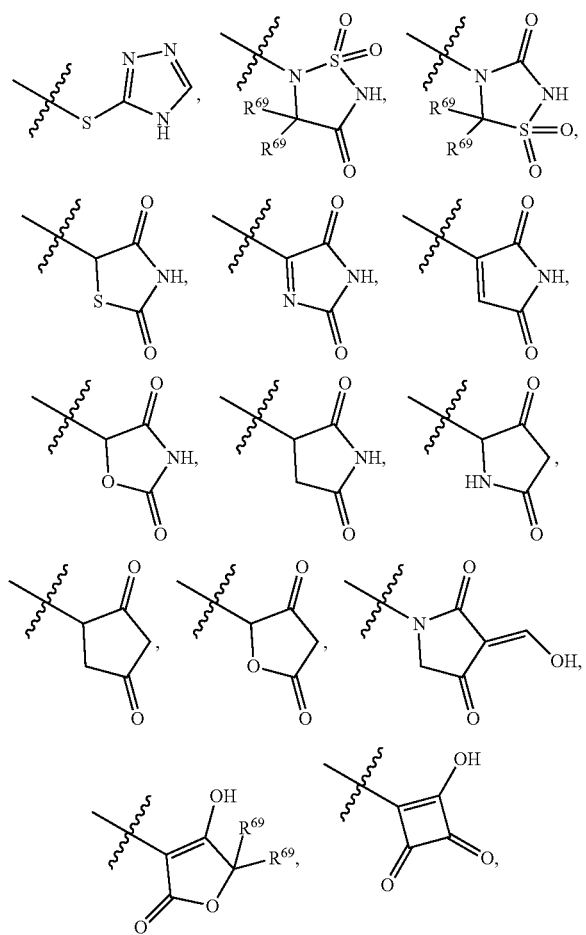

In one embodiment, the compound of Formula IV is substituted with a $R^{150}$ substituent.

Pharmaceutical compositions comprising a compound or salt of Formula I, Formula II, Formula III, or Formula IV together with a pharmaceutically acceptable carrier are also disclosed.

In one embodiment, the disorder is associated with the alternative Complement cascade pathway. In yet another embodiment, the disorder is associated with the Complement classical pathway. In a further embodiment, the disorder is associated with the Complement lectin pathway. Alternatively, the active compound or its salt or prodrug may act through a different mechanism of action than the Complement cascade, or in particular as a Complement Factor B inhibitor, to treat the disorder described herein.

In one embodiment, a method for the treatment of paroxysmal nocturnal hemoglobinuria (PNH) is provided that includes the administration of an effective amount of a compound to a host of Formula I, Formula II, Formula III, or Formula IV or a pharmaceutically acceptable salt thereof, optionally in a pharmaceutically acceptable carrier. In another embodiment, a method for the treatment of wet or dry age-related macular degeneration (AMD) in a host is provided that includes the administration of an effective amount of a compound of Formula I, Formula II, Formula III, or Formula IV or a pharmaceutically acceptable salt thereof, optionally in a pharmaceutically acceptable carrier. In another embodiment, a method for the treatment of rheumatoid arthritis in a host is provided that includes the administration of an effective amount of a compound of Formula Formula I, Formula II, Formula III, or Formula IV or a pharmaceutically acceptable salt thereof, optionally in a pharmaceutically acceptable carrier. In another embodiment, a method for the treatment of multiple sclerosis in a host is provided that includes the administration of an effective amount of a compound of Formula I, Formula II, Formula III, or Formula IV or a pharmaceutically acceptable salt thereof, optionally in a pharmaceutically acceptable carrier.

In other embodiments, an active compound or its salt or prodrug as described herein can be used to treat fatty liver disease and conditions stemming from fatty liver disease, nonalcoholic steatohepatitis (NASH), liver inflammation, cirrhosis, and liver failure, dermatomyositis, or amyotrophic lateral sclerosis.

The active compound or its pharmaceutically acceptable salt, prodrug or a pharmaceutical composition thereof as disclosed herein is also useful for administration in combination or alternation with a second pharmaceutical agent for use in ameliorating or reducing a side effect of the second pharmaceutical agent. For example, in one embodiment, the active compound may be used in combination with an adoptive cell transfer therapy to reduce an inflammatory response associated with such therapy, for example, a cytokine mediated response such as cytokine response syndrome. In another embodiment, the adoptive cell transfer therapy is a chimeric antigen receptor T-Cell (CAR T) or a dendritic cell used to treat a hematologic or solid tumor, for example, a B-cell related hematologic cancer. In another embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19. In another embodiment, the associated inflammatory response is a cytokine mediated response.

Another embodiment is provided that includes the administration of an effective amount of an active compound or a pharmaceutically acceptable salt thereof, optionally in a pharmaceutically acceptable carrier to a host to treat an ocular, pulmonary, gastrointestinal, or other disorder that can benefit from topical or local delivery.

Any of the compounds described herein (Formula I, Formula II, Formula III, or Formula IV) can be administered to the eye in any desired form of administration, including via intravitreal, intrastromal, intracameral, sub-tenon, subretinal, retro-bulbar, peribulbar, suprachoroidal, conjunctival, subconjunctival, episcleral, posterior juxtascleral, circumcorneal, and tear duct injections, or through a mucus, mucin, or a mucosal barrier, in an immediate or controlled release fashion.

In other embodiments of the invention, an active compound provided herein can be used to treat or prevent a disorder in a host mediated by Complement Factor B, or by an excessive or detrimental amount of $C3(H_2O)B$ complex in the Complement pathway. As examples, the invention includes methods to treat or prevent Complement associated disorders that are induced by antibody-antigen interactions, a component of an immune or autoimmune disorder or by ischemic injury. The invention also provides methods to decrease inflammation or an immune response, including an autoimmune response, where mediated or affected by Complement Factor B.

The present invention thus includes at least the following features:

(i) a compound of Formula I, Formula II, Formula III, or Formula IV or a pharmaceutically acceptable salt or prodrug thereof, for use in treating or preventing a disorder listed in the methods of treatment including but not limited to the development of fatty liver disease and conditions stemming from fatty liver disease, such as nonalcoholic steatohepatitis (NASH), liver inflammation, cirrhosis, or liver failure; dermatomyositis; amyotrophic lateral sclerosis; cytokine or inflammatory reactions in response to biotherapeutics (e.g. CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(ii) a pharmaceutically acceptable composition of a compound of Formula I, Formula II, Formula III, or Formula IV or its pharmaceutically acceptable salt in a pharmaceutically acceptable carrier;

(iii) a compound selected from Formula I, Formula II, Formula III, or Formula IV or a pharmaceutically acceptable salt or prodrug thereof, for use in treating or preventing a disorder mediated by the Complement pathway, and for example, cascade Factor B;

(iv) use of a compound of Formula I, Formula II, Formula III, or Formula IV, as described herein, or a pharmaceutically acceptable salt or prodrug thereof, in the manufacture of a medicament for treating or preventing a disorder listed in the methods of treatment, including but not limited to the development of fatty liver disease and conditions stemming from fatty liver disease, such as nonalcoholic steatohepatitis (NASH), liver inflammation, cirrhosis, liver failure; dermatomyositis; amyotrophic lateral sclerosis; cytokine or inflammatory reactions in response to biotherapeutics (e.g., CAR T-cell therapy); paroxysmal nocturnal hemoglobinuria (PNH), rheumatoid arthritis, multiple sclerosis, age-related macular degeneration (AMD), retinal degeneration, other ophthalmic diseases (e.g., geographic atrophy), a respiratory disease or a cardiovascular disease;

(v) a process for manufacturing a medicament intended for the therapeutic use for treating or preventing a disorder listed in the methods of treatment, or generally for treating or preventing disorders mediated by Complement cascade Factor B, characterized in that a compound selected from Formula I, Formula II, Formula III, or Formula IV or an embodiment of the active compound is used in the manufacture;

(vi) a compound selected from Formula I, Formula II, Formula III, or Formula IV or a salt thereof as described herein in substantially pure form (e.g., at least 90 or 95%):

(vii) a compound of Formula I, Formula II, Formula III, or Formula IV as described herein, or a pharmaceutically acceptable salt or prodrug thereof, for use in treating a medical disorder which is an inflammatory or immune condition, a disorder mediated by the Complement cascade (including a dysfunctional cascade), a disorder or abnormality of a cell that adversely affects the ability of the cell to engage in or respond to normal Complement activity, or an undesired complement-mediated response to a medical treatment, such as surgery or other medical procedure or a pharmaceutical or biopharmaceutical drug administration, a blood transfusion, or other allogeneic tissue or fluid administration.

DETAILED DESCRIPTION

I. Terminology

Compounds are described using standard nomenclature. Unless defined otherwise, all technical and scientific terms used herein have the same meaning as is commonly understood by one of skill in the art to which this invention belongs.

The compounds in any of the Formulas described herein include racemates, enantiomers, mixtures of enantiomers, diastereomers, mixtures of diastereomers, tautomers, N-oxides, isomers; such as rotamers, as if each is specifically described.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds of Formula I, Formula II, Formula III, or Formula IV with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$ $^{31}P$, $^{32}P$, $^{35}S$, $^{36}Cl$, and $^{125}I$ respectively. In one embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used. In one embodiment, the isotopic substitution is deuterium for hydrogen at one or more locations on the molecule to improve the performance of the drug, for example, the pharmacodynamics, pharmacokinetics, biodistribution, half-life, stability, AUC, $T_{max}$, $C_{max}$, etc. For example, the deuterium can be bound to carbon in a location of bond breakage during metabolism (an α-deuterium kinetic isotope effect) or next to or near the site of bond breakage (a β-deuterium kinetic isotope effect).

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one embodiment, deuterium is 90, 95 or 99% enriched at a desired location. Unless otherwise stated, the enrichment at any point is above natural abundance and enough to alter a detectable property of the drug in a human.

In one embodiment, the substitution of a hydrogen atom for a deuterium atom can be provided in any of A, C, L or B. In one embodiment, the substitution of a hydrogen atom for a deuterium atom occurs within an R group selected from any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{101}$, $R^{102}$, $R^{114}$, $R^{115}$, $R^{116}$, $R^{117}$, $R^{118}$, $R^{119}$, $R^{120}$, $R^{150}$, and $R^{152}$. For example, when any of the R groups are, or contain for example through substitution, methyl, ethyl, or methoxy, the alkyl residue may be optionally deuterated (in non-limiting embodiments, $CDH_2$, $CD_2H$, $CD_3$, $CH2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be optionally deuterated.

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)NH$_2$ is attached through carbon of the keto (C═O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., ═O) then two hydrogens on the atom are replaced. For example, a pyridyl group substituted by oxo is a pyridone. Combinations of substituents and/or variables are permissible only if such combinations result in stable compounds or useful synthetic intermediates.

A stable active compound refers to a compound that can be isolated and can be formulated into a dosage form with a shelf life of at least one month. A stable manufacturing intermediate or precursor to an active compound is stable if it does not degrade within the period needed for reaction or other use. A stable moiety or substituent group is one that does not degrade, react or fall apart within the period necessary for use. Non-limiting examples of unstable moieties are those that combine heteroatoms in an unstable arrangement, as typically known and identifiable to those of skill in the art.

Where a group can be optionally substituted or unsubstituted it is not substituted unless specified. Optional substituents include, but are not limited to, e.g., halogen (which can independently be F, Cl, Br or I); amino; cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; alkylthio including those having one or more thioether linkages; alkylsulfinyl; alkylsulfonyl groups including those having one or more sulfonyl linkages; sulfonamide groups including those having one or more sulfonyl linkages; sulfanilamide; phosphate; phosphonate; aminoalkyl groups including groups having one or more N atoms; aryl (e.g., phenyl, biphenyl, naphthyl, or the like, each ring either substituted or unsubstituted aromatic); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated, unsaturated, or aromatic heterocyclic group having 1 to 3 separate or fused rings with one or more nitrogen, sulfur, or oxygen atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, $C_1$-$C_6$alkyl, $C_2$-$C_6$alkenyl, $C_2$-$C_6$alkynyl, —$C_1$-$C_6$alkoxy, $C_2$-$C_6$alkanoyl, $C_1$-$C_6$alkylester, (mono- and di-$C_1$-$C_6$alkylamino)$C_0$-$C_2$alkyl, $C_1$-$C_2$haloalkyl, hydoxy$C_1$-$C_6$alkyl, carboxamide, ester, carbamate, urea, sulfonamide, —$C_1$-$C_6$alkyl(heterocyclyl), —$C_1$-$C_6$alkyl(heteroaryl), —$C_1$-$C_6$alkyl($C_3$-$C_7$cycloalkyl), —O$C_1$-$C_6$alkyl($C_3$-$C_7$cycloalkyl), B(OH)$_2$, phosphate, phosphonate and $C_1$-$C_2$haloalkoxy.

"Alkyl" is a branched or straight chain saturated aliphatic hydrocarbon group. In one embodiment, the alkyl group contains from 1 to about 12 carbon atoms, more generally from 1 to about 6 carbon atoms or from 1 to about 4 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted as described above. In an alternative embodiment, trimethylsilyl can be used instead of t-butyl.

In an alternative embodiment, when a term is used that includes "alk" then "cycloalkyl" or "carbocyclic" can be considered part of the definition, unless unambiguously excluded by the context. For example, and without limitation, the terms alkyl, alkenyl, alkynyl, alkoxy, alkanoyl, haloalkyl, aminoalkyl, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Non-limiting examples are $C_2$-$C_8$alkenyl, $C_2$-$C_6$alkenyl and $C_2$-$C_4$alkenyl. The specified ranges as used herein indicate an alkenyl group having each member of the range described as an independent species, as described above for the alkyl moiety. Examples of alkenyl include, but are not limited to, ethenyl and propenyl. In an alternative embodiment, the alkenyl group is optionally substituted as described above.

"Alkynyl" is a branched or straight chain aliphatic hydrocarbon group having one or more carbon-carbon triple bonds that may occur at any stable point along the chain, for example, $C_2$-$C_8$alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted as described above.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly, an "alkylthio" or a "thioalkyl" group is an alkyl group as defined above with the indicated number of carbon atoms covalently bound through a sulfur bridge (—S—). In an alternative embodiment, the alkoxy group is optionally substituted as described above. In an alternative embodiment, the thioalkyl group is optionally substituted as described above.

"Alkanoyl" is an alkyl group as defined above covalently bound through a carbonyl (C=O) bridge. The carbonyl carbon is included in the number of carbons, that is $C_2$alkanoyl is a CH$_3$(C=O)— group. In an alternative embodiment, the alkanoyl group is optionally substituted as described above.

"Alkylester" is an alkyl group as defined herein covalently bound through an ester linkage. The ester linkage may be in either orientation, e.g., a group of the formula —O(C=O)alkyl or a group of the formula —(C=O)Oalkyl.

"Amino" is —NH$_2$.

"Amide" or "carboxamide" is —C(O)NR$^a$R$^b$ wherein R$^a$ and R$^b$ are each independently selected from hydrogen, alkyl, for example, $C_1$-$C_6$alkyl, alkenyl, for example, $C_2$-$C_6$alkenyl, alkynyl, for example, $C_2$-$C_6$alkynyl, —$C_0$-$C_4$alkyl($C_3$-$C_7$cycloalkyl), —$C_0$-$C_4$alkyl($C_3$-$C_7$heterocycloalkyl), —$C_0$-$C_4$alkyl(aryl), and —$C_0$-$C_4$alkyl(heteroaryl); or together with the nitrogen to which they are bonded, R$^a$ and R$^b$ can form a $C_3$-$C_7$heterocyclic ring. In an alternative embodiment, the R$^a$ and R$^b$ groups are each independently optionally substituted as described above.

As used herein, "carbocyclyl", "carbocyclic", "carbocycle" or "cycloalkyl" is a saturated or partially unsaturated (i.e., not aromatic) group containing all carbon ring atoms and from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 9 ring carbon atoms ("$C_{3-9}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_5$), cyclooctenyl ($C_5$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), and the like. As the foregoing examples illustrate, in certain embodiments, the carbocyclyl group can be saturated or can contain one or more carbon-carbon double or triple bonds. In an alternative embodiment "Carbocyclyl" also includes ring systems wherein the carbocyclyl ring, as defined above, is fused with one or more heterocyclyl, aryl or heteroaryl groups wherein the point of attachment is on the carbocyclyl ring, and in such instances, the number of carbons continue to designate the number of carbons in the carbocyclic ring system. In an alternative embodiment, each instance of carbocycle is optionally substituted with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

"Cycloalkylalkyl" is a cycloalkyl as defined herein attached through an alkyl group. Non-limiting examples of cycloalkylalkyl groups include:

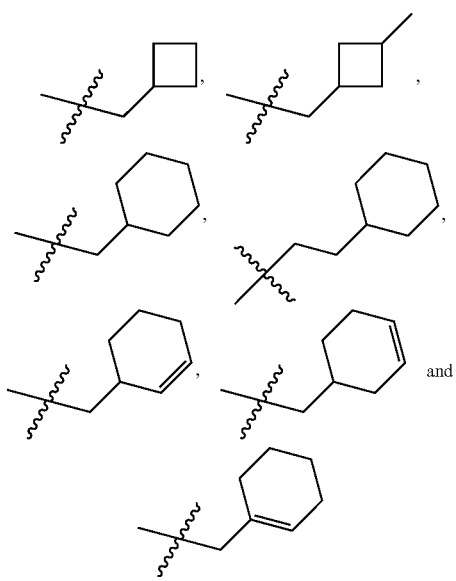

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and pentafluoroethyl.

"Haloalkoxy" indicates a haloalkyl group as defined herein attached through an oxygen bridge (oxygen of an alcohol radical).

"Alkoxyalkyl" is an alkyl group as previously described, substituted with at least one hydroxyl substituent.

"Aminoalkyl" is an alkyl group as previously described, substituted with at least one amino substituent.

"Halo" or "halogen" indicates independently any of fluoro, chloro, bromo or iodo.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C6-14 aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2 or 3 heteroatoms independently selected from nitrogen, oxygen, phosphorus, sulfur, silicon and boron, to form, for example, a 3,4-methylenedioxyphenyl group. In one embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl.

"Arylalkyl" is an aryl group as defined herein attached through an alkyl group. Non-limiting examples of arylalkyl groups include:

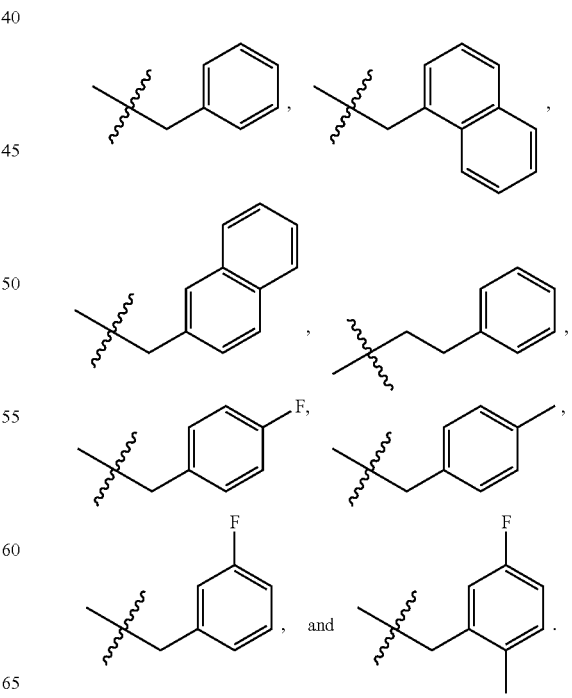

"Aryloxy" is an aryl group as defined herein attached through a —O— linker. Non-limiting examples of aryloxy groups include:

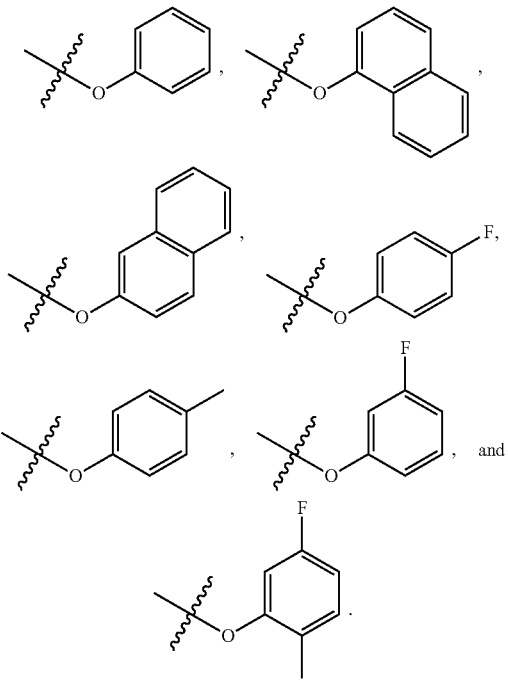

The term "heterocycle," or "heterocyclic ring" as used herein refers to a saturated or a partially unsaturated (i.e., having one or more double and/or triple bonds within the ring without aromaticity) cyclic moiety of 3 to about 12, and more typically 3, 5, 6, 7, 8, 9, or 10 ring atoms in which at least one ring atom is a heteroatom selected from nitrogen, oxygen, phosphorus, sulfur, silicon and boron, the remaining ring atoms being carbon, where one or more ring atoms is optionally substituted independently with one or more substituents described above. A heterocycle may be a monocycle having 3 to 7 ring members (2 to 6 carbon atoms and 1 to 4 heteroatoms selected from nitrogen, oxygen, phosphorus, sulfur, silicon and boron) or a bicycle having 6 to 10 ring members (4 to 9 carbon atoms and 1 to 6 heteroatoms selected from nitrogen, oxygen, phosphorus, sulfur, silicon and boron), for example: a bicyclo [4,5], [5,5], [5,6], or [6,6] system. In one embodiment, the only heteroatom is nitrogen. In one embodiment, the only heteroatom is oxygen. In one embodiment, the only heteroatom is sulfur, boron or silicon. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, pyrrolidinyl, dihydrofuranyl, tetrahydrothienyl, tetrahydropyranyl, dihydropyranyl, tetrahydrothiopyranyl, piperidino, piperidonyl, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, dihydroisoquinolinyl, tetrahydroisoquinolinyl, pyrazolidinylimidazolinyl, imidazolidinyl, 2-oxa-5-azabicyclo[2.2.2] octane, 3-oxa-8-azabicyclo[3.2.1]octane, 8-oxa-3-azabicyclo[3.2.1]octane, 6-oxa-3-azabicyclo[3.1.1]heptane, 2-oxa-5-azabicyclo [2.2.1]heptane, 3-azabicyco[3.1.0]hexanyl, 3-azabicyclo [4.1.0]heptanyl, azabicyclo[2.2.2]hexanyl, 3H-indolyl, quinolizinyl, N-pyridyl ureas, and pyrrolopyrimidine. Spiro moieties are also included within the scope of this definition. Examples of a heterocyclic group wherein 1 or 2 ring carbon atoms are substituted with oxo (═O) moieties are pyrimidinonyl and 1,1-dioxo-thiomorpholinyl. In an alternative embodiment, the heterocycle groups herein are optionally substituted independently with one or more substituents described herein.

"Heterocycloalkyl" is a heterocycle group as defined herein attached through an alkyl group. Non-limiting examples of heterocycloalkyl groups include:

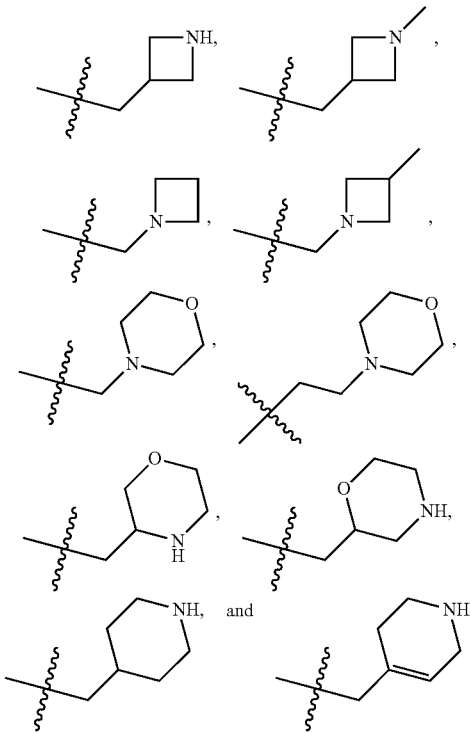

"Heteroaryl" indicates a stable monocyclic aromatic ring which contains from 1 to 3, or in some embodiments from 1, 2 or 3 heteroatoms selected from nitrogen, oxygen, phosphorus, sulfur, silicon and boron with remaining ring atoms being carbon, or a stable bicyclic or tricyclic system containing at least one 4 to 7 or 5- to 7-membered aromatic ring which contains from 1 to 3, or in some embodiments from 1 to 2, heteroatoms selected from nitrogen, oxygen, phosphorus, sulfur, silicon and boron with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 to 7 ring atoms. In some embodiments, bicyclic heteroaryl groups are 8- to 10-membered heteroaryl groups, that is, groups containing 8 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. In an alternative embodiment heteroaryl groups are optionally substituted independently with one or more substituents described herein.

"Heteroarylalkyl" is a heteroaryl group as defined herein attached through an alkyl group. Non-limiting examples of heteroarylalkyl groups include:

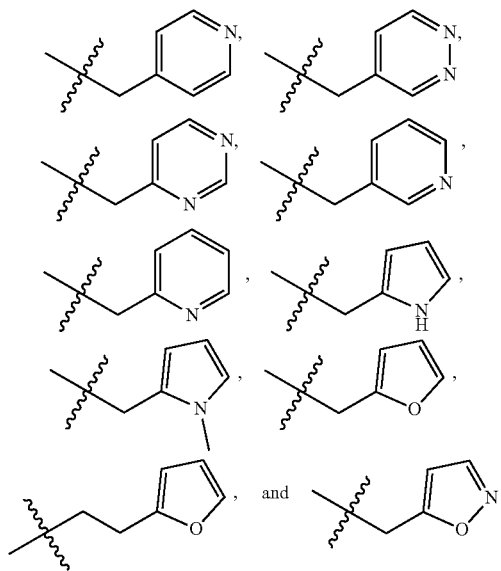

The term "mono- and/or di-alkylamino" indicate a secondary or tertiary alkylamino group, wherein the alkyl groups are independently selected alkyl groups, as defined herein. The point of attachment of the alkylamino group is on the nitrogen. Examples of mono- and di-alkylamino groups include ethylamino, dimethylamino, and methylpropyl-amino.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

"Pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, including but not limited to by modulation of the Complement Factor B pathway. Typically, the host is a human. A "patient" or "host" or "subject" also refers to for example, a mammal, primate (e.g., human), cows, sheep, goat, horse, dog, cat, rabbit, rat, mice, fish, bird, chicken, and the like.

A "prodrug" as used herein, means a compound which when administered to a host in vivo is converted into a parent drug. As used herein, the term "parent drug" means any of the presently described chemical compounds herein. Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others. In certain embodiments, the prodrug renders the parent compound more lipophilic. In certain embodiments, a prodrug can be provided that has several prodrug moieties in linear, branched or cyclic manner. For example, nonlimiting embodiments include the use of a divalent linker moiety such as a dicarboxylic acid, amino acid, diamine, hydroxycarboxylic acid, hydroxyamine, dihydroxy compound, or other compound that has at least two functional groups that can link the parent molecule with another prodrug moiety, and is typically biodegradable in vivo. In some embodiments, 2, 3, 4 or 5 prodrug biodegradable moieties are covalently bound in sequence, branched or cyclic fashion to the parent compound. Nonlimiting examples of prodrugs according to the present invention are formed with:

a. a carboxylic acid on the parent drug and a hydroxylated prodrug moiety to form an ester;
b. a carboxylic acid on the parent drug and an amine prodrug to form an amide;
c. an amino on the parent drug and a carboxylic acid prodrug moiety to form an amide,
d. an amino on the parent drug and a sulfonic acid to form a sulfonamide;
e. a sulfonic acid on the parent drug and an amino on the prodrug moiety to form a sulfonamide;
f. a hydroxyl group on the parent drug and a carboxylic acid on the prodrug moiety to form an ester;
g. a hydroxyl on the parent drug and a hydroxylated prodrug moiety to form an ether;
h. a phosphonate on the parent drug and a hydroxylated prodrug moiety to form a phosphonate ester;
i. a phosphoric acid on the parent drug and a hydroxylated prodrug moiety to form a phosphate ester;
j. a hydroxyl on the parent drug and a phosphonate on the prodrug to form a phosphonate ester;
k. a hydroxyl on the parent drug and a phosphoric acid prodrug moiety to form a phosphate ester;
l. a carboxylic acid on the parent drug and a prodrug of the structure HO—(CH$_2$)$_2$—O—(C$_{2-24}$ aliphatic group), for example, HO—(CH$_2$)$_2$—O—(C$_{2-24}$ alkyl group) to form an ester;
m. a carboxylic acid on the parent drug and a prodrug of the structure HO—(CH$_2$)$_2$—S—(C$_{2-24}$ aliphatic group), for example, HO—(CH$_2$)$_2$—S—(C$_{2-24}$ alkyl group) to form a thioester;
n. a hydroxyl on the parent drug and a prodrug of the structure HO—(CH$_2$)$_2$—O—(C$_{2-24}$ aliphatic group), for example, HO—(CH$_2$)$_2$—O—(C$_{2-24}$ alkyl group) to form an ether;
o. a carboxylic acid on the parent drug and a prodrug of the structure HO—(CH$_2$)$_2$—S—(C$_{2-24}$ aliphatic group), for example, HO—(CH$_2$)$_2$—S—(C$_{2-24}$ alkyl group), to form a thioether; and
p. a carboxylic acid, oxime, hydrazide, hydrazone, amine or hydroxyl on the parent compound and a prodrug moiety that is a biodegradable polymer or oligomer including but not limited to polylactic acid, polylactide-co-glycolide, polyglycolide, polyethylene glycol, polyanhydride, polyester, polyamide or a peptide. An exemplary synthesis of Oxime linkages is provided in the paper published by Jin et. al. titled "Oxime Linkage: A Robust Tool for the Design of PH-Sensitive Polymeric Drug Carriers" in BioMacromolecules, 2011, 12(10), 3460-3468.

In one embodiment, a prodrug is provided by attaching a natural or non-natural amino acid to an appropriate functional moiety on the parent compound, for example, oxygen, nitrogen or sulfur, and typically oxygen or nitrogen, usually in a manner such that the amino acid can be cleaved in vivo to provide the parent drug. The amino acid can be used alone or covalently linked (straight, branched or cyclic) to one or more other prodrug moieties to modify the parent drug to achieve the desired performance, such as increased half-life, lipophilicity, or other drug delivery or pharmacokinetic properties. The amino acid can be any compound with an amino group and a carboxylic acid, which includes an aliphatic amino acid, alkyl amino acid, aromatic amino acid, heteroaliphatic amino acid, heteroalkyl amino acid, or heterocyclic amino acid or heteroaryl amino acid.

"Providing a compound with at least one additional active agent" means the compound and the additional active agent (s) are provided simultaneously in a single dosage form, provided concomitantly in separate dosage forms, or provided in separate dosage forms for administration separated by some amount of time that is within the time in which both the compound and the at least one additional active agent are within the blood stream of a patient. In certain embodiments, the compound and the additional active agent need not be prescribed for a patient by the same medical care worker. In certain embodiments, the additional active agent or agents need not require a prescription. Administration of the compound or the at least one additional active agent can occur via any appropriate route, for example, oral tablets, oral capsules, oral liquids, inhalation, injection, suppositories, parenteral, sublingual, buccal, intravenous, intraaortal, transdermal, polymeric controlled delivery, non-polymeric controlled delivery, nano or microparticles, liposomes, and/or topical contact.

A "therapeutically effective amount" of a pharmaceutical composition/combination of this invention means an amount effective, when administered to a host, to provide a therapeutic benefit such as an amelioration of symptoms or reduction or diminution of the disease itself. In one embodiment, a therapeutically effective amount is an amount sufficient to prevent a significant increase or will significantly reduce the detectable level of Complement Factor B in the patient's blood, serum, or tissues.

II. Detailed Description of the Active Compounds

According to the present invention, a compound of Formula I, Formula II, Formula III, or Formula IV is provided:

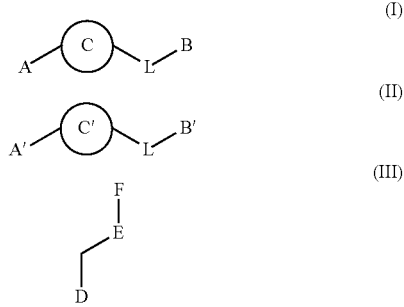

(IV)

as well as the pharmaceutically acceptable salts and compositions thereof. Formula I, Formula II, Formula III, and Formula IV can be considered to comprise a quinazoline (A or A'), a central core (C or C'), and a L-B or L-B' substituent. In one embodiment, the compound is an inhibitor of Complement Factor B, and therefore can be used in an effective amount to treat a host in need of Complement Factor B modulation. In another embodiment, the compound acts through a mechanism other than inhibition of Complement B to treat a disorder described herein in a host, typically a human.

Prior published quinazoline containing compounds are described in the following disclosures: Senta Pharmaceuticals Corp. patent publication WO2005/112938 titled "Disalt inhibitors of IL-12 production"; Sumitomo Pharmaceuticals Co. patent publication JP2000/281660 titled "Quinazolines and pharmaceuticals for treatment of allergic diseases and cartilage disorders"; Novartis patent publication WO1997/020820 titled "Heteroaryl compounds-NPY receptor subtype Y5 modulators"; Astellas Pharma Inc. patent publication WO2005/123697 titled "Preparation of quinazoline derivatives as CCR4 function controllers"; WUXI MChem Pharmatech Co. patent publication CN102516232 titled "One kind of ErbB2 selective small molecule inhibitors and their applications"; Painceptor Pharma Corp. patent publication WO2007/071055 titled "Compositions and methods for modulating gated ion channels"; Mediolanum Farmaceutici SRL patent publication WO1996/02524 titled "Phenylcarbamate derivatives suitable to the use as anticholinesterase substances"; Merck patent publication WO1997/11698 titled "Alpha 1b adrenergic receptor antagonist"; Recordati Chem Pharm patent publication WO2000/67735 titled "Use of selective antagonists of the alpha 1b-adrenergic receptor for improvement of sexual dysfunction"; Chemrx Advanced Technologies patent publication WO2001/168615 titled "Quinazoline synthesis".

Non-limiting examples of compounds falling within Formula I with variations in the variables e.g. A, C, L and B, are illustrated below. The disclosure includes all combinations of these definitions so long as a stable compound results.

Formulas V through XIX

In one aspect, the disclosure includes compounds and salts of Formulas V-XIX for any use and in any composition described in this application.

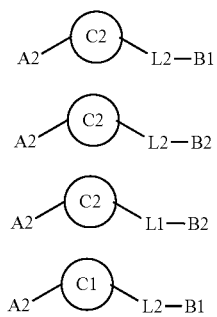

Formula V

Formula VI

Formula VII

Formula VIII

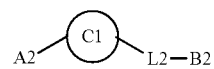

Formula IX

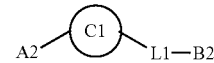

Formula X

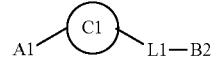

Formula XI

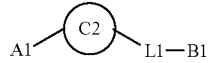

Formula XII

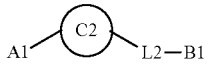

Formula XIII

Formula XIV

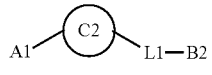

Formula XV

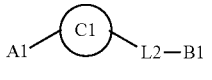

Formula XVI

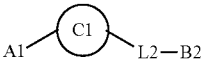

Formula XVII

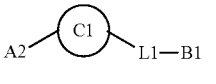

Formula XVIII

Formula XIX

Formulas IA-IG

To further illustrate the invention, various embodiments of Formula IA, IB, IC and ID are provided. These are presented by way of example to show some of the variations among presented compounds within the invention and can be applied to any of the Formulas herein.

In one aspect, this disclosure includes compounds and salts of Formula IA:

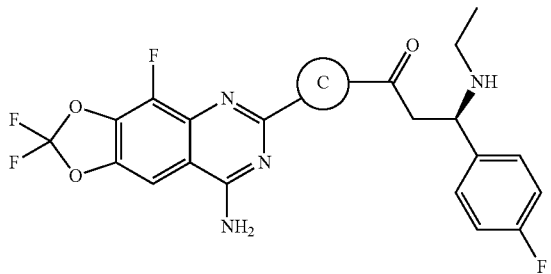

(IA)

wherein C may carry any of the definitions set forth herein for this variable.

In another aspect, this disclosure includes compounds and salts of Formula IB:

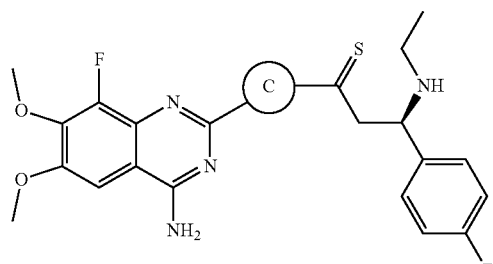

(IB)

wherein C may carry any of the definitions set forth herein for this variable.

In another aspect, this disclosure includes compounds and salts of Formula IC:

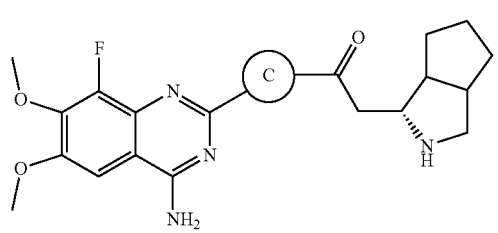

(IC)

wherein C may carry any of the definitions set forth herein for this variable.

In another aspect, this disclosure includes compounds and salts of Formula ID, Formula IE, Formula IF, and Formula IG:

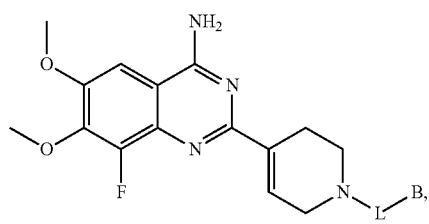

(ID)

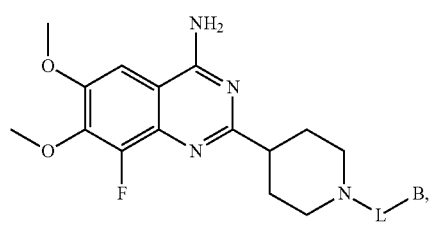

(IE)

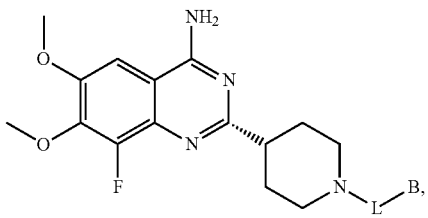

(IF)

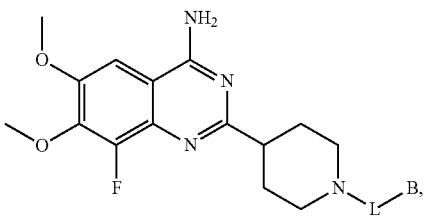

(IG)

wherein L and B may carry any of the definitions set forth herein for these variables.

In another aspect, this disclosure includes compounds and salts of Formula IIA, Formula IIB, Formula IIC, and Formula IID:

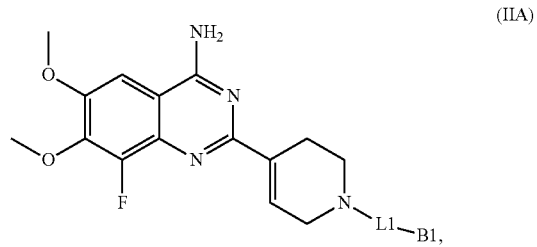

(IIA)

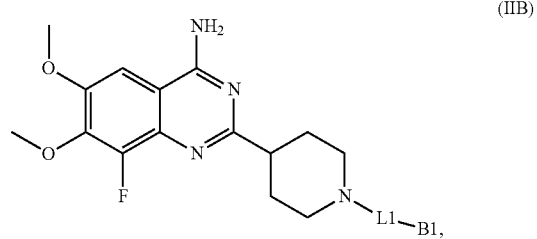

(IIB)

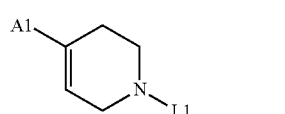

(IIC)

and

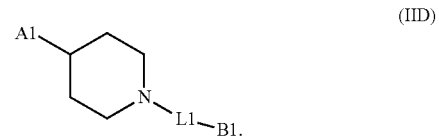

(IID)

Embodiments of $R^{150}$
In one embodiment $R^{150}$ is selected from the below:
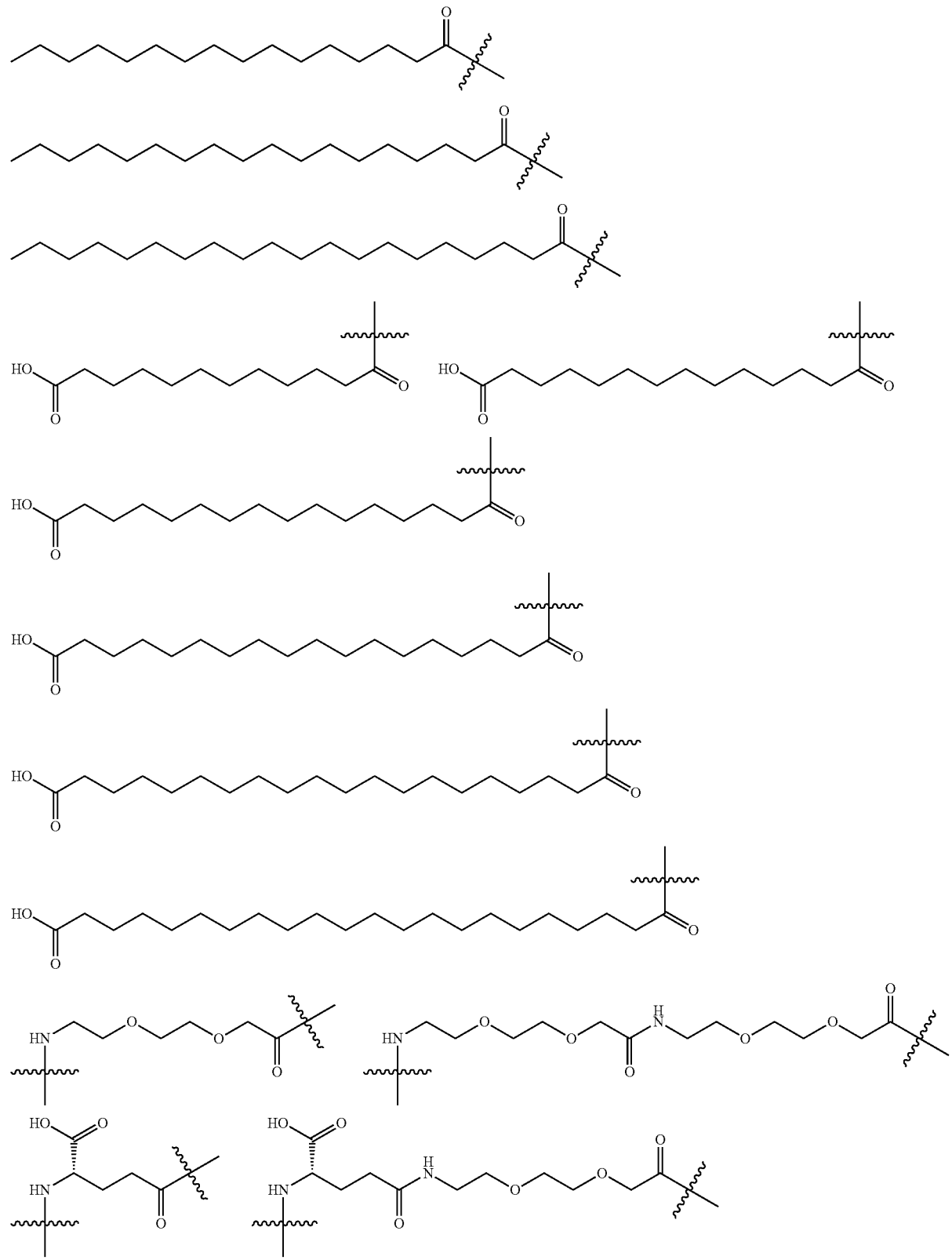

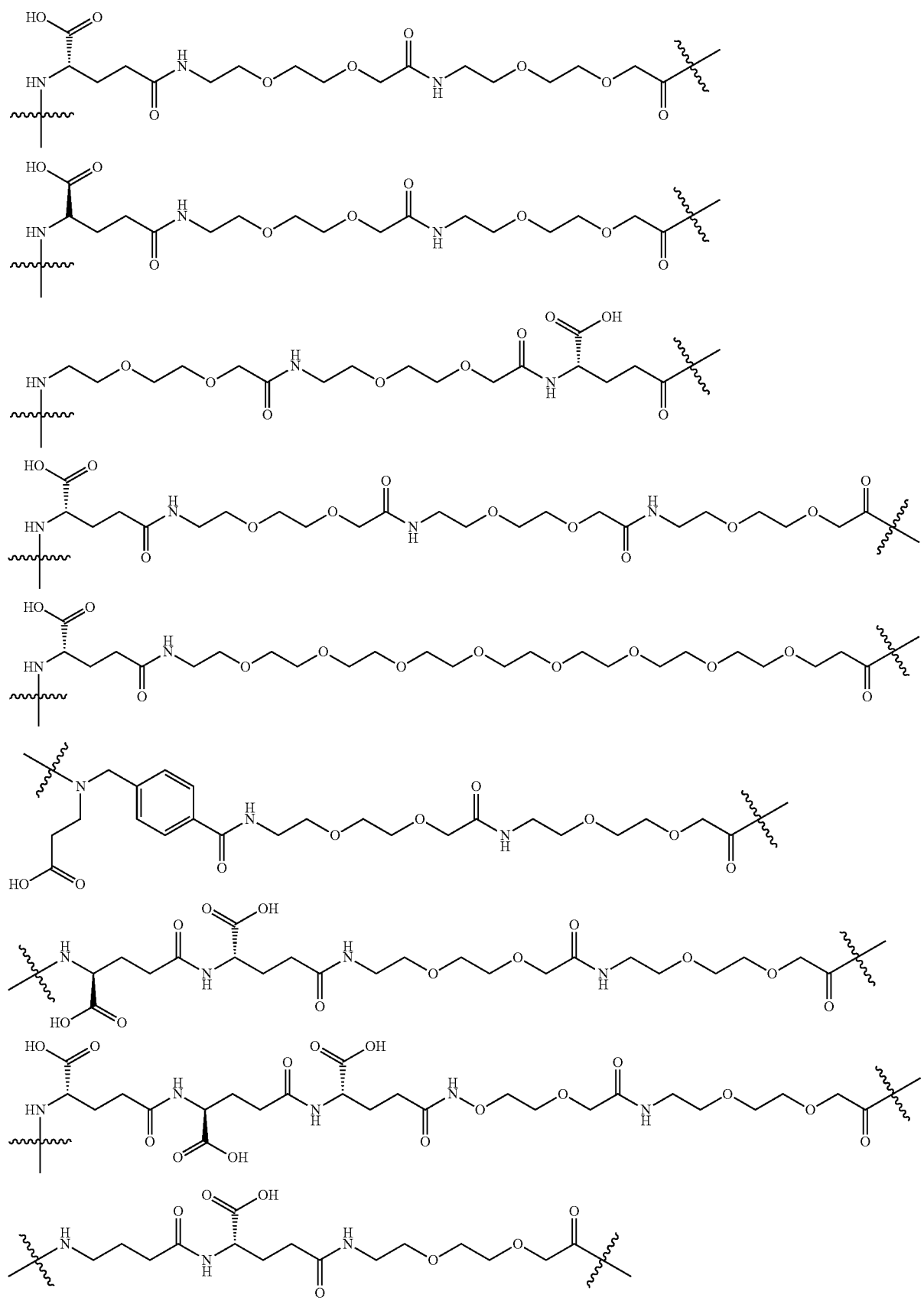

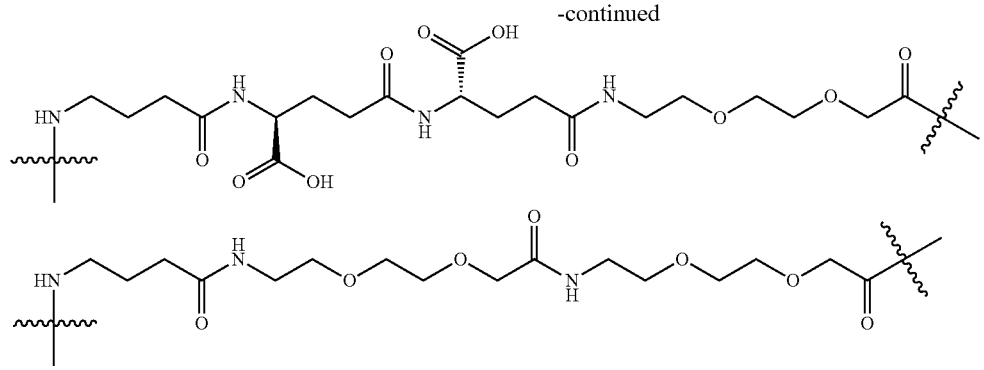

wherein if the moiety is shown as a divalent species, it can be capped with hydrogen, methyl, alkyl, haloalkyl, another bioactive moiety, or additional prodrug moiety.

III. Pharmaceutical Preparations

Active compounds described herein can be administered to a host in need thereof as the neat chemical, but are more typically administered as a pharmaceutical composition that includes an effective amount for a host, typically a human, in need of such treatment of an active compound as described herein or its pharmaceutically acceptable salt, prodrug, isotopic analog, or isolated isomer thereof. Thus, in one embodiment, the disclosure provides pharmaceutical compositions comprising an effective amount of compound or pharmaceutically acceptable salt, prodrug, isotopic analog, or isolated isomer thereof together with at least one pharmaceutically acceptable carrier for any of the uses described herein. The pharmaceutical composition may contain a compound or salt as the only active agent, or, in an alternative embodiment, the compound and at least one additional active agent.

An effective amount of an active compound as described herein, or the active compound described herein in combination or alternation with, or preceded by, concomitant with or followed by another active agent, can be used in an amount sufficient to (a) inhibit the progression of a disorder mediated by the Complement pathway, including an inflammatory, immune, including an autoimmune, disorder or Complement Factor B related disorder; (b) cause a regression of an inflammatory, immune, including an autoimmune, disorder or Complement Factor B related disorder; (c) cause a cure of an inflammatory, immune, including an autoimmune, disorder or Complement Factor B related disorder; or inhibit or prevent the development of an inflammatory, immune, including an autoimmune, disorder or Complement Factor B related disorder. Accordingly, an effective amount of an active compound or its salt or composition described herein will provide a sufficient amount of the active agent when administered to a patient provides a clinical benefit.

The exact amount of the active compound or pharmaceutical composition described herein to be delivered to the host, typically a human, in need thereof, will be determined by the health care provider to achieve the desired clinical benefit.

In certain embodiments, the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound, or its salt or prodrug. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound, or its salt.

The amount of active compound in the dosage form is calculated without reference to the salt. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The pharmaceutical composition may for example include a molar ratio of the active compound and an additional active agent that achieves the desired result. For example, the pharmaceutical composition may contain a molar ratio of about 0.5:1, about 1:1, about 2:1, about 3:1 or from about 1.5:1 to about 4:1 of an additional active agent in combination with the active compound (additional active agent: active compound), or its salt, described herein. In one embodiment, the additional active agent is an anti-inflammatory or immunosuppressing agent. Compounds disclosed herein or used as described herein may be administered orally, topically, parenterally, by inhalation or spray, sublingually, via implant, including ocular implant, transdermally, via buccal administration, rectally, as an ophthalmic solution, injection, including ocular injection, intravenous, intraaortal, intracranial, subdermal, intraperitoneal, subcutaneous, transnasal, sublingual, intrathecal, or rectal or by other means, in dosage unit formulations containing conventional pharmaceutically acceptable carriers. For ocular delivery, the compound can be administered, as desired, for example, as a solution, suspension, or other formulation via intravitreal, intrastromal, intracameral, sub-tenon, sub-retinal, retro-bulbar, peribulbar, suprachorodial, subchorodial, chorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device, injection, or topically administered formulation, for example a solution or suspension provided as an eye drop.

The pharmaceutical composition may be formulated as any pharmaceutically useful form, e.g., as an aerosol, a cream, a gel, a gel cap, a pill, a microparticle, a nanoparticle, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution or suspension. Some dosage forms, such as tablets and capsules, are subdivided into suitably sized unit doses containing appropriate quantities of the active components, e.g., an effective amount to achieve the desired purpose.

Pharmaceutical compositions, and methods of manufacturing such compositions, suitable for administration as contemplated herein are known in the art. Examples of known techniques include, for example, U.S. Pat. Nos. 4,983,593, 5,013,557, 5,456,923, 5,576,025, 5,723,269, 5,858,411, 6,254,889, 6,303,148, 6,395,302, 6,497,903, 7,060,296, 7,078,057, 7,404,828, 8,202,912, 8,257,741, 8,263,128, 8,337,899, 8,431,159, 9,028,870, 9,060,938, 9,211,261, 9,265,731, 9,358,478, and 9,387,252, incorporated by reference herein.

The pharmaceutical compositions contemplated here can optionally include a carrier. Carriers must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. Classes of carriers include, but are not limited to binders, buffering agents, coloring agents, diluents, disintegrants, emulsifiers, fillers, flavorants, glidents, lubricants, pH modifiers, preservatives, stabilizers, surfactants, solubilizers, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Examples of other matrix materials, fillers, or diluents include lactose, mannitol, xylitol, microcrystalline cellulose, calcium diphosphate, and starch. Examples of surface active agents include sodium lauryl sulfate and polysorbate 80. Examples of drug complexing agents or solubilizers include the polyethylene glycols, caffeine, xanthene, gentisic acid and cylodextrins.

Examples of disintegrants include sodium starch gycolate, sodium alginate, carboxymethyl cellulose sodium, methyl cellulose, colloidal silicon dioxide, and croscarmellose sodium. Examples of binders include methyl cellulose, microcrystalline cellulose, starch, and gums such as guar gum, and tragacanth. Examples of lubricants include magnesium stearate and calcium stearate. Examples of pH modifiers include acids such as citric acid, acetic acid, ascorbic acid, lactic acid, aspartic acid, succinic acid, phosphoric acid, and the like; bases such as sodium acetate, potassium acetate, calcium oxide, magnesium oxide, trisodium phosphate, sodium hydroxide, calcium hydroxide, aluminum hydroxide, and the like, and buffers generally comprising mixtures of acids and the salts of said acids. Optional other active agents may be included in a pharmaceutical composition, which do not substantially interfere with the activity of the compound of the present invention.

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions can be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal or parenteral (including intramuscular, intra-arterial, intrathecal, subcutaneous and intravenous) administration or in a form suitable for administration by inhalation or insufflation. The preferred manner of administration is intravenous or oral using a convenient daily dosage regimen which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet, capsule, a softgel capsule or can be an aqueous or nonaqueous solution, suspension or syrup. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the active agent can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as an continuous infusion system. A formulation provided by the disclosure can be administered using a syringe, injector, pump, or any other device recognized in the art for parenteral administration.

In certain embodiments, the pharmaceutical composition for administration further includes a compound or salt of Formula I, Formula II, Formula III, or Formula IV and optionally comprises one or more of a phosphoglyceride; phosphatidylcholine; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerol succinate; diphosphatidyl glycerol (DPPG); hexanedecanol; fatty alcohol such as polyethylene glycol (PEG); polyoxyethylene-9-lauryl ether; a surface active fatty acid, such as palmitic acid or oleic acid; fatty acid; fatty acid monoglyceride; fatty acid diglyceride; fatty acid amide; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebroside; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipid; synthetic and/or natural detergent having high surfactant properties; deoxycholate; cyclodextrin; chaotropic salt; ion pairing agent; glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid; pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan, mannitol, sorbitol, xylitol, erythritol, maltitol, and lactitol, a pluronic polymer, polyethylene, polycarbonate (e.g. poly(1,3-dioxan-2one)), polyanhydride (e.g. poly(sebacic anhydride)), polypropylfumerate, polyamide (e.g. polycaprolactam), polyacetal, polyether, polyester (e.g., polylactide, polyglycolide, polylactide-co-glycolide, polycaprolactone, polyhydroxyacid (e.g. poly((β-hydroxyalkanoate))), poly(orthoester), polycyanoacrylate, polyvinyl alcohol, polyurethane, polyphosphazene, polyacrylate, polymethacrylate, polyurea, polystyrene, and polyamine, polylysine, polylysine-PEG copolymer, and poly (ethyleneimine), poly(ethylene imine)-PEG copolymer, glycerol monocaprylocaprate, propylene glycol, Vitamin E TPGS (also known as d-α-Tocopheryl polyethylene glycol 1000 succinate), gelatin, titanium dioxide, polyvinylpyrrolidone (PVP), hydroxypropyl methyl cellulose (HPMC), hydroxypropyl cellulose (HPC), methyl cellulose (MC), block copolymers of ethylene oxide and propylene oxide (PEO/PPO), polyethyleneglycol (PEG), sodium carboxymethylcellulose (NaCMC), hydroxypropylmethyl cellulose acetate succinate (HPMCAS).

In some embodiments, the pharmaceutical preparation may include polymers for controlled delivery of the described compounds, including, but not limited to pluronic polymers, polyesters (e.g., polylactic acid, poly(lactic-co-glycolic acid), polycaprolactone, polyvalerolactone, poly(1, 3-dioxan-2one)); polyanhydrides (e.g., poly(sebacic anhydride)); polyethers (e.g., polyethylene glycol); polyurethanes; polymethacrylates; polyacrylates; and polycyanoacrylates. In some embodiments, polymers may be modified with polyethylene glycol (PEG), with a carbohydrate, and/or with acyclic polyacetals derived from polysaccharides. See, e.g., Papisov, 2001, ACS Symposium Series, 786:301, incorporated by reference herein.

The compounds of the present invention can be formulated as particles. In one embodiment, the particles are or include microparticles. In an alternative embodiment, the particles are or include nanoparticles.

In an additional alternative embodiment, common techniques for preparing particles include, but are not limited to, solvent evaporation, solvent removal, spray drying, phase inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

In one embodiment, the particles are derived through a solvent evaporation method. In this method, a compound described herein (or polymer matrix and one or more compounds described herein) is dissolved in a volatile organic solvent, such as methylene chloride. The organic solution containing a compound described herein is then suspended in an aqueous solution that contains a surface active agent such as poly(vinyl alcohol). The resulting emulsion is stirred until most of the organic solvent evaporated, leaving solid nanoparticles or microparticles. The resulting nanoparticles or microparticles are washed with water and dried overnight in a lyophilizer. Nanoparticles with different sizes and morphologies can be obtained by this method. Pharmaceutical compositions which contain labile polymers, such as certain polyanhydrides, may degrade during the fabrication process due to the presence of water. For these polymers, methods which are performed in completely or substantially anhydrous organic solvents can be used to make the particles.

Solvent removal can also be used to prepare particles from a compound that is hydrolytically unstable. In this method, the compound (or polymer matrix and one or more compounds) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

In one embodiment, an active compound as described herein is administered to a patient in need thereof as particles formed by solvent removal. In another embodiment, the present invention provides particles formed by solvent removal comprising a compound of the present invention and one or more pharmaceutically acceptable excipients as defined herein. In another embodiment, the particles formed by solvent removal comprise a compound of the present invention and an additional therapeutic agent. In a further embodiment, the particles formed by solvent removal comprise a compound of the present invention, an additional therapeutic agent, and one or more pharmaceutically acceptable excipients. In another embodiment, any of the described particles formed by solvent removal can be formulated into a tablet and then coated to form a coated tablet. In an alternative embodiment, the particles formed by solvent removal are formulated into a tablet but the tablet is uncoated.

In one embodiment, the particles are derived by spray drying. In this method, a compound (or polymer matrix and one or more compounds) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment, an active compound as described herein is administered to a patient in need thereof as a spray dried dispersion (SDD). In another embodiment, the present invention provides a spray dried dispersion (SDD) comprising a compound of the present invention and one or more pharmaceutically acceptable excipients as defined herein. In another embodiment, the SDD comprises a compound of the present invention and an additional therapeutic agent. In a further embodiment, the SDD comprises a compound of the present invention, an additional therapeutic agent, and one or more pharmaceutically acceptable excipients. In another embodiment, any of the described spray dried dispersions can be coated to form a coated tablet. In an alternative embodiment, the spray dried dispersion is formulated into a tablet but is uncoated. Particles can be formed from the active compound as described herein using a phase inversion method. In this method, the compound (or polymer matrix and one or more active compounds) is dissolved in a suitable solvent, and the solution is poured into a strong non-solvent for the compound to spontaneously produce, under favorable conditions, microparticles or nanoparticles.

The method can be used to produce nanoparticles in a wide range of sizes, including, for example, from nanoparticles to microparticles, typically possessing a narrow particle size distribution.

In one embodiment, an active compound as described herein is administered to a patient in need thereof as particles formed by phase inversion. In another embodiment, the present invention provides particles formed by phase inversion comprising a compound of the present invention and one or more pharmaceutically acceptable excipients as defined herein. In another embodiment, the particles formed by phase inversion comprise a compound of the present invention and an additional therapeutic agent. In a further embodiment, the particles formed by phase inversion comprise a compound of the present invention, an additional therapeutic agent, and one or more pharmaceutically acceptable excipients. In another embodiment, any of the described particles formed by phase inversion can be formulated into a tablet and then coated to form a coated tablet.

In an alternative embodiment, the particles formed by phase inversion are formulated into a tablet but the tablet is uncoated.

Techniques for particle formation using coacervation are known in the art, for example, as described in GB-B-929 406; GB-B-929 40 1; and U.S. Pat. Nos. 3,266,987, 4,794, 000, and 4,460,563. Coacervation involves the separation of a compound (or polymer matrix and one or more compounds) solution into two immiscible liquid phases. One phase is a dense coacervate phase, which contains a high concentration of the compound, while the second phase contains a low concentration of the compound. Within the dense coacervate phase, the compound forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

In one embodiment, an active compound as described herein is administered to a patient in need thereof as particles formed by coacervation. In another embodiment, the present invention provides particles formed by coacervation comprising a compound of the present invention and one or more pharmaceutically acceptable excipients as defined herein. In another embodiment, the particles formed by coacervation comprise a compound of the present invention and an additional therapeutic agent. In a further embodiment, the particles formed by coacervation comprise a compound of the present invention, an additional therapeutic agent, and one or more pharmaceutically acceptable excipients. In another embodiment, any of the described particles formed by coacervation can be formulated into a tablet and then coated to form a coated tablet. In an alternative embodiment, the particles formed by coacervation are formulated into a tablet but the tablet is uncoated.

Methods for very low temperature casting of controlled release microspheres are described in U.S. Pat. No. 5,019,400 to Gombotz et al. In this method, the compound is dissolved in a solvent. The mixture is then atomized into a vessel containing a liquid non-solvent at a temperature below the freezing point of the drug solution which freezes the compound droplets. As the droplets and non-solvent for the compound are warmed, the solvent in the droplets thaws and is extracted into the non-solvent, hardening the microspheres.

In one embodiment, a compound of the present invention is administered to a patient in need thereof as particles formed by low temperature casting. In another embodiment, the present invention provides particles formed by low temperature casting comprising a compound of the present invention and one or more pharmaceutically acceptable excipients as defined herein. In another embodiment, the particles formed by low temperature casting comprise a compound of the present invention and an additional therapeutic agent. In a further embodiment, the particles formed by low temperature casting comprise a compound of the present invention, an additional therapeutic agent, and one or more pharmaceutically acceptable excipients. In another embodiment, any of the described particles formed by low temperature casting can be formulated into a tablet and then coated to form a coated tablet. In an alternative embodiment, the particles formed by low temperature casting are formulated into a tablet but the tablet is uncoated.

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based compound delivery can be used to release compounds at a sustained rate and thus lower the frequency of administration, deliver drugs in a targeted manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Methods for producing nanoparticles are known in the art. For example, see Muller, R. H., et al., Solid lipid nanoparticles (SLN) for controlled drug delivery—a review of the state of the art, Eur. H. Pharm. Biopharm., 50:161-177, 2000; U.S. Pat. No. 8,691,750 to Consien et al.; WO 2012/145801 to Kanwar. U.S. Pat. No. 8,580,311 to Armes, S. et al.; Petros, R. A. and DeSimone, J. M., Strategies in the design of nanoparticles for therapeutic applications, Nature Reviews/Drug Discovery, vol. 9:615-627, 2010; U.S. Pat. Nos. 8,465,775; 8,444,899; 8,420,124; 8,263,129; 8,158,728; 8,268,446; Pellegrino et al., 2005, Small, 1:48; Murray et al., 2000, Ann. Rev. Mat. Sci., 30:545; and Trindade et al., 2001, Chem. Mat., 13:3843; all incorporated herein by reference. Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)), U.S. Pat. No. 5,543,158 to Gref et al., or WO publication WO2009/051837 by Von Andrian et al. Zauner et al., 1998, Adv. Drug Del. Rev., 30:97; and Kabanov et al., 1995, Bioconjugate Chem., 6:7; (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372; Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633; U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181; Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732; C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010); U.S. Pat. No. 6,632,671 to Unger Oct. 14, 2003, all incorporated herein by reference.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In another embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In some embodiments, a compound described herein may be covalently coupled to a polymer used in the nanoparticle, for example a polystyrene particle, PLGA particle, PLA particle, or other nanoparticle.

The pharmaceutical compositions can be formulated for oral administration. These compositions can contain any amount of active compound that achieves the desired result, for example between 0.1 and 99 weight % (wt. %) of the compound and usually at least about 5 wt. % of the compound. Some embodiments contain at least about 10%, 15%, 20%, 25 wt. % to about 50 wt. % or from about 5 wt. % to about 75 wt. % of the compound.

Pharmaceutical compositions suitable for rectal administration are typically presented as unit dose suppositories. These may be prepared by admixing the active compound with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Pharmaceutical compositions suitable for transdermal administration may also be delivered by iontophoresis (see, for example, Pharmaceutical Research 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Pharmaceutical compositions suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Additional non-limiting examples of inhalation drug delivery devices and methods include, for example, U.S. Pat. No. 7,383,837 titled "Inhalation device" (SmithKline Beecham Corporation); WO/2006/033584 titled "Powder inhaler" (Glaxo SmithKline Pharmaceuticals SA); WO/2005/044186 titled "Inhalable pharmaceutical formulations employing desiccating agents and methods of administering the same" (Glaxo Group Ltd and SmithKline Beecham Corporation); U.S. Pat. No. 9,095,670 titled "Inhalation device and method of dispensing medicament", U.S. Pat. No. 8,205,611 titled "Dry powder inhaler" (Astrazeneca AB); WO/2013/038170 titled "Inhaler" (Astrazeneca AB and Astrazeneca UK Ltd.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Many methods and devices for drug delivery to the eye are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277,830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.). Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of methods and devices for drug delivery to the eye include, for example, WO2011/106702 and U.S. Pat. No. 8,889,193 titled "Sustained delivery of therapeutic agents to an eye compartment", WO2013/138343 and U.S. Pat. No. 8,962,577 titled "Controlled release formulations for the delivery of HIF-1 inhibitors", WO/2013/138346 and US2013/0272994 titled "Non-Linear Multiblock Copolymer-Drug Conjugates for the Delivery of Active Agents", WO2005/072710 and U.S. Pat. No. 8,957,034 titled "Drug and Gene Carrier Particles that Rapidly Move Through Mucus Barriers", WO2008/030557, US2010/0215580, US2013/0164343 titled "Compositions and Methods for Enhancing Transport Through Mucous", WO2012/061703, US2012/0121718, and US2013/0236556 titled "Compositions and Methods Relating to Reduced Mucoadhesion", WO2012/039979 and US2013/0183244 titled "Rapid Diffusion of Large Polymeric Nanoparticles in the Mammalian Brain", WO2012/109363 and US2013/0323313 titled "Mucus Penetrating Gene Carriers", WO 2013/090804 and US2014/0329913 titled "Nanoparticles with enhanced mucosal penetration or decreased inflammation", WO2013/110028 titled "Nanoparticle formulations with enhanced mucosal penetration", WO2013/166498 and US2015/0086484 titled "Lipid-based drug carriers for rapid penetration through mucus linings" (The Johns Hopkins University); WO2013/166385 titled "Pharmaceutical Nanoparticles Showing Improved Mucosal Transport", US2013/0323179 titled "Nanocrystals, Compositions, And Methods that Aid Particle Transport in Mucus" (The Johns Hopkins University and Kala Pharmaceuticals, Inc.); WO/2015/066444 titled "Compositions and methods for ophthalmic and/or other applications", WO/2014/020210 and WO/2013/166408 titled "Pharmaceutical nanoparticles showing improved mucosal transport" (Kala Pharmaceuticals, Inc.); U.S. Pat. No. 9,022,970 titled "Ophthalmic injection device including dosage control device", WO/2011/153349 titled "Ophthalmic compositions comprising pbo-peo-pbo block copolymers", WO/2011/140203 titled "Stabilized ophthalmic galactomannan formulations", WO/2011/068955 titled "Ophthalmic emulsion", WO/2011/037908 titled "Injectable aqueous ophthalmic composition and method of use therefor", US2007/0149593 titled "Pharmaceutical Formulation for Delivery of Receptor Tyrosine Kinase Inhibiting (RTKi) Compounds to the Eye", U.S. Pat. No. 8,632,809 titled "Water insoluble polymer matrix for drug delivery" (Alcon, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

IV. Methods of Treatment

In one aspect, an active compound or its salt or composition, as described herein (e.g. Formula I, Formula II, Formula III, or Formula IV), is used to treat a medical disorder which is an inflammatory or immune condition, a disorder mediated by the Complement cascade (including a dysfunctional cascade), a disorder or abnormality of a cell that adversely affects the ability of the cell to engage in or respond to normal Complement activity, or an undesired complement-mediated response to a medical treatment, such as surgery or other medical procedure or a pharmaceutical or biopharmaceutical drug administration, a blood transfusion, or other allogeneic tissue or fluid administration.

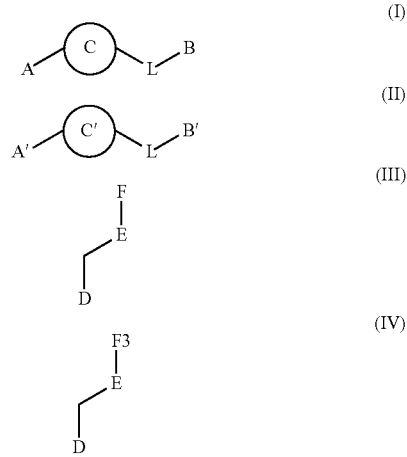

In one embodiment, the disorder is selected from fatty liver and conditions stemming from fatty liver, such as nonalcoholic steatohepatitis (NASH), liver inflammation, cirrhosis and liver failure. In another embodiment of the present invention, a method is provided for treating fatty liver disease in a host by administering an effective amount of an active compound or its salt or composition as described herein.

In another embodiment, an active compound or its salt or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a subject in need thereof an effective amount of an active compound or its salt or composition as described herein.

In another embodiment, the present invention provides a method of treating or preventing amyotrophic lateral sclerosis by administering to a subject in need thereof an effective amount of an active compound or its salt or composition as described herein.

In another embodiment, the present invention provides a method of treating or preventing abdominal aortic aneurysm, hemodialysis complications, hemolytic anemia, or hemodialysis by administering to a subject in need thereof an effective amount of an active compound or its salt or composition as described herein.

In another embodiment, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of an active compound or its salt or composition as described herein. Various types of cytokine or inflammatory reactions may occur in response to a number of factors, such as the administrations of biotherapeutics. In one embodiment, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

Fatal cytokine storms have been observed in response to infusion with several monoclonal antibody therapeutics. See, Abramowicz D, et al. "Release of tumor necrosis factor, interleukin-2, and gamma-interferon in serum after injection of OKT3 monoclonal antibody in kidney transplant recipients" Transplantation (1989) 47(4):606-8; Chatenoud L, et al. "In vivo cell activation following OKT3 administration. Systemic cytokine release and modulation by corticosteroids" Transplantation (1990) 49(4):697-702; and Lim L C, Koh L P, and Tan P. "Fatal cytokine release syndrome with chimeric anti-$CD_{20}$ monoclonal antibody rituximab in a 71-year-old patient with chronic lymphocytic leukemia" J. Clin Oncol. (1999) 17(6):1962-3.

Also contemplated herein, is the use of an active compound or its salt or composition as described herein to mediate an adverse immune response in patients receiving bi-specific T-cell engagers (BiTE). A bi-specific T-cell engager directs T-cells to target and bind with a specific antigen on the surface of a cancer cell. For example, Blinatumomab (Amgen), a BiTE has recently been approved as a second line therapy in Philadelphia chromosome-negative relapsed or refractory acute lymphoblastic leukemia. Blinatumomab is given by continuous intravenous infusion in 4-week cycles. The use of BiTE agents has been associated with adverse immune responses, including cytokine release syndrome. The most significantly elevated cytokines in the CRS associated with ACT include IL-10, IL-6, and IFN-γ (Klinger et al., Immunopharmacologic response of patients with B-lineage acute lymphoblastic leukemia to continuous infusion of T cell-engaging $CD_{19}$/$CD_3$-bispecific BiTE antibody blinatumomab. Blood (2012) 119:6226-6233).

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In one embodiment, the present invention provides a method of treating or preventing a C3 glomurenopathy by administering to a subject in need thereof an effective amount of an active compound or its salt or composition as described herein. In another embodiment, the disorder is selected from dense deposit disease (DDD) and C3 glomerulonephritis (C3GN).

In one embodiment, the present invention provides a method of treating or preventing a IC-MPGN by administering to a subject in need thereof an effective amount of an active compound or its salt or composition as described herein.

In one embodiment, the present invention provides a method of treating or preventing a paroxysmal nocturnal hemoglobinuria (PNH) by administering to a subject in need thereof an effective amount of an active compound or its salt or composition as described herein.

In another embodiment, the present invention provides a method of treating or preventing age-related macular degeneration (AMD) by administering to a subject in need thereof an effective amount of an active compound or its salt or composition as described herein.

In one embodiment, the present invention provides a method of treating or preventing rheumatoid arthritis by administering to a subject in need thereof an effective amount of an active compound or its salt or composition as described herein.

In one embodiment, the present invention provides a method of treating or preventing multiple sclerosis by administering to a subject in need thereof an effective amount of an active compound or its salt or composition as described herein.

In another embodiment, the present invention provides a method of treating or preventing myasthenia gravis by administering to a subject in need thereof an effective amount of an active compound or its salt or composition as described herein.

In one embodiment, the present invention provides a method of treating or preventing atypical hemolytic uremic syndrome (aHUS) by administering to a subject in need thereof an effective amount of an active compound or its salt or composition as described herein.

In another embodiment, the present invention provides a method of treating or preventing neuromyelitis optica (NMO) by administering to a subject in need thereof an effective amount of an active compound or its salt or composition as described herein.

In yet another embodiment, the present invention provides a method of treating or preventing a disorder as described below by administering to a subject in need thereof an effective amount of an active compound or its salt or composition as described herein, including:

vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In an additional embodiment, the disorder is selected from: acute myocardial infarction, aneurysm, cardiopulmonary bypass, dilated cardiomyopathy, Complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from: atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis; angioedema, low platelets (HELLP) syndrome, sickle cell disease, platelet refractoriness, red cell casts, or typical or infectious hemolytic uremic syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, or catastrophic antiphospholipid syndrome.

In another embodiment, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration;

pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In a further embodiment, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis; inclusion body myositis, intestinal ischemia, iridocyclitis, iritis, juvenile chronic arthritis, Kawasaki's disease (arteritis), or lipiduria; membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis *nodosa* (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thryoiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss.

In one embodiment, an active compound or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitonial fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, *pityriasis lichenoides et varioliformis acuta*, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion, or central retinal vein occulusion (CVRO).

In some embodiments, Complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by an active compound or its salt or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable Complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, in plants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of sickle cell in a host is provided that includes the administration of an effective amount of an active compound or its salt or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of an active compound or its salt or composition as described herein. In one embodiment, a method for the treatment of ANCA-vasculitis in a host is provided that includes the administration of an effective amount of an active compound or its salt or composition as described herein. In one embodiment, a method for the treatment of IgA nephropathy in a host is provided that includes the administration of an effective amount of an active compound or its salt or composition as described herein. In one embodiment, a method for the treatment of rapidly progressing glomerulonephritis (RPGN), in a host is provided that includes the administration of an effective amount of an active compound or its salt or composition as described herein. In one embodiment, a method for the treatment of lupus nephritis, in a host is provided that includes the administration of an effective amount of an active compound or its salt or composition as described herein. In one embodiment, a method for the treatment of hemorrhagic dengue fever, in a host is provided that includes the administration of an effective amount of an active compound or its salt or composition as described herein.

In an additional alternative embodiment, an active compound or its salt or composition as described herein is used in the treatment of an autoimmune disorder.

The Complement pathway enhances the ability of antibodies and phagocytic cells to clear microbes and damaged cells from the body. It is part of the innate immune system and in healthy individuals is an essential process. Inhibiting the Complement pathway will decrease the body's immune system response. Therefore, it is an object of the present invention to treat autoimmune disorders by administering an effective does of an active compound or its salt or composition as described herein to a subject in need thereof.

In one embodiment, the autoimmune disorder is caused by activity of the Complement system. In one embodiment, the autoimmune disorder is caused by activity of the alternative Complement pathway. In one embodiment, the autoimmune disorder is caused by activity of the classical Complement pathway. In another embodiment, the autoimmune disorder is caused by a mechanism of action that is not directly related to the Complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, an active compound or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MIll scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment, an active compound or its salt or composition as described herein is provided at an effective dose to treat a patient with type 1 diabetes. In one embodiment, an active compound or its salt or composition as described herein is provided at an effective dose to treat a patient with type 2 diabetes.

Type 1 diabetes is an autoimmune disease. An autoimmune disease results when the body's system for fighting infection (the immune system) turns against a part of the body. The pancreas then produces little or no insulin.

V. Combination Therapy

In one embodiment, an active compound or its salt or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In one embodiment, an active compound or its salt or composition as described herein may be provided in combination or alternation with at least one additional inhibitor of the Complement system or a second active compound with a different biological mechanism of action. In the description below and herein generally, whenever any of the terms referring to an active compound or its salt or composition as described herein are used, it should be understood that pharmaceutically acceptable salts, prodrugs or compositions are considered included, unless otherwise stated or inconsistent with the text.

In non-limiting embodiments, an active compound or its salt or composition as described herein may be provided together with a protease inhibitor, a soluble Complement regulator, a therapeutic antibody (monoclonal or polyclonal), Complement component inhibitor, receptor agonist, or siRNA.

In other embodiments, an active compound described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, an active compound as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, an active compound as described herein can be administered in combination or alternation with an anti-IL6 antibody, including but not limited to tocilizumab (Actemra) and siltuximab (Sylvant). In an alternative embodiment, an active compound as described herein can be administered in combination or alternation with an IL17 inhibitor, including but not limited to secukibumab (Cosentyx).

In an alternative embodiment, an active compound as described herein can be administered in combination or alternation with a p40 (IL12/IL23) inhibitor, including but not limited to ustekinumab (Stelara).

In an alternative embodiment, an active compound as described herein can be administered in combination or alteration with an IL23 inhibitor, including but not limited to risankizumab. In an alternative embodiment, an active compound as described herein can be administered in combination or alteration with an anti-interferon α antibody, for example but not limited to sifalimumab.

In an alternative embodiment, an active compound as described herein can be administered in combination or alteration with a kinase inhibitor, for example but not limited to a JAK1/JAK3 inhibitor, for example but not limited to tofacitinib (Xelianz). In an alternative embodiment, an active compound as described herein can be administered in combination or alteration with a JAK1/JAK2 inhibitor, for example but not limited to baracitibib.

In an alternative embodiment, an active compound as described herein can be administered in combination or alteration with an anti-VEGF agent, for example but not limited to: aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids.

In another embodiment, an active compound as described herein can be administered in combination or alternation with an immune checkpoint inhibitor. Non-limiting examples of checkpoint inhibitors include anti-PD-1 or anti-PDL1 antibodies, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.), atezolizumab, durvalumab, and KN035, or anti-CTLA4 antibodies, for example Ipilimumab, Tremelimumab, AGEN1884 and AGEN2041 (Agenus).

Non-limiting examples of active agents that can be used in combination with active compounds described herein are:

Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);

Soluble Complement regulators: Soluble Complement receptor 1 (TP10) (Avant Immunotherapeutics); sCR1-sLex/TP-20 (Avant Immunotherapeutics); MLN-2222/CAB-2 (Millenium Pharmaceuticals); Mirococept (Inflazyme Pharmaceuticals);

Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);

Complement component inhibitors: Compstatin/POT-4 (Potentia Pharmaceuticals); ARC1905 (Archemix); 4(1MEW)APL-1,APL-2 (Appelis); CP40/AMY-101,PEG-Cp40 (Amyndas);

PDGF inhibitors: Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil;

Anti-factor H or anti-factor B agents: Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas);

Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH;

Anti-CR3, anti-MASP2, anti C1s, and anti-C1n molecules: Cynryze (ViroPharma/Baxter); TNT003 (True North); OMS721 (Omeros); OMS906 (Omeros); and Imprime PGG (Biothera);

Receptor agonists: PMX-53 (Peptech Ltd.); JPE-137 (Jerini); JSM-7717 (Jerini);

Others: Recombinant human MBL (rhMBL; Enzon Pharmaceuticals);

Imides and glutarimide derivatives such as thalidomide, lenalidomide, pomalidomide;

Additional non-limiting examples that can be used in combination or alternation with an active compound or its salt or composition as described herein include the following.

| Non-limiting examples of potential therapeutics for combination therapy | | | |
|---|---|---|---|
| Name | Target | Company | Class of Molecule |
| LFG316 | C5 | Novartis/Morphosys | Monoclonal antibody |
| 4(1MEW)APL-1, APL-2 | C3/C3b | Apellis | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101, PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |

-continued

Non-limiting examples of potential therapeutics for combination therapy

| Name | Target | Company | Class of Molecule |
|---|---|---|---|
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-05aR-151, NN8209; Anti-05aR-215, NN8210 | C5aR | Novo Nordisk | Monoclonal Antibody |
| Imprime PGG | CR3 | Biothera | Soluble beta-glucan |

In one embodiment, an active compound or its salt or composition as described herein may be provided together with a compound that inhibits an enzyme that metabolizes an administered protease inhibitor. In another embodiment, a compound or salt may be provided together with ritonavir.

In one embodiment, an active compound or its salt or composition as described herein may be provided in combination with a Complement C5 inhibitor or C5 convertase inhibitor. In another embodiment, an active compound or its salt or composition as described herein may be provided in combination with eculizumab, a monoclonal antibody directed to the Complement factor C5 and manufactured and marketed by Alexion Pharmaceuticals under the tradename Soliris. Eculizumab has been approved by the U.S. FDA for the treatment of PNH and aHUS.

In one embodiment, an active compound or its salt or composition as described herein may be provided together with a compound that inhibits Complement factor D. In another embodiment of the invention, an active compound or its salt or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age-related macular degeneration" describes certain Factor D inhibitors; Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B. V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In another embodiment, an active compound or its salt or composition as described herein is administered with a Complement Factor D inhibitor described in PCT/US16/48688 titled "Alkyne Compounds for Treatment of Medical Disorders", PCT/US16/48690 titled "Amide Compounds for Treatment of Medical Disorders", PCT/US16/48693 titled "Amino Compounds for Treatment of Medical Disorders", PCT/US16/48695 titled "Carbamate, Ester, and Ketone Compounds for Treatment of Medical Disorders", PCT/US16/48696 titled "Aryl, Heteroaryl, and Heterocyclic Compounds for Treatment of Medical Disorders", PCT/

US16/48701 titled "Ether Compounds for Treatment of Medical Disorders", PCT/US16/48704 titled "Phosphonate Compounds for Treatment of Medical Disorders", PCT/US16/486707 titled "Compounds for Treatment of Medical Disorders", PCT/US16/48709 titled "Disubstituted Compounds for Treatment of Medical Disorders", PCT/US16/48797 titled "Alkyne Compounds for Treatment of Immune and Inflammatory Disorders", PCT/US16/48779 titled "Amide Compounds for Treatment of Immune and Inflammatory Disorders", PCT/US16/48783 titled "Amino Compounds for Treatment of Immune and Inflammatory Disorders", PCT/US16/48795 titled "Carbamate, Ester, and Ketone Compounds for Treatment of Immune and Inflammatory Disorders", PCT/US16/48788 titled "Aryl, Heteroaryl, and Heterocyclic Compounds for Treatment of Immune and Inflammatory Disorders", PCT/US16/48793 titled "Ether Compounds for Treatment of Immune and Inflammatory Disorders", PCT/US16/48799 titled "Phosphonate Compounds for Treatment of Immune and Inflammatory Disorders", PCT/US16/48787 titled "Compounds for Treatment of Immune and Inflammatory Disorders", PCT/US16/48800 titled "Disubstituted Compounds for Treatment of Immune and Inflammatory Disorders", In one embodiment, an active compound or its salt or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus, anti-PDGFR molecule, and combinations thereof.

In one embodiment of the present invention, an active compound or its salt or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g., ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA41g (Abatacept), belatacept, LFA31g, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukimumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromethalone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, an active compound or its salt or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), sal salate (Di salcid), difluni sal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, an active compound or its salt or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656, 667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methyl-propanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a subject in need thereof an effective amount of an active compound or its salt or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); Cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids, including, but not limited to, triamcinolone acetonide.

In one embodiment, the present invention provides a method of treating or preventing age-related macular degeneration (AMD) by administering to a subject in need thereof an effective amount of an active compound or its salt or composition as described herein in combination with a Complement C5 inhibitor, for example, a Complement C5 inhibitor described herein and in the table above titled Non-limiting examples of potential therapeutics for combination therapy, including, but not limited to, eculizumab; LFG316 (Novartis/Morphosys); Anti-05 siRNA (Alnylam); ARC 1005 (Novo Nordisk); Coversin (Volution Immuno-Pharmaceuticals); Mubodine (Adienne Pharma); RA101348 (Ra Pharma); SOBI002 (Swedish Orphan Biovitrum); SOMAmers (SomaLogic); Erdigna (Adienne Pharma); ARC1905 (Opthotech); MEDI7814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-05aR-151, NN8209; Anti-05aR-215, NN8210 (Novo Nordisk).

In one embodiment, the present invention provides a method of treating or preventing age-related macular degeneration (AMD) by administering to a subject in need thereof an effective amount of an active compound or its salt or composition as described herein in combination with anti-properidin agent, for example, an anti-properidin agent as described above, including but not limited to NM9401 (Novelmed).

In one embodiment, the present invention provides a method of treating or preventing age-related macular degeneration (AMD) by administering to a subject in need thereof an effective amount of an active compound or its salt or composition as described herein in combination with a Complement C3 inhibitor for example, a Complement C3 inhibitor described above, including, but not limited to, a compstatin or compstatin analogue, for example Compstatin/POT-4 (Potentia Pharmaceuticals); ARC1905 (Archemix); 4(1MEW)APL-1,APL-2 (Appelis); CP40/AMY-101, PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Toni Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In one embodiment, the present invention provides a method of treating or preventing age-related macular degeneration (AMD) by administering to a subject in need thereof an effective amount of an active compound or its salt or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In one embodiment, the present invention provides a method of treating or preventing age-related macular degeneration (AMD) by administering to a subject in need thereof an effective amount of an active compound or its salt or composition as described herein in combination with an anti-MASP2, anti-Cls or anti-CR3 molecules, for example, but not limited to: Cynryze (ViroPharma/Baxter); TNT003 (True North); OMS721 (Omeros); OMS906 (Omeros); and Imprime PGG (Biothera).

In one embodiment, the present invention provides a method of treating or preventing age-related macular degeneration (AMD) by administering to a subject in need thereof an effective amount of an active compound or its salt or composition as described herein in combination with an PDGF inhibitor, for example as described herein including but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil.

In one embodiment, the present invention provides a method of treating or preventing paroxysmal nocturnal hemoglobinuria (PNH) by administering to a subject in need thereof an effective amount of an active compound or its salt or composition as described herein with an additional inhibitor of the Complement system or another active compound with a different biological mechanism of action. In another embodiment, the present invention provides a method of treating or preventing paroxysmal nocturnal hemoglobinuria (PNH) by administering to a subject in need thereof an effective amount of an active compound or its salt or composition as described herein in combination or alternation with eculizumab. In another embodiment, the present invention provides a method of treating or preventing paroxysmal nocturnal hemoglobinuria (PNH) by administering to a subject in need thereof an effective amount of an active compound or its salt or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes. In another embodiment, the additional agent is a Complement component inhibitor, for example but not limited to Compstatin/POT-4 (Potentia Pharmaceuticals); ARC1905 (Archemix); 4(1MEW)APL-1,APL-2 (Appelis); CP40/AMY-101,PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a Complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Toni Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In one embodiment, the present invention provides a method of treating or preventing rheumatoid arthritis by administering to a subject in need thereof an effective amount of a composition comprising an active compound or its salt or composition as described herein in combination or alternation with an additional inhibitor of the Complement system, or an active agent that functions through a different mechanism of action. In another embodiment, the present invention provides a method of treating or preventing rheumatoid arthritis by administering to a subject in need thereof an effective amount of an active compound or its salt or composition as described herein in combination or alternation with methotrexate. In certain embodiments, an active compound or its salt or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying anti-rheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of an active compound or its salt or composition as described herein in combination or alternation with an additional inhibitor of the Complement system, or an active agent that functions through a different mechanism of action. In another embodiment, the present invention provides a method of treating or preventing multiple sclerosis by administering to a subject in need thereof an effective amount of an active compound or its salt or composition as described herein in combination or alternation with a corticosteroid. Examples of corticosteroids include, but are not limited to, prednisone, dexamethasone, solumedrol, and methylprednisolone. In one embodiment, an active compound or its salt or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H.P. Acthar Gel (ACTH), or a combination thereof.

In one embodiment, an active compound or its salt or composition as described herein is useful in a combination with another pharmaceutical agent to ameliorate or reduce a side effect of the agent. For example, in one embodiment, an active compound or its salt or composition as described herein may be used in combination with adoptive cell transfer therapies to reduce an associated inflammatory response associated with such therapies, for example, a cytokine mediated response such as cytokine release syndrome. In another embodiment, the adoptive cell transfer therapy includes the use of a chimeric antigen receptor T-Cell (CAR T). In another embodiment, the adoptive cell transfer therapy includes the use of a chimeric antigen receptor T-Cell (CAR T) or a dendritic cell to treat a hematologic or solid tumor, for example, a B-cell related hematologic cancer. In another embodiment, the hematologic or solid tumor is acute lymphoblastic leukemia (ALL), acute myeloid leukemia (AML), non-Hodgkin's lymphoma, chronic lymphocytic leukemia (CLL), pancreatic cancer, glioblastoma, or a cancer that expresses CD19.

In an additional alternative embodiment, an active compound or its salt or composition as described herein may be provided in combination with eculizumab for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, an active compound or its salt or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, the additional agent is a Complement component inhibitor, for example but not limited to Compstatin/POT-4 (Potentia Pharmaceuticals); ARC1905 (Archemix); 4(1MEW)APL-1,APL-2 (Appelis); CP40/AMY-101,PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a Complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Toni Pharmaceuticals); Bikaciomab, NM9308 (Novelmed); CVF, HC-1496 (InCode) ALXN1102/ALXN1103 (TT30) (Alexion Pharmaceuticals); rFH (Opthnerion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In one embodiment, an active compound or its salt or composition as described herein may be provided in combination with rituxan for the treatment of a Complement mediated disorder. In another embodiment, the Complement mediated disorder is, for example, rheumatoid arthritis, Granulomatosis with Polyangiitis (GPA) (Wegener's Granulomatosis), and Microscopic Polyangiitis (MPA). In another embodiment, the disorder is Lupus.

In one embodiment, an active compound or its salt or composition as described herein may be provided in combination with cyclophosphamide for the treatment of a Complement mediated disorder. In another embodiment, the disorder is an autoimmune disease. In another embodiment, the Complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, an active compound or its salt or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, an active compound or its salt or composition as described herein may be provided in combination with methotrexate for the treatment of Lupus.

In another embodiment, an active compound or its salt or composition as described herein may be provided in combination with azathioprine for the treatment of Lupus.

In another embodiment, an active compound or its salt or composition as described herein may be provided in combination with a non-steroidal anti-inflammatory drug for the treatment of Lupus.

In another embodiment, an active compound or its salt or composition as described herein may be provided in combination with a corticosteroid for the treatment of Lupus.

In another embodiment, an active compound or its salt or composition as described herein may be provided in combination with a belimumab (Benlysta) for the treatment of Lupus.

In another embodiment, an active compound or its salt or composition as described herein may be provided in combination with hydroxychloroquine (Plaquenil) for the treatment of Lupus.

In another embodiment, an active compound or its salt or composition as described herein may be provided in combination with sifalimumab for the treatment of Lupus.

In another embodiment, an active compound or its salt or composition as described herein may be provided in combination with OMS721 (Omeros) for the treatment of a Complement mediated disorder. In one embodiment, an active compound or its salt or composition as described herein may be provided in combination with OMS906 (Omeros) for the treatment of a Complement mediated disorder. In one embodiment, the Complement mediated disorder is, for example, thrombotic thrombocytopenic purpura (TTP) or aHUS.

In one embodiment, an active compound or its salt or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In one embodiment, an active compound or its salt or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, an active compound or its salt or composition as described herein may be provided in combination with an anti-cytokine inhibitor including, but are not limited to, adalimumab, infliximab, etanercept, protopic, efalizumab, alefacept, anakinra, siltuximab, secukinumab, ustekinumab, golimumab, and tocilizumab, or a combination thereof. Additional anti-inflammatory agents that can be used in combination with an active compound or its salt or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann- LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibition); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble Complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine). In a specific embodiment, an active compound or its salt or composition as described herein may be provided in combination with a corticosteroid for the treatment or prevention of cytokine or inflammatory reactions in response to the administration of pharmaceuticals or biotherapeutics. In another embodiment, an active compound or its salt or composition as described herein may be provided in combination with etarnercept for the treatment or prevention of cytokine or inflammatory reactions in response to the administration of pharmaceuticals or biotherapeutics. In another embodiment, an active compound or its salt or composition as described herein may be provided in combination with tocilizumab for the treatment or prevention of cytokine or inflammatory reactions in response to the administration of pharmaceuticals or biotherapeutics. In another embodiment, an active compound or its salt or composition as described herein may be provided in combination with etarnercept and tocilizumab for the treatment or prevention of cytokine or inflammatory reactions in response to the administration of pharmaceuticals or biotherapeutics. In another embodiment, an active compound or its salt or composition as described herein may be provided in combination with infliximab for the treatment or prevention of cytokine or inflammatory reactions in response to the administration of pharmaceuticals or biotherapeutics. In another embodiment, an active compound or its salt or composition as described herein may be provided in combination with golimumab for the treatment or prevention of cytokine or inflammatory reactions in response to the administration of pharmaceuticals or biotherapeutics.

VI. Combinations for Prophylactic or Concomitant Anti-Bacterial Therapy

In one aspect of the present invention, a method is provided for treating a host in need thereof that comprises administering an effective amount of a prophylactic anti-bacterial vaccine prior to administration of an active compound or its salt or composition for any of the disorders described herein. In another aspect of the present invention, a method is provided for treating a host in need thereof that comprises administering an effective amount of a prophylactic anti-bacterial drug, such as a pharmaceutical drug, prior to administration of an active compound or its salt or composition for any of the disorders described herein. In one aspect of the present invention, a method is provided for treating a host in need thereof that comprises administering an effective amount of an anti-bacterial vaccine after administration of an active compound or its salt or composition for any of the disorders described herein. In another aspect of the present invention, a method is provided for treating a host in need thereof that comprises administering an effective amount of an anti-bacterial drug, such as a pharmaceutical drug, after administration of an active compound or its salt or composition for any of the disorders described herein. In one embodiment, the disorder is PNH, C3G, or aHUS. In one embodiment, the host has received an organ or other tissue or biological fluid transplant. In one embodiment, the host is also administered eculizumab. In one aspect of the present invention, an active compound or its salt or composition as described herein is administered to a host concomitantly to a subject following the prophylactic administration of a vaccine against a bacterial infection. In another embodiment, the Complement mediated disorder is PNH, C3G, or aHUS. In another embodiment, the subject has received an organ or other tissue or biological fluid transplant. In another embodiment, the subject is also administered eculizumab.

In one aspect of the present invention, an active compound or its salt or composition as described herein is administered to a subject concomitantly with the prophylactic administration of a vaccine against a bacterial infection. In one embodiment, the Complement mediated disorder is PNH, C3G, or aHUS. In another embodiment, the subject has received an organ or other tissue or biological fluid transplant. In another embodiment, the subject is also administered eculizumab. In one aspect of the present invention, an active compound or its salt or composition as described herein is administered to a subject and, during the administration period of the compound or salt, a vaccine against a bacterial infection is administered to the subject. In one embodiment, the Complement mediated disorder is PNH, C3G, or aHUS. In another embodiment, the subject has received an organ or other tissue or biological fluid transplant. In another embodiment, the subject is also administered eculizumab.

In one aspect of the present invention, the subject is administered an active compound or its salt or composition as described herein in combination with an antibiotic compound for the duration of Factor B inhibitor administration. In one embodiment, the Complement mediated disorder is PNH, C3G, or aHUS. In one embodiment, the subject has received an organ or other tissue or biological fluid transplant. In one embodiment, the subject is also administered eculizumab.

In one aspect of the present invention, an active compound or its salt or composition as described herein is administered to a subject following the prophylactic administration of a vaccine against a bacterial infection, and in combination with an antibiotic compound for the duration of Factor B inhibitor administration. In one embodiment, the Complement mediated disorder is PNH or aHUS. In one embodiment, the subject has received an organ or other tissue or biological fluid transplant. In one embodiment, the subject is also administered eculizumab.

In another embodiment, the subject, prior to receiving an active compound or its salt or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib). In one embodiment, the subject is vaccinated against a bacterial infection caused by *Streptococcus pneumoniae*. In one embodiment, the subject is vaccinated against a bacterial infection caused by the bacterium *Nisseria meningitidis, Haemophilus influenzae,* or *Streptococcus pneumoniae*, or a combination of one or more of *Nisseria meningitidis, Haemophilus influenzae,* or *Streptococcus pneumoniae*. In one embodiment, the subject is vaccinated against a bacterial infection caused by the bacterium *Nisseria meningitidis, Haemophilus influenzae,* and *Streptococcus pneumoniae*.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium *Nisseria meningitidis, Haemophilus influenzae,* or *Streptococcus pneunemoniae*, or a combination of one or more of *Nisseria meningitidis, Haemophilus influenzae,* or *Streptococcus pneumoniae*, and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis,*

In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *haemophilus* b conjugate (prp-t) vaccine (ActHIB, Sanofi; Hibrix, GSK), *haemophilus* b conjugate (hboc) vaccine (HibTITER, Neuron Biotech), *haemophilus* b conjugate (prp-omp) vaccine (PedvaxHIB, Merck), *haemophilus* b conjugate (prp-t) vaccine/meningococcal conjugate vaccine (MenHibrix, GSK), *haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guerin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *haemophilus* influenza type B (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a Factor B inhibitor described herein. In one embodiment, the subject is administered an antibiotic compound for the duration of administration of the active compound to reduce the development of a bacterial infection. Antibiotic compounds for concomitant administration with a Factor B inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Sumamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen),azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen),oxacillin (Prostaphlin), penicillin G (Pentids),penicillin V (Veetids (Pen-Vee-K), piperacillin (Pipracil), penicillin G (Pfizerpen), temocillin (Negaban),ticarcillin (Ticar), amoxicillin/clavulanate (Augmentin), ampicillin/sulbactam (Unasyn), piperacillin/tazobactam (Zosyn), ticarcillin/clavulanate (Timentin),bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (NegGram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (MicroSulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (B actrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

VII. Nanoparticle Compositions or Carriers

In one aspect of the present invention, an effective amount of an active compound as described herein is incorporated into a nanoparticle, e.g. for convenience of delivery and/or extended release delivery. The use of materials in nanoscale provides one the ability to modify fundamental physical properties such as solubility, diffusivity, blood circulation half-life, drug release characteristics, and/or immunogenicity. A number of nanoparticle-based therapeutic and diagnostic agents have been developed for the treatment of cancer, diabetes, pain, asthma, allergy, and infections. These nanoscale agents may provide more effective and/or more convenient routes of administration, lower therapeutic toxicity, extend the product life cycle, and ultimately reduce health-care costs. As therapeutic delivery systems, nanoparticles can allow targeted delivery and controlled release.

In addition, nanoparticle-based drug delivery can be used to release drugs at a sustained rate and thus lower the frequency of administration, deliver drugs in a target manner to minimize systemic side effects, or deliver two or more drugs simultaneously for combination therapy to generate a synergistic effect and suppress drug resistance. A number of nanotechnology-based therapeutic products have been approved for clinical use. Among these products, liposomal drugs and polymer-based conjugates account for a large proportion of the products. See, Zhang, L., et al., Nanoparticles in Medicine: Therapeutic Applications and Developments, Clin. Pharm. and Ther., 83(5):761-769, 2008.

Solid lipid nanoparticles (SLN) can be produced in a controlled fashion when a fraction of lipid in the crystalline alpha form can be created and preserved. By doing this, the SLN carrier has a built in trigger mechanism as lipids transform from the alpha to beta form and consequently control drug release. Drug release profiles can be modified according to the composition of the lipid matrix, surfactant concentration and production parameters. See, Muller, R. H., et al., Solid lipid nanoparticles (SLN) for controlled drug delivery—a review of the state of the art, Eur. H. Pharm. Biopharm., 50:161-177, 2000. Consien et al. have recently disclosed lipid nanoparticles having novel amino-lipids that form lipid nanoparticles and their use for the intracellular delivery of biologically active compounds, e.g., nucleic acids. See, U.S. Pat. No. 8,691,750 to Consien et al.

Kanwar has disclosed alginate adsorbed chitosan adsorbed lactoferrin adsorbed calcium phosphate nanoparticles and the controlled release of lactoferrin from the nanoparticles. See, WO 2012/145801 to Kanwar. In addition, Armes et al. have disclosed polymer-templated core-shell nanoparticles adapted to facilitate controlled release of at least one active agent into a system in response to controlled changes in the pH of the system. See, U.S. Pat. No. 8,580,311 to Armes, S. et al. incorporated by reference herein.

Petros and DeSimone have recently reviewed strategies in the design of nanoparticles. In addition, the authors reviewed their PRINT (particle replication in non-wetting templates) technology for generating microparticles and nanoparticles. See, Petros, R. A. and DeSimone, J. M., Strategies in the design of nanoparticles for therapeutic applications, Nature Reviews/Drug Discovery, vol. 9:615-627, 2010. Importantly, the authors disclosed the production of nanoparticles in which a single parameter (shape or size) can be altered independently of all other particle attributes. The authors concluded their paper by outlining several particle characteristics that have emerged as being central to the function of engineered nanoparticles. These parameters include particle size, particle shape, surface characteristics and the ability to release therapeutics. Additional nanoparticle fabrication methods can also be found in U.S. Pat. Nos. 8,465,775, 8,444,899, 8,420,124, 8,263,129, 8,158,728 and 8,268,446 all hereby incorporated by reference.

Nanoparticles may be prepared using a wide variety of methods known in the art. For example, nanoparticles can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

In some embodiments, the compounds described herein can be associated with a nanoparticle, such as a polymeric nanoparticle. Nanoparticles may comprise natural polymers, including but not limited to chitosan, alginate, dextran, gelatin, and albumin, and synthetic polymers such as, but not limited to, poly(lactide-co-glycolide) (PLGA), (3-hydroxybutyrate-co-3-hydroxyvalerate) (PHBV), poly(sebacic anhydride), poly(ε-caprolactone), polystyrene, thermoresponsive (i.e., NIPAAm and CMCTS-g-PDEA) and pH-responsive (i.e., Eudragit L100, Eudragit S and AQOAT AS-MG) polymers, either pegylated or non-pegylated.

In one embodiment, the polymeric particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm. In one embodiment, the compounds described herein are covalently coupled to a polystyrene particle, PLGA particle, PLA particle, or other nanoparticle.

In some embodiments, the nanoparticle can be solid or hollow and can comprise one or more layers. In some embodiments, each layer has a unique composition and unique properties relative to the other layer(s). To afford but one example, the nanoparticle may have a core/shell structure, wherein the core is one layer (e.g. a polymeric core) and the shell is a second layer (e.g. a lipid bilayer or monolayer). In some embodiments, the nanoparticle may comprise a plurality of different layers. In some embodiments, a compound described herein can be incorporated into or surrounded by one or more layers. In one embodiment, the nanoparticle comprises a liquid lipid core.

In some embodiments, the nanoparticles comprising a compound described herein may optionally comprise one or more lipids. In some embodiments, a nanoparticle may comprise a liposome. In some embodiments, a nanoparticle may comprise a lipid bilayer. In some embodiments, a nanoparticle may comprise a lipid monolayer. In some embodiments, a nanoparticle may comprise a micelle. In some embodiments, a nanoparticle may comprise a core comprising a polymeric matrix surrounded by a lipid layer (e.g., lipid bilayer, lipid monolayer, etc.). In some embodiments, a nanoparticle may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In other embodiments, the nanoparticle may comprise metal particles, quantum dots, ceramic particles, etc. In some embodiments, a non-polymeric nanoparticle is an aggregate of non-polymeric components, such as an aggregate of metal atoms (e.g., gold atoms).

In some embodiments, nanoparticles may optionally comprise one or more amphiphilic entities. In some embodiments, an amphiphilic entity can promote the production of nanoparticles with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making nanoparticles useful in the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween® 85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of nanoparticles to be used in accordance with the present invention.

In some embodiments, a nanoparticle may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In some embodiments, the nanoparticle does not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

In some embodiments, the associated nanoparticle can comprise one or more polymers. In some embodiments, the nanoparticle comprises one or more polymers that are a non-methoxy-terminated, pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticles are non-methoxy-terminated, pluronic polymers. In some embodiments, all of the polymers that make up the nanoparticle are non-methoxy-terminated, pluronic polymers. In some embodiments, the nanoparticle comprises one or more polymers that are a non-methoxy-terminated polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticles are non-methoxy-terminated polymers. In some embodiments, all of the polymers that make up the nanoparticle are non-methoxy-terminated polymers. In some embodiments, the nanoparticle comprises one or more polymers that do not comprise pluronic polymer. In some embodiments, at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 97%, or 99% (weight/weight) of the polymers that make up the nanoparticle do not comprise pluronic polymer. In some embodiments, all of the polymers that make up the nanoparticles do not comprise pluronic polymer. In some embodiments, such a polymer can be surrounded by a coating layer (e.g., liposome, lipid monolayer, micelle, etc.). In some embodiments, various elements of the nanoparticle can be coupled with the polymer.

Other examples of polymers include, but are not limited to polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly((β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, nanoparticles include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, the polymer can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a nanoparticles comprising a hydrophilic polymeric matrix generates a hydrophilic environment within the nanoparticle. In some embodiments, polymers can be hydrophobic. In some embodiments, a nanoparticles comprising a hydrophobic polymeric matrix generates a hydrophobic environment within the nanoparticle. Selection of the hydrophilicity or hydrophobicity of the polymer may have an impact on the nature of materials that are incorporated (e.g., coupled) within the nanoparticle.

In some embodiments, the polymer may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al.

In some embodiments, the polymer may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, the polymer may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, the polymer can be a cationic polymer. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly(amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the nanoparticles may not comprise (or may exclude) cationic polymers.

In some embodiments, the polymer can be a degradable polyester, for example, bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

Polymers can be linear or branched polymers. In some embodiments, the polymer can be a dendrimer. In some embodiments, polymers can be substantially cross-linked to one another. In some embodiments, polymers can be substantially free of cross-links. In some embodiments, polymers can be used without undergoing a cross-linking step. It is further to be understood that a nanoparticle may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

The compounds of the present invention can be coupled to a nanoparticle by any of a number of methods. Generally, the coupling can be a result of bonding between the compound and the nanoparticle. This bonding can result in the compound being attached to the surface of the nanoparticle and/or contained within (encapsulated) the nanoparticle. In some embodiments, however, the compounds are encapsulated by the nanoparticle as a result of the structure of the nanoparticle rather than bonding to the nanoparticle. In some embodiments, the nanoparticle comprises a polymer as provided herein, and the compounds described herein are coupled to the nanoparticle. A compound described herein may be encapsulated into nanoparticles as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al., "Surface-modified PLGA-based Nanoparticles that can Efficiently Associate and Deliver Virus-like Particles" Nanomedicine. 5(6):843-853 (2010). Other methods suitable for encapsulating the compounds described herein may be used, including without limitation methods disclosed in U.S. Pat. No. 6,632,671 to Unger Oct. 14, 2003.

In certain embodiments, nanoparticles are prepared by a nanoprecipitation process or spray drying. Conditions used in preparing nanoparticles may be altered to yield particles of a desired size or property (e.g., hydrophobicity, hydrophilicity, external morphology, "stickiness," shape, etc.). The method of preparing the nanoparticles and the conditions (e.g., solvent, temperature, concentration, air flow rate, etc.) used may depend on the materials to be coupled to the nanoparticles and/or the composition of the polymer matrix. If particles prepared by any of the above methods have a size range outside of the desired range, particles can be sized, for example, using a sieve.

In one embodiment of the present invention, PRINT technology is used to manufacture nanoparticles comprising a compound described herein.

In another embodiment, provided herein are liposome based nanoparticles comprising a compound described herein. In another embodiment, a liposome based nanoparticle comprises a compound described herein formulated for controlled-release.

In one embodiment, provided herein are polymer based nanoparticles comprising a compound described herein. In another embodiment, provided herein are polymer based nanoparticles comprising a compound described herein formulated for controlled-release.

In one embodiment, nanoparticles are comprised of albumin and a compound described herein. In another embodiment, nanoparticles are comprised of a polysaccharide and a compound described herein. In another embodiment, nanoparticles are comprised of a metal and a compound described herein. In another embodiment, nanoparticles are comprised of gold and a compound described herein. In another embodiment, nanoparticles are comprised of iron oxide and a compound described herein. In another embodiment, nanoparticles are comprised of silicon and a compound described herein.

In regard to polymers used for the production of nanoparticles, several reviews are available. See, for example, Soppimath, K. S., et al., Biodegradable polymeric nanoparticles as drug delivery devices, J. Controlled Release, 70:1-20, 2001, Agnihotri, S. A., et al., Recent advances on chitosan-based micro- and nanoparticle delivery, J. Controlled Release, 100(1):5-28, 2004, Ganta, S, et al., A review of stimuli-responsive nanocarriers for drug and gene delivery, J. Controlled Release, 126(3):187-204, 2008, Danhier, F. et al., PLGA-based nanoparticles: An overview of biomedical applications, J. Controlled Release, 161(2):505-522, 2012, In one embodiment, nanoparticles are comprised of L-glutamic acid copolymers and a compound described herein. In another embodiment, nanoparticles are comprised of L-alanine copolymers and a compound described herein. In another embodiment, nanoparticles are comprised of L-lysine copolymers and a compound described herein. In another embodiment, nanoparticles are comprised of L-tyrosine copolymers and a compound described herein. In other embodiment, nanoparticles are comprised of poly(lactic-co-glycolic acid) and a compound described herein. In another embodiment, nanoparticles are comprised of methoxy-PEG-poly(D,L-lactide) and a compound described herein. In another embodiment, nanoparticles are comprised of HPMA copolymer and a compound described herein. In one embodiment, nanoparticles are comprised of polycyclodextran and a compound described herein. In one embodiment, nanoparticles are comprised of polyglutamate and a compound described herein. In another embodiment, nanoparticles are comprised of poly(iso-hexyl-cyanoacrylate) and a compound described herein. In one embodiment, nanoparticles are comprised of poly-L-lysine and a compound described herein. In another embodiment, nanoparticles are comprised of PEG and a compound described herein. In one embodiment, nanoparticles are made of combinations of polymers and a compound described herein.

In one embodiment, a compound disclosed herein is delivered using intravitreal drug-delivery nanoparticles ("nanosponges"), which are three-dimensional nano-networks formed from degradable materials, in particular, formed by crosslinking degradable linear polyesters. In various embodiments, nanosponges can refer to compositions comprising one or more disclosed compounds of the invention or one or more products of the disclosed methods. In particular, nanosponges can refer to disclosed compounds or products encapsulating one or more pharmaceutically active agent or biologically active agent, for example, agents disclosed herein. In a further aspect, a nanosponge is an ocular delivery platform (degradable polyester nanoparticle pharmaceutical or biologically active agent complex) and can comprise one or more degradable cross-linked polyester nanoparticles and one or more biologically active agents, one or more pharmaceutically active agents, and/or one or more imaging agents, as disclosed herein. In one embodiment, a nanosponge is an ocular delivery platform for treatment and/or prevention of eye diseases (e.g., glaucoma, age-related macular degeneration) and cancer (e.g., intraocular melanoma).

VIII. Compounds of the Present Invention

Process of Preparation of Compounds of the Present Invention

ABBREVIATIONS

ACN Acetonitrile
Ac Acetyl
Ac₂O Acetic anhydride
AcOEt Ethyl acetate
AcOH Acetic acid
Boc₂O di-tert-butyl dicarbonate
Bu Butyl
CBz Carboxybenzyl
CH₃OH, MeOH Methanol
DCM, CH₂Cl₂ Dichloromethane
DMA N,N-dimethylacetamide
DMAP 4-Dimethylaminopyridine
DMF N,N-dimethylformamide
DMS Dimethyl sulfide
DMSO Dimethyl sulfoxide
Et Ethyl
Et₃N, TEA Triethylamine
EtOAc Ethyl acetate
EtOH Ethanol N,N,N',N'-Tetramethyl-O-(1H-benzotriazol-1-yl)uronium
HBTU hexafluorophosphate
HCl Hydrochloric acid
HMTA Hexamethylentetramine
iBu, i-Bu, isoBu Isobutyl
iPr, i-Pr, isoPr Isopropyl
ⁱPr₂NEt N,N-diisopropylethylamine
K₂CO₃ Potassium carbonate
LAH Lithium aluminum hydride
LDA Lithium diisopropylamide
LiOH Lithium hydroxide
Me Methyl
Na₂SO₄ Sodium sulfate
NaCl Sodium chloride
NaH Sodium hydride
NaHCO₃ Sodium bicarbonate
NEt₃ Trimethylamine
Pd(PPh₃)₂Cl₂ Bis(triphenylphosphine)palladium(II) dichloride
Pd(PPh₃)₄ Tetrakis(triphenylphosphine)palladium(0)
Pd/C Palladium on carbon
PhtNK Potassium pthalimide
PPh₃ Triphenylphosphine
Pr Propyl
Py, py Pyridine
RT Room temperature
TBAF Tetra-n-butylammonium fluoride
TBAHS Tetrabutylammonium hydrogen sulfate
TBDMS tert-butyldimethylsilyl
tBu, t-Bu, tert-Bu Tertbutyl
tBuOK Potassium tert-butoxide TEA Trimethylamine
TFA Trifluoroacetic acid
THF Tetrahydrofuran
tR Retention time
Ts Tosyl
TsCl Tosyl chloride General Methods All nonaqueous reactions were performed under an atmosphere of dry argon or nitrogen gas using anhydrous solvents. The progress of reactions and the purity of target compounds were determined using one of the two liquid chromatography (LC) methods listed below. The structure of starting materials, intermediates, and final products were confirmed by standard analytical techniques, including NMR spectroscopy and mass spectrometry.

LC Method A
Instrument: Waters Acquity Ultra Performance LC
Column: ACQUITY UPLC BEH C18 2.1×50 mm, 1.7
Column Temperature: 40° C.
Mobile Phase: Eluent A: H₂O+0.05% FA; Eluent B: CH₃CN+0.05% FA
Flow Rate: 0.8 mL/min
Gradient: 0.24 min @ 15% B, 3.26 min gradient (15-85% B), then 0.5 min @ 85% B.
Detection: UV (PDA), ELS, and MS (SQ in EI mode)

LC Method B
Instrument: Shimadzu LC-2010A HT
Column: Athena, C18-WP, 50×4.6 mm, 5
Column Temperature: 40° C.
Mobile Phase: Eluent A: H₂O/CH₃OH/FA=90/10/0.1; Eluent B: H₂O/CH₃OH/FA=10/90/0.1
Flow Rate: 3 mL/min
Gradient: 0.4 min @ 30% B, 3.4 min gradient (30-100% B), then 0.8 min @ 100% B
Detection: UV (220/254 nm)

LC Method C
Instrument: Agilent 1200 series LC system with mass detector
Column: Zorbax XDB C18, 50×4.6 mm, 5 μm
Column Temperature: 25° C.
Mobile Phase: Eluent A: H₂O+0.1% FA; Eluent B: CH₃CN
Flow Rate: 1.5 mL/min
Gradient:

| Time (min) | 0.0 | 3.0 | 5.0 | 5.5 | 7.0 |
|---|---|---|---|---|---|
| % B | 5.0 | 95 | 95 | 5.0 | 5.0 |

Detection: UV (PDA, 210-400 nm) and MS (SQ multimode ESI+APCI)

Example 1. General Route of Synthesis

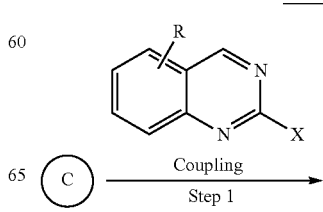

Scheme 1-1

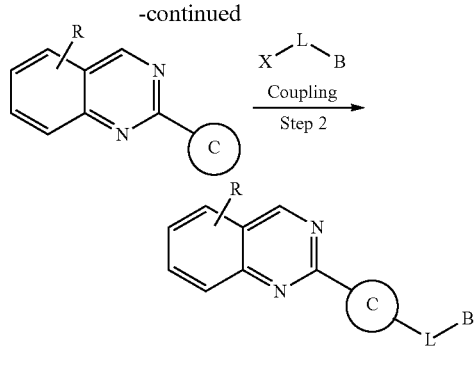

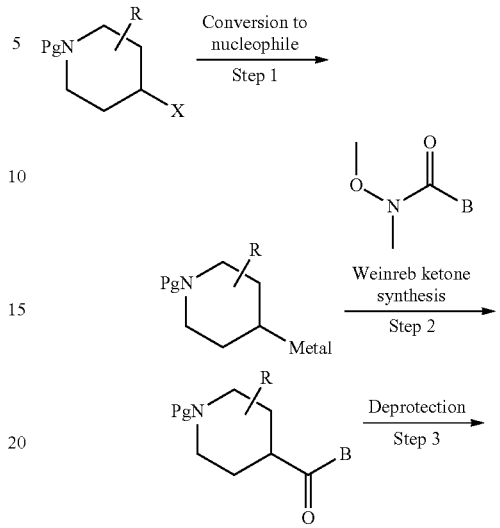

Scheme 1-1: A compound of the present invention can be prepared, for example, from a central core moiety. In Step 1 the central core is coupled to an appropriately substituted quinazoline as known in the art to afford a species of Formula A-C. In Step 2 the A-C species is coupled to an appropriately substituted linker with a B moiety to afford a compound of Formula I.

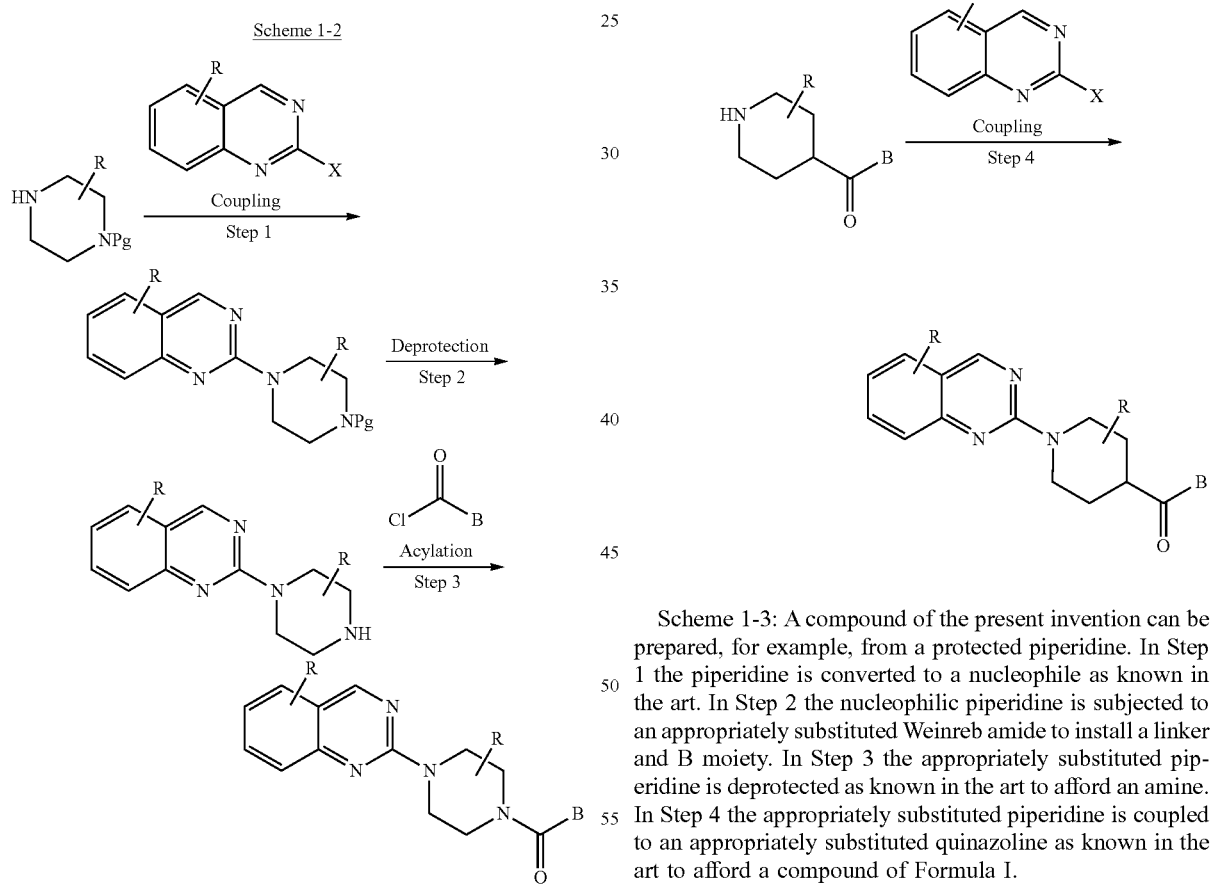

Scheme 1-3: A compound of the present invention can be prepared, for example, from a protected piperidine. In Step 1 the piperidine is converted to a nucleophile as known in the art. In Step 2 the nucleophilic piperidine is subjected to an appropriately substituted Weinreb amide to install a linker and B moiety. In Step 3 the appropriately substituted piperidine is deprotected as known in the art to afford an amine. In Step 4 the appropriately substituted piperidine is coupled to an appropriately substituted quinazoline as known in the art to afford a compound of Formula I.

Scheme 1-2: A compound of the present invention can be prepared, for example, from a protected piperazine. In Step 1 the piperazine is coupled to an appropriately substituted quinazoline as known in the art to afford a species of Formula A-C. In Step 2 the piperazine is deprotected as known in the art to afford a nucleophilic amine. In Step 3 the piperazine is subjected to an appropriately substituted acyl chloride to afford a compound of Formula I.

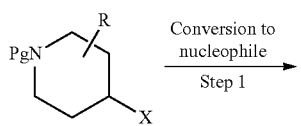

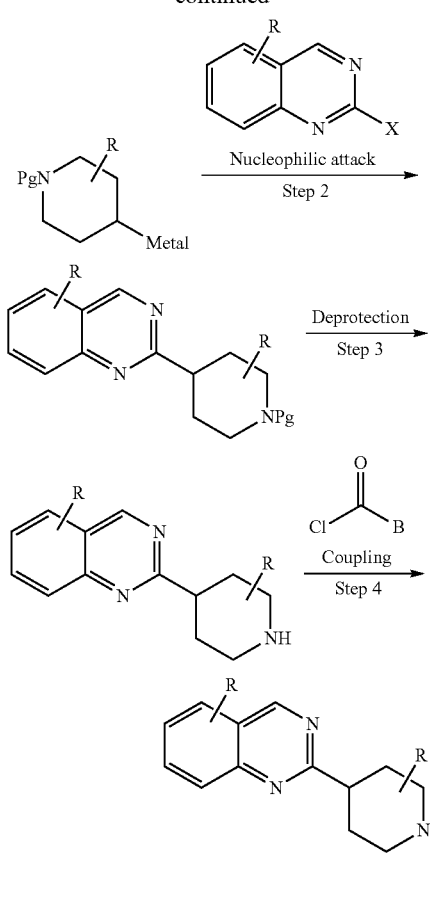
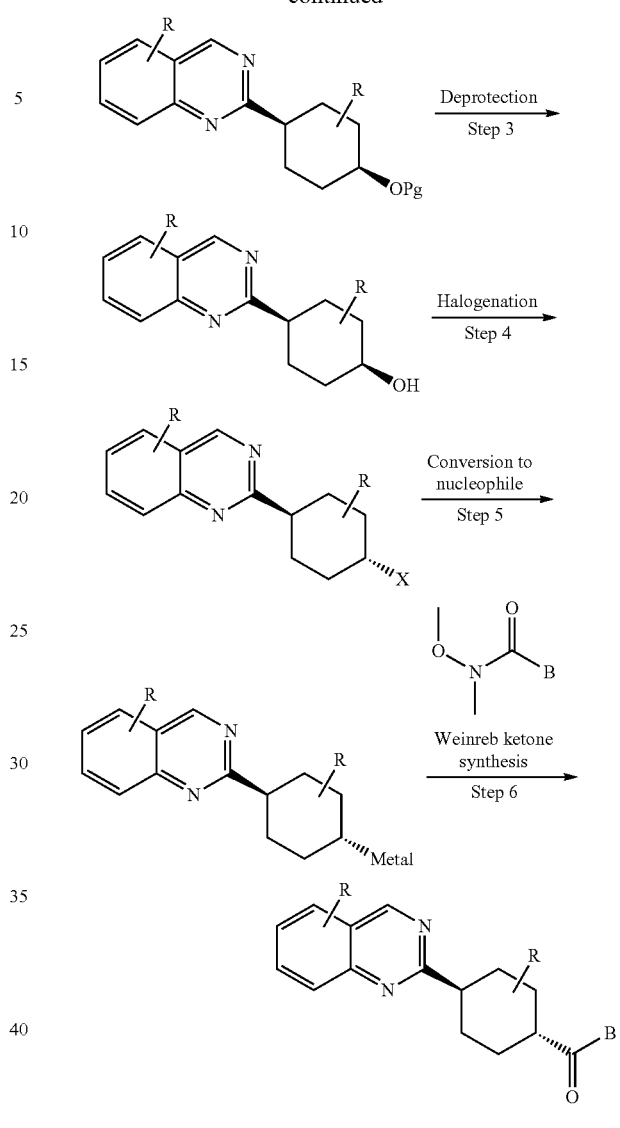

Scheme 1-4: A compound of the present invention can be prepared, for example, from a protected piperidine. In Step 1 the piperidine is converted to a nucleophile as known in the art. In Step 2 the nucleophilic piperidine is subjected to an appropriately substituted quinazoline to install the A moiety. In Step 3 the appropriately substituted piperidine is deprotected as known in the art to afford an amine. In Step 4 the appropriately substituted piperidine is subjected to an acyl chloride as known in the art to afford a compound of Formula I.

Scheme 1-5

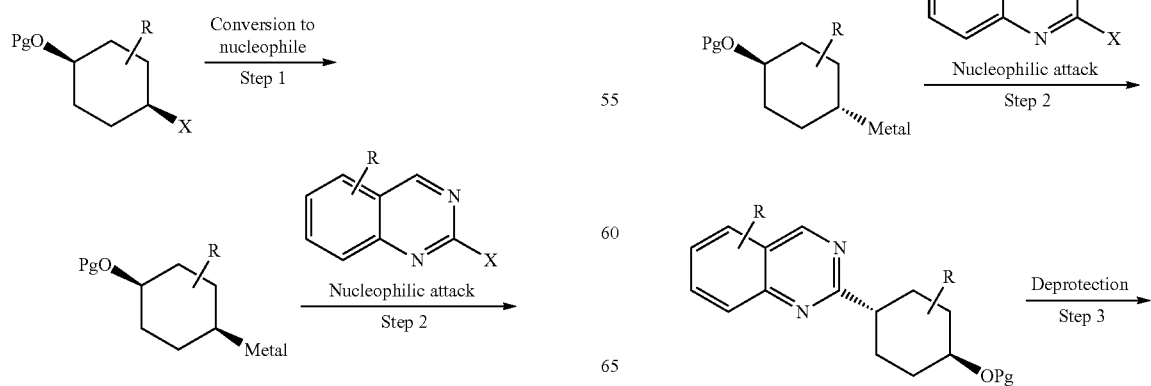

153
-continued

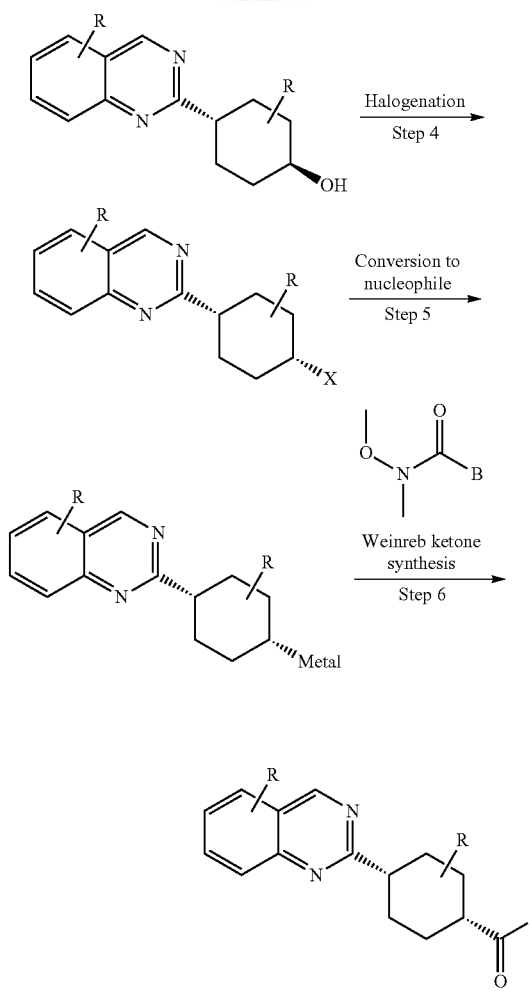

154
-continued

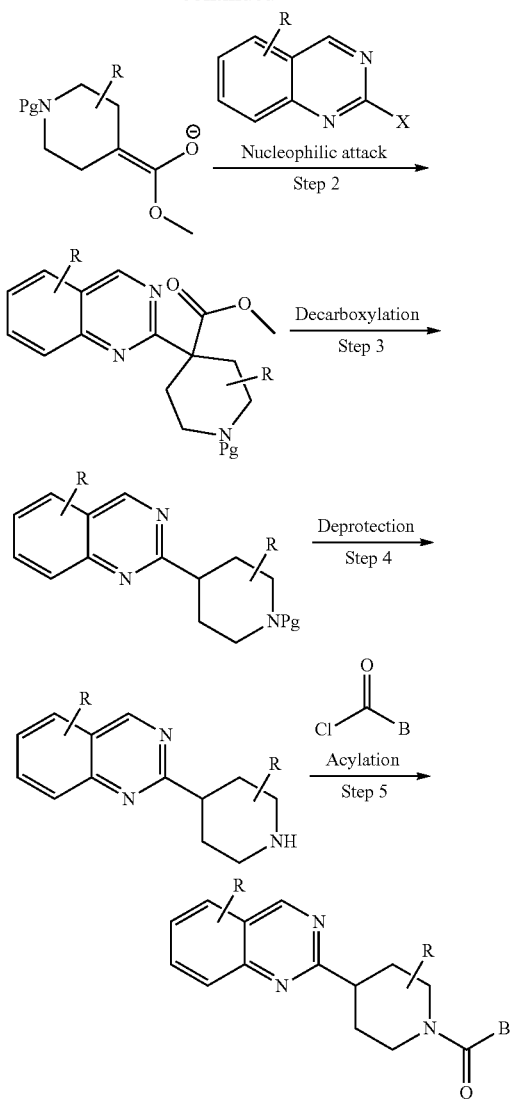

Scheme 1-5: A compound of the present invention can be prepared, for example, from a protected carbocycle. In Step 1 the protected cyclohexanol is converted to a nucleophile as known in the art. In Step 2 the nucleophilic cyclohexanol is subjected to an appropriately substituted quinazoline to install the A moiety. In Step 3 the appropriately substituted cyclohexanol is deprotected as known in the art to afford an alcohol. In Step 4 the appropriately substituted cyclohexanol is halogenated as known in the art to afford a halide. In Step 5 the appropriately substituted halide is converted to a nucleophile as known in the art. In Step 6 the appropriately substituted cyclohexyl nucleophile is subjected to a Weinreb amide to afford a compound of Formula I.

Scheme 1-6

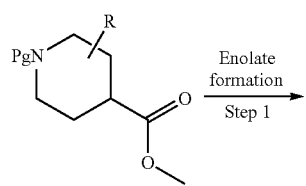

Scheme 1-6: A compound of the present invention can be prepared, for example, from a protected piperidine. In Step 1 the piperidine is converted to an enolate as known in the art. In Step 2 the nucleophilic piperidine is subjected to an appropriately substituted quinazoline halide to afford a quaternary piperidine. In Step 3 the appropriately substituted piperidine is decarboxylated as known in the art to afford an A-C species. In Step 4 the appropriately substituted piperidine is deprotected as known in the art. In Step 5 the appropriately substituted piperidine is subjected to an acyl chloride to afford a compound of Formula I.

Scheme 1-7

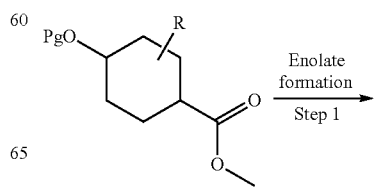

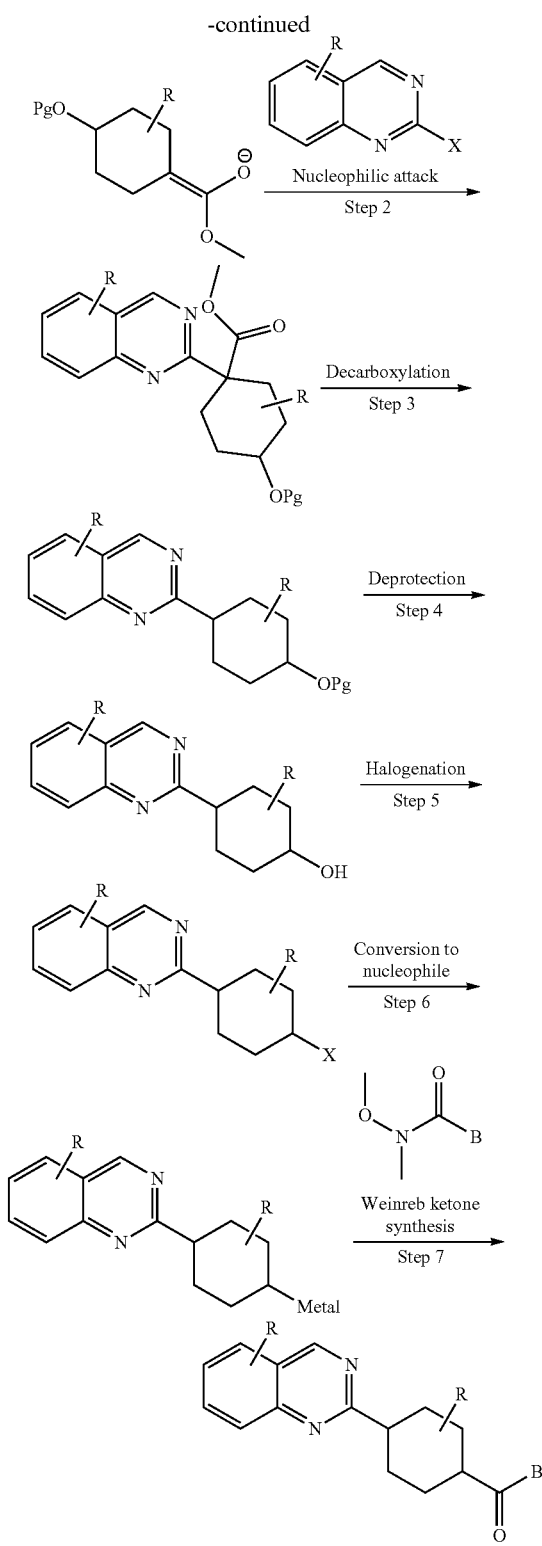

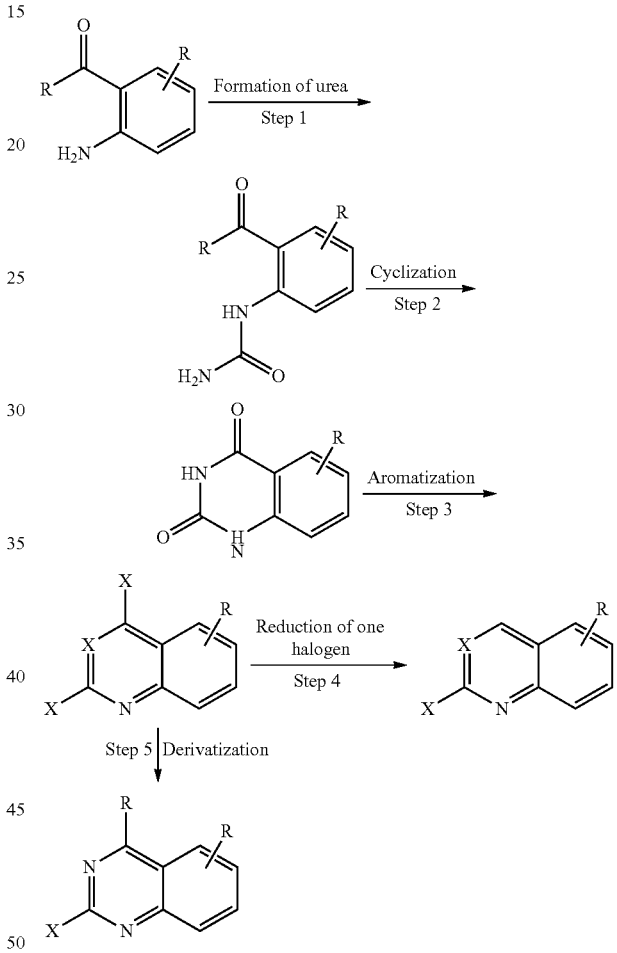

carbocycle is deprotected as known in the art to afford an alcohol. In Step 5 the appropriately substituted cyclohexanol is halogenated as known in the art to afford a halide. In Step 6 the appropriately substituted halide is converted to a nucleophile as known in the art. In Step 7 the appropriately substituted cyclohexyl nucleophile is subjected to a Weinreb amide to afford a compound of Formula I.

Example 2. Synthesis of Quinazoline (A) Moieties

Scheme 2-1: An A ring of the present invention can be prepared, for example, from an aniline. In Step 1 the appropriately substituted aniline is converted to a urea as known in the art. In Step 2 the appropriately substituted urea cyclizes by nucleophilic attack of the carbonyl moiety with subsequent loss of R to afford a heterocycle. In Step 3 the appropriately substituted heterocycle is aromatized as known in the art to afford a halogenated quinazoline which can be optionally further modified in Step 4 and Step 5. In Step 4 the appropriately substituted quinazoline is reduced as known in the art to the halogenated species which can be used as described in example 1. In Step 5 the appropriately substituted dihalide is instead further derivatized as known in the art to afford a halogenated species which can be used as described in example 1.

Scheme 1-7: A compound of the present invention can be prepared, for example, from a protected carbocycle. In Step 1 the appropriately substituted carbocycle is converted to an enolate as known in the art. In Step 2 the nucleophilic carbocycle is subjected to an appropriately substituted quinazoline halide to afford a quaternary carbocycle. In Step 3 the appropriately substituted carbocycle is decarboxylated as known in the art. In Step 4 the appropriately substituted Scheme 2-2

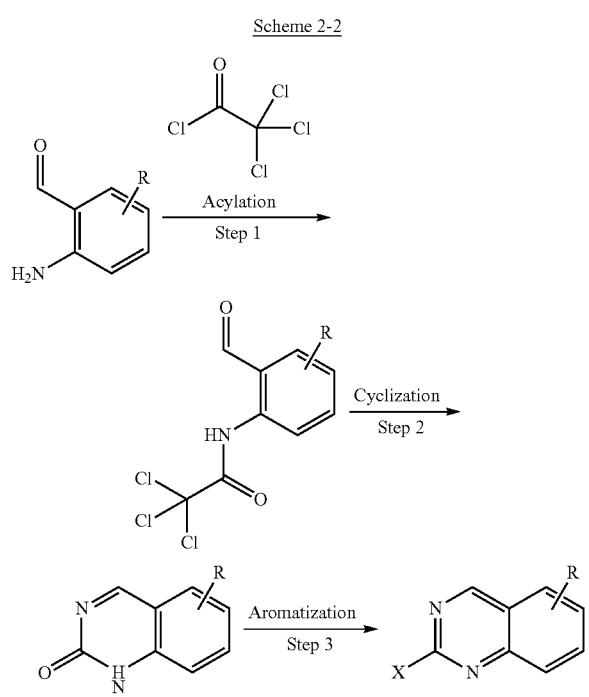

Scheme 2-2: An A ring of the present invention can be prepared, for example, from an aniline. In Step 1 the appropriately substituted aniline is acylated with 2,2,2-trichloroacetyl chloride to afford an amide. In Step 2 the appropriately substituted amide is cyclized as known in the art to afford a heterocycle. In Step 3 the appropriately substituted heterocycle is aromatized as known in the art to afford a halogenated quinazoline.

Scheme 2-3

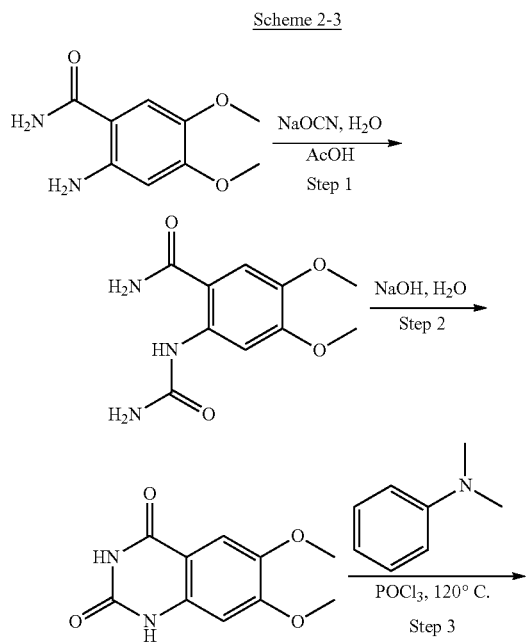

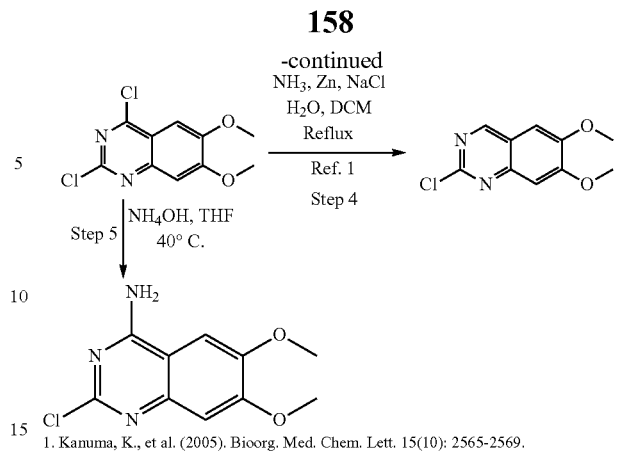

1. Kanuma, K., et al. (2005). Bioorg. Med. Chem. Lett. 15(10): 2565-2569.

Scheme 2-3: An A ring of the present invention can be prepared, for example, from 2-amino-4,5-dimethoxybenzamide. In Step 1 the appropriately substituted aniline is subjected to sodium cyanate to afford a urea. In Step 2 the appropriately substituted urea cyclizes upon addition of a strong base affording ammonia and a heterocycle. In Step 3 the appropriately substituted heterocycle is stirred in POCl$_3$ at elevated temperatures to afford a halogenated quinazoline which can be optionally further modified in Step 4 and Step 5. In Step 4 the appropriately substituted quinazoline is reduced selectively as known in the art to a mono-halogenated species. In Step 5 the appropriately substituted dihalide is subjected to ammonia hydroxide to afford a derivatized quinazoline.

Scheme 2-4

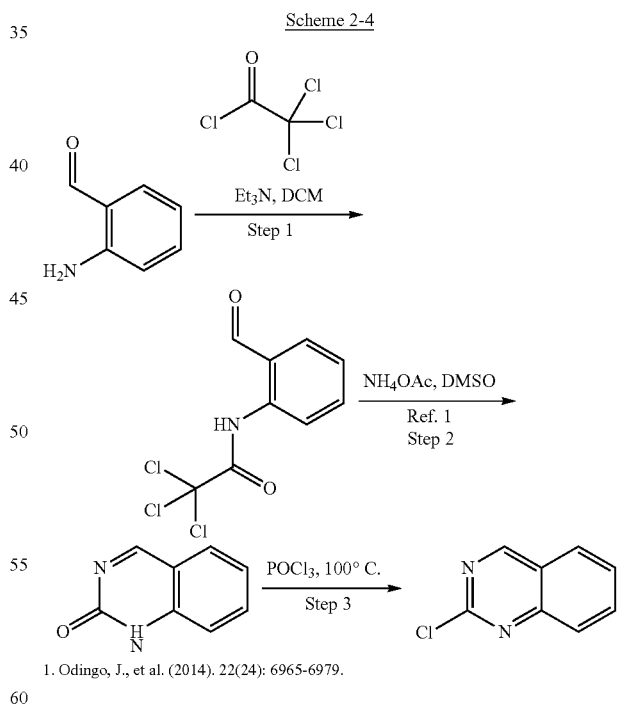

1. Odingo, J., et al. (2014). 22(24): 6965-6979.

Scheme 2-4: An A ring of the present invention can be prepared, for example, from 2-aminobenzaldehyde. In Step 1 the appropriately substituted aniline is acylated with 2,2,2-trichloroacetyl chloride to afford an amide. In Step 2 the appropriately substituted amide is subjected to ammonium acetate in DMSO to afford a heterocycle. In Step 3 the appropriately substituted heterocycle is stirred in POCl₃ at high temperatures to afford a halogenated quinazoline.

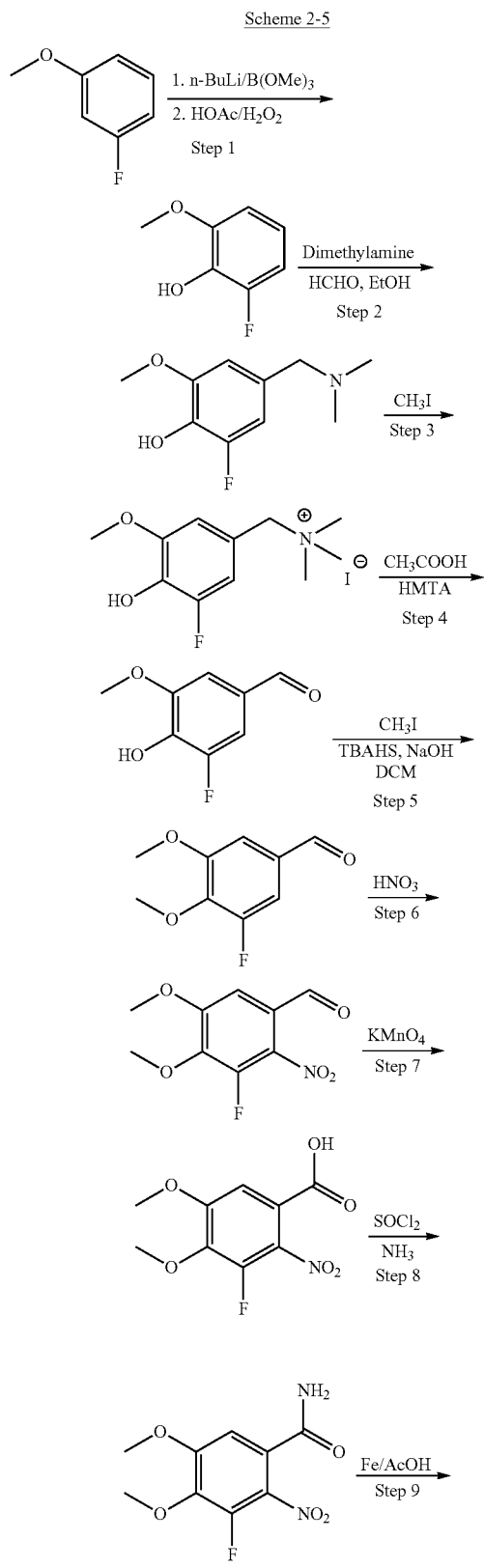

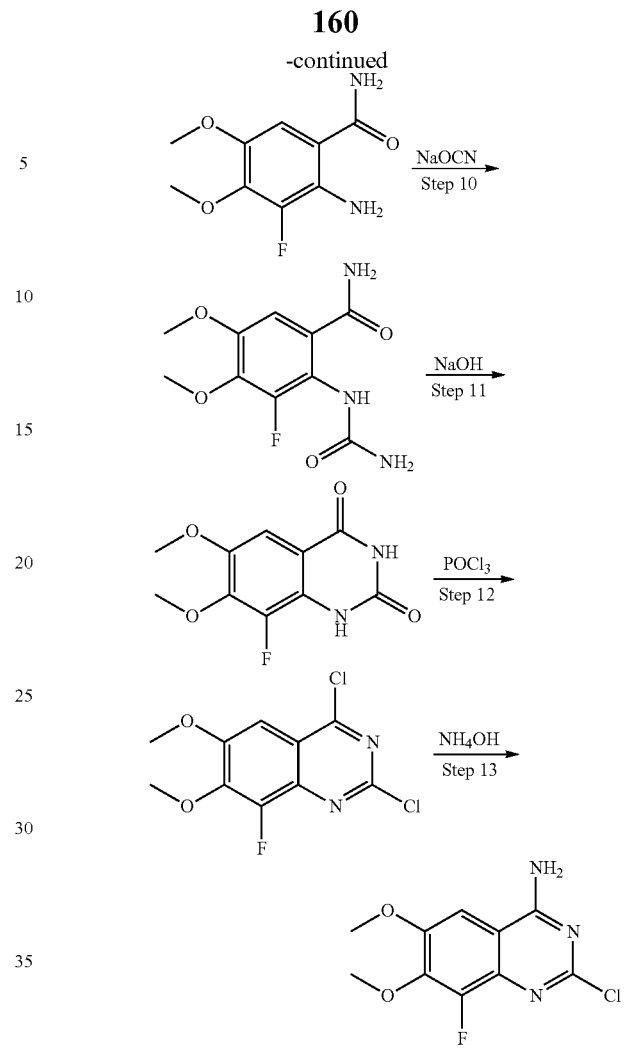

Scheme 2-5: An A ring of the present invention can be prepared, for example, from 1-fluoro 3-methoxy benzene, and with appropriate choice of chemical reagents and reactions, highly functionalized quinazolines can be formed as known in the art.

Example 3. Synthesis of Central Core (C) Moieties

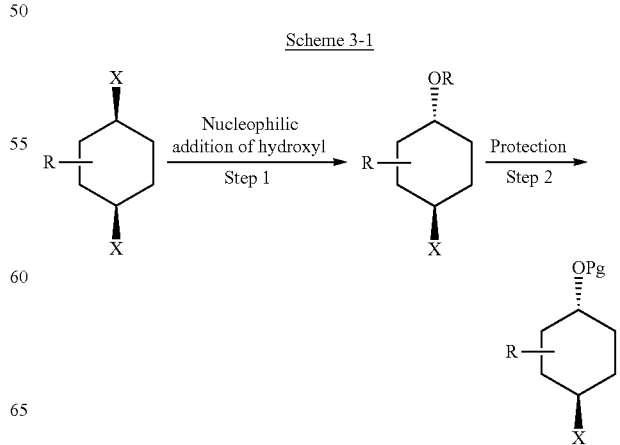

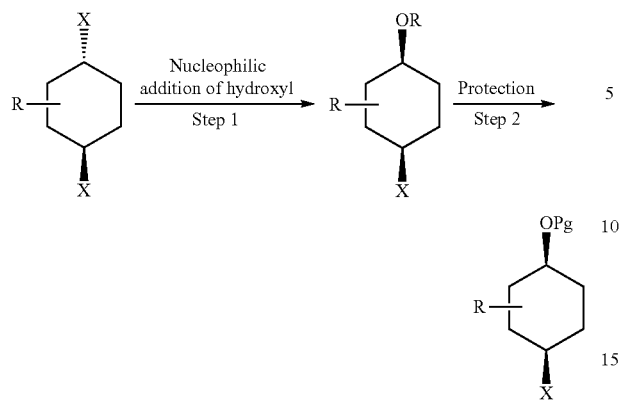

Scheme 3-1: A central core of the present invention can be prepared, for example, from a halogenated cyclohexane. In Step 1 the appropriately substituted cyclohexane is subjected to nucleophilic attack by a hydroxyl species to invert a stereocenter and afford a cis or trans species depending on the choice of starting material. In Step 2 the cis or trans cyclohexane is appropriately protected to be used as described in Example 1.

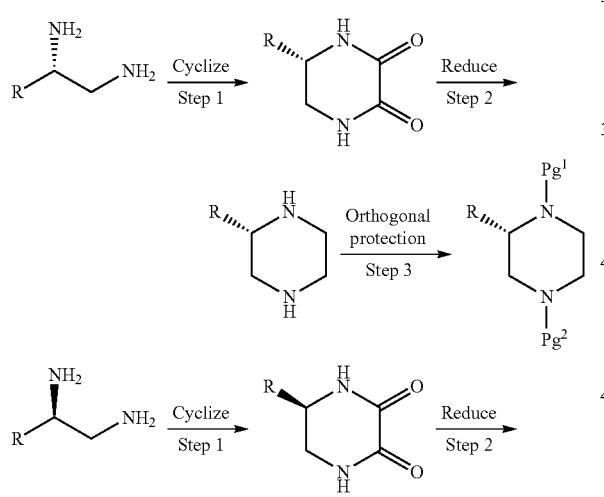

Scheme 3-2: A central core of the present invention can be prepared, for example, from a chiral diamine. In Step 1 the appropriately substituted diamine is cyclized as known in the art to afford an R or S piperazine dione depending on choice of chiral starting material. In Step 2 the R or S piperazine dione is reduced as known in the art to afford a piperazine. In Step 3 the R or S piperazine is appropriately protected to be used as described in example 1.

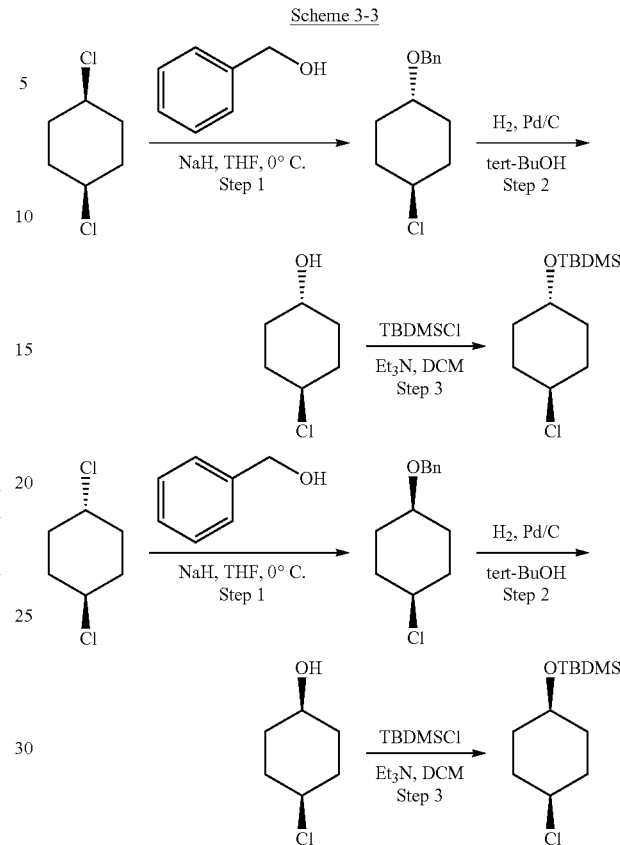

Scheme 3-3: A central core of the present invention can be prepared, for example, from cis or trans dichloro cyclohexane. In Step 1 the appropriately substituted cyclohexane is subjected to benzyl alcohol and sodium hydride to afford a cis or trans ether depending on the choice of starting material. In Step 2 the appropriately substituted benzyl ether is hydrogenated with hydrogen and palladium to afford a cyclohexanol. In Step 3 the appropriately substituted cyclohexanol is subjected to a silyl chloride to afford a silyl ether.

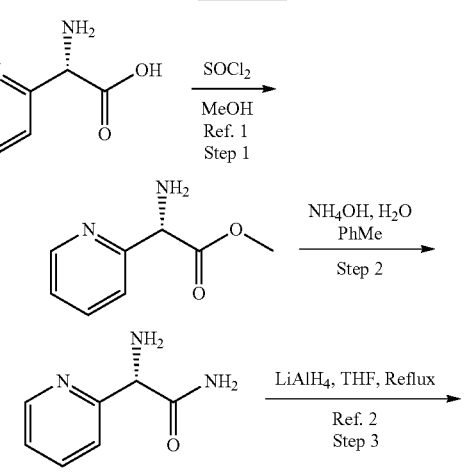

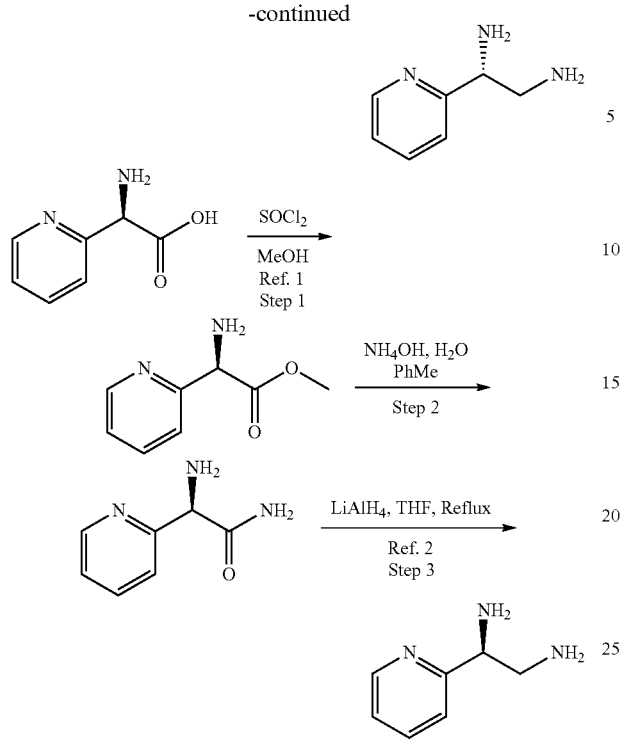

1. Kudelko, A., et al. (2013). Tetrahedron Lett. 54(35): 4637-4640. 2. Malkov, A. V., et al. (2006). Chem. - Eur. J. 12(26): 6910-6929.

Scheme 3-4: A chiral diamine useful in the present invention can be prepared, for example, from a chiral amino acid. In Step 1 the appropriately substituted amino acid is subjected to thionyl chloride followed by a workup with methanol to afford an ester as reported by Kudelko and coworkers. In Step 2 the R or S ester is subjected to ammonium acetate to afford an amide. In Step 3 the R or S amide is reduced as reported by Malkov and coworkers to afford a chiral diamine which can be used in Scheme 3-5.

Scheme 3-5

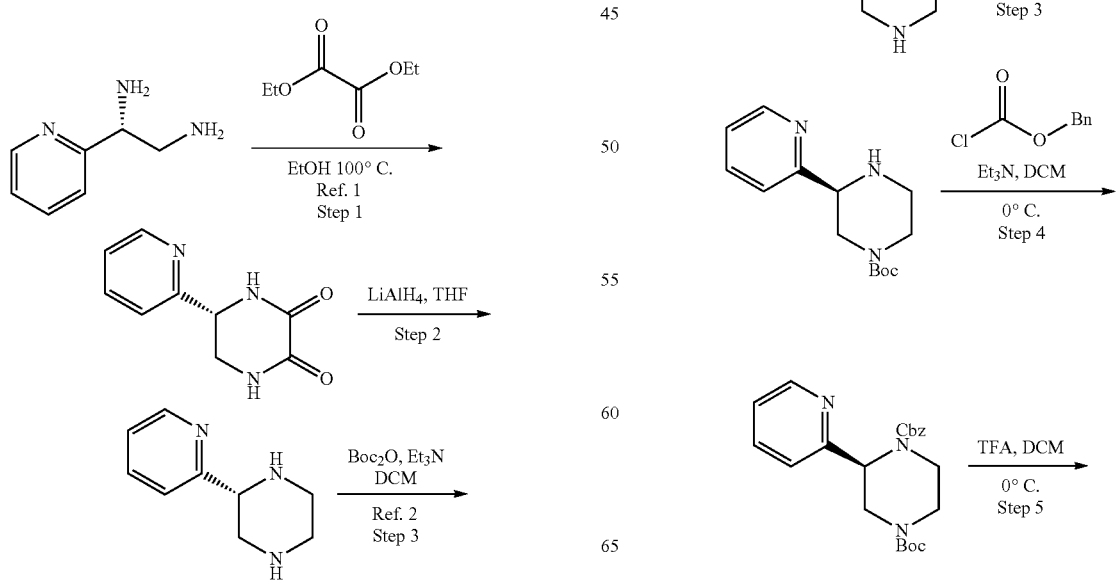

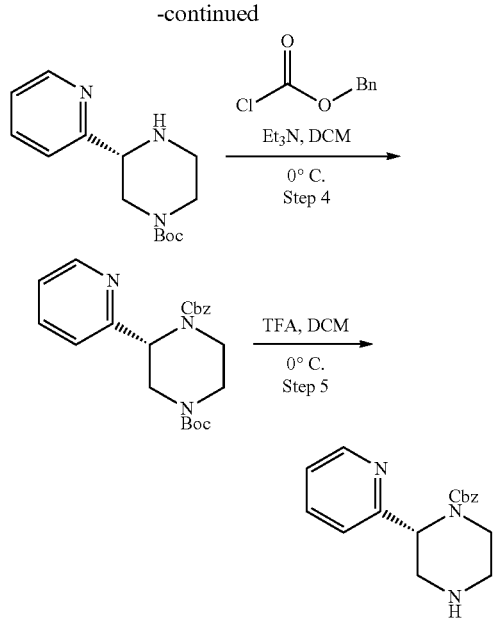

165

-continued

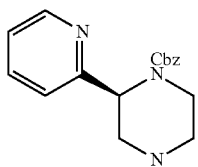

1. Guandalini, L., et al. (2015). Bioorg. Med. Chem. Lett. 25(8): 1700-1704. 2. WO 2009150129

Scheme 3-5: A central core of the present invention can be prepared, for example, from a chiral diamine. In Step 1 the appropriately substituted diamine is subjected to diethyl oxalate and heat to afford a chiral piperazine dione. In Step 2 the R or S piperazine dione is reduced with lithium aluminum hydride to afford a chiral piperazine. In Step 3 the R or S piperazine mono-protected with Boc at the less hindered amine to afford a Boc-protected piperazine. In Step 4 the R or S Boc-protected piperazine is protected with benzyl chloroformate to afford an orthogonally protected species. In Step 5 the R or S piperazine is selectively deprotected with acidic conditions to afford the Cbz-protected piperazine.

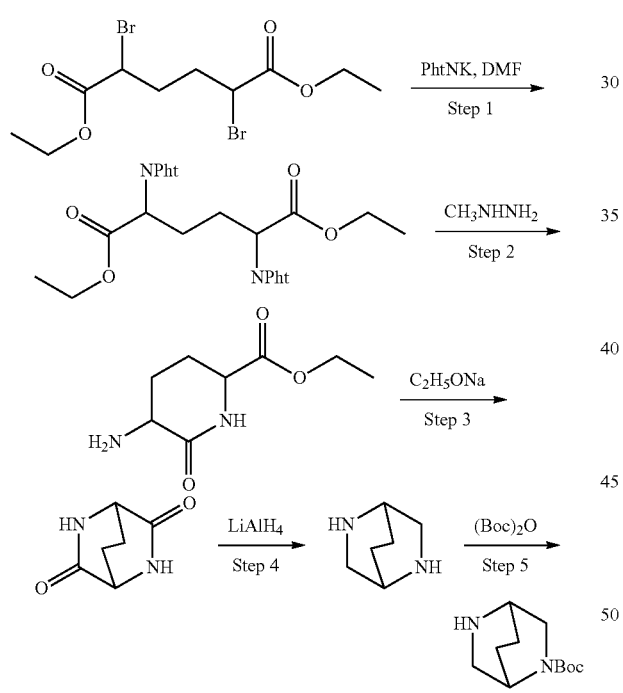

Scheme 3-6

Scheme 3-6: A central core of the present invention can be prepared, for example, from diethyl 2,5-dibromohexanedioate. In Step 1 diethyl 2,5-dibromohexanedioate is subjected to potassium phthalimide to afford a protected diamino species. In Step 2 the appropriately substituted protected diamino species is deprotected with methyl hydrazine followed by an intramolecular cyclization to afford a piperidine. In Step 3 the appropriately substituted piperidine is subjected to a base to afford a bridged piperazine dione. In Step 4 the appropriately substituted dione is reduced with lithium aluminum hydride to afford a bridged piperazine. In Step 5 the appropriately substituted piperazine is mono Boc-protected to afford a central core moiety.

166

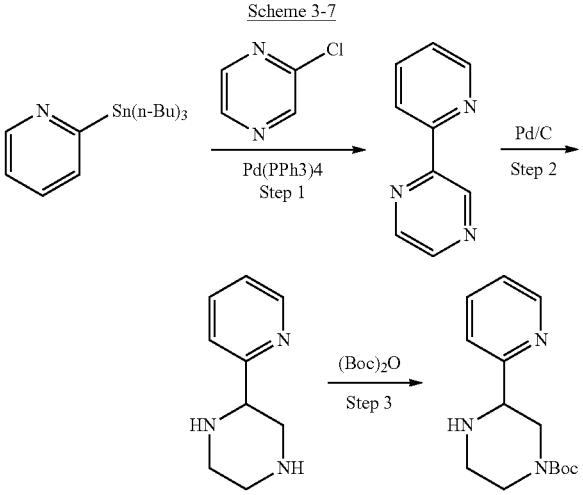

Scheme 3-7

Scheme 3-7: A central core of the present invention can be prepared, for example, from 2-(tributylstannyl)pyridine. In Step 1 2-(tributylstannyl)pyridine is subjected to 2-chloropyrazine in the presence of palladium catalyst to afford a biheteroaryl species. In Step 2 the appropriately substituted biheteroaryl species is hydrogenated with palladium on carbon as known in the art to afford a substituted piperazine. In Step 3 the appropriately substituted piperazine is mono Boc-protected to afford a central core moiety.

Example 4. Synthesis of L-B Moieties

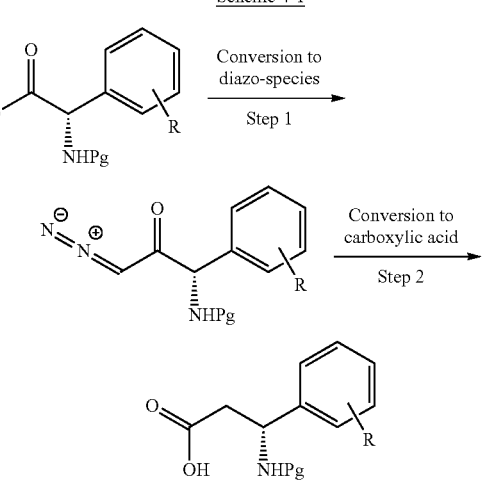

Scheme 4-1

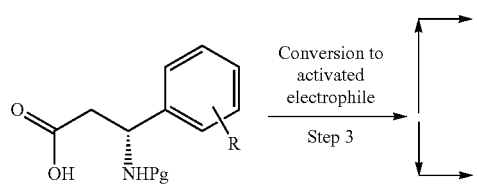

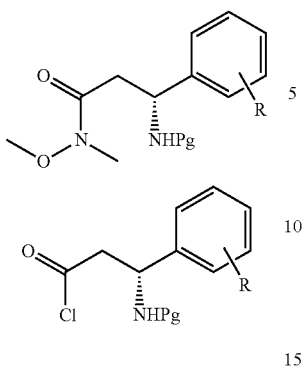

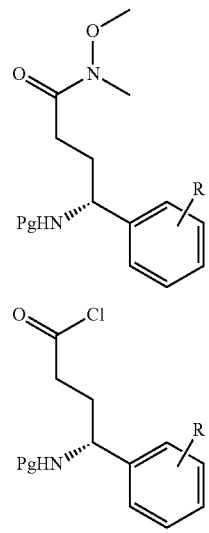

Scheme 4-1: A L-B moiety of the present invention can be prepared, for example, from an amino acid. In Step 1 the appropriately substituted amino acid is converted to a diazo species as known in the art to add a carbon. In Step 2 the appropriately substituted diazo-species is converted to a carboxylic acid as known in the art to afford a beta amino acid. In Step 3 the appropriately substituted beta amino acid is converted to an activated electrophile which can be used as described in Example 1.

Scheme 4-2: A L-B moiety of the present invention can be prepared, for example, from a beta amino acid. In Step 1 the appropriately substituted beta amino acid is converted to a diazo species as known in the art to add a carbon. In Step 2 the appropriately substituted diazo-species is converted to a carboxylic acid as known in the art to afford a gamma amino acid. In Step 3 the appropriately substituted gamma amino acid is converted to an activated electrophile which can be used as described in Example 1.

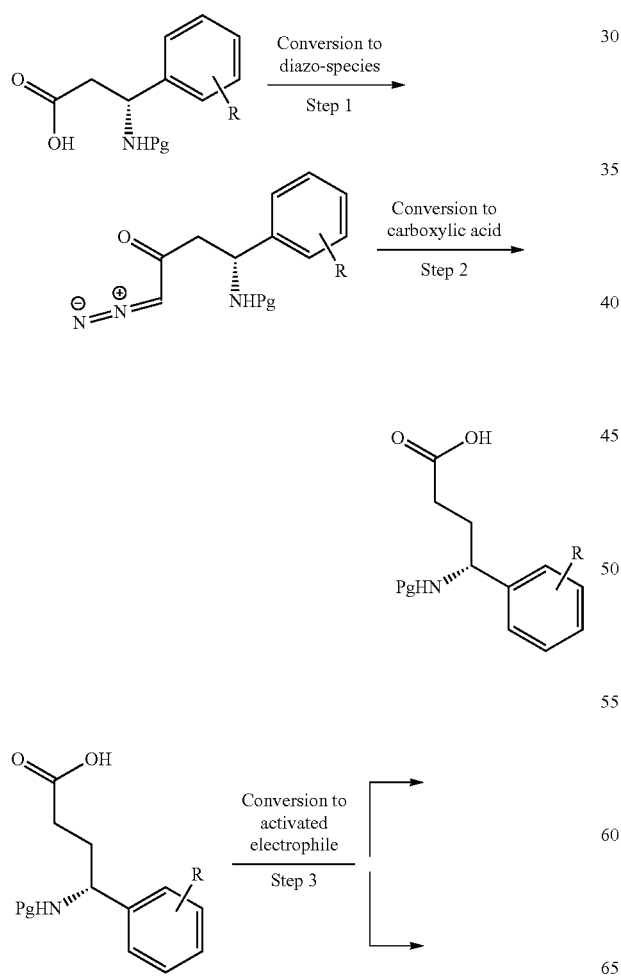

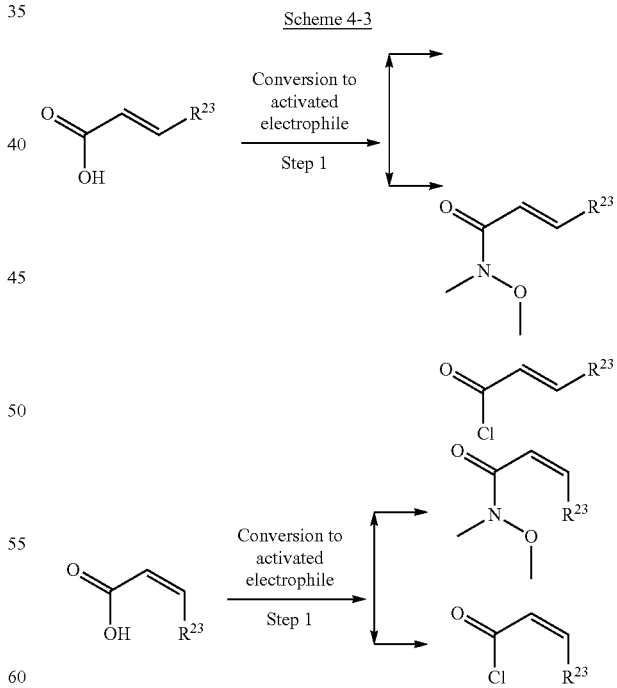

Scheme 4-3: A L-B moiety of the present invention can be prepared, for example, from a carboxylic acid. In Step 1 the appropriately substituted carboxylic acid is converted to an activated electrophile as known in the art to afford a species that can be used as described in Example 1.

Scheme 4-4

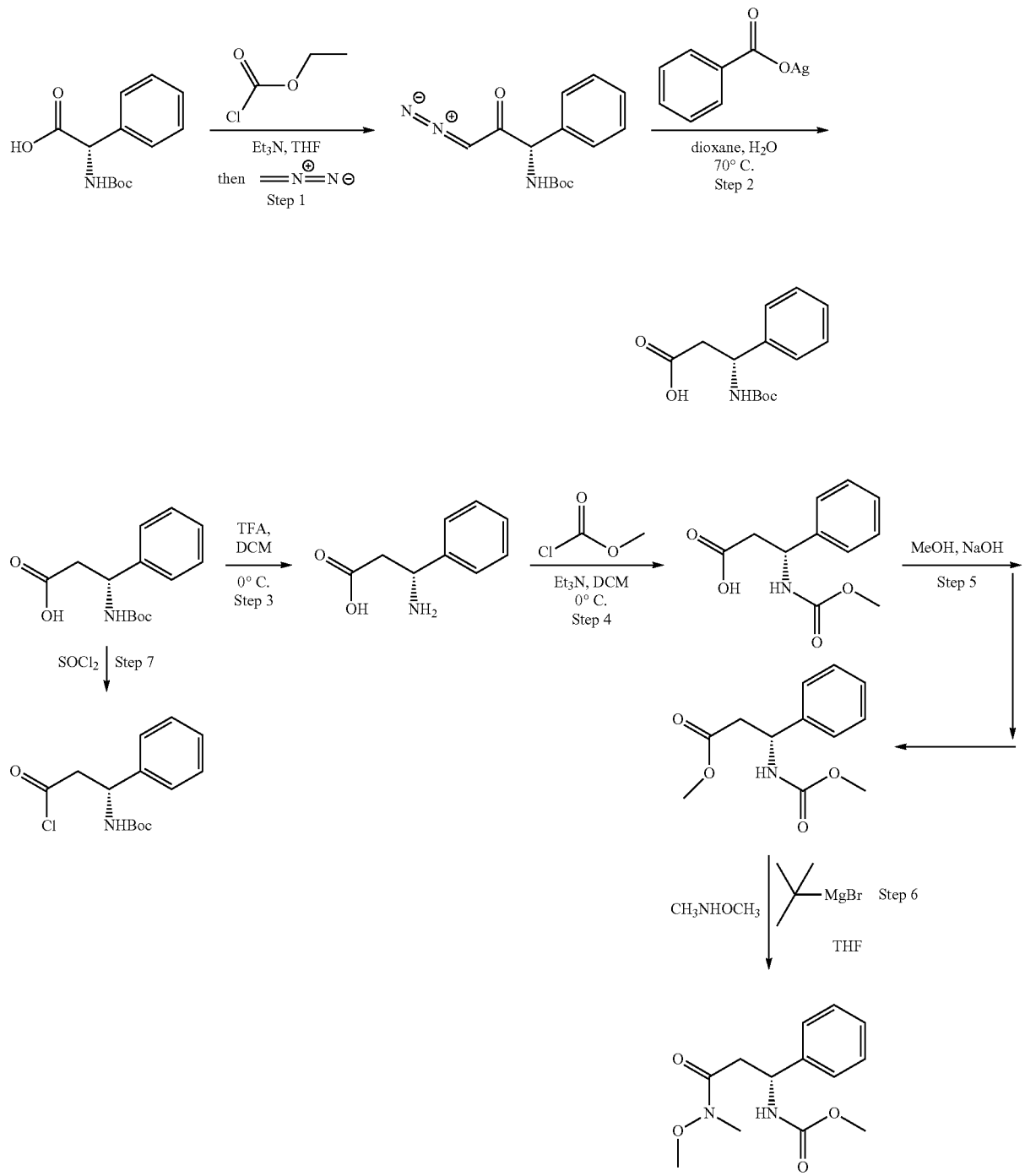

Scheme 4-4: A L-B moiety of the present invention can be prepared, for example, from an amino acid. In Step 1 the appropriately substituted Boc-protected amino acid is subjected to ethyl chloroformate to form a mixed anhydride which is then reacted with diazomethane to afford a diazo-species. In Step 2 the appropriately substituted diazo-species is subjected to silver benzoate to afford a beta amino acid. In Step 3 the appropriately substituted beta amino acid is deprotected with trifluoroacetic acid to afford an amine. In Step 4 the appropriately substituted beta amino acid is subjected to methyl chloroformate to afford a carbamate/anhydride species, the mixed anhydride is cleaved upon workup to afford a carbamate. In Step 5 the appropriately substituted carboxylic acid is esterified as known in the art to afford a methyl ester. In Step 6 the appropriately substituted methyl ester is converted to a Weinreb amide by use of Weinreb's amine and a bulky Grignard reagent. Alternatively, in Step 7 the appropriately substituted beta amino acid is converted to an acyl chloride by thionyl chloride.

Scheme 4-5

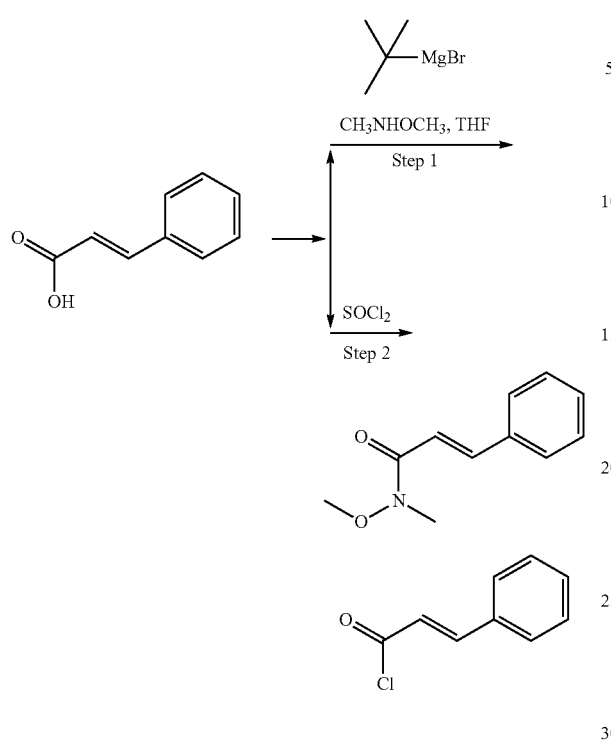

Scheme 4-6

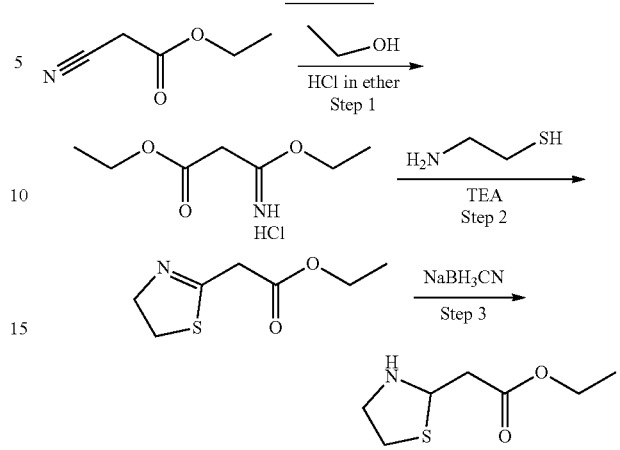

Scheme 4-6: A L-B moiety of the present invention can be prepared, for example, from ethyl 2-cyanoacetate. In Step 1 ethyl 2-cyanoacetate is converted to ethyl 3-ethoxy-3-iminopropanoate as known in the art. In Step 2 ethyl 3-ethoxy-3-iminopropanoate is subjected to 2-aminoethane-1-thiol in the presence of base to afford a dihydrothiazole. In Step 3 the appropriately substituted dihydrothiazole is reduced with a hydride to afford a thiazolidine.

Example 5. Representative Synthesis of Compounds of Formula I

Scheme 5-1

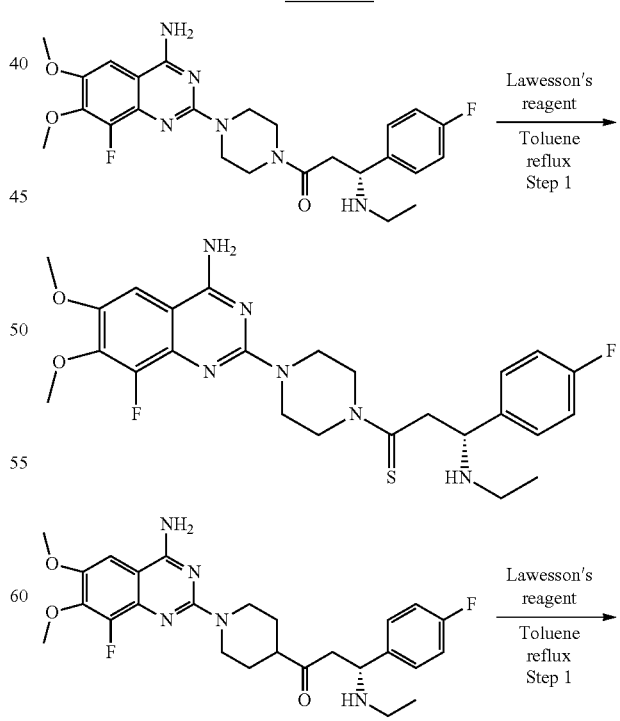

Scheme 4-5: A L-B moiety of the present invention can be prepared, for example, from cinnamic acid or the cis analog of cinnamic acid. In Step 1 the appropriately substituted carboxylic acid is converted to a Weinreb amide by use of Weinreb's amine and a bulky Grignard reagent. Alternatively, in Step 2 the appropriately substituted carboxylic acid is converted to an acyl chloride by thionyl chloride.

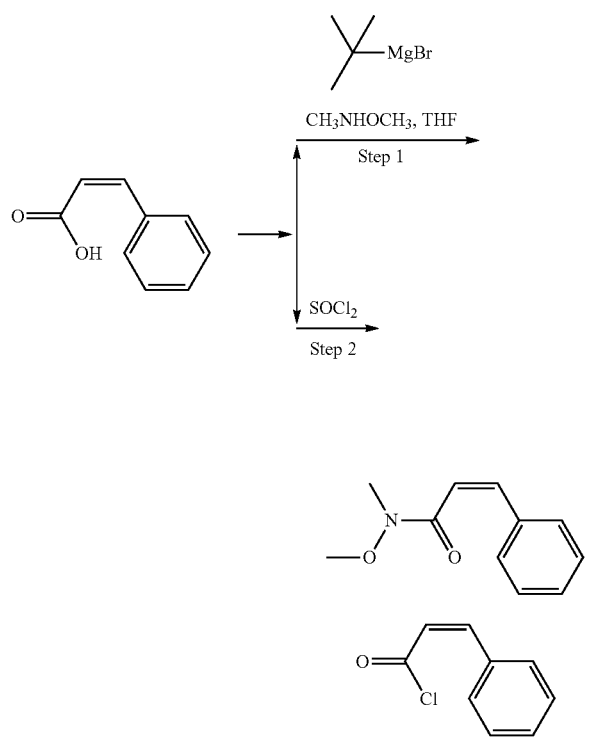

-continued

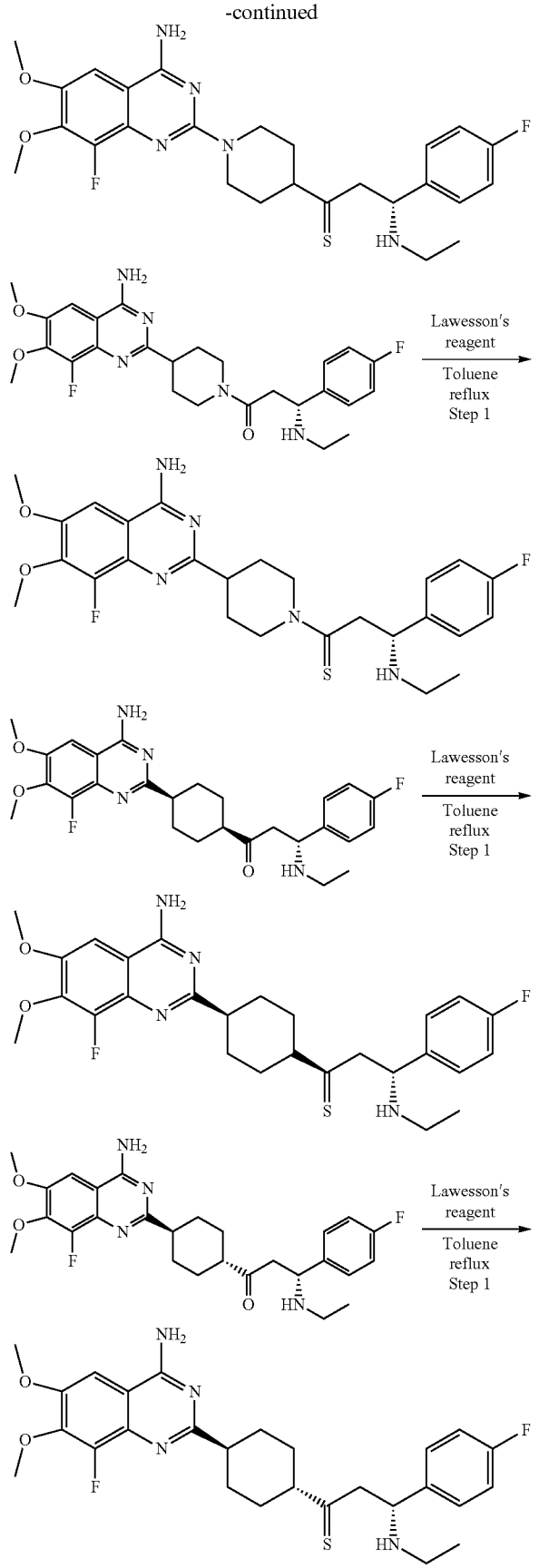

Scheme 5-1: A compound of the present invention can be prepared, for example, from an amide or ketone. In Step 1 the appropriately substituted amide or ketone is subjected to Lawesson's reagent in toluene at reflux to afford a thione or thioamide of Formula I.

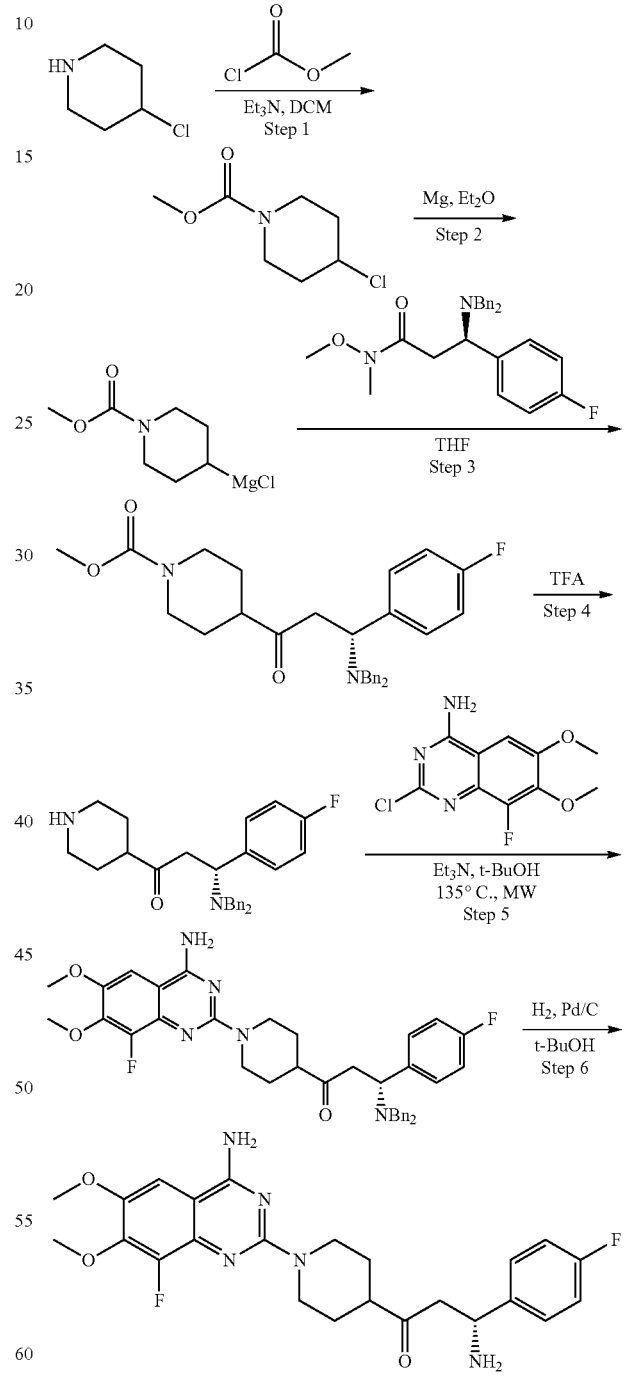

Scheme 5-2: A compound of the present invention can be prepared, for example, from 4-chloropiperidine. In Step 1 the appropriately substituted piperidine is subjected to methyl chloroformate to afford a carbamate protected piperidine. In Step 2 the appropriately substituted halide is converted to a Grignard reagent as known in the art. In Step 3 the appropriately substituted Grignard reagent is converted to a ketone via the Weinreb ketone synthesis. In Step 4 the appropriately substituted piperidine is deprotected with strongly acidic conditions to afford a nucleophilic piperidine. In Step 5 the appropriately substituted piperidine is subjected to a quinazoline at high temperatures to afford a protected compound of Formula I. In Step 6 hydrogenation on a parr hydrogenator with palladium on carbon affords a compound of Formula I.

-continued

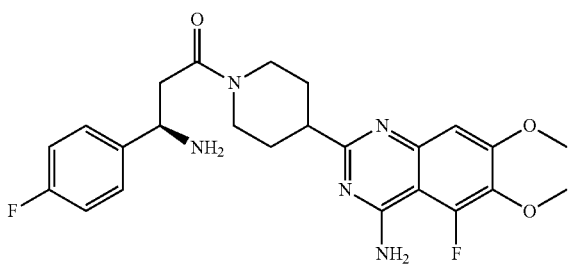

1. WO 2010-US47430

Scheme 5-3: A compound of the present invention can be prepared, for example, from 4-chloropiperidine. In Step 1 the appropriately substituted piperidine is subjected to methyl chloroformate to afford a carbamate protected piperidine. In Step 2 the appropriately substituted halide is converted to a Grignard reagent as known in the art. In Step 3 the appropriately substituted Grignard reagent is subjected to an aryl quinazoline in the presence of Palladium, [1,1'-bis(diphenylphosphino-κP)ferrocene]dichloro-, (SP-4-2)-, compd, with dichloromethane (1:1) to afford a quinazoline substituted piperidine. In Step 4 the appropriately substituted piperidine is deprotected with strongly acidic conditions to afford a nucleophilic piperidine. In Step 5 the appropriately substituted piperidine is subjected to an acyl chloride to afford a protected compound of Formula I. In Step 6 hydrogenation on a parr hydrogenator with palladium on carbon affords a compound of Formula I.

Scheme 5-3

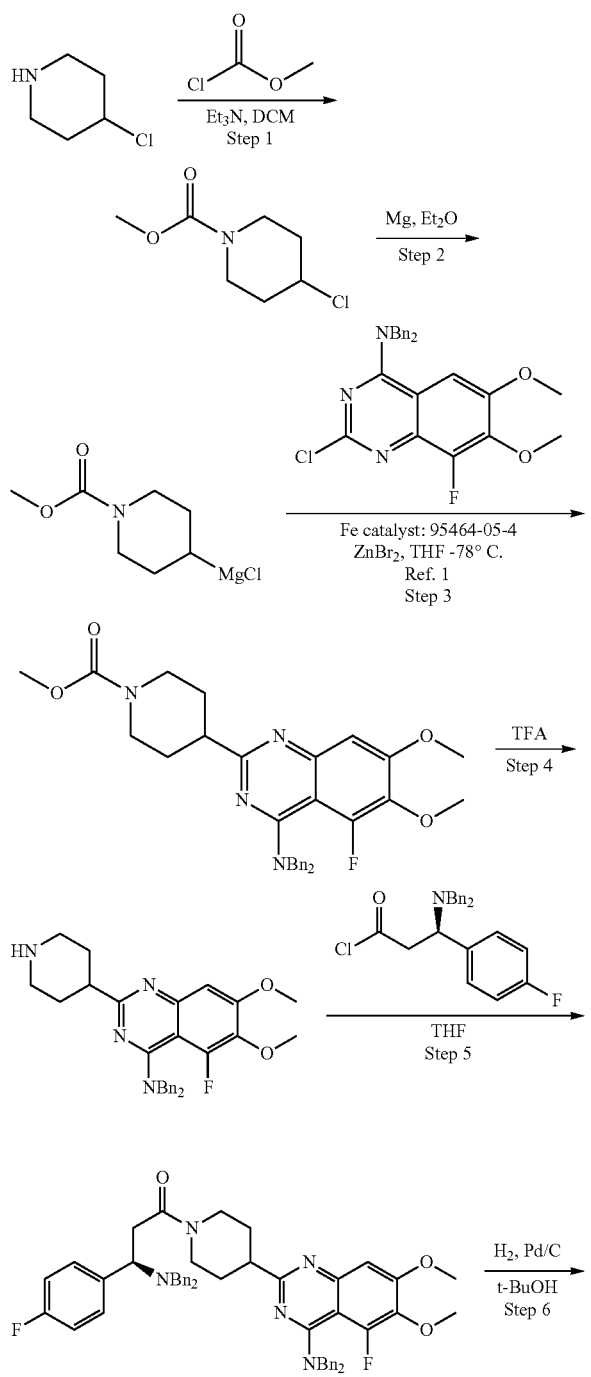

Scheme 5-4

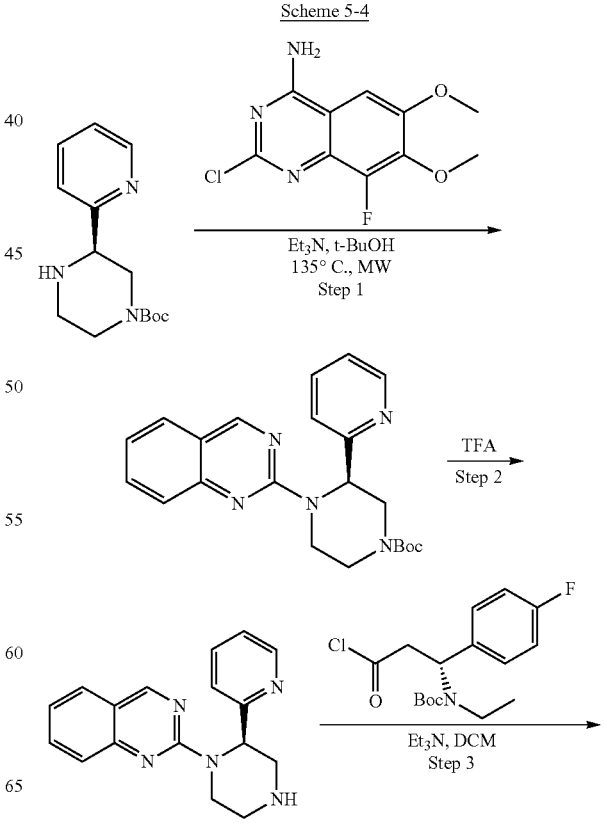

177
-continued

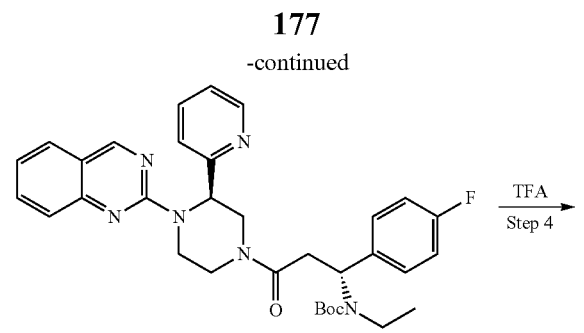

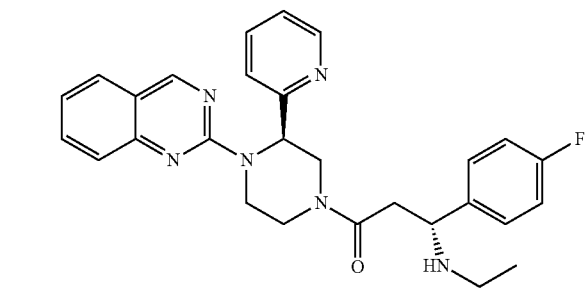

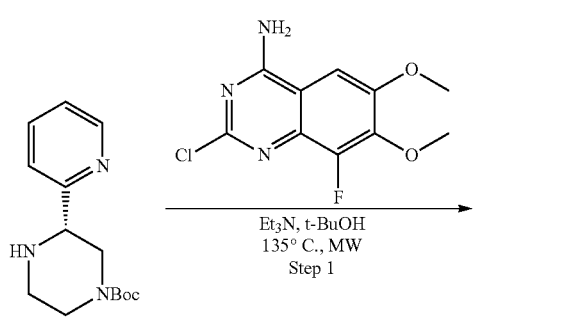

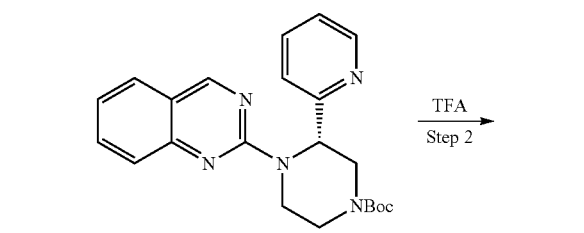

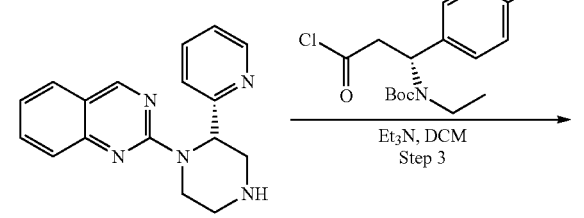

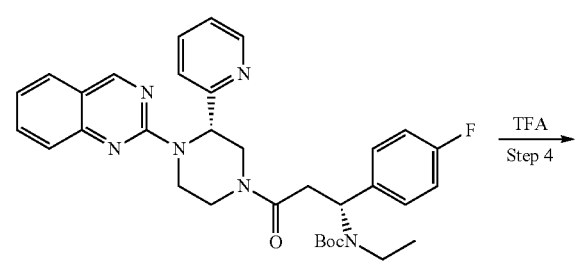

178
-continued

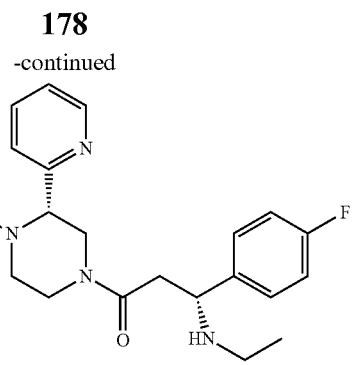

Scheme 5-4: A compound of the present invention can be prepared, for example, from an aryl substituted piperazine. In Step 1 the appropriately substituted piperazine is subjected to a quinazoline at high temperatures to afford an A-C species. In Step 2 the appropriately substituted Boc-protected piperazine is deprotected with strong acid to afford a nucleophilic piperazine. In Step 3 the appropriately substituted piperazine is subjected to an acyl chloride to afford a protected species of Formula I. In Step 4 the protected species of Formula I is deprotected with strong acid to afford a compound of Formula I.

Scheme 5-5

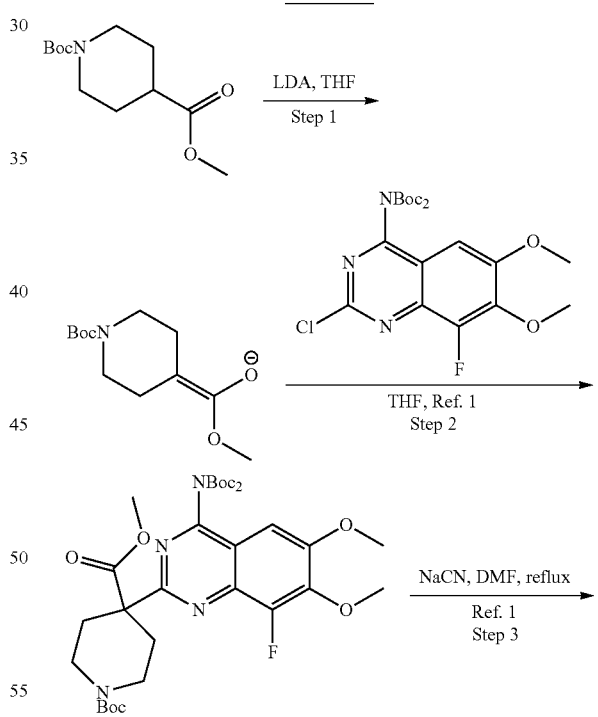

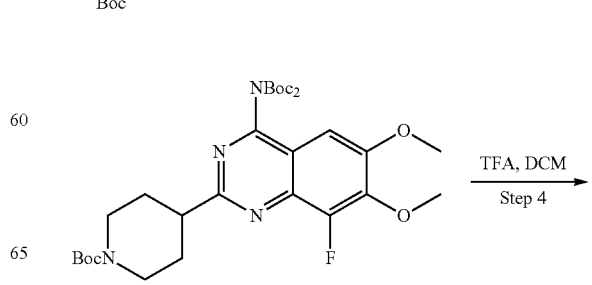

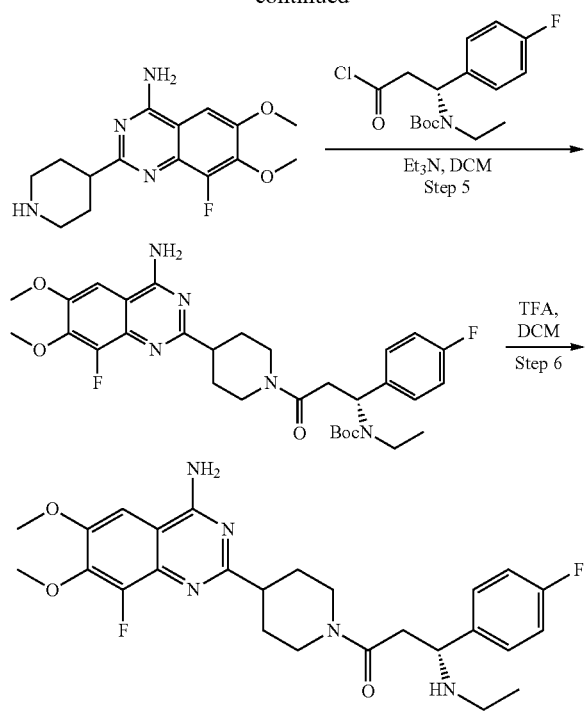

1. US20050096327

Scheme 5-5: A compound of the present invention can be prepared, for example, from an ester. In Step 1 the appropriately substituted ester is subjected to lithium diisopropyl amide to afford an enolate which is subsequently trapped in Step 2 with a quinazoline halide. In Step 3 the appropriately substituted Boc-protected piperidine is decarboxylated in the presence of sodium cyanide with heat to afford a quinazoline substituted piperidine. In Step 4 the appropriately substituted piperidine is globally deprotected with acid to afford a nucleophilic piperidine. In Step 5 the appropriately substituted piperidine is subjected to an acyl chloride to afford a protected species of Formula I. In Step 6 the protected species of Formula I is deprotected with acid to afford a compound of Formula I.

Scheme 5-6

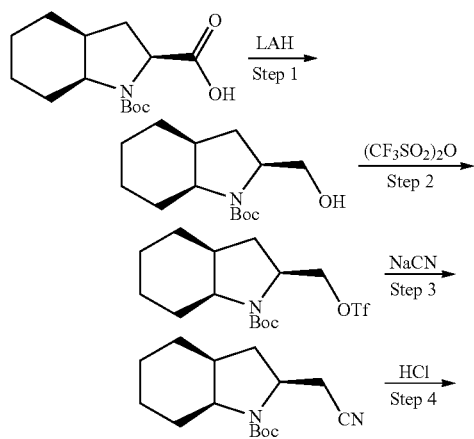

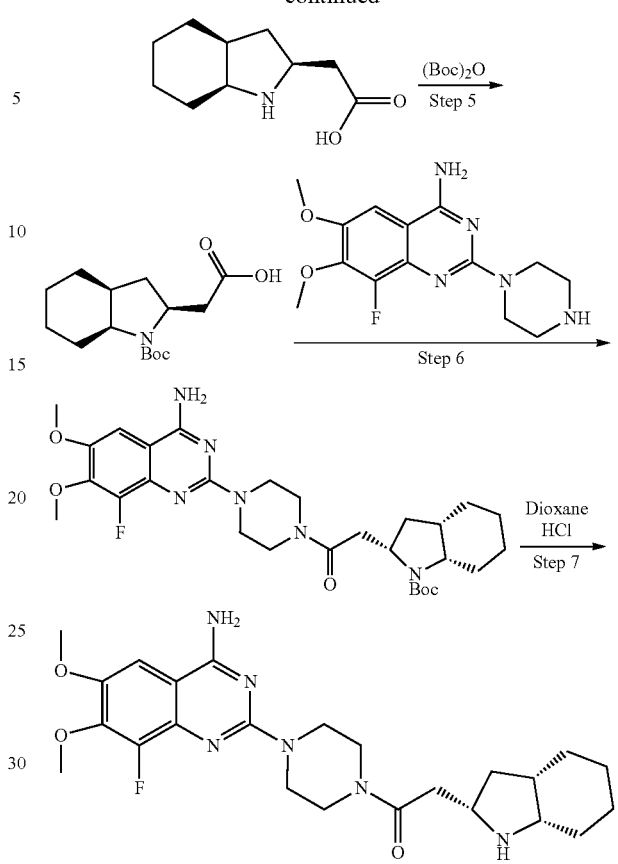

Scheme 5-6: A compound of the present invention can be prepared, for example, from a carboxylic acid. In Step 1 the appropriately substituted acid is subjected to lithium aluminum hydride to afford an alcohol. In Step 2 the appropriately substituted alcohol is converted to a triflate as known in the art. In Step 3 the appropriately substituted triflate is subjected to nucleophilic addition of sodium cyanide to afford a cyano species. In Step 4 the appropriately substituted cyano species is hydrated to a carboxylic acid in the presence of strong aqueous acid. In Step 5 the appropriately substituted amine is Boc-protected. In Step 6 the appropriately substituted acid is coupled to an A-C moiety as known in the art to afford a protected species of Formula I. In Step 7 the protected species of Formula I is deprotected with acid to afford a compound of Formula I.

Scheme 5-7

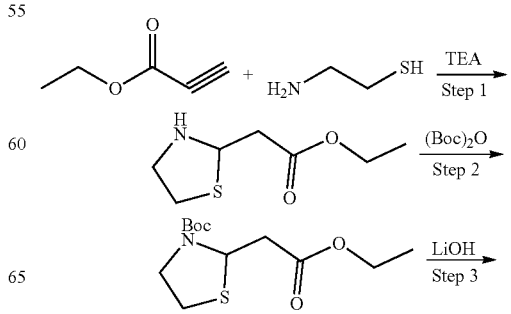

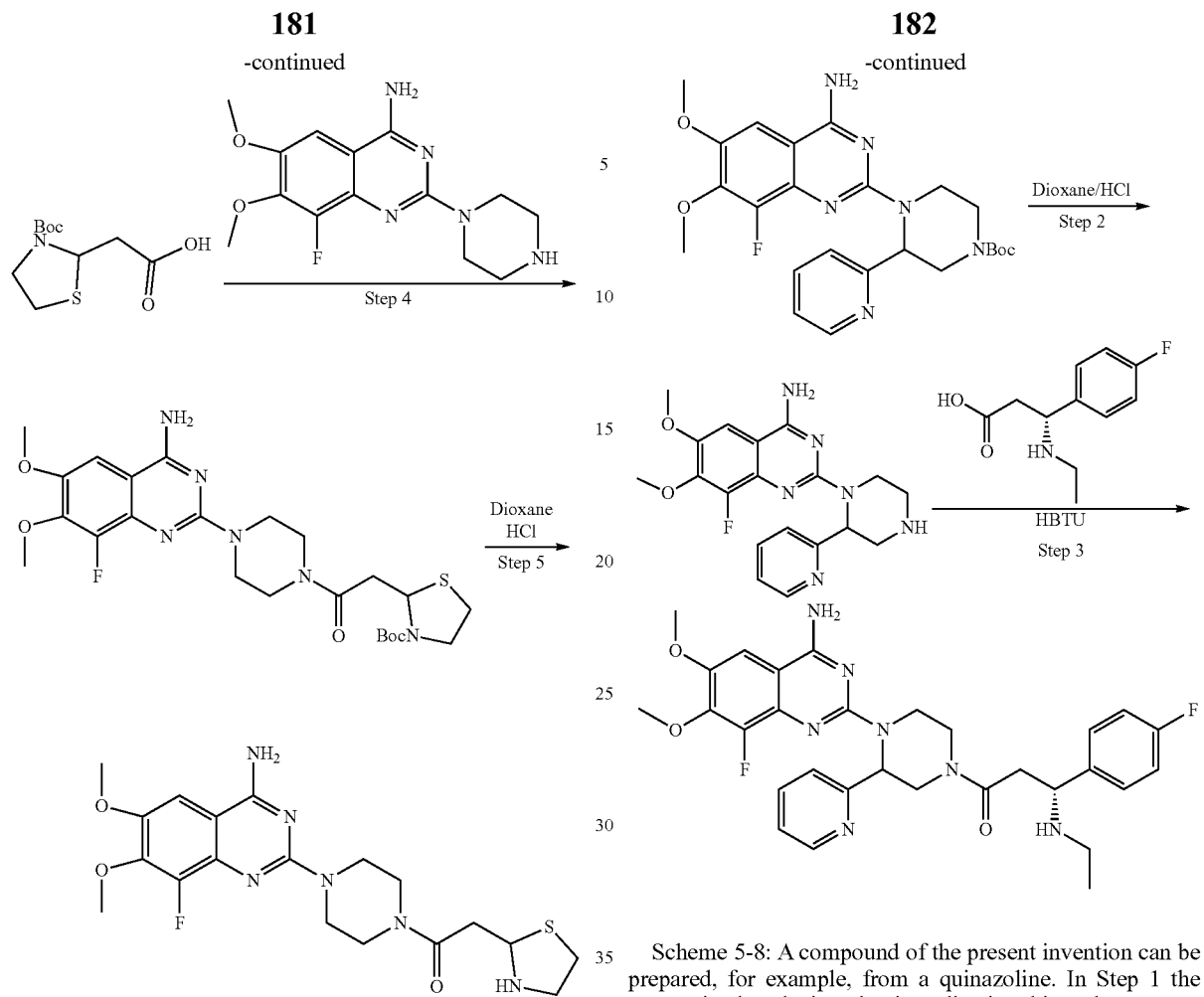

Scheme 5-7: A compound of the present invention can be prepared, for example, from an alkyne. In Step 1 the appropriately substituted alkyne is subjected to 2-aminoethane-1-thiol in the presence of a base to afford a thiazolidine. In Step 2 the appropriately substituted thiazolidine is Boc-protected as known in the art. In Step 3 the appropriately substituted ester is saponified to afford an acid. In Step 4 the appropriately substituted acid is coupled to an A-C moiety as known in the art to afford a protected species of Formula I. In Step 5 the protected species of Formula I is deprotected with acid to afford a compound of Formula I.

Scheme 5-8: A compound of the present invention can be prepared, for example, from a quinazoline. In Step 1 the appropriately substituted quinazoline is subjected to a mono protected piperazine to afford a protected A-C moiety. In Step 2 the protected A-C moiety is deprotected as known in the art to afford a free amine. In Step 3 the appropriately substituted amine is coupled to a B-L moiety to afford a compound of Formula I.

Example 6. Synthesis of Compounds of the Present Invention and Intermediates Thereof

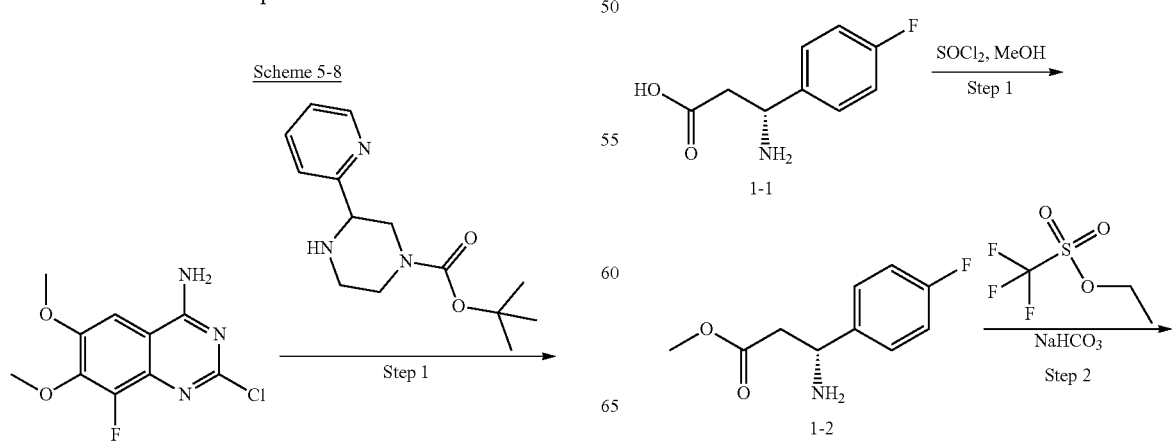

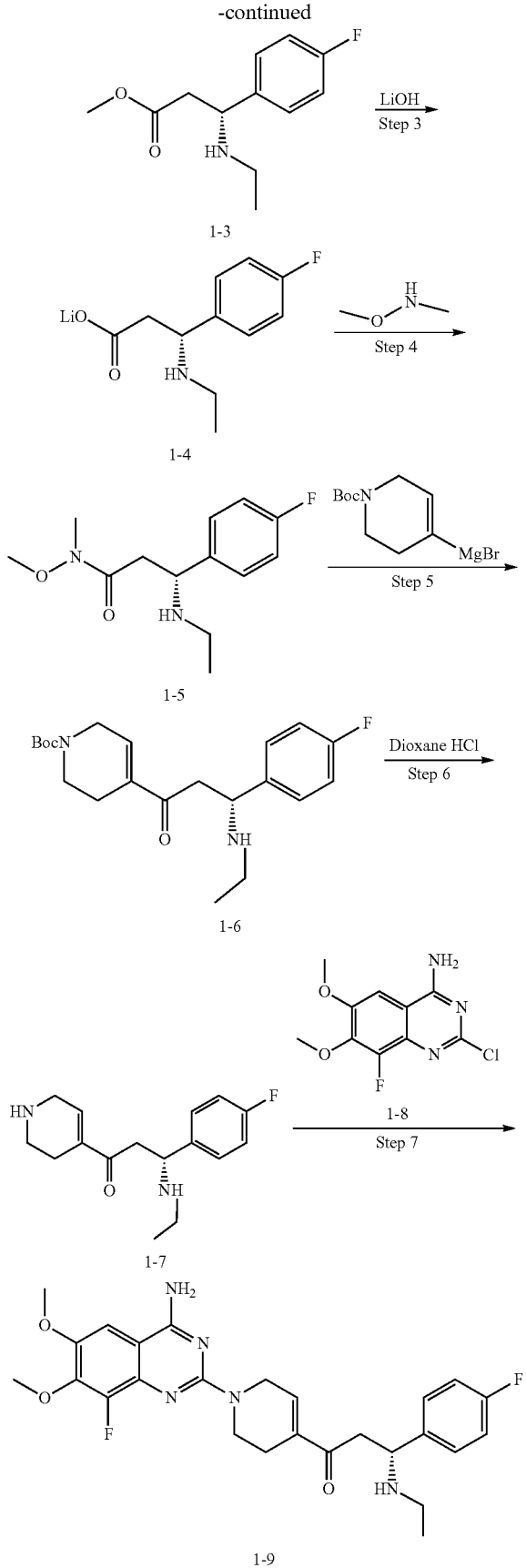

Step 1: Methyl (R)-3-amino-3-(4-fluorophenyl)propanoate (1-2)

To a solution of (R)-3-amino-3-(4-fluorophenyl)propanoic acid (1 equiv) in MeOH (10 vol) at 0° C. is added SOCl₂ (4 equiv). The reaction mixture is stirred at room temperature for 12 hours and then concentrated. The resulting mixture is quenched with saturated NaHCO₃ solution and extracted with ethyl acetate. The organic layer is separated, dried over anhydrous Na₂SO₄, filtered and then concentrated to afford compound 1-2.

Step 2: Methyl (R)-3-(ethylamino)-3-(4-fluorophenyl)propanoate (1-3)

To a solution of compound 1-2 (1 equiv), aqueous NaHCO₃ (5 equiv) in EtOAc (10 vol) at 0° C. is added a solution of ethyl trifluoromethanesulfonate (1.2 equiv) in EtOAc (5 vol). The reaction mixture is stirred at room temperature for 2 hours and then quenched with saturated NaHCO₃ solution. The resulting mixture is extracted with ethyl acetate. The organic layer is separated, dried over anhydrous Na₂SO₄, filtered and then concentrated. The residue is purified by column chromatography on silica gel to afford compound 1-3.

Step 3: Lithium (R)-3-(ethylamino)-3-(4-fluorophenyl)propanoate (1-4)

To a solution of compound 1-3 (1 equiv) in THF (10 vol) at 0° C. is added LiOH (2 equiv). The reaction mixture is stirred at 65° C. for 2 hours and then concentrated. The residue is re-crystallized from MTBE to afford compound 1-4.

Step 4: (R)-3-(Ethylamino)-3-(4-fluorophenyl)-N-methoxy-N-methylpropanamide (1-5)

To a solution of compound 1-4 (1 equiv) and N,O-dimethylhydroxylamine hydrochloride (1.2 equiv) in DMF (10 vol) at 0° C. is added DIPEA (4 equiv) and HATU (1.2 equiv). The reaction mixture is stirred at room temperature for 12 hours and then quenched with water. The resulting mixture is extracted with ethyl acetate. The organic layer is separated, dried over anhydrous Na₂SO₄, filtered and then concentrated. The residue is purified by column chromatography on silica gel to afford compound 1-5.

Step 5: tert-Butyl (R)-4-(3-(ethylamino)-3-(4-fluorophenyl)propanoyl)piperidine-1-carboxylate (1-6)

To a solution of compound 1-5 (1 equiv) in THF (10 vol) at −78° C. under nitrogen atmosphere is added (1-(tert-butoxycarbonyl)piperidin-4-yl)magnesium bromide in ether (1.5 equiv). The reaction mixture is stirred at −78° C. for 1 hour and then quenched with saturated aqueous ammonium chloride solution. The resulting mixture is extracted with ethyl acetate. The organic layer is separated, dried over anhydrous Na₂SO₄, filtered and then concentrated. The residue is purified by column chromatography on silica gel to afford compound 1-6.

Step 6: (R)-3-(Ethylamino)-3-(4-fluorophenyl)-1-(piperidin-4-yl)propan-1-one (1-7)

To a solution of compound 1-6 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 1-7.

Step 7: (R)-1-(1-(4-Amino-8-fluoro-6,7-dimethoxy-quinazolin-2-yl)piperidin-4-yl)-3-(ethylamino)-3-(4-fluorophenyl)propan-1-one (1-9)

To a solution of compound 1-7 (1 equiv) and compound 1-8 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 1-9.

Step 1: tert-Butyl 8-(4-amino-8-fluoro-6,7-dimethoxyquinazolin-2-yl)-3,8-diazabicyclo[3.2.1]octane-3-carboxylate (2-2)

To a mixture of 2-chloro-8-fluoro-6,7-dimethoxyquinazolin-4-amine (1 equiv) and TEA (1.5 equiv) in isopentyl alcohol (10 vol) is added tert-butyl 3,8-diazabicyclo[3.2.1]octane-3-carboxylate (2 equiv). The reaction mixture is stirred at 120° C. for 16 hours and then concentrated. The residue is re-crystallized from MTBE to afford compound 2-2.

Step 2: 2-(3,8-Diazabicyclo[3.2.1]octan-8-yl)-8-fluoro-6,7-dimethoxyquinazolin-4-amine (2-3)

To a solution of compound 2-2 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 2-3.

Step 3: (3R)-1-(8-(4-Amino-8-fluoro-6,7-dimethoxyquinazolin-2-yl)-3,8-diazabicyclo[3.2.1]octan-3-yl)-3-(ethylamino)-3-(4-fluorophenyl)propan-1-one (2-5)

To a solution of compound 2-3 (1 equiv) and compound 2-4 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 2-5.

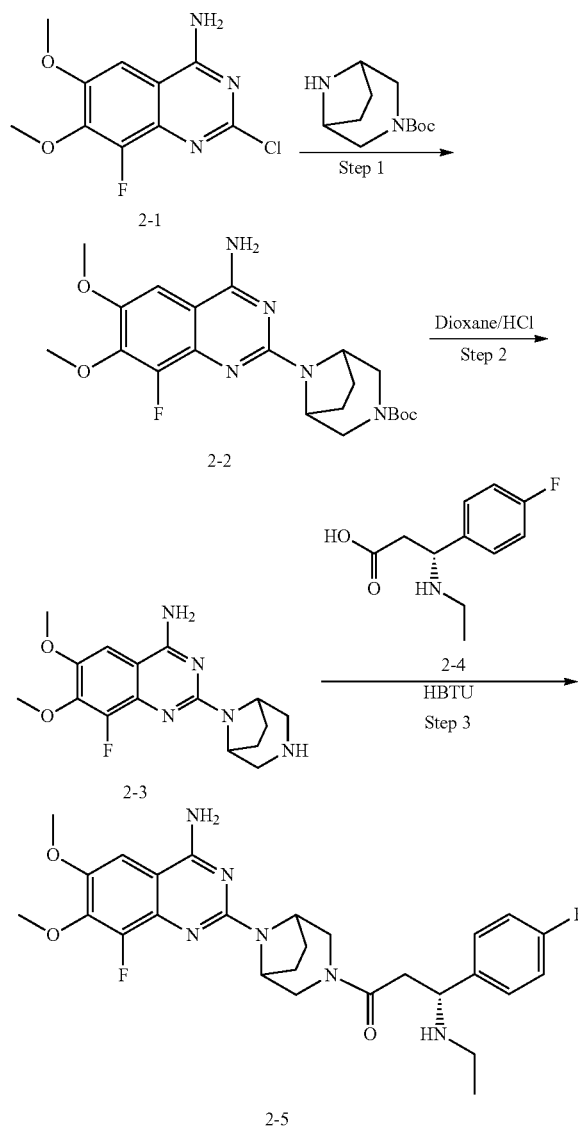

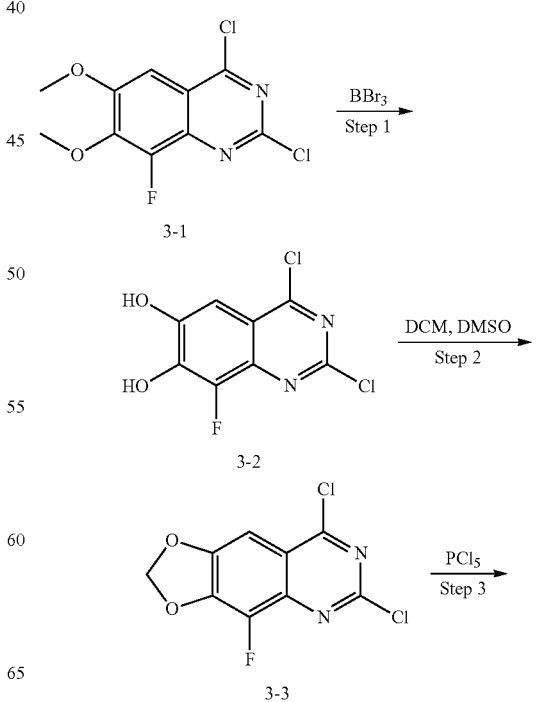

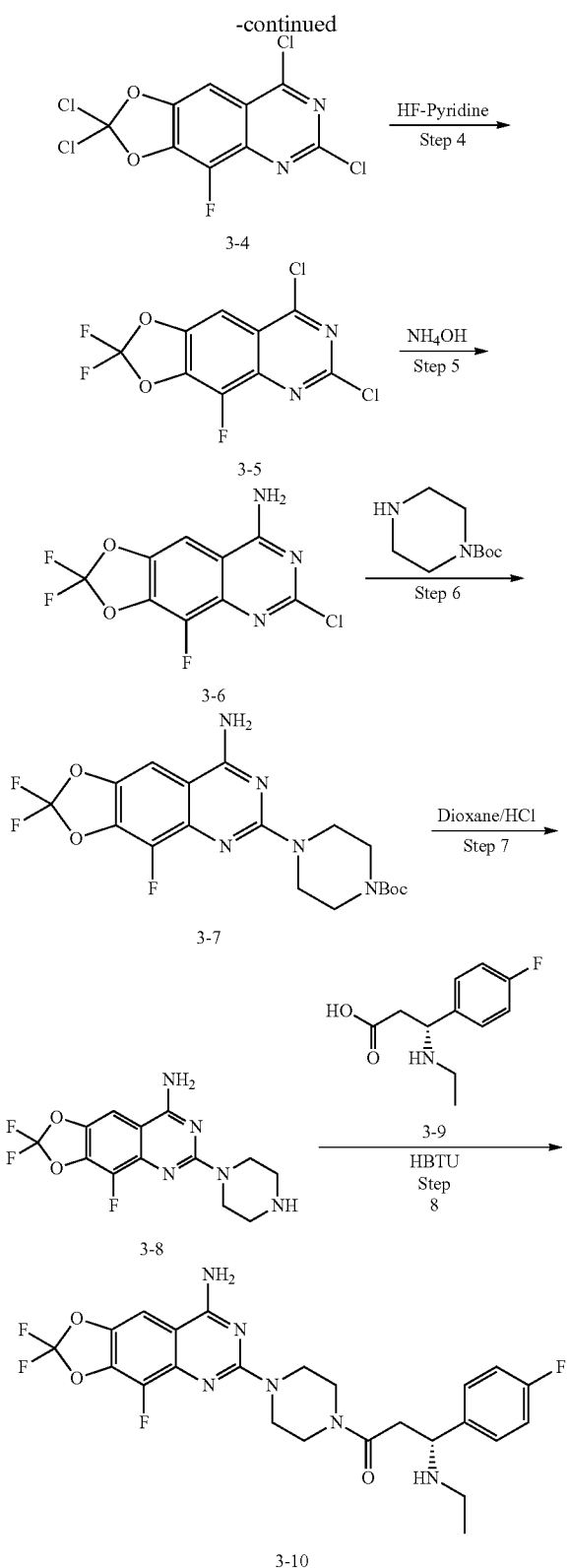

BBr₃ in DCM (2 equiv). The reaction mixture is stirred at room temperature for 4 hours and then concentrated. The residue is re-crystallized from MTBE to afford compound 3-2.

Step 2: 6,8-Dichloro-4-fluoro-[1,3]dioxolo[4,5-g]quinazoline (3-3)

To a solution of compound 3-2 (1 equiv) and NaOH (4 equiv) in DMSO (3 vol) at 80° C. is added a preheated mixture of dichloromethane (1.5 vol) and DMSO (2 vol). The reaction mixture is stirred at 80° C. for 12 hours and then quenched with water. The resulting mixture is extracted with ethyl acetate. The organic layer is separated, dried over anhydrous Na₂SO₄, filtered and then concentrated. The residue is purified by column chromatography on silica gel to afford compound 3-3.

Step 3: 2,2,6,8-Tetrachloro-4-fluoro-[1,3]dioxolo[4,5-g]quinazoline (3-4)

To a solution of compound 3-3 (1 equiv) in toluene (10 vol) at 0° C. is added PCl₅ (2 equiv). The reaction mixture is stirred at 90° C. for 4 hours and then concentrated. The resulting mixture is quenched with saturated NaHCO₃ solution and extracted with ethyl acetate. The organic layer is separated, dried over anhydrous Na₂SO₄, filtered and then concentrated. The residue is purified by column chromatography on silica gel to afford compound 3-4.

Step 4: 6,8-Dichloro-2,2,4-trifluoro-[1,3]dioxolo[4,5-g]quinazoline (3-5)

A mixture of compound 3-4 (1 equiv) and HF-pyridine (5 equiv) is stirred at −10° C. for 5 hours and then quenched with ice. The resulting mixture is extracted with ethyl acetate. The organic layer is separated, dried over anhydrous Na₂SO₄, filtered and then concentrated. The residue is purified by column chromatography on silica gel to afford compound 3-5.

Step 5: 6-Chloro-2,2,4-trifluoro-[1,3]dioxolo[4,5-g]quinazolin-8-amine (3-6)

To a solution of compound 3-5 (1 equiv) in THF (10 vol) is added 25% solution of NH₄OH (5 vol). The reaction mixture is stirred at 40° C. for 16 hours and then concentrated. The residue is taken in water and stirred for 30 minutes. The resultant solid is filtered and dried to afford compound 3-6.

Step 6: tert-Butyl 4-(8-amino-2,2,4-trifluoro-[1,3]dioxolo[4,5-g]quinazolin-6-yl)piperazine-1-carboxylate (3-7)

To a solution of compound 3-6 (1 equiv) and TEA (1.5 equiv) in isopentyl alcohol (10 vol) is added tert-butyl piperazine-1-carboxylate (2 equiv). The reaction mixture is stirred at 120° C. for 16 hours and then concentrated. The residue is re-crystallized from MTBE to afford compound 3-7.

Step 7: 2,2,4-Trifluoro-6-(piperazin-1-yl)-[1,3]dioxolo[4,5-g]quinazolin-8-amine (3-8)

To a solution of compound 3-7 (1 equiv) in 1,4-dioxane (2 vol) at 0° C. is added 4 N HCl in dioxane (10 vol). The Step 1: 2,4-Dichloro-8-fluoroquinazoline-6,7-diol (3-2)

To a solution of 2,4-dichloro-8-fluoro-6,7-dimethoxyquinazoline (1 equiv) in DCM (10 vol) at 0° C. is added 1 M reaction mixture is stirred at room temperature for 4 hours and then concentrated. The residue is taken up in MTBE and stirred for 30 minutes. The resultant solid is filtered and dried to afford compound 3-8.

Step 8: (R)-1-(4-(8-Amino-2,2,4-trifluoro-[1,3]di-oxolo[4,5-g]quinazolin-6-yl)piperazin-1-yl)-3-(eth-ylamino)-3-(4-fluorophenyl)propan-1-one (3-10)

To a solution of compound 3-8 (1 equiv) and compound 3-9 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 3-10.

Step 1: tert-Butyl 4-(4-amino-8-fluoro-6,7-dime-thoxyquinazolin-2-yl)-3,6-dihydropyridine-1(2H)-carboxylate (4-2)

To a mixture of 2-chloro-8-fluoro-6,7-dimethoxyquinazo-lin-4-amine (1 equiv) and tert-butyl 4-(4,4,5,5-tetramethyl-1,3,2-dioxaborolan-2-yl)-3,6-dihydropyridine-1(2H)-car-boxylate (1.1 equiv) in DMF (10 vol) is added $PdCl_2(PPh_3)_2$ (0.1 equiv) and potassium acetate (2 equiv). After degassing with nitrogen, the resulting mixture is stirred at 100° C. for 12 hours and then cooled to room temperature. Water is added to the reaction mixture and the resulting mixture is extracted with ethyl acetate. The organic layer is separated, dried over anhydrous $Na_2SO_4$, filtered and then concentrated. The residue is purified by column chromatography on silica gel to afford compound 4-2.

Step 2: 8-Fluoro-6,7-dimethoxy-2-(1,2,3,6-tetrahy-dropyridin-4-yl)quinazolin-4-amine (4-3)

To a solution of compound 4-2 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 4-3.

Step 3: (R)-1-(4-(4-Amino-8-fluoro-6,7-dimethoxy-quinazolin-2-yl)-3,6-dihydropyridin-1(2H)-yl)-3-(ethylamino)-3-(4-fluorophenyl)propan-1-one (4-5)

To a solution of compound 4-3 (1 equiv) and compound 4-4 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 4-5.

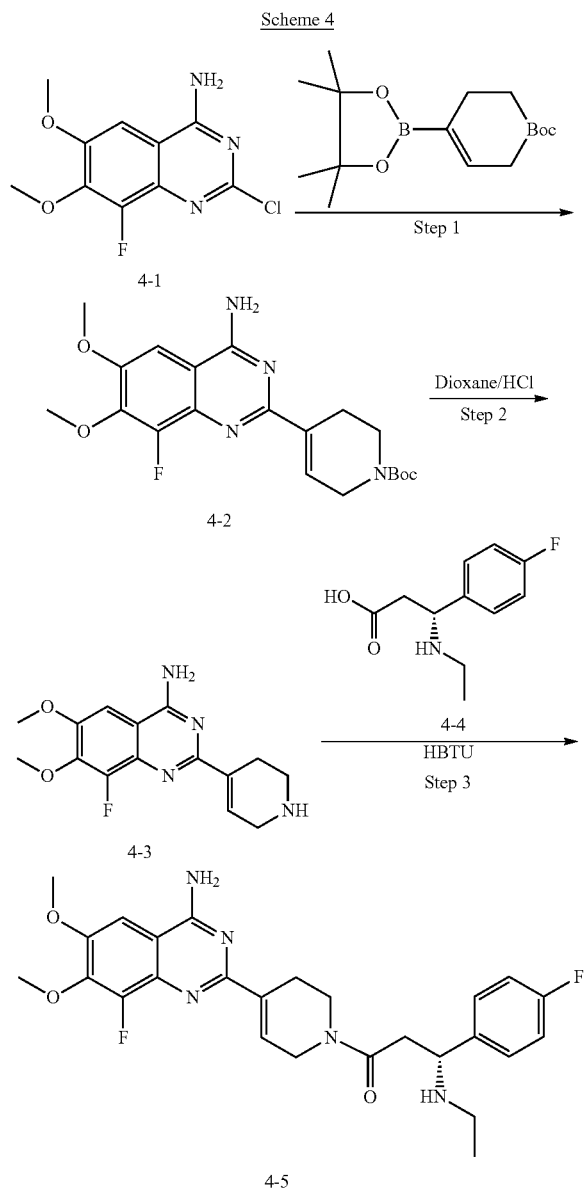

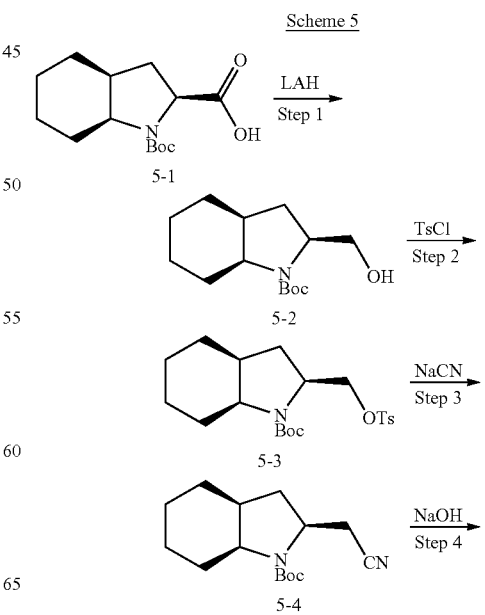

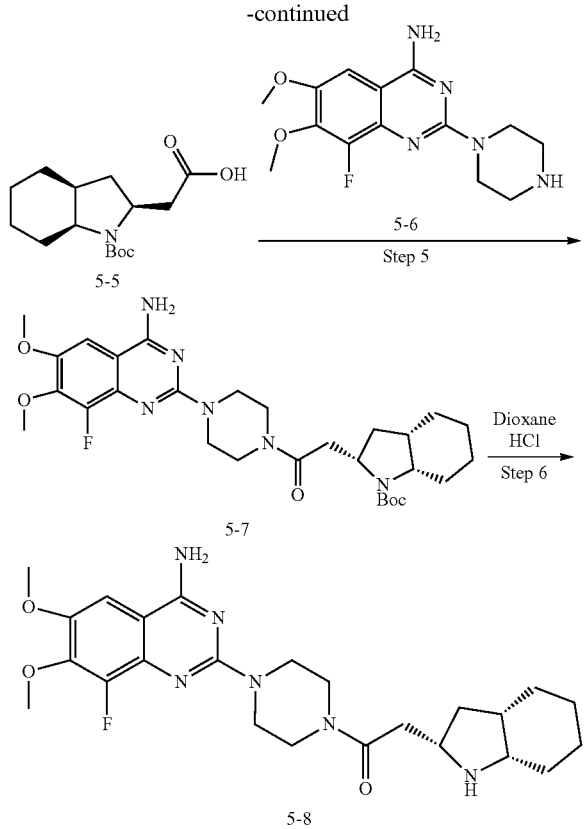

Step 1: tert-Butyl (2S,3aS,7aS)-2-(hydroxymethyl) octahydro-1H-indole-1-carboxylate (5-2)

To a solution of (2S,3aS,7aS)-1-(tert-butoxycarbonyl)octahydro-1H-indole-2-carboxylic acid (I equiv) in THF (50 vol) at 0° C. under nitrogen atmosphere i s added LiAlH$_4$(2.5 equiv). The reaction mixture is stirred at room temperature for 16 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 5-2.

Step 2: tert-Butyl (2S,3aS,7aS)-2-((tosyloxy) methyl)octahydro-1H-indole-1-carboxylate (5-3)

To a solution of compound 5-2 (1 equiv), TEA (3 equiv) and DMAP (0.1 equiv) in DCM (10 vol) at 0° C. is added 4-toluenesulfonyl chloride (1.5 equiv). The reaction mixture is stirred at room temperature for 12 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 5-3.

Step 3: tert-Butyl (2S,3aS,7aS)-2-(cyanomethyl) octahydro-1H-indole-1-carboxylate (5-4)

To a solution of compound 5-3 (1 equiv) in DMSO (10 vol) is added NaCN (3 equiv). The reaction mixture is stirred at 90° C. for 16 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 5-4.

Step 4: 2-02S,3aS,7aS)-1-(tert-Butoxycarbonyl) octahydro-1H-indol-2-yl)acetic Acid (5-5)

To a solution of compound 5-4 (1 equiv) in MeOH (30 vol) at 0° C. is added 30% aqueous NaOH solution (4 vol). The reaction mixture is stirred at 100° C. for 16 hours and then concentrated. The resulting mixture is acidified with 1.5 N HCl and extracted with ethyl acetate. The organic layer is separated, dried over anhydrous Na$_2$SO$_4$, filtered and then concentrated. The residue is purified by column chromatography on silica gel to afford compound 5-5.

Step 5: tert-Butyl (2S,3aS,7aS)-2-(2-(4-(4-amino-8-fluoro-6,7-dimethoxyquinazolin-2-yl)piperazin-1-yl)-2-oxoethyl)octahydro-1H-indole-1-carboxylate (5-7)

To a solution of compound 5-5 (1 equiv) and compound 5-6 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 5-7.

Step 6: 1-(4-(4-Amino-8-fluoro-6,7-dimethoxyquinazolin-2-yl)piperazin-1-yl)-2-((2S,3aS,7aS)-octahydro-1H-indol-2-yl)ethan-1-one (5-8)

To a solution of compound 5-7 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 5-8.

Scheme 6

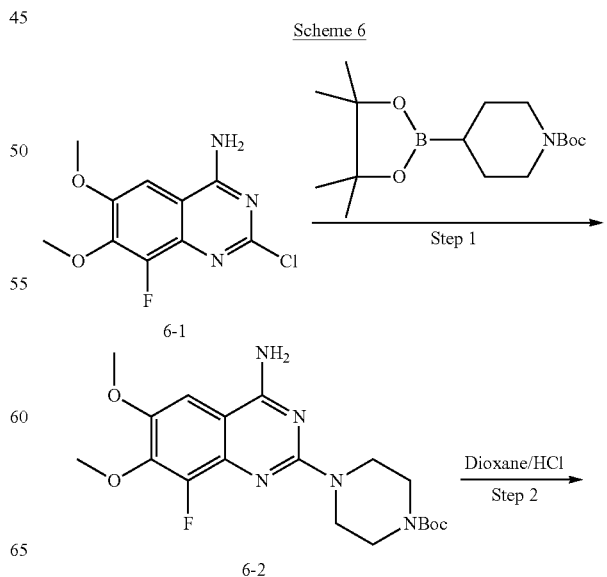

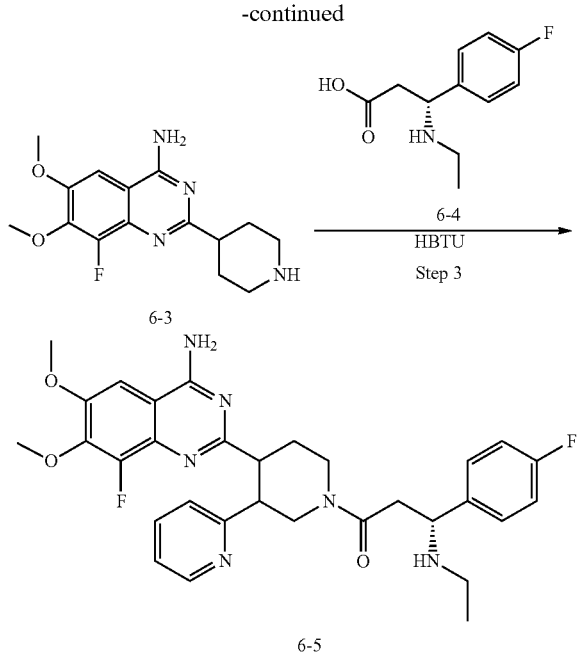

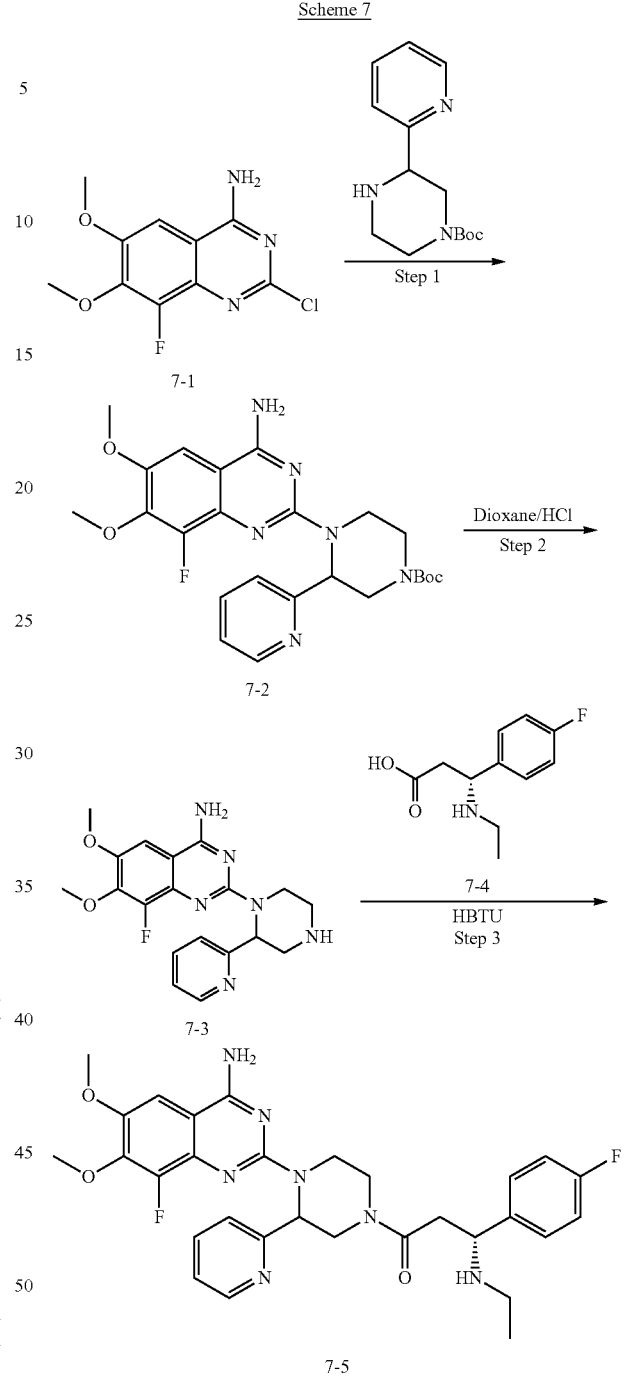

Scheme 7

Step 1: tert-Butyl 4-(4-amino-8-fluoro-6,7-dimethoxyquinazolin-2-yl)piperidine-1-carboxylate (6-2)

To a mixture of 2-chloro-8-fluoro-6,7-dimethoxyquinazolin-4-amine (1 equiv) and tert-butyl 4-(4,4,5,5-tetramethyl-1,3,2-dioxaborolan-2-yl)piperidine-1-carboxylate (1.1 equiv) in DMF (10 vol) is added $PdCl_2(PPh_3)_2$ (0.1 equiv) and potassium acetate (2 equiv). After degassing with nitrogen, the resulting mixture is stirred at 100° C. for 12 hours and then cooled to room temperature. Water is added to the reaction mixture and the resulting mixture is extracted with ethyl acetate. The organic layer is separated, dried over anhydrous $Na_2SO_4$, filtered and then concentrated. The residue is purified by column chromatography on silica gel to afford compound 6-2.

Step 2: 8-Fluoro-6,7-dimethoxy-2-(piperidin-4-yl)quinazolin-4-amine (6-3)

To a solution of compound 6-2 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 6-3.

Step 3: (R)-1-(4-(4-Amino-8-fluoro-6,7-dimethoxyquinazolin-2-yl)piperidin-1-yl)-3-(ethylamino)-3-(4-fluorophenyl)propan-1-one (6-5)

To a solution of compound 6-3 (1 equiv) and compound 6-4 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 6-5.

Step 1: tert-Butyl 4-(4-amino-8-fluoro-6,7-dimethoxyquinazolin-2-yl)-3-(pyridin-2-yl)piperazine-1-carboxylate (7-2)

To a mixture of 2-chloro-8-fluoro-6,7-dimethoxyquinazolin-4-amine (1 equiv) and TEA (1.5 equiv) in isopentyl alcohol (10 vol) is added tert-butyl 3-(pyridin-2-yl)piperazine-1-carboxylate (2 equiv). The reaction mixture is stirred at 120° C. for 16 hours and then concentrated. The residue is re-crystallized from MTBE to afford compound 7-2.

Step 2: 8-Fluoro-6,7-dimethoxy-2-(2-(pyridin-2-yl)piperazin-1-yl)quinazolin-4-amine (7-3)

To a solution of compound 7-2 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 7-3.

Step 3: (3R)-1-(4-(4-Amino-8-fluoro-6,7-dimethoxyquinazolin-2-yl)-3-(pyridin-2-yl)piperazin-1-yl)-3-(ethylamino)-3-(4-fluorophenyl)propan-1-one (7-5)

To a solution of compound 7-3 (1 equiv) and compound 7-4 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 7-5.

Scheme 8

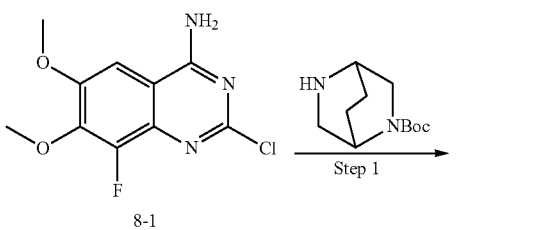

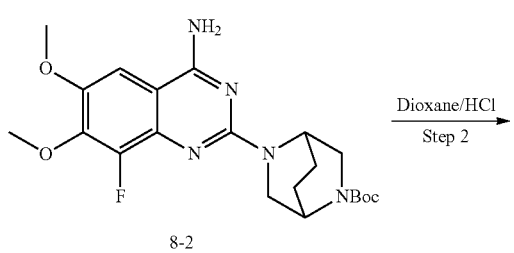

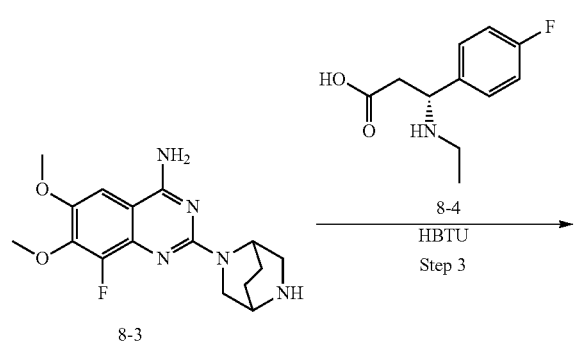

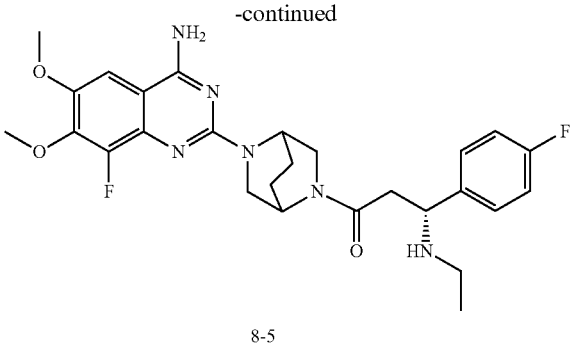

8-5

Step 1: tert-Butyl 5-(4-amino-8-fluoro-6,7-dimethoxyquinazolin-2-yl)-2,5-diazabicyclo[2.2.2]octane-2-carboxylate (8-2)

To a mixture of 2-chloro-8-fluoro-6,7-dimethoxyquinazolin-4-amine (1 equiv) and TEA (1.5 equiv) in isopentyl alcohol (10 vol) is added tert-butyl 2,5-diazabicyclo[2.2.2]octane-2-carboxylate (2 equiv). The reaction mixture is stirred at 120° C. for 16 hours and then concentrated. The residue is re-crystallized from MTBE to afford compound 8-2.

Step 2: tert-Butyl 5-(4-amino-8-fluoro-6,7-dimethoxyquinazolin-2-yl)-2,5-diazabicyclo[2.2.2]octane-2-carboxylate (8-3)

To a solution of compound 8-2 (1 equiv) in 1,4-dioxane (2 vol) at 0° C. is added 4 N HCl in dioxane (10 vol). The reaction mixture is stirred at room temperature for 4 hours and then concentrated. The residue is taken in MTBE and stirred for 30 minutes. The resultant solid is filtered and dried to afford compound 8-3.

Step 3: (3R)-1-(5-(4-Amino-8-fluoro-6,7-dimethoxyquinazolin-2-yl)-2,5-diazabicyclo[2.2.2]octan-2-yl)-3-(ethylamino)-3-(4-fluorophenyl)propan-1-one (8-5)

To a solution of compound 8-3 (1 equiv) and compound 8-4 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 8-5.

Scheme 9

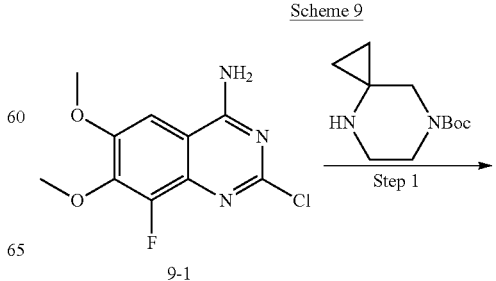

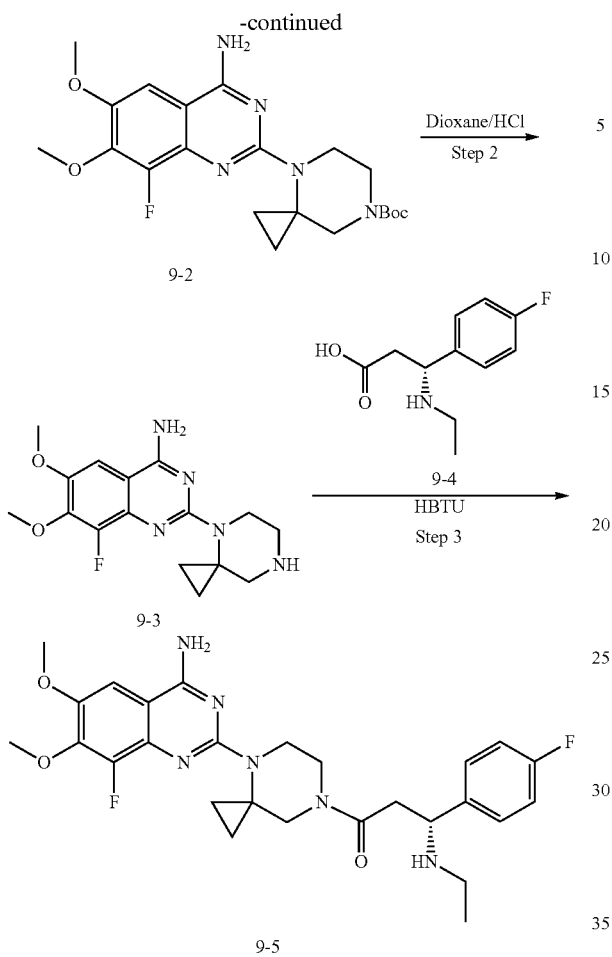

at room temperature for 16 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 9-5.

Scheme 10

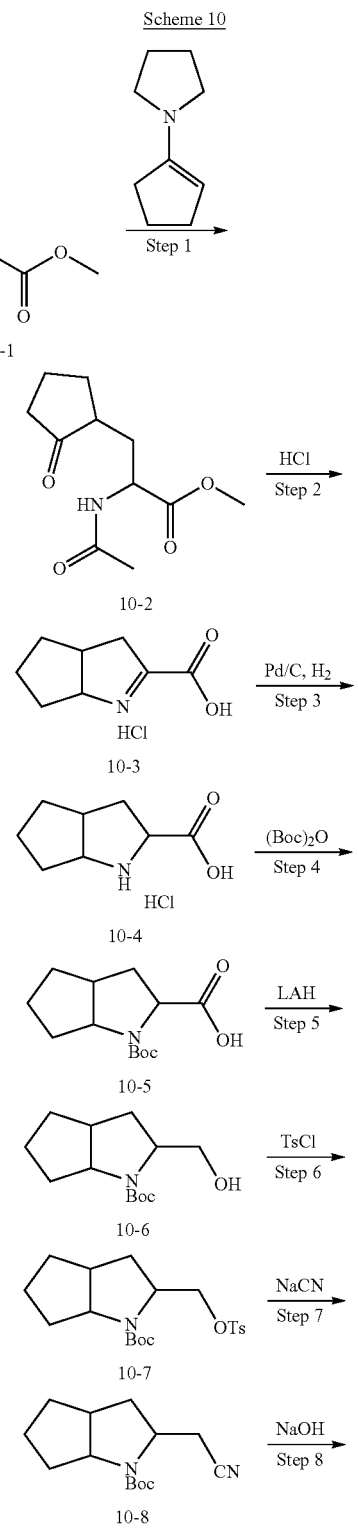

Step 1: tert-Butyl 4-(4-amino-8-fluoro-6,7-dimethoxyquinazolin-2-yl)-4,7-diazaspiro[2.5]octane-7-carboxylate (9-2)

To a mixture of 2-chloro-8-fluoro-6,7-dimethoxyquinazolin-4-amine (1 equiv) and TEA (1.5 equiv) in isopentyl alcohol (10 vol) is added tert-butyl 4,7-diazaspiro[2.5]octane-7-carboxylate (2 equiv). The reaction mixture is stirred at 120° C. for 16 hours and then concentrated. The residue is re-crystallized from MTBE to afford compound 9-2.

Step 2: 8-Fluoro-6,7-dimethoxy-2-(4,7-diazaspiro[2.5]octan-4-yl)quinazolin-4-amine (9-3)

To a solution of compound 9-2 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 9-3.

Step 3: (R)-1-(4-(4-Amino-8-fluoro-6,7-dimethoxyquinazolin-2-yl)-4,7-diazaspiro[2.5]octan-7-yl)-3-(ethylamino)-3-(4-fluorophenyl)propan-1-one (9-5)

To a solution of compound 9-3 (1 equiv) and compound 9-4 (1 equiv) in DMF (10 vol) at 0° C. is added DIPEA (5 equiv) and HBTU (1.2 equiv). The reaction mixture is stirred

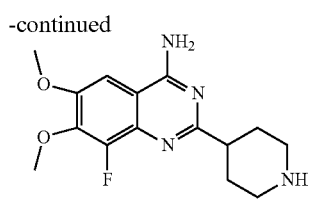

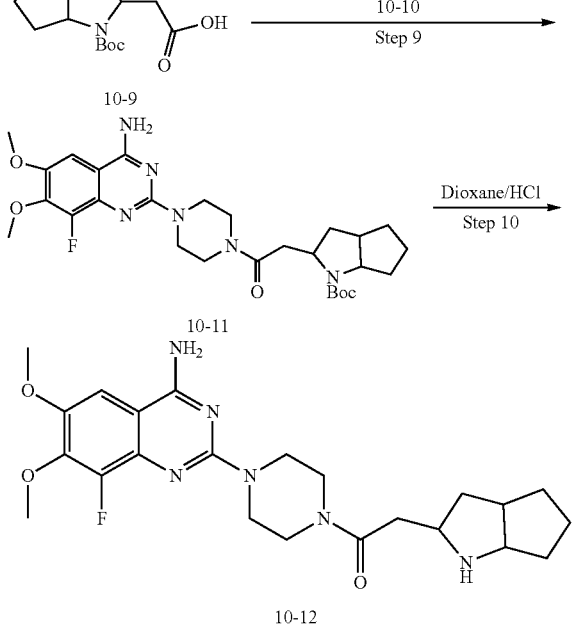

Step 1: Methyl 2-acetamido-3-(2-oxocyclopentyl)propanoate (10-2)

To a solution of methyl 2-(chloromethyl)-4-oxopentanoate (1 equiv) and 1-(cyclopent-1-en-1-yl)pyrrolidine (1.2 equiv) in toluene (10 vol) at 0° C. is added TEA (2.5 equiv). The reaction mixture is stirred at room temperature for 6 hours and then concentrated. The resulting mixture is acidified with concentrated HCl and extracted with ethyl acetate. The organic layer is separated, dried over anhydrous $Na_2SO_4$, filtered and then concentrated. The residue is purified by column chromatography on silica gel to afford compound 10-2.

Step 2: 3,3a,4,5,6,6a-Hexahydrocyclopenta[b]pyrrole-2-carboxylic acid hydrochloride (10-3)

To a solution of compound 10-2 (1 equiv) and 5 N HCl (4 vol) is stirred at room temperature for 5 hours and then concentrated to afford compound 10-3.

Step 3: Octahydrocyclopenta[b]pyrrole-2-carboxylic acid hydrochloride (10-4)

To a solution of compound 10-3 (1 equiv) in glacial acetic acid (10 Vol) is added 10% Pd/C. The reaction mixture is hydrogenated under pressure of 5 kg/cm² at 60° C. for 12 h. The resulting mixture is filtered and concentrated. The residue is taken in acetone and stirred for 30 minutes. The resultant solid is filtered and dried to afford compound 10-4.

Step 4: 1-(tert-Butoxycarbonyl)octahydrocyclopenta[b]pyrrole-2-carboxylic Acid (10-5)

To a solution of compound 10-4 (1 equiv) and 2 M NaOH (2 equiv) in THF (10 vol) at 0° C. is added Boc anhydride (1.2 equiv). The reaction mixture is stirred at room temperature for 16 hours and then quenched with 1 M HCl. The resulting mixture is extracted with ethyl acetate. The organic layer is separated, dried over anhydrous $Na_2SO_4$, filtered and then concentrated. The residue is re-crystallized from MTBE to afford compound 10-5.

Step 5: tert-Butyl 2-(hydroxymethyl)hexahydrocyclopenta[b]pyrrole-1(2H)-carboxylate (10-6)

To a solution of compound 10-5 (1 equiv) in THF (50 vol) at 0° C. under nitrogen atmosphere is added $LiAlH_4$ (2.5 equiv). The reaction mixture is stirred at room temperature for 16 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 10-6.

Step 6: tert-Butyl 2-((tosyloxy)methyl)hexahydrocyclopenta[b]pyrrole-1(2H)-carboxylate (10-7)

To a solution of compound 10-6 (1 equiv), TEA (3 equiv) and DMAP (0.1 equiv) in DCM (10 vol) at 0° C. is added 4-toluenesulfonyl chloride (1.5 equiv). The reaction mixture is stirred at room temperature for 12 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 10-7.

Step 7: tert-Butyl 2-(cyanomethyl)hexahydrocyclopenta[b]pyrrole-1(2H)-carboxylate (10-8)

To a solution of compound 10-7 (1 equiv) in DMSO (10 vol) is added NaCN (3 equiv). The reaction mixture is stirred at 90° C. for 16 hours and then quenched with water. The resulting mixture is extracted with ethyl acetate. The organic layer is separated, dried over anhydrous $Na_2SO_4$, filtered and then concentrated. The residue is purified by column chromatography on silica gel to afford compound 10-8.

Step 8: 2-(1-(tert-Butoxycarbonyl)octahydrocyclopenta[b]pyrrol-2-yl)acetic Acid (10-9)

To a solution of compound 10-8 (1 equiv) in MeOH (30 vol) at 0° C. is added 30% aqueous NaOH solution (4 vol). The reaction mixture is stirred at 100° C. for 16 hours and then concentrated. The resulting mixture is acidified with 1.5 N HCl and extracted with ethyl acetate. The organic layer is separated, dried over anhydrous $Na_2SO_4$, filtered and then concentrated. The residue is purified by column chromatography on silica gel to afford compound 10-9.

Step 9: tert-Butyl 2-(2-(4-(4-amino-8-fluoro-6,7-dimethoxyquinazolin-2-yl)piperazin-1-yl)-2-oxoethyl)hexahydrocyclopenta[b]pyrrole-1(2H)-carboxylate (10-11)

To a solution of compound 10-9 (1 equiv) and compound 10-10 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous Na₂SO₄, filtered and then concentrated. The residue is purified by column chromatography on silica gel to afford compound 10-11.

Step 10: 1-(4-(4-Amino-8-fluoro-6,7-dimethoxyquinazolin-2-yl)piperazin-1-yl)-2-(octahydrocyclopenta[b]pyrrol-2-yl)ethan-1-one (10-12)

To a solution of compound 10-11 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 10-12.

Scheme 11

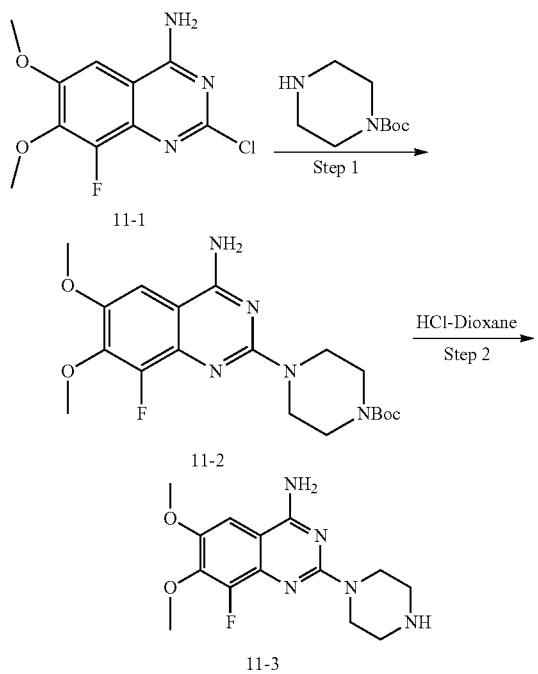

Step 1: tert-Butyl 4-(4-amino-8-fluoro-6,7-dimethoxyquinazolin-2-yl)piperazine-1-carboxylate (11-2)

To a mixture of 2-chloro-8-fluoro-6,7-dimethoxyquinazolin-4-amine (1 equiv) and TEA (1.5 equiv) in isopentyl alcohol (10 vol) is added tert-butyl piperazine-1-carboxylate (2 equiv). The reaction mixture is stirred at 120° C. for 16 hours and then concentrated. The residue is re-crystallized from MTBE to afford compound 11-2.

Step 2: 8-Fluoro-6,7-dimethoxy-2-(piperazin-1-yl)quinazolin-4-amine (11-3)

To a solution of compound 22-2 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 11-3.

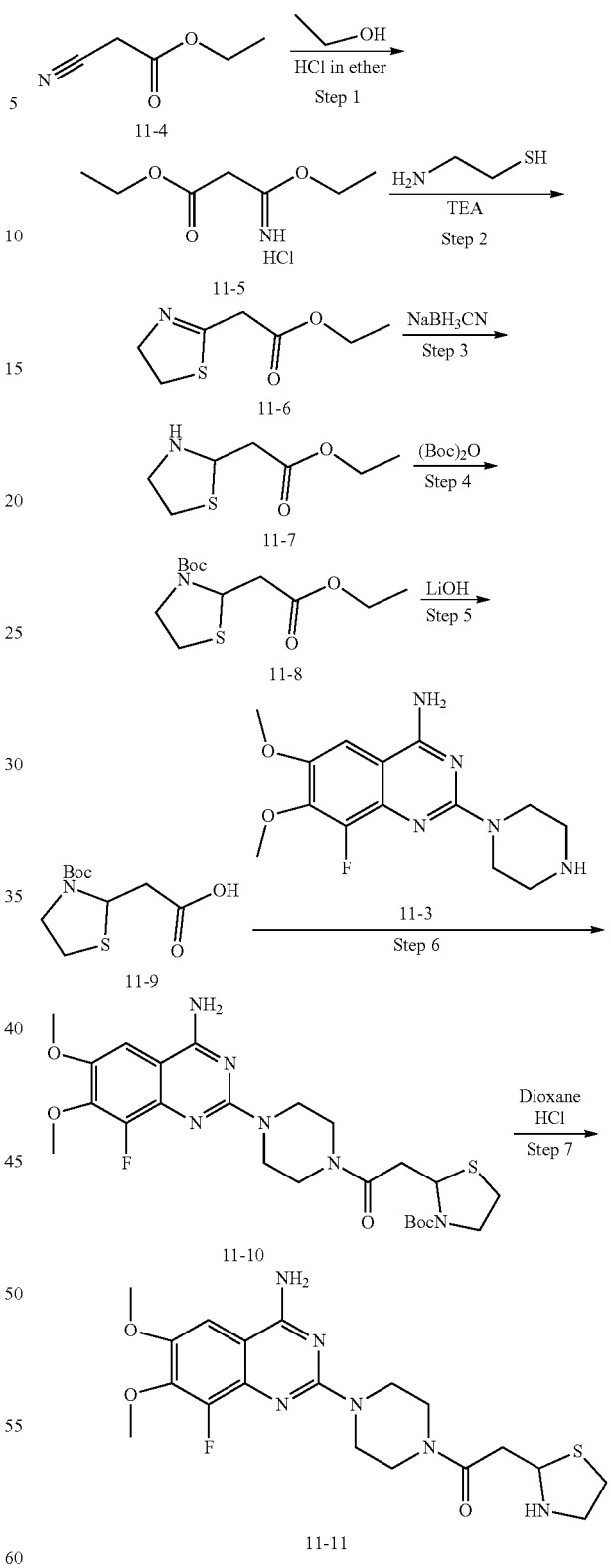

Step 1: Ethyl 3-ethoxy-3-iminopropanoate hydrochloride (11-5)

To a solution of compound 11-4 (1 equiv) and ethanol (1 equiv) in anhydrous diethyl ether (5 vol) at 0° C. is bubbled with HCl gas until saturated. The reaction mixture is stirred at room temperature for 16 hours and then concentrated. The residue is re-crystallized from MTBE to afford compound 11-5.

Step 2: Ethyl 2-(4,5-dihydrothiazol-2-yl)acetate (11-6)

To a solution of compound 11-5 (1 equiv) and 2-aminoethane-1-thiol hydrochloride (1 equiv) in ethanol (10 vol) at 0° C. is added TEA (5 equiv). The reaction mixture is stirred at 80° C. for 3 hours and then concentrated. The residue is purified by column chromatography on silica gel to afford compound 11-6.

Step 3: Ethyl 2-(thiazolidin-2-yl)acetate (11-7)

To a solution of compound 11-6 (1 equiv) and 4.5 M HCl in MeOH (2 equiv) in MeOH (10 vol) at 0° C. is added sodium cyanoborohydride (1 equiv). The reaction mixture is stirred at 0° C. for 1 hour and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 11-7.

Step 4: tert-Butyl 2-(2-ethoxy-2-oxoethyl)thiazolidine-3-carboxylate (11-8)

To a solution of compound 11-7 (1 equiv), DMAP (0.1 equiv) and TEA (2 equiv) in DCM (10 vol) at 0° C. is added Boc anhydride (2 equiv). The reaction mixture is stirred at room temperature for 16 hours and then quenched with water. The resulting mixture is extracted with ethyl acetate. The organic layer is separated, dried over anhydrous Na$_2$SO$_4$, filtered and then concentrated. The residue is re-crystallized from MTBE to afford compound 11-8.

Step 5: 2-(3-(tert-Butoxycarbonyl)thiazolidin-2-yl)acetic Acid (11-9)

To a solution of compound 11-8 (1 equiv) in THF/water (8:2) at 0° C. is added LiOH (3 equiv). The reaction mixture is stirred at room temperature for 2 hours and then quenched with 1 M citric acid. The resulting mixture is extracted with ethyl acetate. The organic layer is separated, dried over anhydrous Na$_2$SO$_4$, filtered and then concentrated. The residue is re-crystallized from MTBE to afford compound 11-9.

Step 6: tert-Butyl 2-(2-(4-(4-amino-8-fluoro-6,7-dimethoxyquinazolin-2-yl)piperazin-1-yl)-2-oxoethyl)thiazolidine-3-carboxylate (11-10)

To a solution of compound 11-9 (1 equiv) and compound 11-3 (1 equiv) in DMF (10 vol) at 0° C. is added DIPEA (5 equiv) and HBTU (1.2 equiv). The reaction mixture is stirred at room temperature for 16 hours and then quenched with water. The resulting mixture is extracted with ethyl acetate. The organic layer is separated, dried over anhydrous Na$_2$SO$_4$, filtered and then concentrated. The residue is purified by column chromatography on silica gel to afford compound 11-10.

Step 7: 1-(4-(4-Amino-8-fluoro-6,7-dimethoxyquinazolin-2-yl)piperazin-1-yl)-2-(thiazolidin-2-yl)ethan-1-one (11-11)

To a solution of compound 11-10 (1 equiv) in 1,4-dioxane (2 vol) at 0° C. is added 4 N HCl in dioxane (10 vol). The reaction mixture is stirred at room temperature for 4 hours and then concentrated. The residue is taken up in MTBE and stirred for 30 minutes. The resultant solid is filtered and dried to afford compound 11-11.

Example 7. Non-Limiting Examples of A-C-L-B Combinations

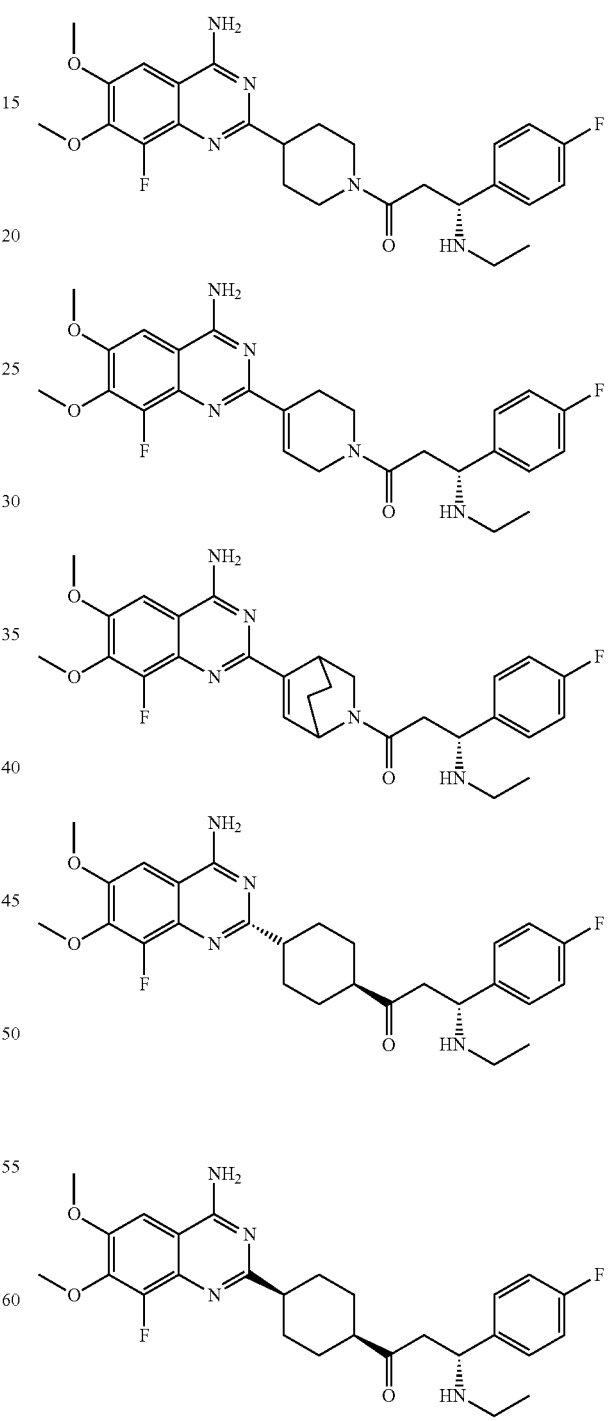

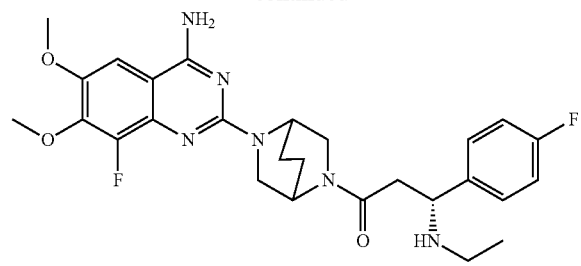
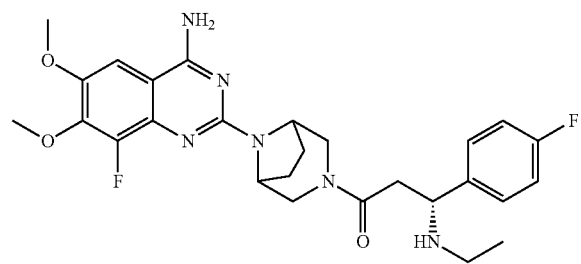
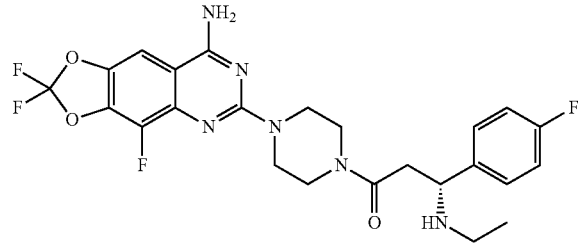
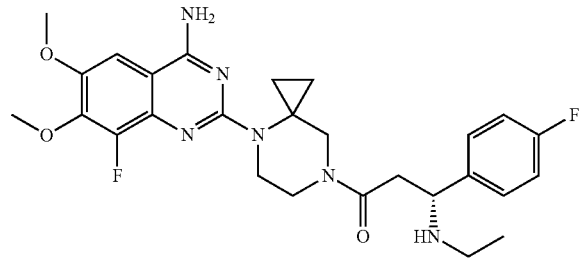
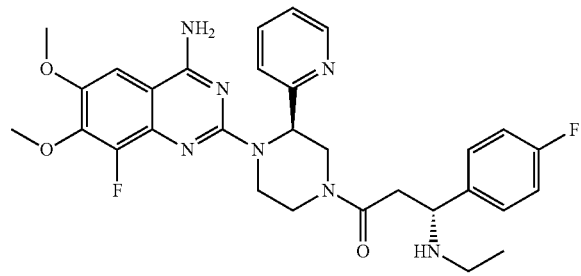
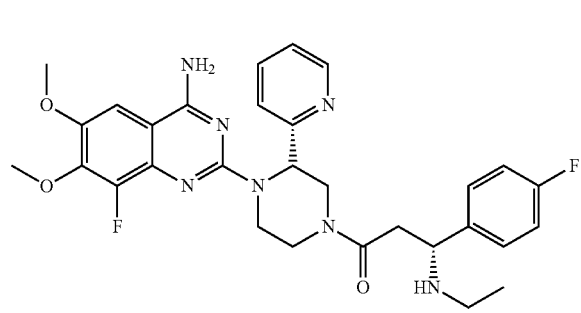
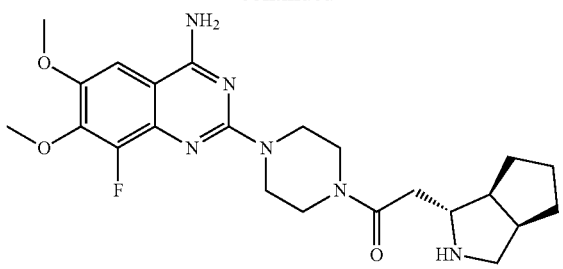
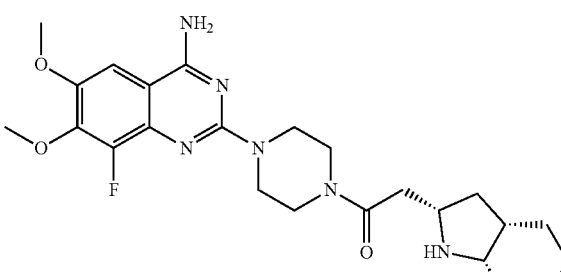
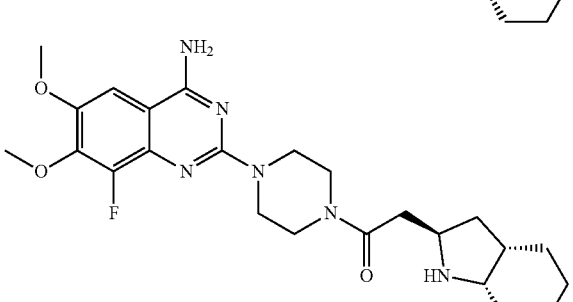
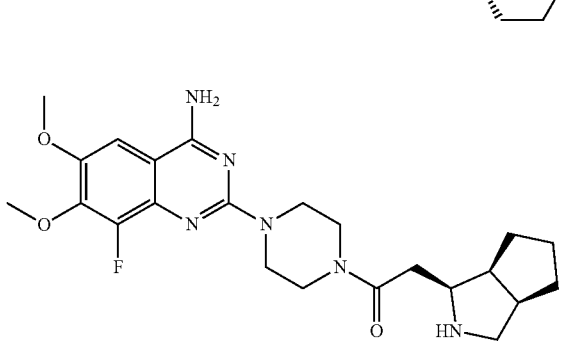
Example 8. Synthesis of Compounds of the Present Invention
Scheme 12: Synthesis of 1-(4-(4-Amino-8-fluro-6,7-dimethoxyquinazolin-2-yl)piperazin-1-yl)-2-(thiazolidin-2-yl)ethan-1-one hydrochloride (COMPOUND 1)
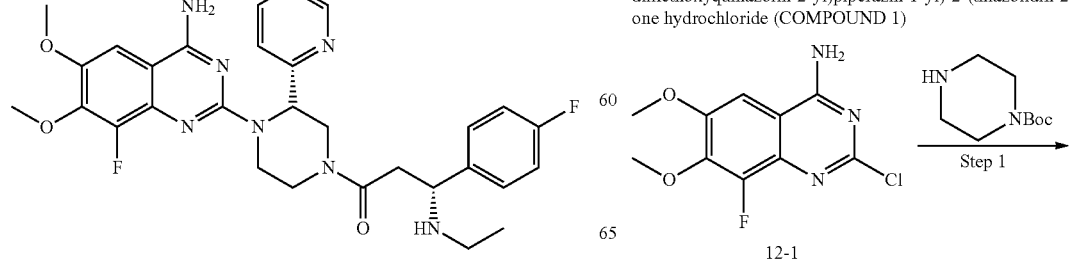
12-1

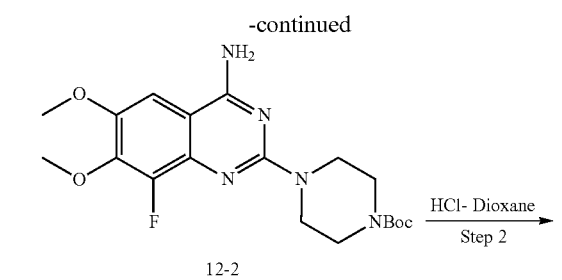

12-2

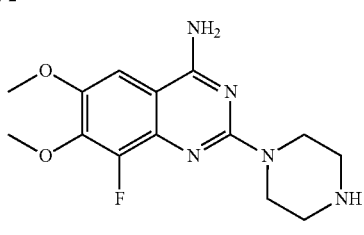

12-3

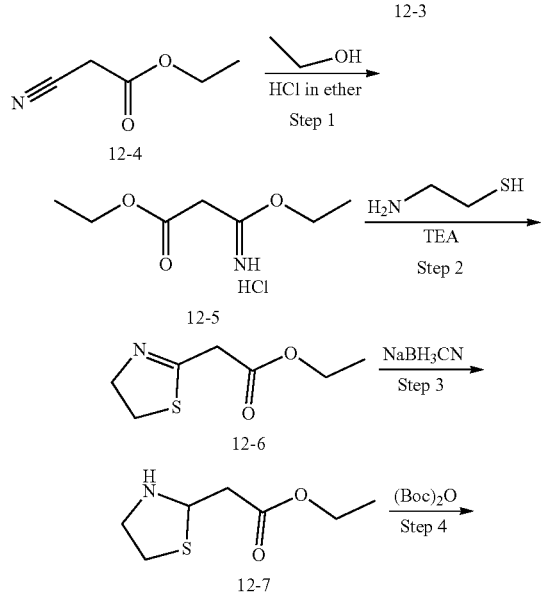

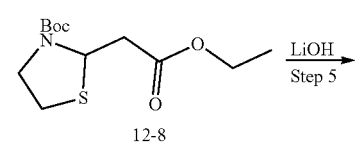

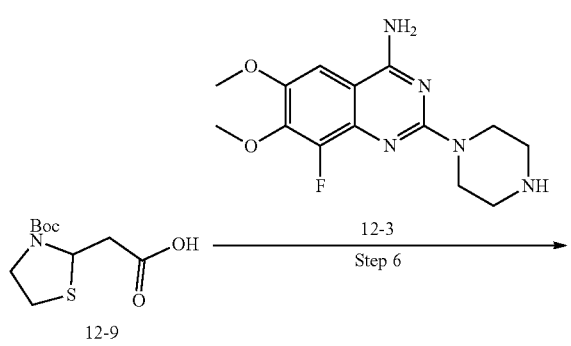

12-9

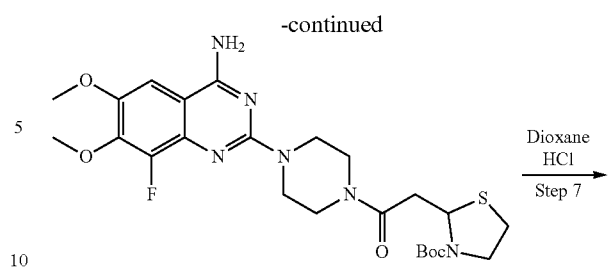

12-10

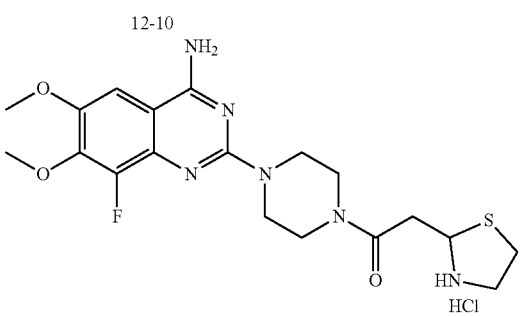

Compound 1

Step 1: tert-Butyl 4-(4-amino-8-fluoro-6,7-dimethoxyquinazolin-2-yl)piperazine-1-carboxylate (12-2)

To a mixture of 2-chloro-8-fluoro-6,7-dimethoxyquinazolin-4-amine (1 equiv) and TEA (1.5 equiv) in isopentyl alcohol (10 vol) was added tert-butyl piperazine-1-carboxylate (2 equiv). The reaction mixture was stirred at 120° C. for 16 hours and concentrated. The residue was re-crystallized from MTBE to afford compound 12-2.

Step 2: 8-Fluoro-6,7-dimethoxy-2-(piperazin-1-yl)quinazolin-4-amine (12-3)

To a solution of compound 12-2 (1 equiv) in 1,4-dioxane (2 vol) at 0° C. was added 4 N HCl in dioxane (10 vol). The reaction mixture was stirred at room temperature for 4 hours and then concentrated. The residue was taken in MTBE and stirred for 30 minutes. The resultant solid was filtered and dried to afford 12-3.

Step 1: Ethyl 3-ethoxy-3-iminopropanoate hydrochloride (12-5)

To a solution of ethyl 2-cyanoacetate (12-4, 1 equiv) and ethanol (1 equiv) in anhydrous diethyl ether (5 vol) at 0° C. was bubbled with HCl gas until saturated. The reaction mixture was stirred at room temperature for 16 hours and then concentrated. The residue was re-crystallized from MTBE to afford compound 12-5.

Step 2: Ethyl 2-(4,5-dihydrothiazol-2-yl)acetate (12-6)

To a solution of compound 12-5 (1 equiv) and 2-aminoethane-1-thiol hydrochloride (1 equiv) in ethanol (10 vol) at 0° C. was added TEA (5 equiv). The reaction mixture was stirred at 80° C. for 3 hours and then concentrated. The residue was purified by column chromatography on silica gel using hexane/EtOAc to afford compound 12-6.

Step 3: Ethyl 2-(thiazolidin-2-yl)acetate (12-7)

To a solution of compound 12-6 (1 equiv) and 4.5 M HCl in MeOH (2 equiv) in MeOH (10 vol) at 0° C. was added sodium cyanoborohydride (1 equiv). The reaction mixture was stirred at 0° C. for 1 hour and then quenched with water. The resulting mixture was extracted with ethyl acetate. The organic layer was separated, dried over anhydrous $Na_2SO_4$, filtered and then concentrated.

The residue was purified by column chromatography on silica gel using hexane/EtOAc to afford compound 12-7.

Step 4: tert-Butyl 2-(2-ethoxy-2-oxoethyl)thiazolidine-3-carboxylate (12-8)

To a solution of compound 12-7 (1 equiv), DMAP (0.1 equiv), and TEA (2 equiv) in DCM (10 vol) at 0° C. was added Boc anhydride (2 equiv). The reaction mixture was stirred at room temperature for 16 hours and then quenched with water. The resulting mixture was extracted with ethyl acetate. The organic layer was separated, dried over anhydrous $Na_2SO_4$, filtered and then concentrated. The residue was re-crystallized from MTBE to afford compound 12-8.

Step 5: 2-(3-(tert-Butoxycarbonyl)thiazolidin-2-yl) acetic Acid (12-9)

To a solution of compound 12-8 (1 equiv) in THF/water (8:2) at 0° C. was added LiOH (3 equiv). The reaction mixture was stirred at room temperature for 2 hours and then quenched with 1 M citric acid. The resulting mixture was extracted with ethyl acetate. The organic layer was separated, dried over anhydrous $Na_2SO_4$, filtered and then concentrated. The residue was re-crystallized from MTBE to afford compound 12-9.

Step 6: tert-Butyl 2-(2-(4-(4-amino-8-fluoro-6,7-dimethoxyquinazolin-2-yl)piperazin-1-yl)-2-oxoethyl)thiazolidine-3-carboxylate (12-10)

To a solution of compound 12-9 (1 equiv) and 12-3 (1 equiv) in DMF (10 vol) at 0° C. was added DIPEA (5 equiv) and HBTU (1.2 equiv). The reaction mixture was stirred at room temperature for 16 hours and then quenched with water. The resulting mixture was extracted with ethyl acetate. The organic layer was separated, dried over anhydrous $Na_2SO_4$, filtered and then concentrated. The residue was purified by column chromatography on silica gel using DCM/MeOH to afford compound 12-10.

Step 7: 1-(4-(4-Amino-8-fluoro-6,7-dimethoxyquinazolin-2-yl)piperazin-1-yl)-2-(thiazolidin-2-yl) ethan-1-one hydrochloride (COMPOUND 1)

To a solution of compound 12-10 (1 equiv) in 1,4-dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford COMPOUND 1.

$^1$H NMR (400 MHz, $CD_3OD$) δ 7.56 (s, 1H), 5.12 (d, J=8.8 Hz, 1H), 4.10 (s, 3H), 4.01-3.93 (m, 7H), 3.79-3.63 (m, 5H), 3.61-3.59 (m, 2H), 3.32-3.24 (m, 3H).

Scheme 13: Synthesis of 1-(4-(4-Amino-8-fluro-6,7-dimethoxyquinazolin-2-yl)piperazin-1-yl)-2-((2S,3aS,6aS)-octahydrocyclopental[b]pyrrol-2-yl)ethan-1-one hydrochloride (COMPOUND 2)

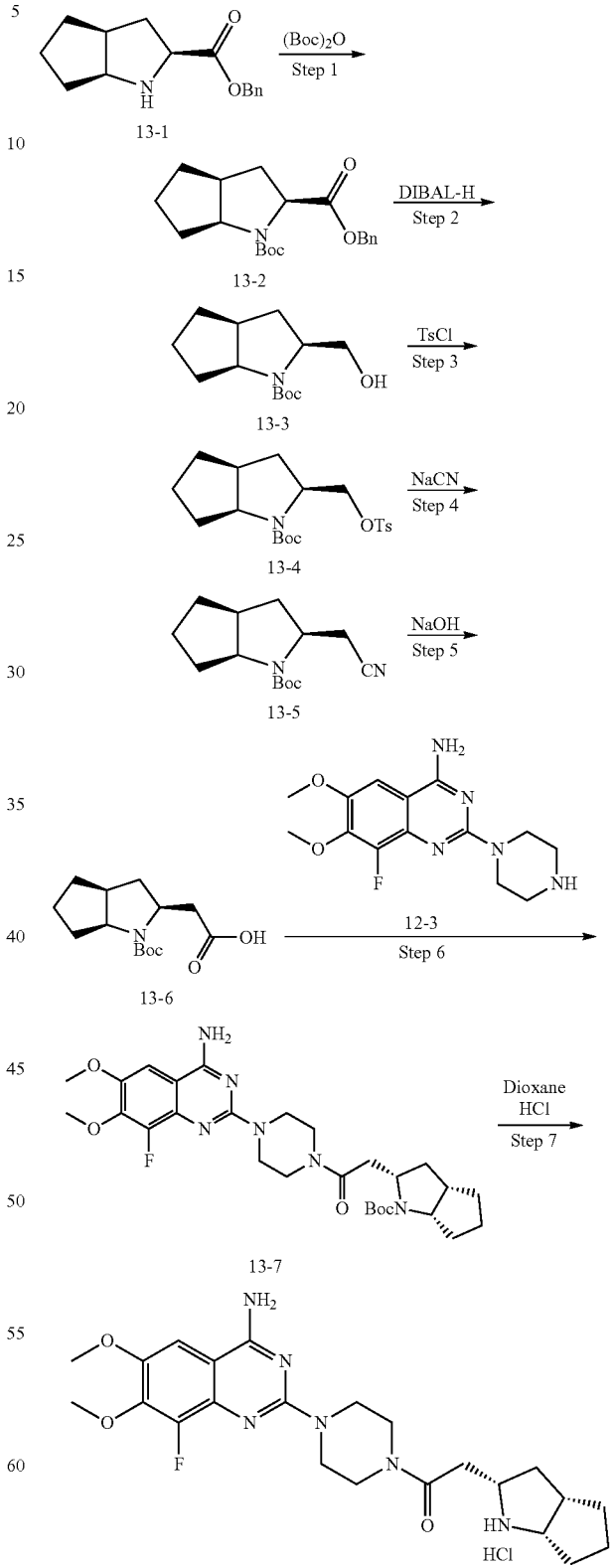

COMPOUND 2

Step 1: 2-Benzyl 1-(tert-butyl) (2S,3aS,6aS)-hexahydrocyclopenta[b]pyrrole-1,2(2H)-dicarboxylate (13-2)

To a solution of benzyl (2S,3aS,6aS)-octahydrocyclopenta[b]pyrrole-2-carboxylate (1) (1 equiv) and DIPEA (1.3 equiv) in DCM (10 vol) at 0° C. was added Boc anhydride (1.1 equiv). The reaction mixture was stirred at room temperature for 5 hours and then quenched with water. The resulting mixture was extracted with DCM. The organic layer was separated, dried over anhydrous $Na_2SO_4$, filtered and then concentrated. The residue was purified by column chromatography on silica gel using hexane/EtOAc to afford compound 13-2.

Step 2: tert-Butyl (2S,3aS,6aS)-2-(hydroxymethyl)hexahydrocyclopenta[b]pyrrole-1(2H)-carboxylate (13-3)

To a solution of compound 13-2 (1 equiv) in THF (50 vol) at −78° C. under nitrogen atmosphere is added DIBAL-H (2 equiv). The reaction mixture was stirred at room temperature for 16 hours and then quenched with saturated $NH_4Cl$ solution. The resulting mixture was extracted with ethyl acetate. The organic layer was separated, dried over anhydrous $Na_2SO_4$, filtered and then concentrated. The residue was purified by column chromatography on silica gel using hexane/EtOAc to afford compound 13-3.

Step 3: tert-Butyl (2S,3aS,6aS)-2-((tosyloxy)methyl)hexahydrocyclopenta[b]pyrrole-1(2H)-carboxylate (13-4)

To a solution of compound 13-3 (1 equiv), TEA (3 equiv) and DMAP (0.1 equiv) in DCM (10 vol) at 0° C. was added 4-toluenesulfonyl chloride (1.5 equiv). The reaction mixture was stirred at room temperature for 12 hours and then quenched with water. The resulting mixture was extracted with ethyl acetate. The organic layer was separated, dried over anhydrous $Na_2SO_4$, filtered and then concentrated. The residue was purified by column chromatography on silica gel using hexane/EtOAc to afford compound 13-4.

Step 4: tert-Butyl (2S,3aS,6aS)-2-(cyanomethyl)hexahydrocyclopenta[b]pyrrole-1(2H)-carboxylate (13-5)

To a solution of compound 13-4 (1 equiv) in DMSO (10 vol) was added NaCN (3 equiv). The reaction mixture was stirred at 90° C. for 16 hours and then quenched with water. The resulting mixture was extracted with ethyl acetate. The organic layer was separated, dried over anhydrous $Na_2SO_4$, filtered and then concentrated. The residue was purified by column chromatography on silica gel using hexane/EtOAc to afford compound 13-5.

Step 5: 2-((2S,3aS,6aS)-1-(tert-Butoxycarbonyl)octahydrocyclopenta[b]pyrrol-2-yl)acetic Acid (13-6)

To a solution of compound 13-5 (1 equiv) in MeOH (30 vol) at 0° C. was added 30% aqueous NaOH solution (4 vol). The reaction mixture was stirred at 100° C. for 16 hours and then concentrated. The resulting mixture is acidified with 1.5 N HCl and extracted with ethyl acetate. The organic layer was separated, dried over anhydrous $Na_2SO_4$, filtered and then concentrated. The residue was purified by column chromatography on silica gel using hexane/EtOAc to afford compound 13-6.

Step 6: tert-Butyl (2S,3aS,6aS)-2-(2-(4-(4-amino-8-fluoro-6,7-dimethoxyquinazolin-2-yl)piperazin-1-yl)-2-oxoethyl)hexahydrocyclopenta[b]pyrrole-1(2H)-carboxylate (13-7)

To a solution of compound 13-6 (1 equiv) and 12-3 (1 equiv) in DMF (10 vol) at 0° C. was added DIPEA (5 equiv) and HBTU (1.2 equiv). The reaction mixture was stirred at room temperature for 16 hours and then quenched with water. The resulting mixture was extracted with ethyl acetate. The organic layer was separated, dried over anhydrous $Na_2SO_4$, filtered and then concentrated. The residue was purified by column chromatography on silica gel using DCM/MeOH to afford compound 13-7.

Step 7: 1-(4-(4-Amino-8-fluoro-6,7-dimethoxyquinazolin-2-yl)piperazin-1-yl)-2-((2S,3aS,6aS)-octahydrocyclopenta[b] pyrrol-2-yl)ethan-1-one hydrochloride (Compound 2)

To a solution of compound 13-7 (1 equiv) in dioxane (2 vol) at 0° C. was added 4 N HCl in dioxane (10 vol). The reaction mixture was stirred at room temperature for 4 hours and then concentrated. The residue was taken in MTBE and stirred for 30 minutes. The resultant solid was filtered and dried to afford COMPOUND 2.

$^1$H NMR (400 MHz, D20) δ 7.11 (s, 1H), 4.08-4.00 (m, 4H), 3.85-3.81 (m, 6H), 3.66-3.61 (m, 5H), 3.05-3.00 (m, 1H), 2.84-2.77 (m, 2H), 2.41-2.34 (m, 1H), 1.74-1.57 (m, 7H), 1.38-1.35 (m, 1H).

Scheme 14: Synthesis of 1-(4-(4-amino-8-fluro-6,7-dimethoxyquinazolin-2-yl)piperazin-1-yl)-2-((2S,3aS,7aS)-octahydro-1H-indol-2-yl)ethan-1-one hydrochloride (COMPOUND 3)

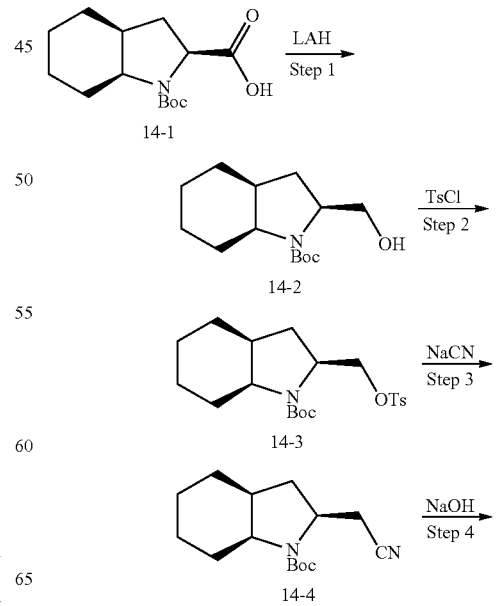

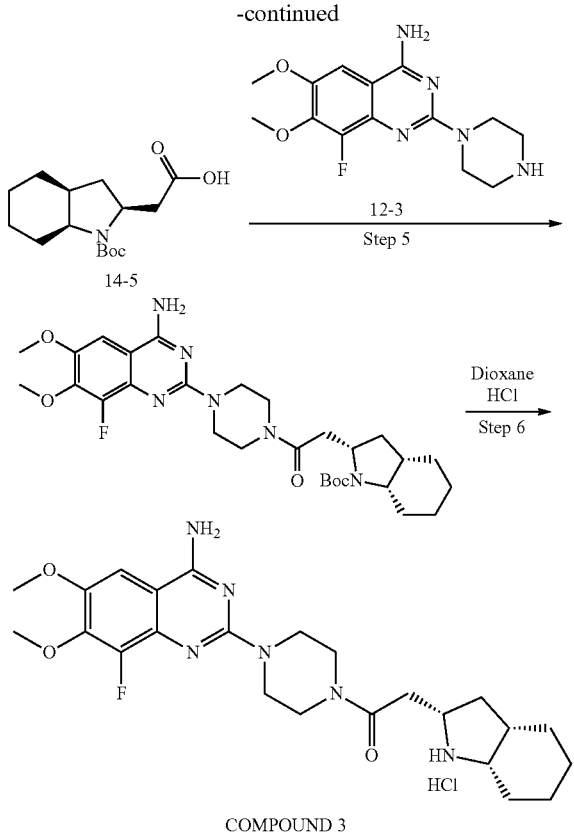

COMPOUND 3

Step 1: tert-Butyl (2S,3aS,7aS)-2-(hydroxymethyl) octahydro-1H-indole-1-carboxylate (14-2)

To a solution of (2S,3aS,7aS)-1-(tert-butoxycarbonyl)octahydro-1H-indole-2-carboxylic acid (1 equiv) in THF (50 vol) at 0° C. under nitrogen atmosphere was added LiAlH$_4$ (2.5 equiv). The reaction mixture was stirred at room temperature for 16 hours and then quenched with potassium sodium tartrate solution. The resulting mixture was extracted with ethyl acetate. The organic layer was separated, dried over anhydrous Na$_2$SO$_4$, filtered and then concentrated. The residue was purified by column chromatography on silica gel using hexane/EtOAc to afford compound 14-2.

Step 2: tert-Butyl (2S,3aS,7aS)-2-((tosyloxy) methyl)octahydro-1H-indole-1-carboxylate (14-3)

To a solution of compound 14-2 (1 equiv), TEA (3 equiv) and DMAP (0.1 equiv) in DCM (10 vol) at 0° C. was added 4-toluenesulfonyl chloride (1.5 equiv). The reaction mixture was stirred at room temperature for 12 hours and then quenched with water. The resulting mixture was extracted with ethyl acetate. The organic layer was separated, dried over anhydrous Na$_2$SO$_4$, filtered and then concentrated. The residue was purified by column chromatography on silica gel using hexane/EtOAc to afford compound 14-3.

Step 3: tert-Butyl (2S,3aS,7aS)-2-(cyanomethyl) octahydro-1H-indole-1-carboxylate (14-4)

To a solution of compound 14-3 (1 equiv) in DMSO (10 vol) was added NaCN (3 equiv). The reaction mixture was stirred at 90° C. for 16 hours and then quenched with water. The resulting mixture was extracted with ethyl acetate. The organic layer was separated, dried over anhydrous Na$_2$SO$_4$, filtered and then concentrated. The residue was purified by column chromatography on silica gel using hexane/EtOAc to afford compound 14-4.

Step 4: 2-((2S,3aS,7aS)-1-(tert-Butoxycarbonyl) octahydro-1H-indol-2-yl)acetic Acid (14-5)

To a solution of compound 14-4 (1 equiv) in MeOH (30 vol) at 0° C. was added 30% aqueous NaOH solution (4 vol). The reaction mixture was stirred at 100° C. for 16 hours and then concentrated. The resulting mixture was acidified with 1.5 N HCl and extracted with ethyl acetate. The organic layer was separated, dried over anhydrous Na$_2$SO$_4$, filtered and then concentrated. The residue was purified by column chromatography on silica gel using DCM/MeOH to afford compound 14-5.

Step 5: tert-Butyl (2S,3aS,7aS)-2-(2-(4-(4-amino-8-fluoro-6,7-dimethoxyquinazolin-2-yl)piperazin-1-yl)-2-oxoethyl)octahydro-1H-indole-1-carboxylate (14-7)

To a solution of compound 14-5 (1 equiv) and 12-3 (1 equiv) in DMF (10 vol) at 0° C. was added DIPEA (5 equiv) and HBTU (1.2 equiv). The reaction mixture was stirred at room temperature for 16 hours and then quenched with water. The resulting mixture was extracted with ethyl acetate. The organic layer was separated, dried over anhydrous Na$_2$SO$_4$, filtered and then concentrated. The residue was purified by column chromatography on silica gel using DCM/MeOH to afford compound 14-7.

Step 6: 1-(4-(4-Amino-8-fluoro-6,7-dimethoxyquinazolin-2-yl)piperazin-1-yl)-2-((2S,3aS,7aS)-octahydro-1H-indol-2-yl)ethan-1-one hydrochloride (Compound 3)

To a solution of compound 7 (1 equiv) in dioxane (2 vol) at 0° C. is added 4 N HCl in dioxane (10 vol). The reaction mixture was stirred at room temperature for 4 hours and then concentrated. The residue was taken up in MTBE and stirred for 30 minutes. The resultant solid was filtered and dried to afford COMPOUND 3.

$^1$H NMR (400 MHz, D20) δ 7.15 (s, 1H), 3.94 (s, 3H), 3.92-3.82 (m, 6H), 3.75-3.64 (m, 5H), 3.46-3.42 (m, 1H), 3.10-3.05 (m, 1H), 2.94-2.88 (m, 1H), 2.33-2.32 (m, 1H), 2.16-2.11 (m, 1H), 1.80-1.78 (m, 2H), 1.75-1.62 (m, 4H), 1.52-1.42 (m, 3H), 1.01-0.99 (m, 2H).

Scheme 15: Synthesis of (R)-1-(4-(4-Amino-8-fluoro-6,7-dimethoxyquinazolin-2-yl)-3,6-dihydropyridin-1(2H)-yl)-3-(ethylamino)-3-(4-fluorophenyl)propan-1-one (COMPOUND 4)

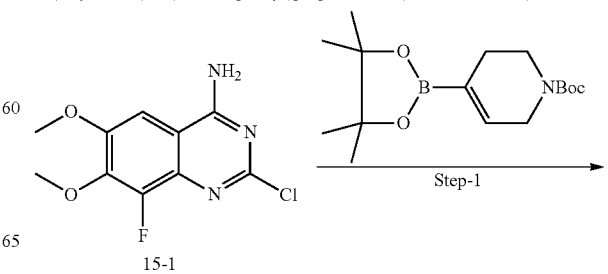

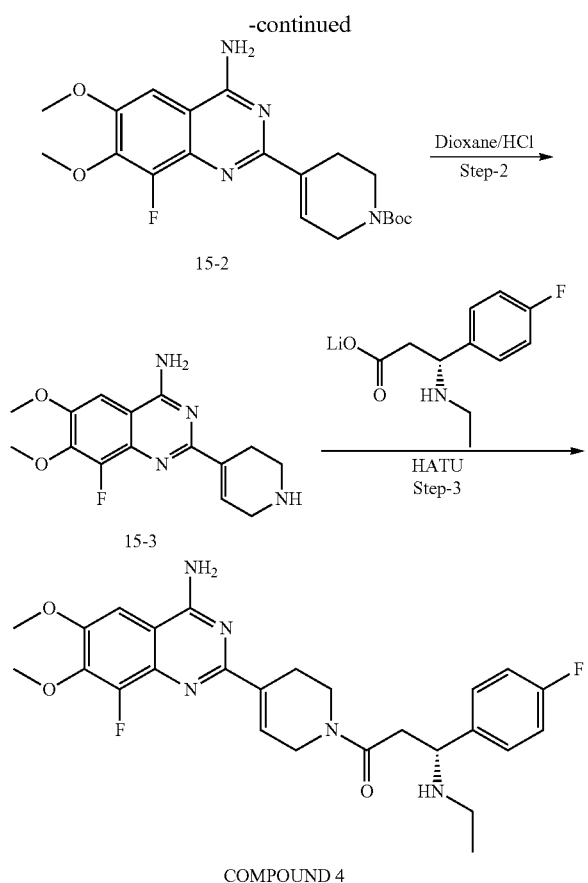

Step 1: tert-Butyl 4-(4-amino-8-fluoro-6,7-dimethoxyquinazolin-2-yl)-3,6-dihydropyridine-1(2H)-carboxylate (15-2)

To a solution of 2-chloro-8-fluoro-6,7-dimethoxyquinazolin-4-amine (1 equiv) in dioxane (10 vol) was added tert-butyl 4-(4,4,5,5-tetramethyl-1,3,2-dioxaborolan-2-yl)-3,6-dihydropyridine-1(2H)-carboxylate (1.1 equiv) and 2 M $Na_2CO_3$ (2 equiv). After degassing with nitrogen, $PdCl_2$$(PPh_3)_2$ (0.1 equiv) was added to the reaction mixture. The resulting mixture was stirred at 80° C. for 12 hours and then cooled to room temperature. Water was added to the reaction mixture and the resulting mixture was extracted with ethyl acetate. The organic layer was separated, dried over anhydrous $Na_2SO_4$, filtered, and then concentrated. The residue was purified by column chromatography on silica gel using hexane/EtOAc to afford compound 15-2.

Step 2: 8-Fluoro-6,7-dimethoxy-2-(1,2,3,6-tetrahydropyridin-4-yl)quinazolin-4-amine (15-3)

To a solution of compound 15-2 (1 equiv) in dioxane (2 vol) at 0° C. was added 4 N HCl in dioxane (10 vol). The reaction mixture was stirred at room temperature for 4 hours and then concentrated. The residue was taken in MTBE and stirred for 30 minutes. The resultant solid was filtered and dried to afford compound 15-3.

Step 3: (R)-1-(4-(4-Amino-8-fluoro-6,7-dimethoxyquinazolin-2-yl)-3,6-dihydropyridin-1(2H)-yl)-3-(ethylamino)-3-(4-fluorophenyl)propan-1-one (Compound 4)

To a solution of compound 15-3 (1 equiv) and lithium (R)-3-(ethylamino)-3-(4-fluorophenyl)propanoate (1 equiv) in DMF (10 vol) at 0° C. was added DIPEA (5 equiv) and HATU (1.2 equiv). The reaction mixture was stirred at room temperature for 16 hours and then quenched with water. The resulting mixture was extracted with ethyl acetate. The organic layer was separated, dried over anhydrous $Na_2SO_4$, filtered and then concentrated. The residue was purified by column chromatography on silica gel using hexane/EtOAc to afford COMPOUND 4.

$^1$H NMR (400 MHz, DMSO-$d_6$) δ 7.60 (s, 2H), 7.53 (s, 1H), 7.45 (d, J=8.6 Hz, 2H), 7.15 (d, J=8.6 Hz, 2H), 7.05-7.01 (m, 1H), 4.19-4.13 (m, 3H), 3.94 (s, 3H), 3.91 (s, 3H), 3.65-3.53 (m, 2H), 2.81-2.67 (m, 2H), 2.59-2.51 (m, 2H), 2.45-2.33 (m, 3H), 0.98-0.96 (m, 3H).

Scheme 16: Synthesis of (R)-1-(4-(4-Amino-8-fluoro-6,7-dimethoxyquinazolin-2-yl)piperidin-1-yl)-3-(ethylamino)-3-(4-fluorophenyl)propan-1-one (COMPOUND 5)

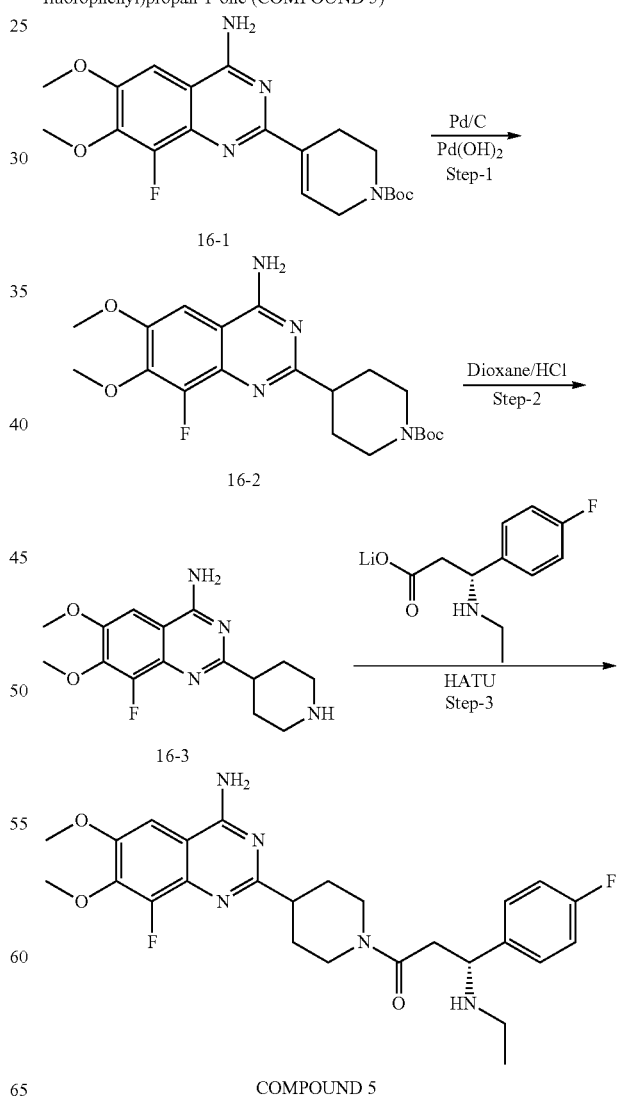

Step 1: tert-Butyl 4-(4-amino-8-fluoro-6,7-dimethoxyquinazolin-2-yl)piperidine-1-carboxylate (16-2)

To a solution of tert-butyl 4-(4-amino-8-fluoro-6,7-dimethoxyquinazolin-2-yl)-3,6-dihydropyridine-1(2H)-carboxylate (1 equiv) in THF/MeOH (1:1, 10 Vol) was added Pd/C (10%) and Pd(OH)$_2$ (10%). The reaction mixture was hydrogenated under pressure of 1 kg/cm$^2$ at room temperature for 12 hours. The resulting mixture was filtered and concentrated. The residue was taken up in MTBE and stirred for 30 minutes. The resultant solid was filtered and dried to afford compound 16-2.

Step 2: 8-Fluoro-6,7-dimethoxy-2-(piperidin-4-yl)quinazolin-4-amine (16-3)

To a solution of compound 16-2 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 16-3.

Step 3: (R)-1-(4-(4-Amino-8-fluoro-6,7-dimethoxyquinazolin-2-yl)piperidin-1-yl)-3-(ethylamino)-3-(4-fluorophenyl)propan-1-one (Compound 5)

To a solution of compound 16-3 (1 equiv) and lithium (R)-3-(ethylamino)-3-(4-fluorophenyl)propanoate (1 equiv) in DMF (10 vol) at 0° C. was added DIPEA (5 equiv) and HATU (1.2 equiv). The reaction mixture was stirred at room temperature for 16 hours and then quenched with water. The resulting mixture was extracted with ethyl acetate. The organic layer was separated, dried over anhydrous Na$_2$SO$_4$, filtered and then concentrated. The residue was purified by column chromatography on silica gel using hexane/EtOAc to afford COMPOUND 5.

$^1$H NMR (400 MHz, CD$_3$OD) δ 7.45 (d, J=8.5 Hz, 2H), 7.38 (s, 1H), 7.13 (d, J=8.6 Hz, 2H), 4.57 (d, J=10 Hz, 1H), 4.27 (q, J=6.7 Hz, 1H), 4.04 (s, 3H), 3.98 (s, 3H), 2.98-2.86 (m, 3H), 2.75 (q, J=11.1 Hz, 1H), 2.64-2.48 (m, 2H), 1.95-1.81 (m, 3H), 1.38-1.29 (m, 1H), 1.17-1.13 (m, 3H), 0.92-0.87 (m, 2H).

Scheme 17: Synthesis of Methyl (R)-4-(4-amino-8-fluoro-6,7-dimeth-oxyquinazolin-2-yl)-1-(3-(ethylamino)-3-(4-fluorophenyl)propanoyl)-1,2,5,6-tetrahydropyridine-3-carboxylate (COMPOUND 6) and synthesis of (R)-4-(4-Amino-8-fluoro-6,7-dimethoxyquinoazolin-2-yl)-1-(3-(ethylamino)-3-(4-fluorophenyl)propanoyl)-1,2,5,6-tetrahydropyridine-3-carboxylic acid (COMPOUND 8)

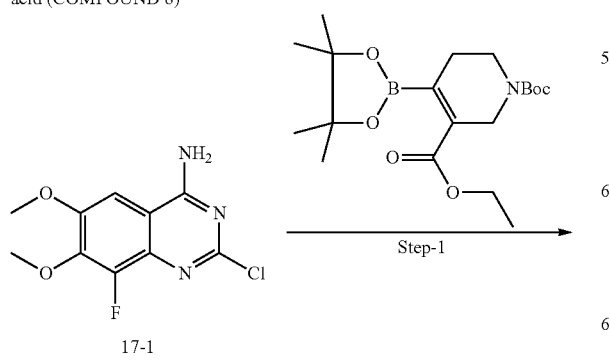

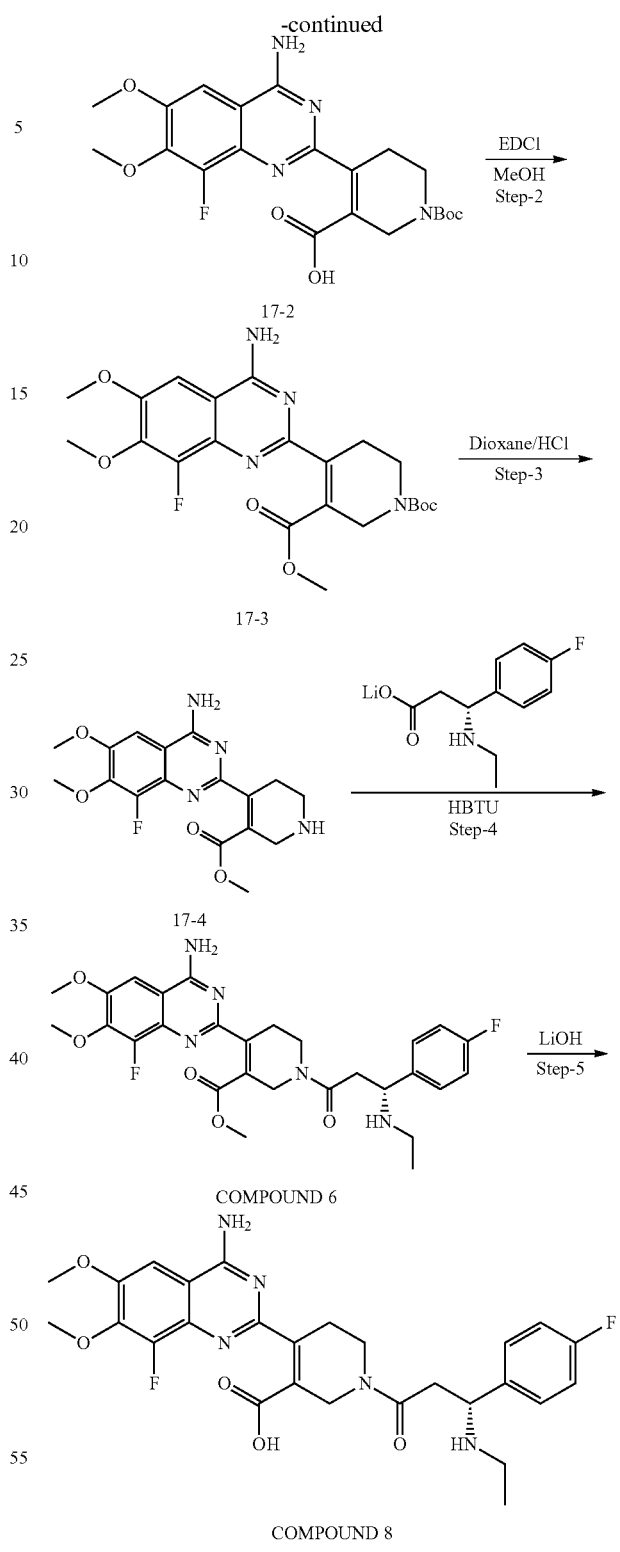

Step 1: 4-(4-Amino-8-fluoro-6,7-dimethoxyquinazolin-2-yl)-1-(tert-butoxycarbonyl)-1,2,5,6-tetrahydropyridine-3-carboxylic Acid (17-2)

To a solution of 2-chloro-8-fluoro-6,7-dimethoxyquinazolin-4-amine (1 equiv) in THF (10 vol) was added 1-(tert-butyl) 3-ethyl 4-(4,4,5,5-tetramethyl-1,3,2-dioxaborolan-2-yl)-5,6-dihydropyridine-1,3(2H)-dicarboxylate (1.1 equiv) and 2 M Na₂CO₃ (2 equiv). After degassing with nitrogen, Pd(PPh₃)₄ (0.1 equiv) was added to the reaction mixture. The resulting mixture was stirred at 100° C. in a sealed tube for 12 hours and then cooled to room temperature. Water was added to the reaction mixture and the resulting mixture was extracted with ethyl acetate. The aqueous layer was separated and acidified with 1 M citric acid. The resulting mixture was extracted with ethyl acetate and dried over anhydrous Na₂SO₄, filtered, and then concentrated to afford compound 17-2.

Step 2: 1-(tert-Butyl) 3-methyl 4-(4-amino-8-fluoro-6,7-dimethoxyquinazolin-2-yl)-5,6-dihydropyridine-1,3(2H)-dicarboxylate (17-3)

To a solution of compound 17-2 (1 equiv) in MeOH (10 vol) at 0° C. was added TEA (2 equiv) and EDCI (1.5 equiv). The reaction mixture was stirred at room temperature for 16 hours and then quenched with water. The resulting mixture was extracted with ethyl acetate. The organic layer was separated, dried over anhydrous Na₂SO₄, filtered and then concentrated. The residue was purified by column chromatography on silica gel using hexane/EtOAc to afford compound 17-3.

Step 3: Methyl 4-(4-amino-8-fluoro-6,7-dimethoxyquinazolin-2-yl)-1,2,5,6-tetrahydropyridine-3-carboxylate (17-4)

To a solution of compound 17-3 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 17-4.

Step 4: Methyl (R)-4-(4-amino-8-fluoro-6,7-dimethoxyquinazolin-2-yl)-1-(3-(ethylamino)-3-(4-fluorophenyl)propanoyl)-1,2,5,6-tetrahydropyridine-3-carboxylate (COMPOUND 6)

To a solution of compound 17-4 (1 equiv) and lithium (R)-3-(ethylamino)-3-(4-fluorophenyl)propanoate (1 equiv) in DMF (10 vol) at 0° C. was added DIPEA (5 equiv) and HATU (1.2 equiv). The reaction mixture was stirred at room temperature for 16 hours and then quenched with water. The resulting mixture was extracted with ethyl acetate. The organic layer was separated, dried over anhydrous Na₂SO₄, filtered, and then concentrated. The residue was purified by column chromatography on silica gel using hexane/EtOAc to afford COMPOUND 6.

¹H NMR (400 MHz, CDCl₃) δ 7.69-7.67 (m, 2H), 7.29-7.28 (m, 1H), 7.16-7.10 (m, 3H), 6.81 (d, J=4.4 Hz, 1H), 5.75-5.68 (m, 2H), 4.38-4.23 (m, 2H), 4.16 (s, 3H), 3.99 (s, 3H), 3.74-3.69 (m, 6H), 2.89-2.73 (m, 2H), 1.35-1.20 (m, 5H).

Step 5: (R)-4-(4-Amino-8-fluoro-6,7-dimethoxyquinazolin-2-yl)-1-(3-(ethylamino)-3-(4-fluorophenyl)propanoyl)-1,2,5,6-tetrahydropyridine-3-carboxylic Acid (Compound 8)

To a solution of COMPOUND 6 (1 equiv) in THF/water (1:1) was added LiOH (1.2 equiv). The reaction mixture was stirred at room temperature for 4 hours and then concentrated. The residue was purified by preparative purification to afford COMPOUND 8.

¹H NMR (400 MHz, CD₃OD) δ 7.72-7.48 (m, 3H), 7.26 (q, J=8.1 Hz, 2H), 4.80 (s, 1H), 4.50-4.42 (m, 2H), 4.13 (s, 3H), 4.03 (s, 3H), 3.80-3.74 (m, 2H), 3.04-2.96 (m, 2H), 2.76-2.70 (m, 2H), 1.56-1.40 (m, 1H), 1.33-1.30 (m, 4H).

Scheme 17: Synthesis of Methyl (R)-4-(4-amino-8-fluoro-6,7-dimeth-oxyquinazolin-2-yl)-1-(3-(ethylamino)-3-(4-fluorophenyl)propanoyl)-1,2,5,6-tetrahydropyridine-3-carboxylate (COMPOUND 6) and synthesis of (R)-4-(4-Amino-8-fluoro-6,7-dimethoxyquinoazolin-2-yl)-1-(3-(ethylamino)-3-(4-fluorophenyl)propanoyl)-1,2,5,6-tetrahydropyridine-3-carboxylic acid (COMPOUND 8)

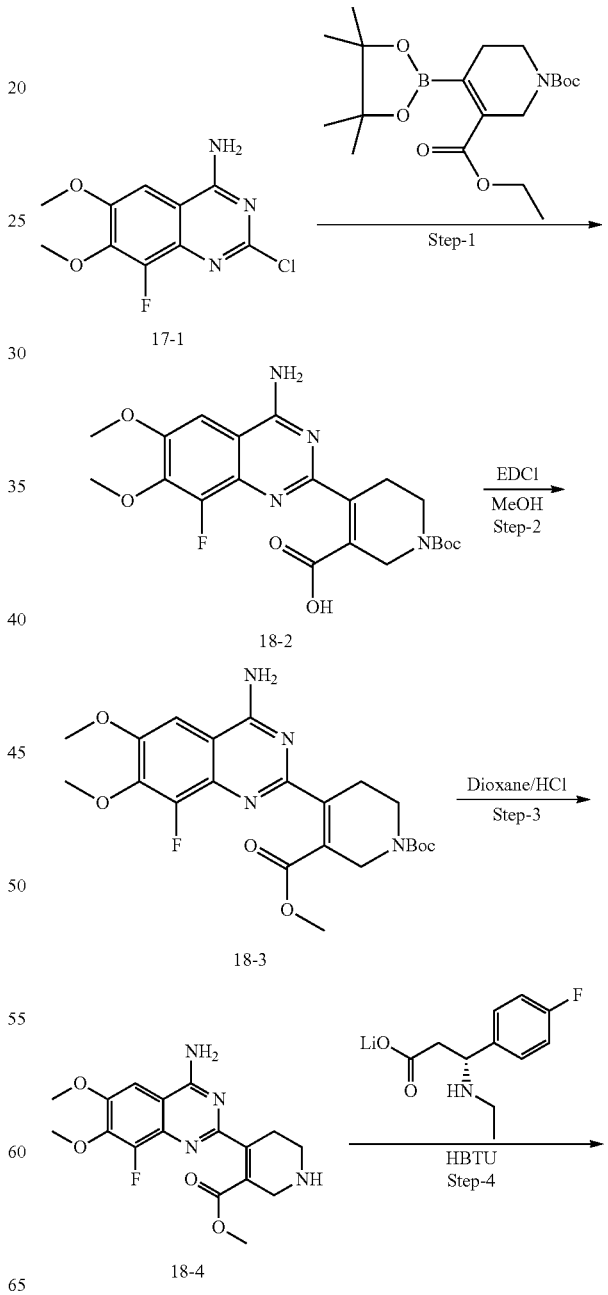

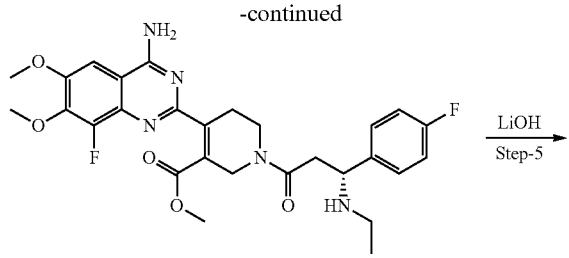

COMPOUND 6

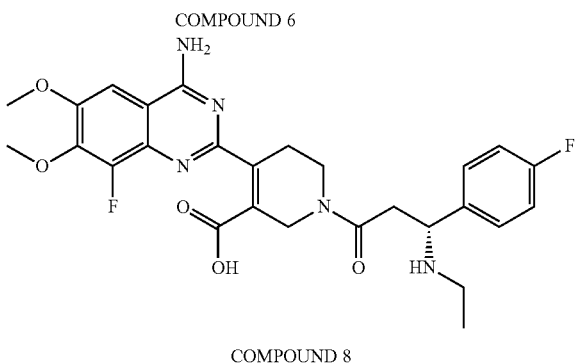

COMPOUND 8

Step 1: 4-(4-Amino-8-fluoro-6,7-dimethoxyquinazolin-2-yl)-1-(tert-butoxycarbonyl)-1,2,5,6-tetrahydropyridine-3-carboxylic Acid (18-2)

To a solution of 2-chloro-8-fluoro-6,7-dimethoxyquinazolin-4-amine (1 equiv) in THF (10 vol) was added 1-(tert-butyl) 3-ethyl 4-(4,4,5,5-tetramethyl-1,3,2-dioxaborolan-2-yl)-5,6-dihydropyridine-1,3(2H)-dicarboxylate (1.1 equiv) and 2 M $Na_2CO_3$ (2 equiv). After degassing with nitrogen, $Pd(PPh_3)_4$ (0.1 equiv) was added to the reaction mixture. The resulting mixture was stirred at 100° C. in a sealed tube for 12 hours and then cooled to room temperature. Water was added to the reaction mixture and the resulting mixture was extracted with ethyl acetate. The aqueous layer was separated and acidified with 1 M citric acid. The resulting mixture was extracted with ethyl acetate and dried over anhydrous $Na_2SO_4$, filtered, and then concentrated to afford compound 18-2.

Step 2: 1-(tert-Butyl) 3-methyl 4-(4-amino-8-fluoro-6,7-dimethoxyquinazolin-2-yl)-5,6-dihydropyridine-1,3(2H)-dicarboxylate (18-3)

To a solution of compound 18-2 (1 equiv) in MeOH (10 vol) at 0° C. was added TEA (2 equiv) and EDCI (1.5 equiv). The reaction mixture was stirred at room temperature for 16 hours and then quenched with water. The resulting mixture was extracted with ethyl acetate. The organic layer was separated, dried over anhydrous $Na_2SO_4$, filtered, and then concentrated. The residue was purified by column chromatography on silica gel using hexane/EtOAc to afford compound 18-3.

Step 3: Methyl 4-(4-amino-8-fluoro-6,7-dimethoxyquinazolin-2-yl)-1,2,5,6-tetrahydropyridine-3-carboxylate (18-3)

To a solution of compound 18-3 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 18-4.

Step 4: Methyl (R)-4-(4-amino-8-fluoro-6,7-dimethoxyquinazolin-2-yl)-1-(3-(ethylamino)-3-(4-fluorophenyl)propanoyl)-1,2,5,6-tetrahydropyridine-3-carboxylate (Compound 6)

To a solution of compound 18-4 (1 equiv) and lithium (R)-3-(ethylamino)-3-(4-fluorophenyl)propanoate (1 equiv) in DMF (10 vol) at 0° C. was added DIPEA (5 equiv) and HATU (1.2 equiv). The reaction mixture was stirred at room temperature for 16 hours and then quenched with water. The resulting mixture was extracted with ethyl acetate. The organic layer was separated, dried over anhydrous $Na_2SO_4$, filtered and then concentrated. The residue was purified by column chromatography on silica gel using hexane/EtOAc to afford COMPOUND 6.

$^1$H NMR (400 MHz, $CDCl_3$) δ 7.69-7.67 (m, 2H), 7.29-7.28 (m, 1H), 7.16-7.10 (m, 3H), 6.81 (d, J=4.4 Hz, 1H), 5.75-5.68 (m, 2H), 4.38-4.23 (m, 2H), 4.16 (s, 3H), 3.99 (s, 3H), 3.74-3.69 (m, 6H), 2.89-2.73 (m, 2H), 1.35-1.20 (m, 5H).

Step 5: (R)-4-(4-Amino-8-fluoro-6,7-dimethoxyquinazolin-2-yl)-1-(3-(ethylamino)-3-(4-fluorophenyl)propanoyl)-1,2,5,6-tetrahydropyridine-3-carboxylic Acid (Compound 8)

To a solution of COMPOUND 6 (1 equiv) in THF/water (1:1) was added LiOH (1.2 equiv). The reaction mixture was stirred at room temperature for 4 hours and then concentrated. The residue was purified by preparative purification to afford COMPOUND 8.

$^1$H NMR (400 MHz, $CD_3OD$) δ 7.72-7.48 (m, 3H), 7.26 (q, J=8.1 Hz, 2H), 4.80 (s, 1H), 4.50-4.42 (m, 2H), 4.13 (s, 3H), 4.03 (s, 3H), 3.80-3.74 (m, 2H), 3.04-2.96 (m, 2H), 2.76-2.70 (m, 2H), 1.56-1.40 (m, 1H), 1.33-1.30 (m, 4H).

Scheme 19: Synthesis of Methyl 4-(4-amino-8-fluoro-6,7-dimethoxyquinazolin-2-yl)-1-((R)-3-(ethylamino)-3-(4-fluorophenyl)propanoyl)piperidine-3-carboxylate (COMPOUND 7) and synthesis of 4-(4-Amino-8-fluoro-6,7-dimethoxyquinazolin-2-yl)-1-((R)-3-(ethylamino)-3-(4-fluorophenyl)propanoyl)piperidine-3-carboxylic acid (COMPOUND 9)

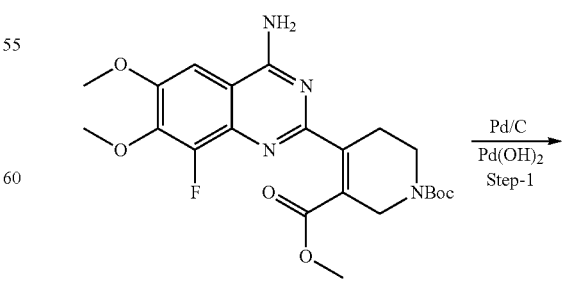

19-1

-continued

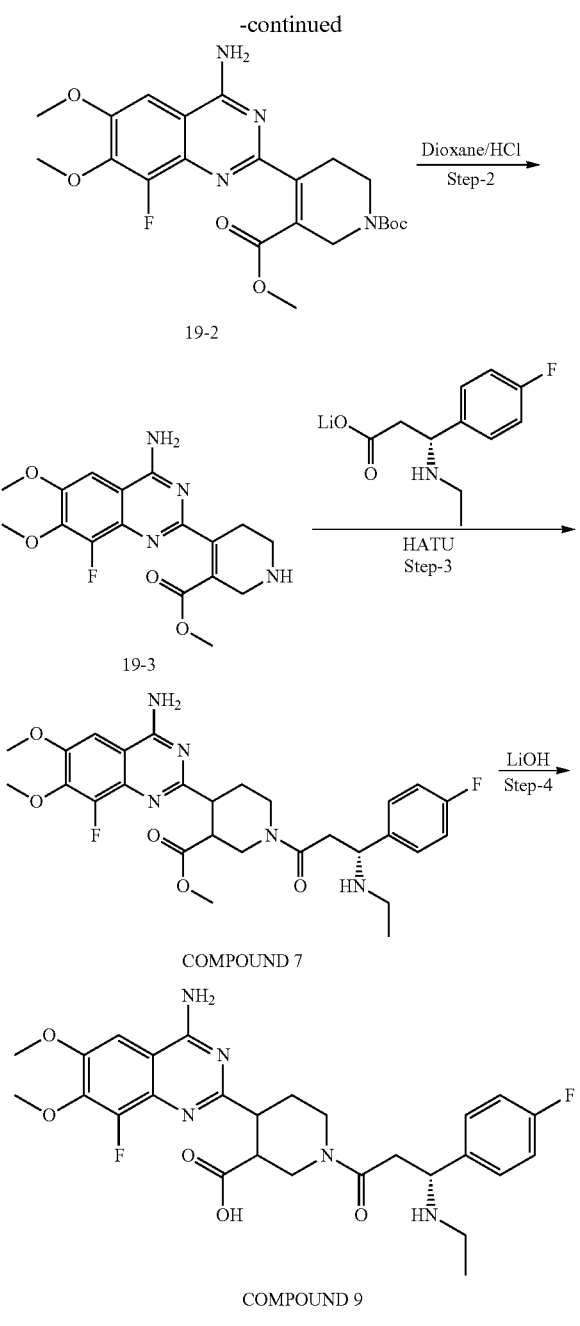

19-2

19-3

COMPOUND 7

COMPOUND 9

Step 1: 1-(tert-Butyl) 3-methyl 4-(4-amino-8-fluoro-6,7-dimethoxyquinazolin-2-yl)piperidine-1,3-dicarboxylate (19-2)

To a solution of 1-(tert-butyl) 3-methyl 4-(4-amino-8-fluoro-6,7-dimethoxyquinazolin-2-yl)-5,6-dihydropyridine-1,3(2H)-dicarboxylate (1 equiv) in THF/MeOH (1:1, 10 Vol) was added Pd/C (10%) and Pd(OH)$_2$ (10%). The reaction mixture was hydrogenated under pressure of 1 kg/cm$^2$ at room temperature for 12 hours. The resulting mixture was filtered and concentrated. The residue was taken up in MTBE and stirred for 30 minutes. The resultant solid was filtered and dried to afford compound 19-2.

Step 2: Methyl 4-(4-amino-8-fluoro-6,7-dimethoxyquinazolin-2-yl)piperidine-3-carboxylate (3)

To a solution of compound 19-2 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 19-3.

Step 3: Methyl 4-(4-amino-8-fluoro-6,7-dimethoxyquinazolin-2-yl)-1-((R)-3-(ethylamino)-3-(4-fluorophenyl)propanoyl)piperidine-3-carboxylate (Compound 7)

To a solution of compound 19-3 (1 equiv) and lithium (R)-3-(ethylamino)-3-(4-fluorophenyl)propanoate (1 equiv) in DMF (10 vol) at 0° C. was added DIPEA (5 equiv) and HATU (1.2 equiv). The reaction mixture was stirred at room temperature for 16 hours and then quenched with water. The resulting mixture was extracted with ethyl acetate. The organic layer was separated, dried over anhydrous Na$_2$SO$_4$, filtered, and then concentrated. The residue was purified by column chromatography on silica gel using hexane/EtOAc to afford COMPOUND 7.

$^1$H NMR (400 MHz, CDCl$_3$) δ 7.71-7.54 (m, 3H), 7.12-7.08 (m, 3H), 6.78-6.75 (m, 1H), 5.55-5.39 (m, 2H), 4.32-4.29 (m, 1H), 4.15 (s, 3H), 3.99 (s, 3H), 3.67-3.63 (m, 3H), 3.55-3.51 (m, 2H), 3.21-3.05 (m, 2H), 2.85-2.61 (m, 2H), 2.35-2.28 (m, 2H), 1.36-1.24 (m, 5H).

Step 5: 4-(4-Amino-8-fluoro-6,7-dimethoxyquinazolin-2-yl)-1-((R)-3-(ethylamino)-3-(4-fluorophenyl)propanoyl)piperidine-3-carboxylic Acid (Compound 9)

To a solution of COMPOUND 7 (1 equiv) in THF/water (1:1) was added LiOH (1.2 equiv). The reaction mixture was stirred at room temperature for 4 hours and then concentrated. The residue was purified by preparative purification to afford COMPOUND 9.

$^1$H NMR (400 MHz, CD$_3$OD) δ 7.62-7.59 (m, 3H), 7.34-7.23 (m, 2H), 5.05 (d, J=13.2 Hz, 1H), 4.82-4.74 (m, 2H), 4.16 (s, 3H), 4.03 (s, 3H), 3.68-3.65 (m, 1H), 3.51-3.37 (m, 2H), 3.27-3.25 (m, 2H), 3.03-2.96 (m, 2H), 2.11-2.06 (m, 1H), 1.67-1.59 (m, 1H), 1.35-1.33 (m, 4H).

Scheme 20: Synthesis of (3R)-1-(4-(4-Amino-8-fluoro-6,7-dimethoxyquinazolin-2-yl)-2,6-dimethyl-3,6-dihydropyridin-1(2H)-yl)-3-(ethylamino)-3-(4-fluorophenyl)propan-1-one (COMPOUND 10)

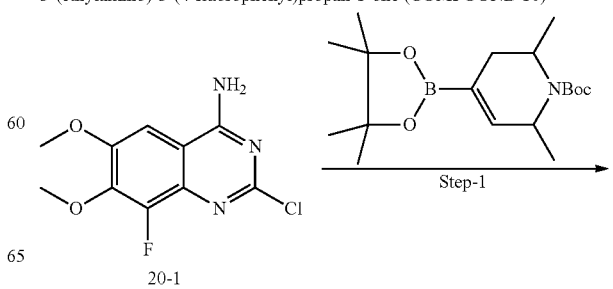

20-1

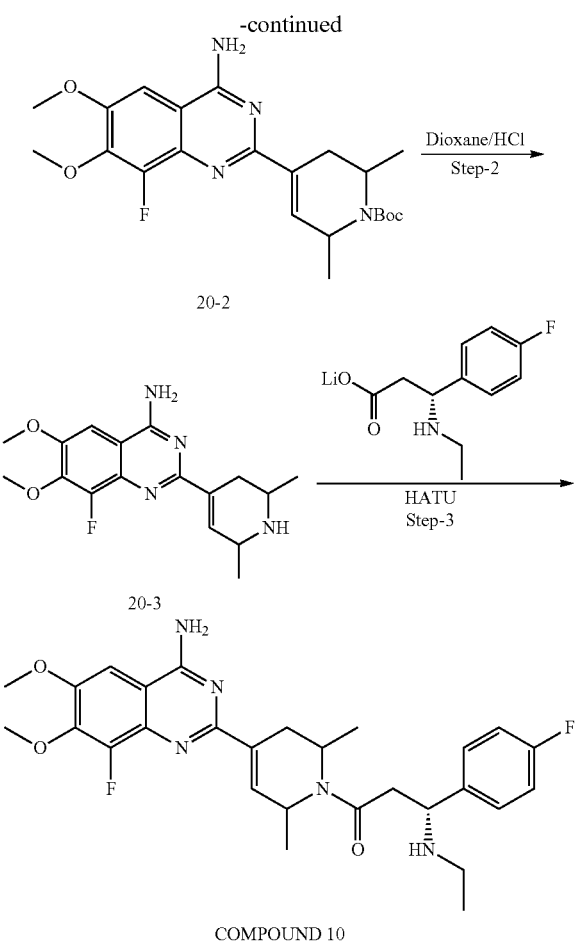

20-2

20-3

COMPOUND 10

Step 1: tert-Butyl 4-(4-amino-8-fluoro-6,7-dimethoxyquinazolin-2-yl)-2,6-dimethyl-3,6-dihydropyridine-1(2H)-carboxylate (20-2)

To a solution of 2-chloro-8-fluoro-6,7-dimethoxyquinazolin-4-amine (1 equiv) in dioxane (10 vol) was added tert-butyl 4-(4,4,5,5-tetramethyl-1,3,2-dioxaborolan-2-yl)-3,6-dihydropyridine-1(2H)-carboxylate (1.1 equiv) and 2 M $Na_2CO_3$ (2 equiv). After degassing with nitrogen, $PdCl_2(PPh_3)_2$ (0.1 equiv) was added to the reaction mixture. The resulting mixture was stirred at 80° C. for 12 hours and then cooled to room temperature. Water was added to the reaction mixture and the resulting mixture was extracted with ethyl acetate. The organic layer was separated, dried over anhydrous $Na_2SO_4$, filtered, and then concentrated. The residue was purified by column chromatography on silica gel using hexane/EtOAc to afford compound 20-2.

Step 2: 2-(2,6-Dimethyl-1,2,3,6-tetrahydropyridin-4-yl)-8-fluoro-6,7-dimethoxyquinazolin-4-amine (20-3)

To a solution of compound 20-2 (1 equiv) in dioxane (2 vol) at 0° C. is added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 20-3.

Step 3: (3R)-1-(4-(4-Amino-8-fluoro-6,7-dimethoxyquinazolin-2-yl)-2,6-dimethyl-3,6-dihydropyridin-1(2H)-yl)-3-(ethylamino)-3-(4-fluorophenyl)propan-1-one (Compound 10)

To a solution of compound 20-3 (1 equiv) and lithium (R)-3-(ethylamino)-3-(4-fluorophenyl)propanoate (1 equiv) in DMF (10 vol) at 0° C. was added DIPEA (5 equiv) and HATU (1.2 equiv). The reaction mixture was stirred at room temperature for 16 hours and then quenched with water. The resulting mixture was extracted with ethyl acetate. The organic layer was separated, dried over anhydrous $Na_2SO_4$, filtered and then concentrated. The residue was purified by column chromatography on silica gel using hexane/EtOAc to afford COMPOUND 10.

$^1$H NMR (400 MHz, DMSO-$d_6$) δ 7.63 (s, 2H), 7.53 (s, 1H), 7.43-7.40 (m, 2H), 7.17-7.12 (m, 3H), 4.51-4.48 (m, 1H), 4.12-4.08 (m, 1H), 3.94 (s, 3H), 3.91 (s, 3H), 3.51-3.49 (m, 2H), 3.18-2.90 (m, 2H), 2.36-2.30 (m, 2H), 1.26 (s, 6H), 1.01-0.95 (m, 5H).

Scheme 21: Synthesis of (3R)-1-(4-(4-Amino-8-fluoro-6,7-dimethoxyquinazolin-2-yl)-2,6-dimethylpiperidin-1-yl)-3-(ethylamino)-3-(4-fluorophenyl)propan-1-one (COMPOUND 11)

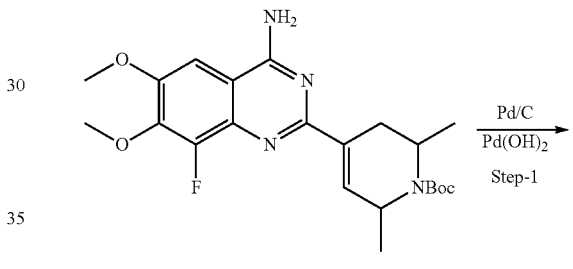

21-1

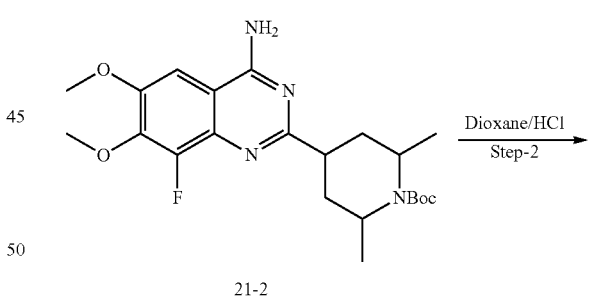

21-2

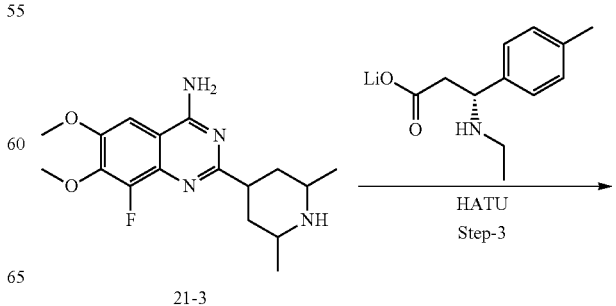

21-3

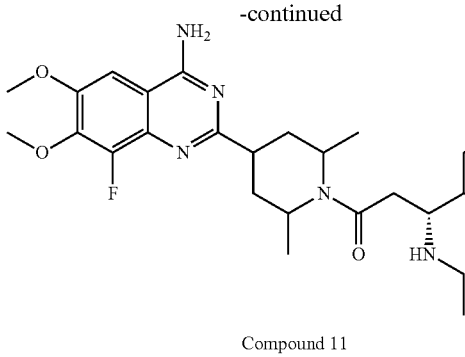

Compound 11

Step 1: tert-Butyl 4-(4-amino-8-fluoro-6,7-dimethoxyquinazolin-2-yl)-2,6-dimethylpiperidine-1-carboxylate (21-2)

To a solution of tert-butyl 4-(4-amino-8-fluoro-6,7-dimethoxyquinazolin-2-yl)-2,6-dimethyl-3,6-dihydropyridine-1(2H)-carboxylate (1 equiv) in THF/MeOH (1:1, 10 Vol) was added Pd/C (10%) and Pd(OH)$_2$ (10%). The reaction mixture was hydrogenated under pressure of 1 kg/cm$^2$ at room temperature for 12 hours. The resulting mixture was filtered and concentrated. The residue was taken up in MTBE and stirred for 30 minutes. The resultant solid was filtered and dried to afford compound 21-2.

Step 2: 2-(2,6-Dimethylpiperidin-4-yl)-8-fluoro-6,7-dimethoxyquinazolin-4-amine (21-3)

To a solution of compound 21-2 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 21-3.

Step 3: (3R)-1-(4-(4-Amino-8-fluoro-6,7-dimethoxyquinazolin-2-A-2,6-dimethylpiperidin-1-yl)-3-(ethylamino)-3-(4-fluorophenyl)propan-1-one (Compound 11)

To a solution of compound 21-3 (1 equiv) and lithium (R)-3-(ethylamino)-3-(4-fluorophenyl)propanoate (1 equiv) in DMF (10 vol) at 0° C. was added DIPEA (5 equiv) and HATU (1.2 equiv). The reaction mixture was stirred at room temperature for 16 hours and then quenched with water. The resulting mixture was extracted with ethyl acetate. The organic layer was separated, dried over anhydrous Na$_2$SO$_4$, filtered, and then concentrated. The residue is purified by column chromatography on silica gel using hexane/EtOAc to afford COMPOUND 11.

$^1$H NMR (400 MHz, CDCl$_3$) δ 7.59 (s, 2H), 7.11-7.07 (m, 2H), 6.81 (d, J=3.6 Hz, 1H), 5.67-5.33 (m, 2H), 4.35-4.28 (m, 1H), 4.16 (s, 3H), 4.01 (s, 3H), 3.73-3.64 (m, 2H), 2.71-2.64 (m, 2H), 2.34-2.31 (m, 2H), 2.12-2.06 (m, 2H), 1.69-1.62 (m, 2H), 0.99-0.82 (m, 9H).

Scheme 22: Synthesis of (R)-1-(4-(8-Amino-2,2,4-trifluoro-[1,3]dioxolo[4,5-g]quinazolin-6-yl)piperazin-1-yl)-3-(ethylamino)-3-(4-fluorophenyl)propan-1-one (COMPOUND 12)

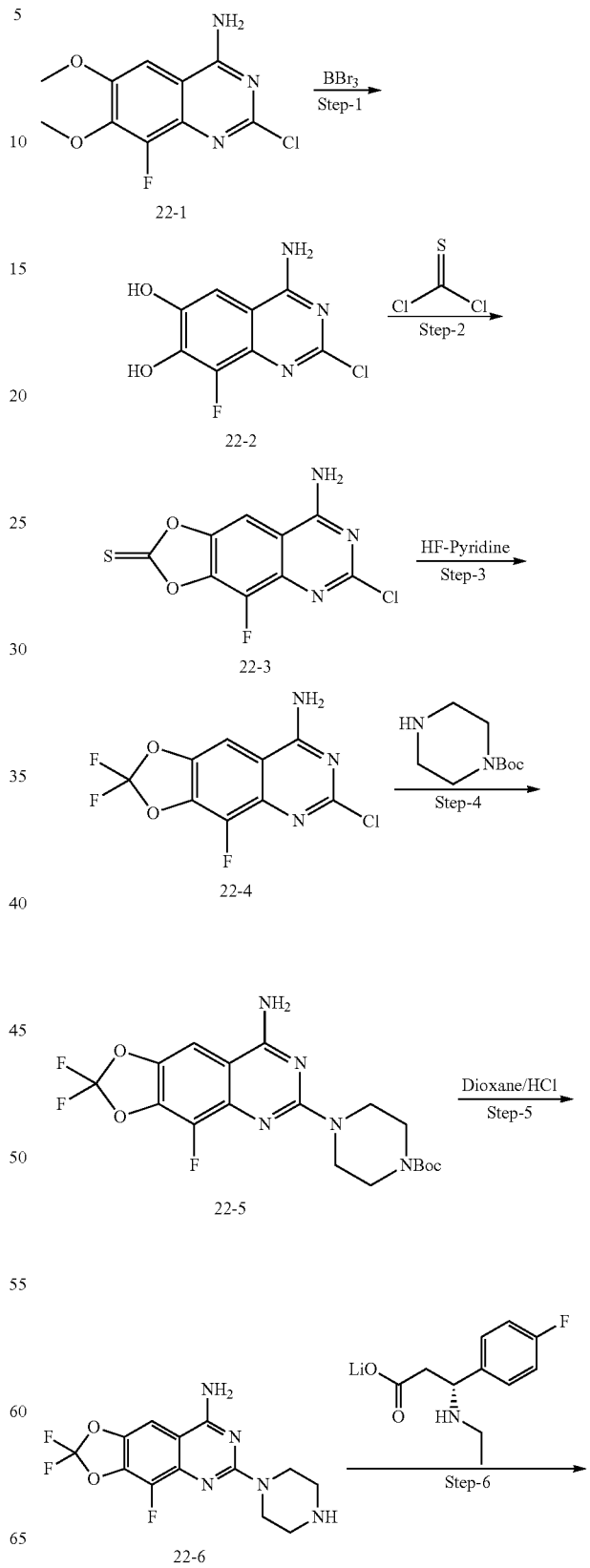

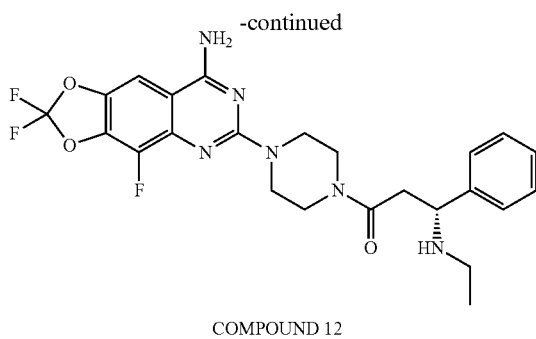

COMPOUND 12

Step 1: 4-Amino-2-chloro-8-fluoroquinazoline-6,7-diol (22-2)

To a solution of 2-chloro-8-fluoro-6,7-dimethoxyquinazolin-4-amine (1 equiv) in DCM (1 vol) at 0° C. was added BBr₃ (10 vol). The reaction mixture was stirred at room temperature for 12 hours and then concentrated. The residue was re-crystallized from MTBE to afford compound 22-2.

Step 2: 8-Amino-6-chloro-4-fluoro-[1,3]dioxolo[4,5-g]quinazoline-2-thione (22-3)

To a solution of NaH (2 equiv) in THF (10 vol) at 0° C. was added compound 22-2 (1 equiv). The reaction mixture was stirred at room temperature for 30 minutes and then cooled to 0° C. Thiophosgene (1.5 equiv) was added to the reaction mixture and the resulting mixture was stirred at room temperature for 5 hours. Water was added to the reaction mixture and the resulting mixture was extracted with ethyl acetate. The organic layer was separated, dried over anhydrous Na₂SO₄, filtered, and then concentrated. The residue was purified by column chromatography on silica gel using hexane/EtOAc to afford compound 22-3.

Step 3: 6-Chloro-2,2,4-trifluoro-[1,3]dioxolo[4,5-g]quinazolin-8-amine (22-4)

To a solution of compound 22-3 (1 equiv) in DCM (10 vol) at −78° C. was added NIS (3 equiv) and HF-pyridine (10 equiv). The reaction mixture was stirred at −78° C. for 1 hour and then quenched with 10% NaHCO₃. The resulting mixture was extracted with DCM. The organic layer was separated, dried over anhydrous Na₂SO₄, filtered and then concentrated. The residue was purified by column chromatography on silica gel using hexane/EtOAc to afford compound 22-4.

Step 4: tert-Butyl 4-(8-amino-2,2,4-trifluoro-[1,3]dioxolo[4,5-g]quinazolin-6-yl)piperazine-1-carboxylate (22-5)

To a solution of compound 22-4 (1 equiv) and TEA (1.5 equiv) in isopentyl alcohol (10 vol) is added tert-butyl piperazine-1-carboxylate (2 equiv). The reaction mixture was stirred at 120° C. for 16 hours and then concentrated. The residue was re-crystallized from MTBE to afford compound 22-5.

Step 5: 2,2,4-Trifluoro-6-(piperazin-1-yl)-[1,3]dioxolo[4,5-g]quinazolin-8-amine (22-6)

To a solution of compound 22-5 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 22-6.

Step 6: (R)-1-(4-(8-Amino-2,2,4-trifluoro-[1,3]dioxolo[4,5-g]quinazolin-6-yl)piperazin-1-yl)-3-(ethylamino)-3-(4-fluorophenyl)propan-1-one (Compound 12)

To a solution of compound 22-6 (1 equiv) and lithium (R)-3-(ethylamino)-3-(4-fluorophenyl)propanoate (1 equiv) in DMF (10 vol) at 0° C. was added DIPEA (5 equiv) and HBTU (1.2 equiv). The reaction mixture was stirred at room temperature for 16 hours and then quenched with water. The resulting mixture was extracted with ethyl acetate. The organic layer was separated, dried over anhydrous Na₂SO₄, filtered and then concentrated. The residue was purified by column chromatography on silica gel using hexane/EtOAc to afford COMPOUND 12.

$^1$H NMR (400 MHz, CD₃OD) δ 7.72 (s, 1H), 7.59-7.56 (m, 2H), 7.23 (t, J=8.8 Hz, 2H), 4.75 (t, J=6.4 Hz, 1H), 3.90-3.85 (m, 4H), 3.72 (t, J=4.8 Hz, 2H), 3.62 (t, J=5.2 Hz, 2H), 3.22-3.24 (m, 2H), 2.94-2.99 (m, 2H), 1.28-1.32 (m, 3H).

Scheme 23: Synthesis of (3R)-1-(8-(4-Amino-8-fluoro-6,7-dimethoxyquinazolin-2-yl)-3,8-diazabicyclo[3.2.1]octan-3-yl)-3-(ethylamino)-3-(4-fluorophenyl)propan-1-one (COMPOUND 13)

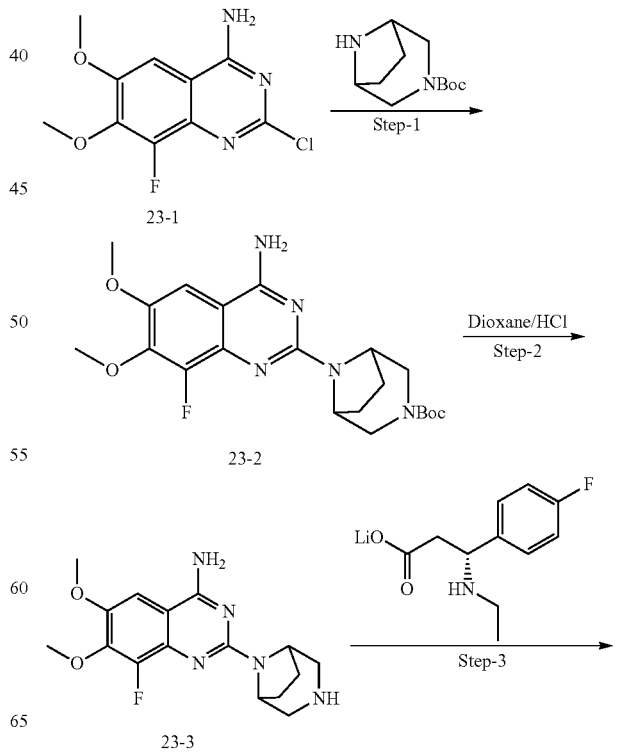

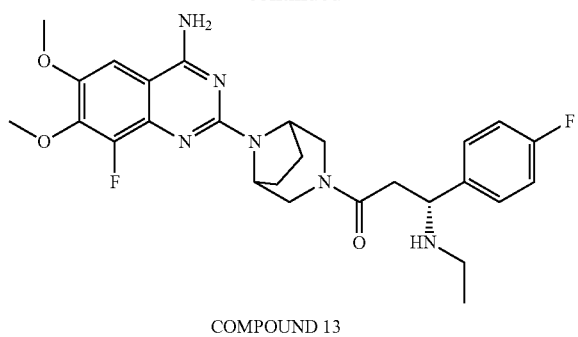

COMPOUND 13

Step 1: tert-Butyl 8-(4-amino-8-fluoro-6,7-dimethoxyquinazolin-2-yl)-3,8-diazabicyclo[3.2.1]octane-3-carboxylate (23-2)

To a mixture of 2-chloro-8-fluoro-6,7-dimethoxyquinazolin-4-amine (1 equiv) and TEA (1.5 equiv) in isopentyl alcohol (10 vol) is added tert-butyl 3,8-diazabicyclo[3.2.1]octane-3-carboxylate (2 equiv). The reaction mixture was stirred at 120° C. for 16 hours and then concentrated. The residue was re-crystallized from MTBE to afford compound 23-2.

Step 2: 2-(3,8-Diazabicyclo[3.2.1]octan-8-yl)-8-fluoro-6,7-dimethoxyquinazolin-4-amine (23-3)

To a solution of compound 23-2 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 23-3.

Step 3: (3R)-1-(8-(4-Amino-8-fluoro-6,7-dimethoxyquinazolin-2-yl)-3,8-diazabicyclo[3.2.1]octan-3-yl)-3-(ethylamino)-3-(4-fluorophenyl)propan-1-one (Compound 13)

To a solution of compound 23-3 (1 equiv) and lithium (R)-3-(ethylamino)-3-(4-fluorophenyl)propanoate (1 equiv) in DMF (10 vol) at 0° C. was added TEA (5 equiv) and HATU (1.2 equiv). The reaction mixture was stirred at room temperature for 16 hours and then quenched with water. The resulting mixture was extracted with ethyl acetate. The organic layer was separated, dried over anhydrous $Na_2SO_4$, filtered and then concentrated. The residue was purified by column chromatography on silica gel using hexane/EtOAc to afford COMPOUND 13.

$^1$H NMR (400 MHz, DMSO-$d_6$) δ 7.42-7.38 (m, 5H), 7.16-7.11 (m, 2H), 4.70-4.67 (m, 2H), 4.14-4.11 (m, 2H), 3.89 (s, 3H), 3.84 (s, 3H), 3.68-3.62 (m, 1H), 3.20-3.15 (m, 2H), 2.80-2.67 (m, 1H), 2.38-2.33 (m, 2H), 1.79-1.70 (m, 2H), 1.61-1.58 (m, 1H), 1.36-1.24 (m, 2H), 1.01-0.81 (m, 4H).

Scheme 24: Synthesis of 1-(3-(4-Amino-8-fluoro-6,7-dimethoxyquinazolin-2-yl)-3,8-diazabicyclo[3.2.1]octan-8-yl)-3-(4-fluorophenyl)prop-2-en-1-one (COMPOUND 14)

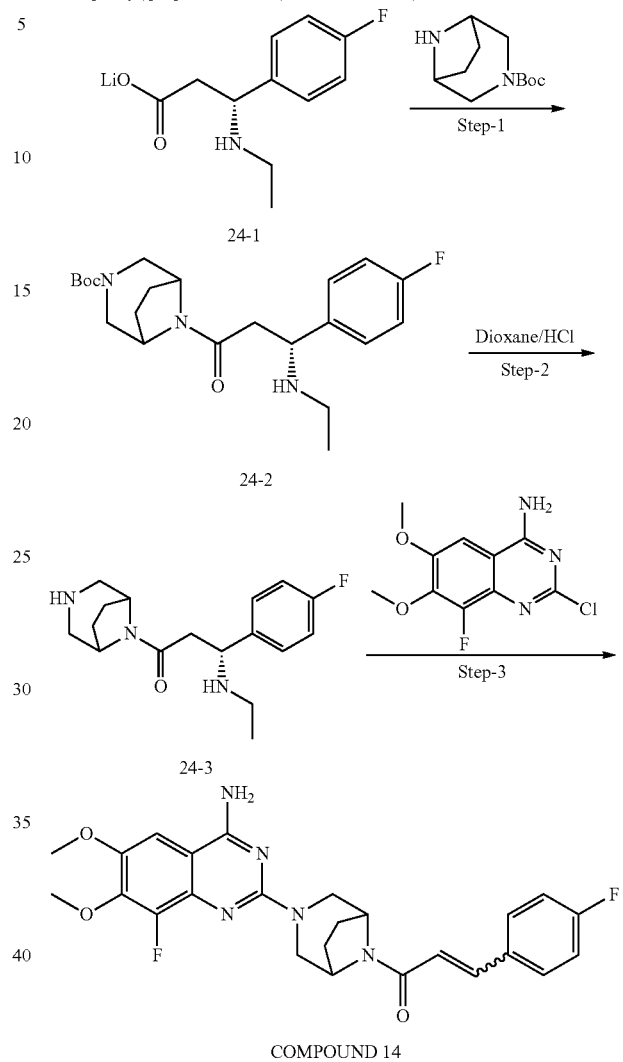

COMPOUND 14

Step 1: tert-Butyl 8-((R)-3-(ethylamino)-3-(4-fluorophenyl)propanoyl)-3,8-diazabicyclo[3.2.1]octane-3-carboxylate (24-2)

To a solution of tert-butyl 3,8-diazabicyclo[3.2.1]octane-3-carboxylate (1 equiv) and lithium (R)-3-(ethylamino)-3-(4-fluorophenyl)propanoate (1 equiv) in DCM (10 vol) at 0° C. was added DIPEA (5 equiv) and T3P (1.2 equiv). The reaction mixture was stirred at room temperature for 16 hours and then quenched with water. The resulting mixture was extracted with DCM. The organic layer was separated, dried over anhydrous $Na_2SO_4$, filtered and then concentrated. The residue was purified by column chromatography on silica gel using hexane/EtOAc to afford compound 24-2.

Step 2: (3R)-1-(3,8-Diazabicyclo[3.2.1]octan-8-yl)-3-(ethylamino)-3-(4-fluorophenyl)propan-1-one (24-3)

To a solution of compound 24-2 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 24-3.

Step 3: 1-(3-(4-Amino-8-fluoro-6,7-dimethoxyquinazolin-2-yl)-3,8-diazabicyclo[3.2.1]octan-8-yl)-3-(4-fluorophenyl)prop-2-en-1-one (Compound 14)

To a mixture of 2-chloro-8-fluoro-6,7-dimethoxyquinazolin-4-amine (1 equiv) and TEA (1.5 equiv) in isopentyl alcohol (10 vol) was added compound 3 (2 equiv). The reaction mixture was stirred at 120° C. for 16 hours and then concentrated. The residue was re-crystallized from MTBE to afford COMPOUND 14.

$^1$H NMR (400 MHz, DMSO-d$_6$) δ 7.85-7.79 (m, 3H), 7.60-7.51 (m, 2H), 7.29-7.18 (m, 4H), 4.95-4.91 (m, 2H), 4.76-4.73 (m, 1H), 4.51-4.49 (m, 1H), 3.97 (s, 3H), 3.88 (s, 3H), 3.20-2.94 (m, 2H), 1.93-1.91 (m, 2H), 1.76-1.68 (m, 2H).

Scheme 25: Synthesis of (3R)-1-(5-(4-Amino-8-fluoro-6,7-dimethoxyquinazolin-2-yl)-2,5-diazabicyclo[2.2.2]octan-2-yl)-3-(ethylamino)-3-(4-fluorophenyl)propan-1-one (COMPOUND 15)

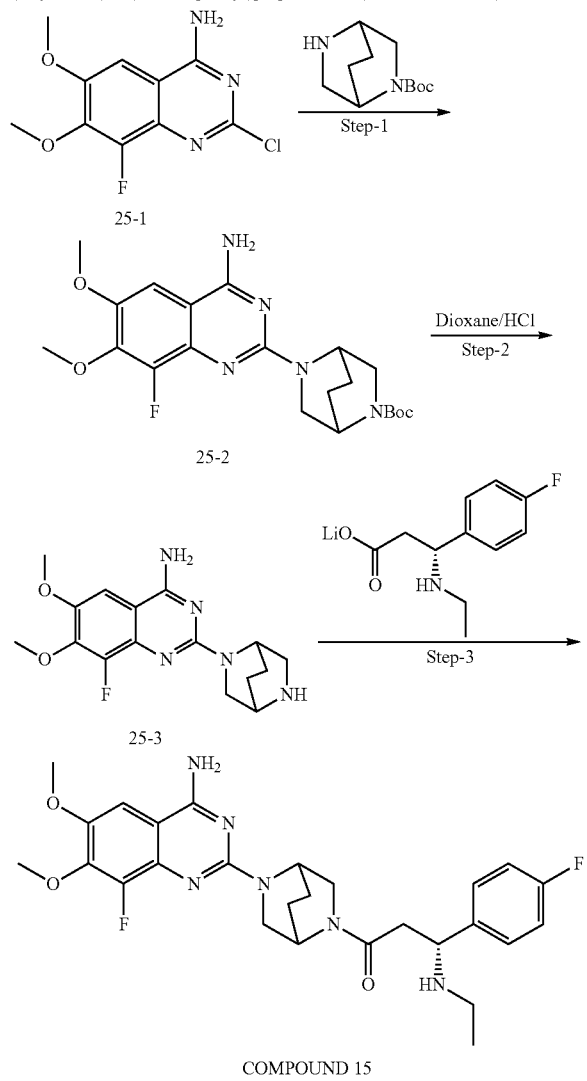

Step 1: tert-Butyl 5-(4-amino-8-fluoro-6,7-dimethoxyquinazolin-2-yl)-2,5-diazabicyclo[2.2.2]octane-2-carboxylate (25-2)

To a mixture of 2-chloro-8-fluoro-6,7-dimethoxyquinazolin-4-amine (1 equiv) and TEA (1.5 equiv) in isopentyl alcohol (10 vol) was added tert-butyl 2,5-diazabicyclo[2.2.2]octane-2-carboxylate (2 equiv). The reaction mixture was stirred at 120° C. for 16 hours and then concentrated. The residue was re-crystallized from MTBE to afford compound 25-2.

Step 2: tert-Butyl 5-(4-amino-8-fluoro-6,7-dimethoxyquinazolin-2-yl)-2,5-diazabicyclo[2.2.2]octane-2-carboxylate (25-3)

To a solution of compound 25-2 (1 equiv) in dioxane (2 vol) at 0° C. was added 4 N HCl in dioxane (10 vol). The reaction mixture was stirred at room temperature for 4 hours and then concentrated. The residue was taken up in MTBE and stirred for 30 minutes. The resultant solid was filtered and dried to afford compound 25-3.

Step 3: (3R)-1-(5-(4-Amino-8-fluoro-6,7-dimethoxyquinazolin-2-yl)-2,5-diazabicyclo[2.2.2]octan-2-yl)-3-(ethylamino)-3-(4-fluorophenyl)propan-1-one (Compound 15)

To a solution of compound 25-3 (1 equiv) and compound 25-4 (1 equiv) in DMF (10 vol) at 0° C. was added TEA (5 equiv) and HATU (1.2 equiv). The reaction mixture was stirred at room temperature for 16 hours and then quenched with water. The resulting mixture was extracted with ethyl acetate. The organic layer was separated, dried over anhydrous Na$_2$SO$_4$, filtered and then concentrated. The residue was purified by column chromatography on silica gel using hexane/EtOAc to afford COMPOUND 15.

$^1$H NMR (400 MHz, DMSO-d$_6$) δ 7.44-7.36 (m, 5H), 7.15-7.03 (m, 2H), 4.95-4.88 (m, 1H), 4.61-4.59 (m, 1H), 4.18-4.12 (m, 1H), 3.87 (s, 3H), 3.82 (s, 3H), 3.68-3.62 (m, 2H), 3.48-3.40 (m, 2H), 2.71-2.66 (m, 2H), 2.37-2.32 (m, 3H), 1.85-1.75 (m, 3H), 1.05-0.96 (m, 3H), 0.85-0.83 (m, 1H).

Scheme 26: Synthesis of 4-((1R)-3-(8-(4-Amino-8-fluoro-6,7-dimethoxyquinazolin-2-yl)-3,8-diazabicyclo[3.2.1]octan-3-yl)-1-(ethylamino)-3-oxopropyl)benzonitrile (COMPOUND 16)

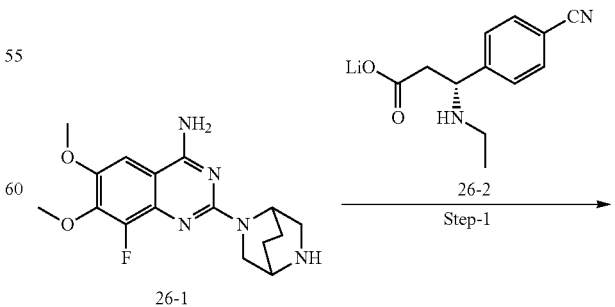

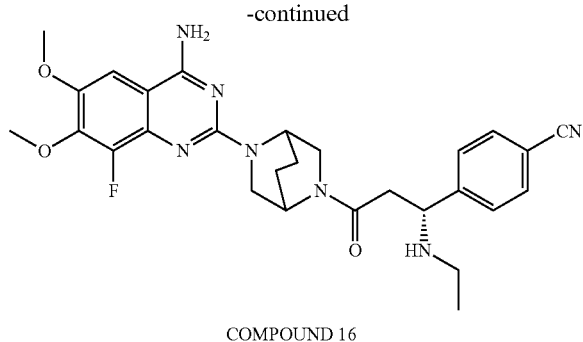

COMPOUND 16

Step 1: 4-((1R)-3-(8-(4-Amino-8-fluoro-6,7-dimethoxyquinazolin-2-yl)-3,8-diazabicyclo[3.2.1]octan-3-yl)-1-(ethylamino)-3-oxopropyl)benzonitrile (Compound 16)

To a solution of 2-(3,8-diazabicyclo[3.2.1]octan-8-yl)-8-fluoro-6,7-dimethoxyquinazolin-4-amine (26-1, 1 equiv) and lithium (R)-3-(4-cyanophenyl)-3-(ethylamino)propanoate (26-2, 1 equiv) in DMF (10 vol) at 0° C. was added TEA (5 equiv) and HBTU (1.2 equiv). The reaction mixture was stirred at room temperature for 16 hours and then quenched with water. The resulting mixture was extracted with ethyl acetate. The organic layer was separated, dried over anhydrous Na$_2$SO$_4$, filtered and concentrated. The residue was purified via preparative HPLC to afford COMPOUND 16.
$^1$H NMR (400 MHz, DMSO-d$_6$) δ 7.79-7.75 (m, 2H), 7.60-7.55 (m, 2H), 7.45-7.38 (m, 3H), 4.70-4.67 (m, 2H), 4.13-4.04 (m, 2H), 3.89 (s, 3H), 3.83 (s, 3H), 3.64-3.60 (m, 1H), 3.17-3.16 (m, 1H), 2.80-2.67 (m, 2H), 2.30-2.26 (m, 2H), 1.91-1.73 (m, 3H), 1.54-1.53 (m, 1H), 1.32-1.31 (m, 1H), 0.97 (t, J=6.5 Hz, 3H).

Scheme 27: Synthesis of (R)-4-(3-(-4(4-Amino-8-fluoro-6,7-dimethoxyquinazolin-2-yl)-3,6-dihydropyridin-1(2H)-yl)-1-(ethylamino)-3-oxopropyl)benzonitrile (COMPOUND 17)

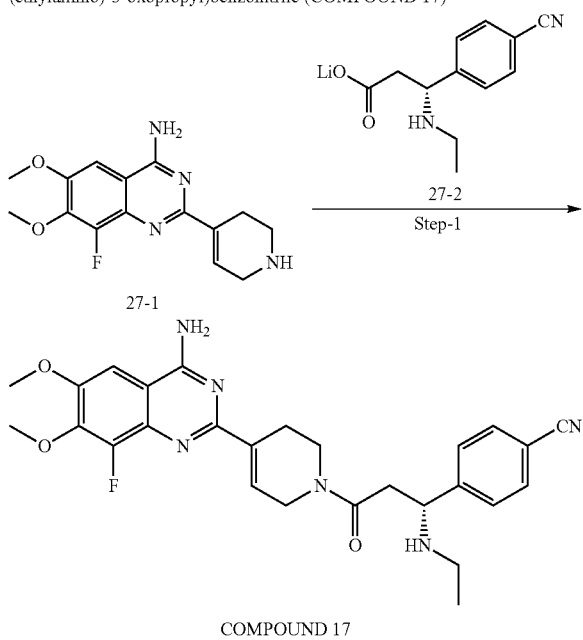

COMPOUND 17

Step 1: (R)-4-(3-(4-(4-Amino-8-fluoro-6,7-dimethoxyquinazolin-2-yl)-3,6-dihydropyridin-1(2H)-yl)-1-(ethylamino)-3-oxopropyl)benzonitrile (Compound 17)

To a solution of 8-fluoro-6,7-dimethoxy-2-(1,2,3,6-tetrahydropyridin-4-yl)quinazolin-4-amine (27-1, 1 equiv) and lithium (R)-3-(4-cyanophenyl)-3-(ethylamino)propanoate (27-2, 1 equiv) in DMF (10 vol) at 0° C. was added TEA (5 equiv) and HBTU (1.2 equiv). The reaction mixture was stirred at room temperature for 16 hours and then quenched with water. The resulting mixture was extracted with ethyl acetate. The organic layer was separated, dried over anhydrous Na$_2$SO$_4$, filtered and concentrated. The residue was purified via preparative HPLC to afford COMPOUND 17.
$^1$H NMR (400 MHz, DMSO-d$_6$) δ 7.77-7.74 (m, 2H), 7.59-7.52 (m, 5H), 7.04-6.98 (m, 1H), 4.21-4.11 (m, 3H), 3.93 (s, 3H), 3.90 (s, 3H), 3.60-3.50 (m, 2H), 2.70-2.66 (m, 4H), 2.34-2.24 (m, 2H), 0.95 (t, J=6.7 Hz, 3H).

Scheme 28: Synthesis of 1-(4-(4-Amino-8-fluoro-6,7-dimethoxyquinazolin-2-yl)-3,6-dihydropyridin-1(2H)-yl)-2-((2S,3aS,7aS)-octahydro-1H-indol-2-yl)ethan-1-one TFA salt (COMPOUND 18)

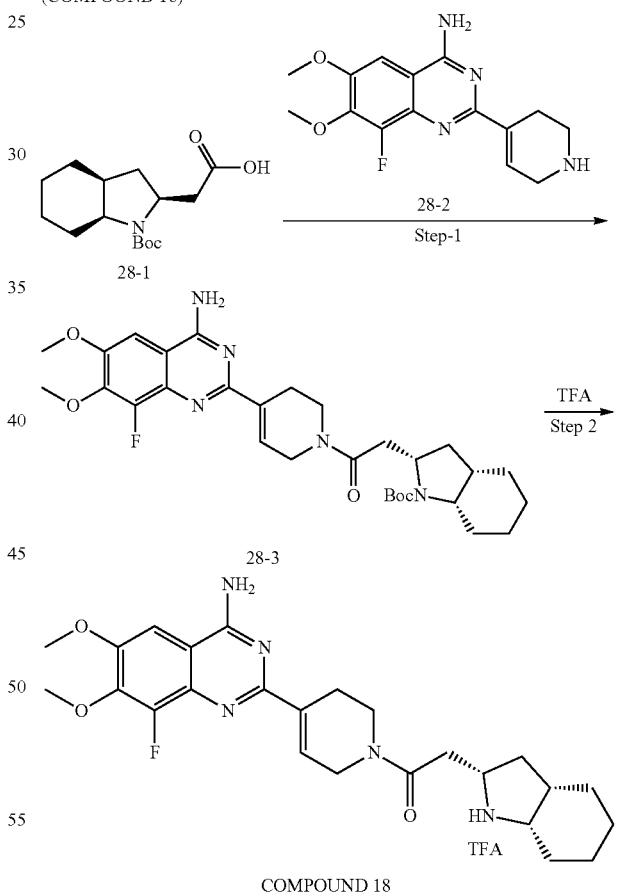

COMPOUND 18

Step 1: tert-butyl (2S,3aS,7aS)-2-(2-(4-(4-Amino-8-fluoro-6,7-dimethoxyquinazolin-2-yl)-3,6-dihydropyridin-1(2H)-yl)-2-oxoethyl)octahydro-1H-indole-1-carboxylate (28-3)

To a solution of 2-((2S,3aS,7aS)-1-(tert-butoxycarbonyl)octahydro-1H-indol-2-yl)acetic acid (28-1, 1 equiv) and 8-fluoro-6,7-dimethoxy-2-(1,2,3,6-tetrahydropyridin-4-yl) quinazolin-4-amine (28-2, 1 equiv) in DMF (10 vol) at 0° C. was added DIPEA (5 equiv) and HBTU (1.2 equiv). The reaction mixture was stirred at room temperature for 16 hours and then quenched with water. The resulting mixture was extracted with ethyl acetate. The organic layer was separated, dried over anhydrous Na₂SO₄, filtered and then concentrated. The residue was purified via column chromatography on silica gel using DCM/MeOH to afford compound 28-3.

Step 2: 1-(4-(4-Amino-8-fluoro-6,7-dimethoxyquinazolin-2-yl)-3,6-dihydropyridin-1(2H)-yl)-2-((2S, 3aS,7aS)-octahydro-1H-indol-2-yl)ethan-1-one TFA Salt (Compound 18)

To a solution of compound 28-3 (1 equiv) in DCM (10 vol) at 0° C. under nitrogen atmosphere was added TFA (5 vol), The reaction mixture was stirred at room temperature for 2 hours. After completion of the reaction, the reaction mixture was concentrated to afford COMPOUND 18.

¹H NMR (400 MHz, D20) δ 7.72 (s, 1H), 6.81-6.80 (m, 1H), 4.25-4.22 (m, 2H), 4.07 (s, 3H), 3.95-3.94 (m, 1H), 3.86 (s, 3H), 3.74-3.59 (m, 3H), 3.13-2.94 (m, 2H), 2.64-2.57 (m, 2H), 2.33-2.32 (m, 1H), 2.15-2.12 (m, 1H), 1.81-1.79 (m, 2H), 1.57-1.55 (m, 4H), 1.35-1.25 (m, 3H).

Scheme 29: Synthesis of 4-(4,4-difluoro-1-((5-methoxy-7-methyl-1H-indol-4-yl)methyl)piperidin-2-yl)benzoic acid (COMPOUND 19)

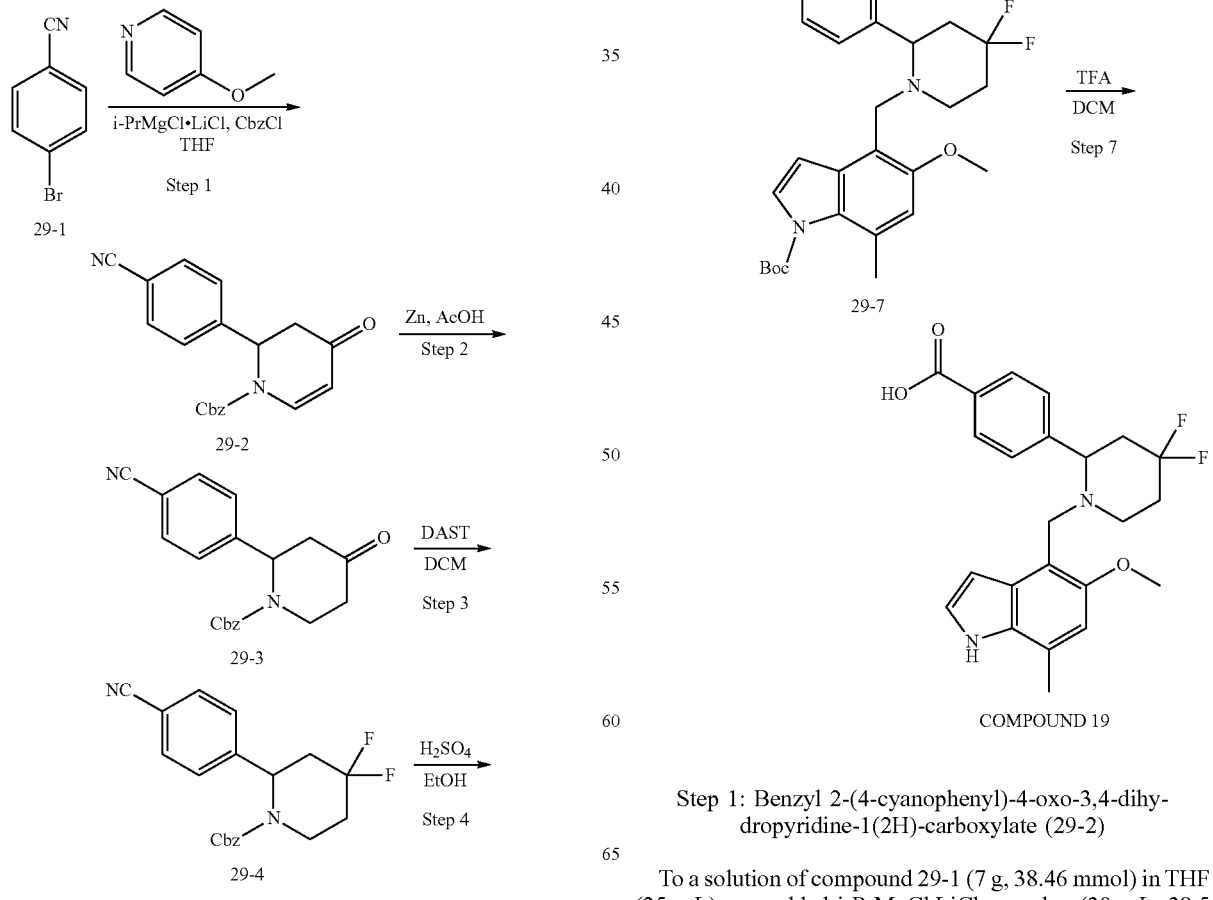

Step 1: Benzyl 2-(4-cyanophenyl)-4-oxo-3,4-dihydropyridine-1(2H)-carboxylate (29-2)

To a solution of compound 29-1 (7 g, 38.46 mmol) in THF (25 mL) was added i-PrMgCl.LiCl complex (30 mL, 38.5 mmol, 1.3 M) under $N_2$ atmosphere at room temperature and the mixture was stirred at room temperature for 1.5 hrs. The mixture was cooled to −5° C. and 4-methoxypyridine (3.8 g, 34.6 mmol) was added followed by drop-wise addition of CbzCl (5.9 g, 34.6 mmol). The reaction was stirred at room temperature for 16 hrs. The reaction mixture was then quenched with 2N HCl and extracted with EtOAc twice. The combined organic phases were washed with brine, dried over $Na_2SO_4$, filtered, and concentrated to dryness. The residue was purified by silica gel column (eluted with petroleum ether/EtOAc=1/1) to give compound 29-2 (2.8 g, 22% yield) as yellow solid. LC/MS (ESI) m/z: 333 $(M+H)^+$.

Step 2: Benzyl 2-(4-cyanophenyl)-4-oxopiperidine-1-carboxylate (29-3)

To a solution of the compound 29-2 (540 mg, 1.62 mmol) in AcOH (5 mL) Zn dust (840 mg, 13 mmol) was added and the reaction mixture was stirred at reflux for 2 hrs. The mixture was diluted with EtOAc and filtered and the filtrate was concentrated to dryness to give crude product, which was purified by silica gel column (eluted with petroleum ether/EtOAc=1/1) to give compound 29-3 (510 mg, 90% yield) as a colorless oil. LC/MS (ESI) m/z: 335 $(M+H)^+$.

Step 3: Benzyl 2-(4-cyanophenyl)-4,4-difluoropiperidine-1-carboxylate (29-4)

To a solution of compound 29-3 (510 mg, 0.51 mmol) in DCM (5 mL) is added DAST (730 mg, 4.6 mmol) at −20° C. under $N_2$ atmosphere and the reaction mixture is stirred at room temperature for 16 hrs. The reaction is quenched with 5% aq.$NaHCO_3$ solution and extracted with DCM twice. The combined organic phases are washed with brine, dried over $Na_2SO_4$, and concentrated to dryness. The residue is purified by silica gel column (eluted with DCM/MeOH=50/1) to give compound 29-4 (183 mg, 33.5% yield) as a light yellow solid. LC/MS (ESI) m/z: 357 $(M+H)^+$.

Step 4: ethyl 4-(4,4-difluoropiperidin-2-yl)benzoate (29-5)

To a solution of the compound 29-4 (180 mg, 0.22 mmol) in EtOH (5 mL) is added conc.$H_2SO_4$ (3 mL, 98%) drop-wiseiy at 0° C. The reaction mixture is stirred at 90° C. for 16 hrs. The mixture is poured into ice-water and the pH is adjusted to 10 by adding 5% aq.$NaHCO_3$ solution. The mixture is extracted with EtOAc twice and the combined organic layers are washed with brine, dried over $Na_2SO_4$, filtered and concentrated to dryness. The residue is purified by silica gel column (eluted with DCM/MeOH=30/1) to give compound 29-5 (126 mg, 72.6% yield) as light yellow solid. LC/MS (ESI) m/z: 270 $(M+H)^+$.

Step 5: tert-butyl 4-((2-(4-(ethoxycarbonyl)phenyl)-4,4-difluoropiperidin-1-yl)methyl)-5-methoxy-7-methyl-1H-indole-1-carboxylate (29-6)

To a mixture of compound 29-5 (120 mg, 0.45 mmol), tert-butyl 4-(hydroxymethyl)-5-methoxy-7-methyl-1H-indole-1-carboxylate (156 mg, 0.54 mmol) and $PPh_3$ (235 mg, 0.9 mmol) in THF (5 mL) is added DIAD (180 mg, 0.9 mmol) drop-wisely at 0° C. under $N_2$ atmosphere. The reaction mixture is stirred at room temperature for 16 hrs. The mixture is concentrated to dryness and the residue is purified by silica gel column (eluted with DCM/MeOH=30/1) to give compound 29-6 (70 mg, 28.6% yield) as a light yellow solid. LC/MS (ESI) m/z: 543 $(M+H)^+$.

Step 6: 4-(1-((1-(tert-butoxycarbonyl)-5-methoxy-7-methyl-1H-indol-4-yl)methyl)-4,4-difluoropiperidin-2-yl)benzoic Acid (29-7)

To a solution of compound 29-6 (50 mg, 0.09 mmol) in THF/water (1 mL/1 mL) is added LiOH (5 mg, 0.2 mmol). The reaction mixture is stirred at room temperature for 2 hrs. The mixture is concentrated to half volume and acidified by adding 1N HCl to pH-3. The mixture is extracted with DCM twice and the combined organic layers are washed with brine, dried over $Na_2SO_4$ and concentrated to give compound 29-7 (35 mg, 73.8% yield) as light yellow solid. LC/MS (ESI) m/z: 515 $(M+H)^+$.

Step 7: 4-(4,4-difluoro-14(5-methoxy-7-methyl-1H-indol-4-yl)methyl)piperidin-2-yl)benzoic Acid (Compound 19)

To a solution of compound 29-7 (35 mg, 0.068 mmol) in DCM (3 mL) is added TFA (1 mL). The reaction mixture is stirred at room temperature for 1 hr. The mixture is concentrated to dryness to give crude product, which is purified by prep.HPLC to give COMPOUND 19 (5.1 mg, 14.6% yield) as white solid. $^1$HNMR (400 MHz, DMSO-$d_6$) δ 11.28 (s, 1H), 9.41 (s, 1H), 8.21 (d, J=13.1 Hz, 1H), 8.07 (s, 1H), 7.85 (d, J=47.4 Hz, 2H), 7.41 (d, J=72.6 Hz, 1H), 6.79 (d, J=49.2 Hz, 1H), 6.43 (s, 1H), 5.00 (s, 1H), 4.40 (s, 1H), 4.10 (s, 1H), 3.81-3.64 (m, 3H), 3.55 (s, 1H), 2.73 (s, 1H), 2.39 (d, J=1.8 Hz, 3H), 2.16 (s, 1H), 1.98-1.77 (m, 1H). LC/MS (ESI) m/z: 415 $(M+H)^+$.

Scheme 30: Synthesis of (1R,4S)-4-((S)-1-((5-Methoxy-7-methyl-1H-indol-4-yl)methyl) piperidin-2-yl)cyclohexanecarboxylic acid (COMPOUND 20)

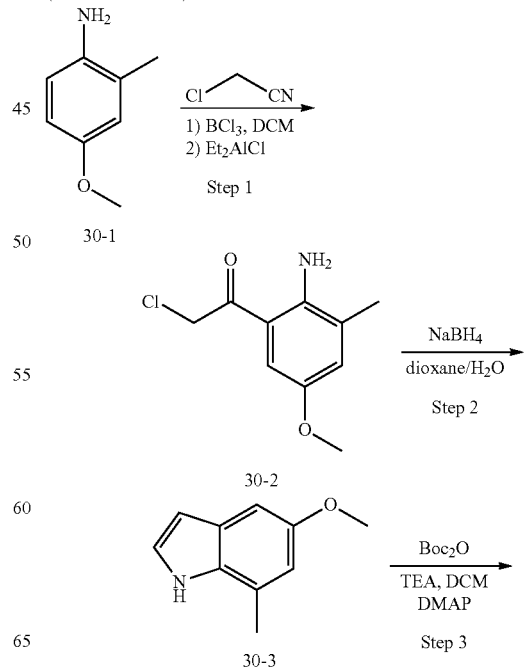

241
-continued
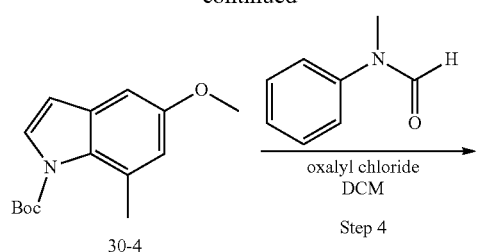
30-4
oxalyl chloride
DCM
Step 4
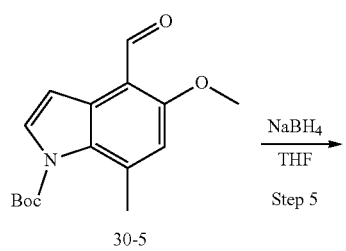
30-5
NaBH₄
THF
Step 5
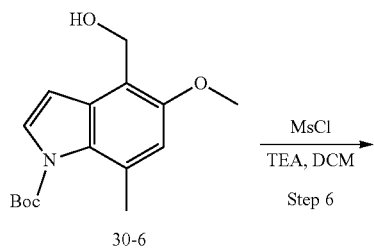
30-6
MsCl
TEA, DCM
Step 6
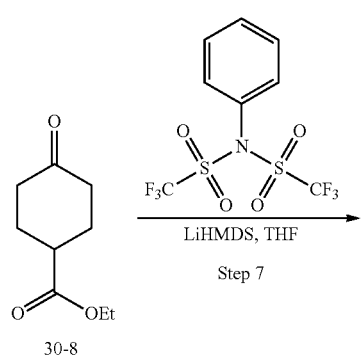
30-7
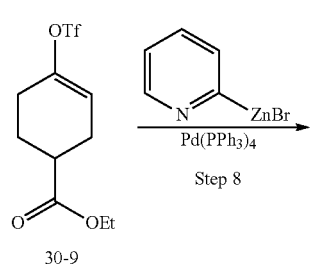
30-8
LiHMDS, THF
Step 7
242
-continued
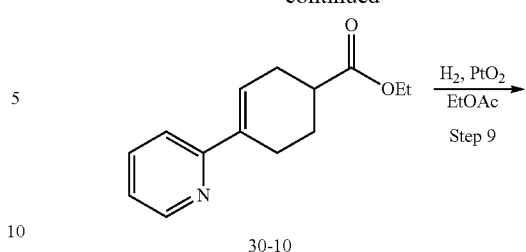
30-10
H₂, PtO₂
EtOAc
Step 9
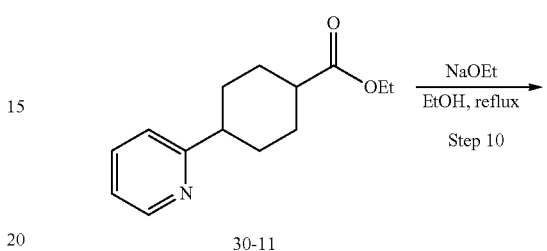
30-11
NaOEt
EtOH, reflux
Step 10
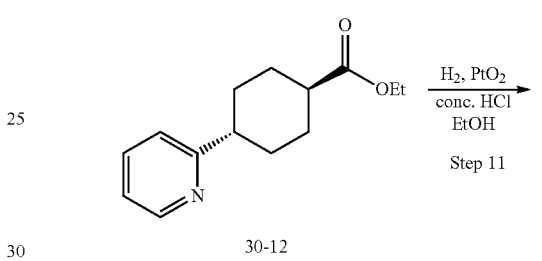
30-12
H₂, PtO₂
conc. HCl
EtOH
Step 11
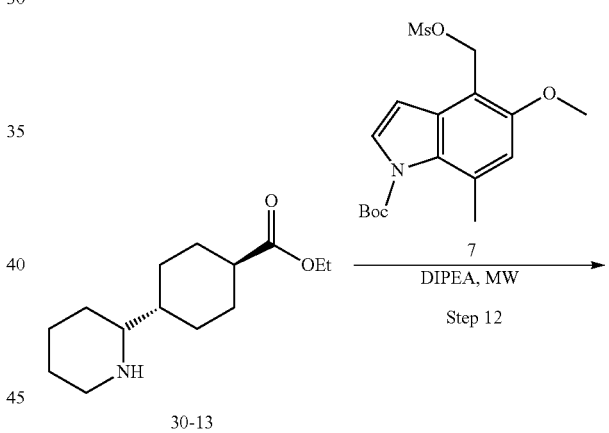
30-13
7
DIPEA, MW
Step 12
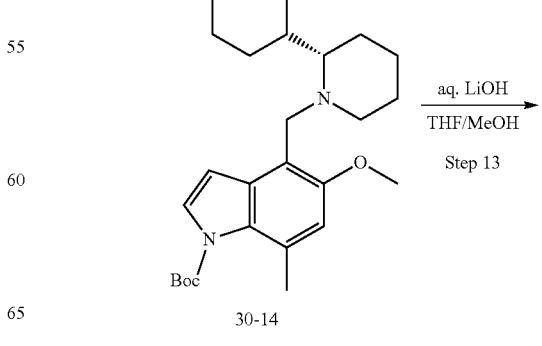
30-14
aq. LiOH
THF/MeOH
Step 13
OTf / ZnBr / Pd(PPh₃)₄
Step 8
30-9

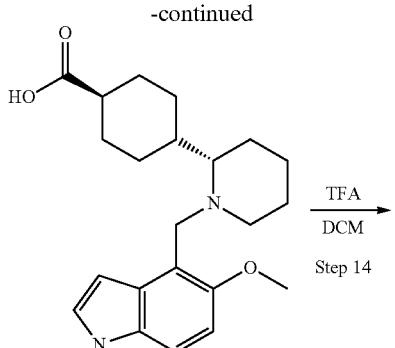

30-15

COMPOUND 20

Step 1: 1-(2-Amino-5-methoxy-3-methylphenyl)-2-chloroethanone (30-2)

To a solution of compound 30-1 (18.6 g, 135.6 mmol) in DCM (20 mL) was added $BCl_3$-THF solution (188.5 ml, 188.5 mmol, 1M) dropwise at −10° C. under $N_2$ atmosphere. Chloroacetonitrile (51.2 g, 684.1 mmol) was added dropwise to the above mixture at 0° C. followed by the dropwise addition of diethylaluminum chloride THF solution (75 mL, 150 mmol, 2M) at 0° C. After addition, the reaction mixture was stirred at room temperature for 16 hours. The reaction mixture was quenched with 5M aqueous HCl at 0° C. and the resulting mixture was extracted with ethyl acetate (300 mL). The organic phase was washed with brine, dried with $Na_2SO_4$ and concentrated to dryness. The residue was purified with silica gel column (eluted with petroleum ether:ethyl acetate=10:1 to 3:1) to afford compound 30-2 (12.6 g, 43.5% yield) as a yellow solid. LC/MS (ESI) m/z: 214 $(M+H)^+$.

Step 2: 5-Methoxy-7-methyl-1H-indole (30-3)

To a mixture of compound 30-2 (3.2 g, 14.977 mmol) in dioxane (27 mL) and water (3 mL) was added $NaBH_4$ (0.567 g, 14.977 mmol) in portions at 0° C. The reaction mixture was stirred at room temperature for 1 hour before it was stirred at 100° C. for 5 hours. The mixture was quenched with water (50 mL) and extracted with ethyl acetate (100 mL). The organic phase was washed with brine, dried with $Na_2SO_4$ and concentrated to dryness. The residue was purified with silica gel column (eluted with petroleum ether: ethyl acetate=10:1 to 3:1) to afford compound 30-3 (1.6 g, 66.3% yield) as a yellow solid. LC/MS (ESI) m/z: 162 $(M+H)^+$.

Step 3: tert-Butyl 5-methoxy-7-methyl-1H-indole-1-carboxylate (30-4)

To a solution of compound 30-3 (1.24 g, 7.69 mmol) in DCM (20 mL) was added di-tert-butyldicarbonate (2.52 g, 11.5 mmol) and catalytic DMAP (0.1 g, 0.769 mmol) at ambient temperature. The reaction mixture was stirred at room temperature for 16 hours. The mixture was diluted with DCM and washed with water and brine, dried over $Na_2SO_4$, filtered and concentrated to dryness. The residue was purified by silica gel column chromatography (eluted with petroleum ether:ethyl acetate=50:1 to 10:1) to afford compound 30-4 (1.91 g, 95.1% yield) a as yellow solid. LC/MS (ESI) m/z: 262 $(M+H)^+$.

Step 4: tert-Butyl 4-formyl-5-methoxy-7-methyl-1H-indole-1-carboxylate (30-5)

To a mixture of N-methylformanilide (1.29 g, 9.57 mmol) in DCM (5 mL) was added oxalyl chloride (1.21 g, 9.57 mmol). The mixture was stirred at 25° C. overnight. A solution of compound 30-4 (1.91 g, 7.31 mmol) in DCM (10 mL) was added to the mixture at −14° C. for 2 hours under $N_2$ atmosphere. After addition, the mixture was stirred for another hour at the same temperature. The reaction was quenched with aqueous $NaHCO_3$ solution and extracted with ethyl acetate (100 mL). The organic phase was washed with brine, dried with $Na_2SO_4$ and concentrated, purified with silica gel column (eluted with petroleum ether:ethyl acetate=50:1 to 30:1) to afford compound 30-5 (0.92 g, 33.2% yield) as a white solid. LC/MS (ESI) m/z: 290 $(M+H)^+$.

Step 5: tert-Butyl 4-(hydroxymethyl)-5-methoxy-7-methyl-1H-indole-1-carboxylate (30-6)

To a solution of tert-butyl 4-formyl-5-methoxy-7-methyl-1H-indole-1-carboxylate (300 mg, 1.0 mmol) in MeOH (4 mL) was added $NaBH_4$ (78.5 mg, 2.1 mmol) at 0° C. and the reaction mixture was stirred at room temperature for 30 minutes. The mixture was evaporated under reduced pressure and the residue was partitioned between EtOAc and water. The organic layer was washed with brine, dried over $Na_2SO_4$ and concentrated to afford compound 30-6 (310 mg, 100% yield) as a yellow solid, which was directly used in the next reaction without further purification. LC/MS (ESI) m/z: 274 $(M-OH)^+$

Step 6: tert-Butyl 5-methoxy-7-methyl-4-(((methylsulfonyl)oxy)methyl)-1H-indole-1-carboxylate (30-7)

To a solution of tert-butyl 4-(hydroxymethyl)-5-methoxy-7-methyl-1H-indole-1-carboxylate (100 mg, 0.34 mmol) in DCM (3 mL) was added TEA (73.4 mg, 0.68 mmol) and MsCl (60 mg, 0.52 mmol) at 0° C. under $N_2$ atmosphere and the reaction mixture was stirred at room temperature overnight. The mixture was poured into ice water (20 mL) and extracted with DCM (2×15 mL). The combined organic layers were dried over $Na_2SO_4$ and concentrated to dryness to afford compound 30-7 (110 mg, 87.6% yield) as yellow solid, which was directly used in the next reaction without further purification. LC/MS (ESI) m/z: 274 (M+H)+.

Step 7: Ethyl 4-(((trifluoromethyl)sulfonyl)oxy) cyclohex-3-enecarboxylate (30-9)

To a solution of ethyl-4-cyclohexanonecarboxylate (1.0 g, 5.88 mmol) in THF (20 mL) was added a 1M solution of lithium bis(trimethylsilyl)amid in THF (7.06 mL, 7.06 mmol) at −65° C. and the mixture was stirred for 1 hour at the same temperature. A solution of N-phenyl-bis(trifluoromethane sulfonimide) (2.5 g, 7.06 mmol) in THF (8 mL) was added dropwise to the mixture and the mixture was stirred at room temperature for 12 hours. The mixture was quenched with 1 M aqueous sodium hydrogen sulfate solution (5.88 mL, 5.88 mmol). The solvent was removed by rotary evaporation (water bath below 40° C.). The residue was partitioned between tert-butyl methyl ether (20 mL) and 0.5 M aqueous sodium hydroxide solution (16 mL). The organic layer was washed with 0.5 M aqueous sodium hydroxide solution, saturated ammonium chloride solution and brine, dried over $Na_2SO_4$ and concentrated under vacuum. The residue was purified by chromatography on silica gel (petroleum ether:EtOAc=25:1 to 20:1) to afford compound 30-9 (1.6 g, yield 90.3%) as a light oil.

Step 8: Ethyl 4-(pyridin-2-yl)cyclohex-3-enecarboxylate (30-10)

A three-neck round-bottom flask with a stir bar was charged with isopropylmagnesium chloride (2.0 M, 2.75 mL, 5.5 mmol, 1.1 equiv). To this mixture was added 2-bromopyridine (0.476 mL, 5.0 mmol, 1.0 equiv) dropwise with the temperature not exceeding 30° C. After 4 hours, zinc chloride (1 M, 7 mL, 7.0 mmol, 1.4 equiv) was added dropwise with the temperature not exceeding 30° C. The mixture was stirred at room temperature for 1 hour.

A mixture of (RS)-4-trifluoromethanesulfonyloxycyclohex-3-enecarboxylic acid ethyl ester (1.6 g, 5.3 mmol) in dry THF (20 mL) was added to the above mixture and the mixture was degassed under $N_2$ atmosphere three times before Pd $(PPh_3)_4$ (404 mg, 0.35 mmol, 0.05 eq) was added. The resulting mixture was stirred at 75° C. under a $N_2$ atmosphere overnight. After cooling to room temperature, the reaction mixture was partitioned between ethyl acetate and water. The organic layer was washed with brine, dried over $Na_2SO_4$ and concentrated to dryness under reduced pressure. The residue was purified by chromatography on silica gel (petroleum ether:EtOAc=20:1 to 15:1) to afford compound 30-10 (560 mg, 45.9% yield) as a light yellow oil. LC/MS (ESI) m/z: 232 (M+H)+

Step 9: Ethyl 4-(pyridin-2-yl)cyclohexanecarboxylate (30-11)

To a solution of ethyl 4-(pyridin-2-yl)cyclohex-3-enecarboxylate (650 mg, 2.81 mmol) in EtOAc (10 mL) was added $PtO_2$ (64 mg, 0.28 mmol) and the reaction mixture was stirred under a $H_2$ balloon at room temperature overnight. The mixture was filtered and the filtrate was concentrated to dryness. The residue was purified by chromatography on silica gel (petroleum ether:EtOAc=20:1 to 15:1) to afford compound 30-11 (450 mg, 68.7% yield) as a light yellow oil. LC/MS (ESI) m/z: 234 (M+H)+.

Step 10: (1R,4R)-Ethyl 4-(pyridin-2-yl)cyclohexanecarboxylate (30-12)

To EtOH (15 mL) was added Na (444 mg, 11.6 mmol) and the mixture was stirred at room temperature until the solution turned clear. Ethyl 4-(pyridin-2-yl)cyclo hexanecarboxylate (450 mg, 1.9 mmol) was added to the above solution and the reaction mixture was stirred at 90° C. for 72 hours. After cooling to 0° C., concentrated $H2SO_4$ (1.7 g, 17.1 mmol) was added and the resulting mixture was stirred at 90° C. for an additional 2 hours. After cooling to room temperature, the mixture was partitioned between EtOAc and aqueous $NaHCO_3$ solution. The organic layer was washed with brine, dried over $Na_2SO_4$, and concentrated under reduced pressure. The residue was purified by chromatography on silica gel (petroleum ether:EtOAc=20:1 to 5:1) to afford compound 30-12 (410 mg, 92.3% yield, 90% ee value) as a brown oil. LC/MS (ESI) m/z: 234 (M+H)+

Step 11: (1S,4R)-Ethyl 4-((S)-piperidin-2-yl)cyclohexanecarboxylate hydrochloride (30-13)

To a solution of (1R,4R)-ethyl 4-(pyridin-2-yl)cyclohexanecarboxylate (200 mg, 0.86 mmol) in EtOH (5 mL) was added concentrated HCl (0.5 mL) and $PtO_2$ (19.5 mg, 0.09 mmol), and the mixture was hydrogenated at 55 Psi for 2 hours. The mixture was filtered and the filtrate was evaporated under reduced pressure. The residue was washed with EtOAc to afford compound 30-13 (180 mg, 87.3% yield) as a white solid. LC/MS (ESI) m/z: 240 (M+H)+.

Step 12: tert-Butyl 4-(((S)-2-((1s,4R)-4-(ethoxycarbonyl)cyclohexyl)piperidin-1-yl) methyl)-5-methoxy-7-methyl-1H-indole-1-carboxylate (30-14)

A mixture of tert-butyl 5-methoxy-7-methyl-4-(((methylsulfonyl)oxy)methyl)-1H-indole-1-carboxylate (100 mg, 0.27 mmol), (1S,4R)-ethyl 4-((S)-piperidin-2-yl) cyclohexanecarboxylate hydrochloride (64.7 mg, 0.27 mmol) and DIPEA (0.14 mL, 0.81 mmol) in MeCN (2 mL) was stirred at 100° C. in a microwave reactor for 1 hour. The mixture was diluted with EtOAc, washed with water and brine, and dried and concentrated to afford crude product. The crude material was purified by preparative TLC (DCM:MeOH=20:1) to afford compound 30-14 (50 mg, 36.2% yield) as a yellow solid. LC/MS (ESI) m/z: 513 (M+H)+.

Step 13: (1R,4S)-4-((S)-1-((1-(tert-Butoxycarbonyl)-5-methoxy-7-methyl-1H-indol-4-yl)methyl) piperidin-2-yl)cyclohexanecarboxylic Acid (30-15)

To a solution of tert-butyl 4-(((S)-2-((1s,4R)-4-(ethoxycarbonyl)cyclohexyl)piperidin-1-yl)methyl)-5-methoxy-7-methyl-1H-indole-1-carboxylate (50 mg, 0.1 mmol) in THF (1 mL) and MeOH (0.5 mL) was added aqueous LiOH solution (0.5 mL, 0.5 mmol, 1M). The reaction mixture was stirred at room temperature overnight. The mixture was acidified by adding 1N HCl and extracting with DCM twice. The combined organic layers were concentrated to dryness to afford 30-15 (45 mg, 95.2% yield) as a light yellow solid.

Step 14: (1R,4S)-4-((S)-1-((5-Methoxy-7-methyl-1H-indol-4-yl)methyl)piperidin-2-yl) cyclohexanecarboxylic Acid (COMPOUND 20)

To a solution of (1R,4S)-4-((S)-1-((1-(tert-butoxycarbonyl)-5-methoxy-7-methyl-1H-indol-4-yl)methyl)piperidin-2-yl)cyclohexanecarboxylic acid (45 mg, 0.093 mmol) in DCM (2 mL) was added TFA (1 mL) and the reaction mixture was stirred at room temperature for 1 hour. The mixture was concentrated to dryness to afford crude product that was purified by preparative HPLC to afford COM- POUND 20 (3.8 mg, 10.6% yield) as a white solid. $^1$H-NMR (400 MHz, CD$_3$OD) δ 7.37 (dd, J=3.1, 1.7 Hz, 1H), 6.85 (s, 1H), 6.57 (dd, J=20.5, 3.2 Hz, 1H), 5.07 (d, J=12.9 Hz, 1H), 4.61 (s, 1H), 4.19 (d, J=12.9 Hz, 1H), 3.94 (d, J=6.6 Hz, 3H), 3.49-3.40 (m, 1H), 3.16-2.96 (m, 2H), 2.55 (s, 3H), 2.45-2.27 (m, 2H), 2.21-1.95 (m, 5H), 1.86-1.75 (m, 2H), 1.73-1.46 (m, 5H), 1.36-1.19 (m, 2H). LC/MS (ESI) m/z: 385 (M+H)$^+$.

Scheme 31: Synthesis of 4-((2S, 4R)-1-((5-Methoxy-7-methyl-1H-indazol-4-yl) methyl)-4-methylpiperidin-2-yl) benzoix acid (COMPOUND 21)

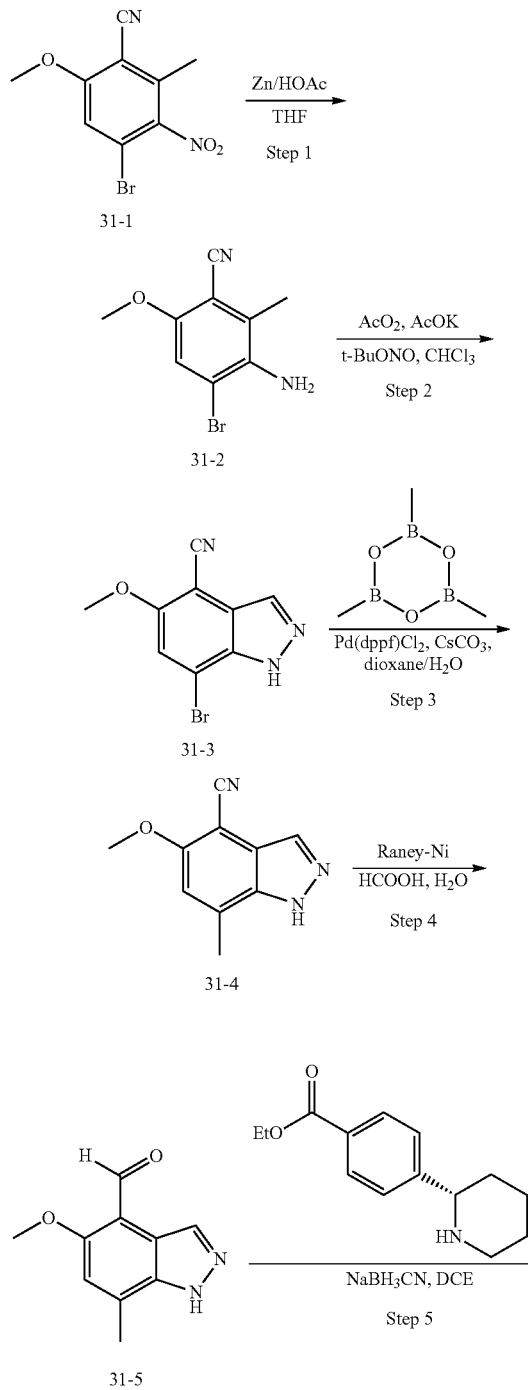

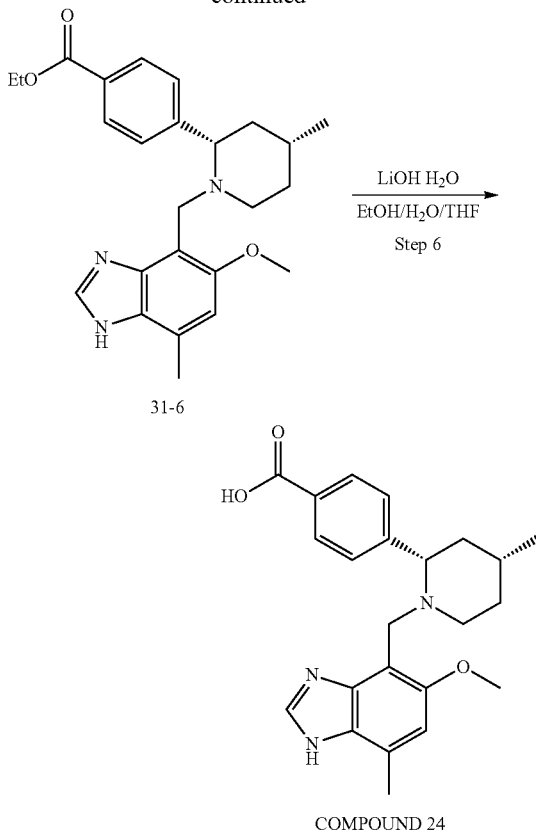

Step 1: 3-Amino-4-bromo-6-methoxy-2-methylbenzonitrile (31-2)

To a solution of compound 31-1 (6.08 g, 22.52 mmol) in a mixture of THF (40 mL) and HOAc (8 mL) was added portion-wise Zn dust (14.64 g, 0.23 mmol) and the reaction mixture was stirred at room temperature for 5 hours. The mixture was diluted with EtOAc and filtered and the filter cake was washed with EtOAc. The filtrate was washed with water, 5% aqueous NaHCO$_3$ solution and brine successively, dried over anhydrous Na$_2$SO$_4$ and concentrated to afford compound 31-2 (4.7 g, 87.0% yield) as a yellow solid. LC/MS (ESI) m/z: 241 (M+H)$^+$.

Step 2: 7-Bromo-5-methoxy-1H-indazole-4-carbonitrile (31-3)

To a solution of compound 31-2 (4.5 g, 18.75 mmol) and potassium acetate (2.21 g, 22.5 mmol) in CHCl$_3$ (50 mL) was added acetic anhydride (5.74 g, 56.25 mmol) dropwise at 0° C. under a N$_2$ atmosphere and the reaction mixture was stirred at room temperature for 1 hour. The reaction mixture was heated to 60° C. and tert-butyl nitrite (3.86 g, 37.5 mmol) was added. The resulting mixture was stirred at 60° C. overnight before the mixture was diluted with water and extracted with DCM twice. The combined organic layers were washed with brine, dried over anhydrous Na$_2$SO$_4$ and concentrated to dryness. The residue was dissolved in MeOH and 6 N HCl (v/v=1:1) and the mixture was stirred at room temperature for 5 hours. The mixture was basified with 10 N aqueous NaOH solution and extracted with DCM twice. The combined organic layers were washed with brine, dried over anhydrous Na$_2$SO$_4$ and concentrated. The residue was purified by column chromatography on silica gel (eluted with petroleum ether/EtOAc=100:1 to 3:1) to afford compound 31-3 (1.8 g, 38.1% yield) as a light yellow solid. LC/MS (ESI) m/z: 252 (M+H)

Step 3:
5-Methoxy-7-methyl-1H-indazole-4-carbonitrile (31-4)

To a solution of compound 31-3 (900 mg, 3.59 mmol) in 1,4-dioxane/H$_2$O (6 mL, v/v=1:1) was added Cs$_2$CO$_3$ (2.34 g, 7.17 mmol), Pd(dppf)Cl2 (262 mg, 0.36 mmol) and 2,4,6-trimethyl-1,3,5,2,4,6-trioxatriborinane (452 mg, 3.59 mmol) in a microwave reactor. The mixture was degassed under a Na atmosphere three times before the mixture was stirred at 120° C. for 3 hours. The mixture was diluted with EtOAc, washed with water and brine, dried over anhydrous Na$_2$SO$_4$ and concentrated to dryness. The residue was purified by column chromatography on silica gel (eluted with petroleum ether/EtOAc=50:1 to 1:1) to afford compound 31-4 (400 mg, 59.7% yield) as a yellow solid. LC/MS (ESI) m/z: 188 (M+H)

Step 4:
5-Methoxy-7-methyl-1H-indazole-4-carbaldehyde (31-5)

To a solution of compound 31-4 (150 mg, 0.80 mmol) in HCOOH (7 mL) and H$_2$O (3 mL) was added Raney nickel (100 mg) and the reaction mixture was stirred at 100° C. under a Na atmosphere overnight. The mixture was diluted with EtOAc and filtered and the filtrate was concentrated to dryness. The residue was basified with 5% aqueous NaHCO$_3$ solution and extracted with DCM twice. The combined organic layers were washed with brine, dried over anhydrous Na$_2$SO$_4$ and concentrated to afford a residue that was purified by column chromatography on silica gel (eluted with DCM/MeOH=200:1 to 30:1) to afford compound 31-5 (40 mg, 26.3% yield) as brown solid. LC/MS (ESI) m/z: 191 (M+H)$^+$.

Step 5: Ethyl 4-((2S, 4R)-1-((5-methoxy-7-methyl-1H-indazol-4-yl) methyl)-4-methylpiperidin-2-yl) benzoate (31-6)

To a solution of compound 31-5 (30 mg, 0.16 mmol) and ethyl 4-((2S, 4R)-4-methylpiperidin-2-yl) benzoate (39 mg, 0.16 mmol) in 1,2-dichloroethane (3 mL) was added NaBH(OAc)$_3$ (100 mg, 0.47 mmol) at 0° C. and the reaction mixture was stirred at room temperature overnight. The mixture was concentrated and the residue was purified by preparative TLC to afford compound 31-6 (15 mg, 22.7% yield) as a milky white solid. LC/MS (ESI) m/z: 422 (M+H)$^+$.

Step 6: 4-((2S, 4R)-14(5-Methoxy-7-methyl-1H-indazol-4-yl) methyl)-4-methylpiperidin-2-yl) benzoic Acid (Compound 21)

To a solution of compound 31-6 (15 mg, 0.036 mmol) in EtOH/H2O/THF (v/v/v=1:1:1, 3 mL) was added LiOH (5 mg, 0.11 mmol, monohydrate) and the reaction mixture was stirred at room temperature for 3 hours. The mixture was acidified with 1N HCl and the mixture was purified by preparative HPLC to afford COMPOUND 24 (2 mg, 12.5% yield) as a white solid. $^1$HNMR (400 MHz, CD$_3$OD) δ 8.12-8.01 (m, 3H), 7.56 (d, J=6.8 Hz, 2H), 7.04 (s, 1H), 3.78 (s, 3H), 3.53-3.44 (m, 1H), 3.17-3.11 (m, 1H), 2.55 (s, 3H), 2.26-2.01 (m, 1H), 1.99-1.85 (m, 1H), 1.85-1.64 (m, 2H), 1.64-1.42 (m, 2H), 1.37-1.32 (m, 2H), 0.97 (s, 3H). LC/MS (ESI) m/z: 394 (M+H)

Scheme 32: Synthesis of 5-Methoxy-7-methyl-4-(((2S, 4R)-4-methyl-2-(4-(S-methylsulfonimidoyl)phenyl)piperidin-1-yl)methyl)-1H-indole (COMPOUND 22)

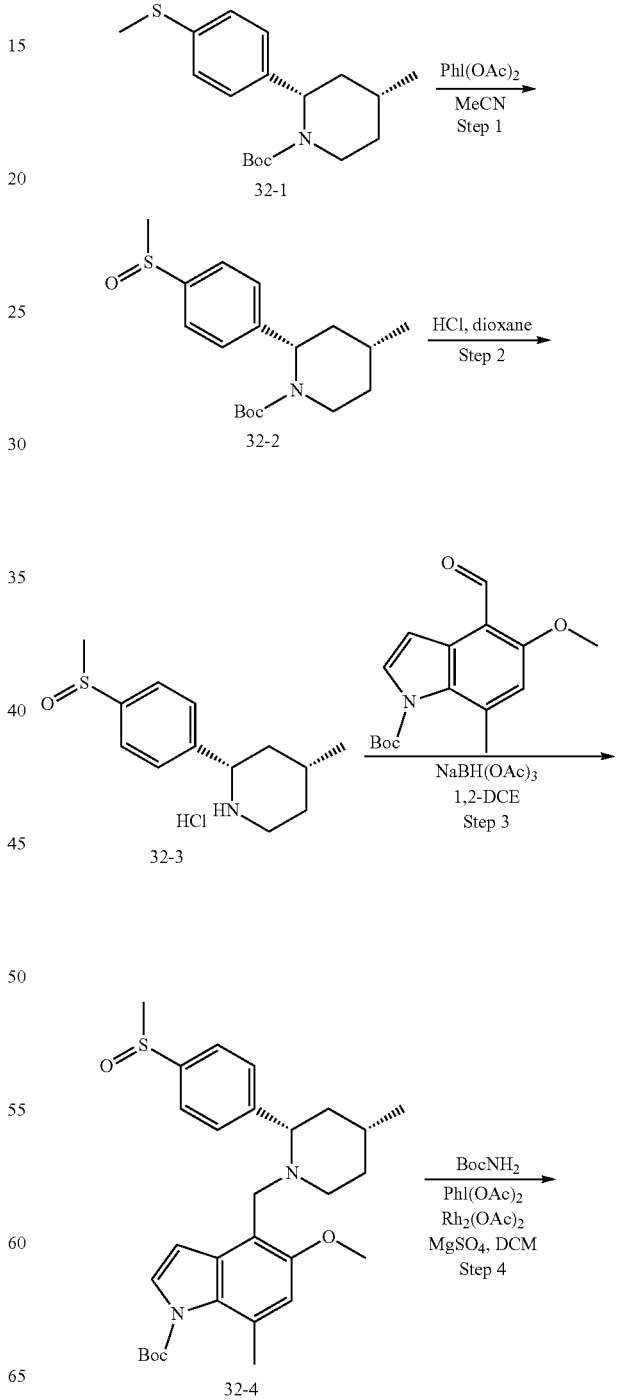

-continued

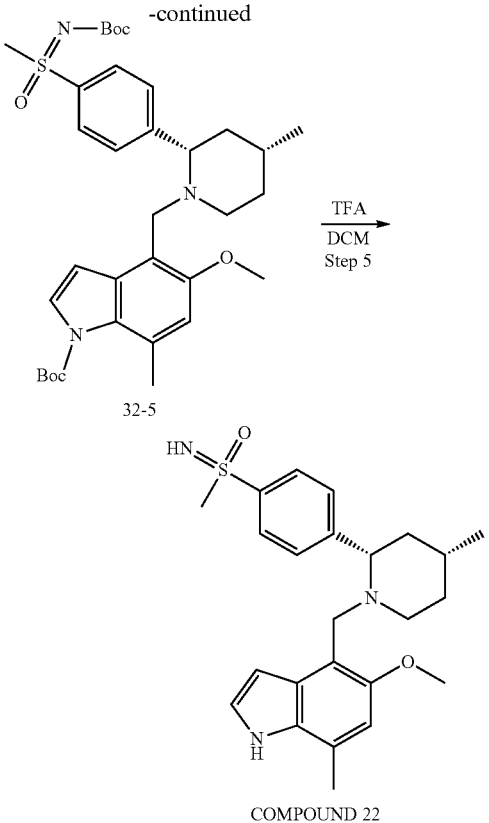

32-5

COMPOUND 22

Step 1: (2S,4R)-tert-Butyl 4-methyl-2-(4-(methyl-sulfinyl)phenyl)piperidine-1-carboxylate (32-2)

To a mixture of compound 32-1 (0.5 g, 1.6 mmol) in MeCN (10 mL) was added (diacetoxyiodo)benzene (565 mg, 1.76 mmol). The reaction mixture was stirred at room temperature for 3 minutes. The reaction was quenched with aqueous $Na_2S_2O_3$ solution and extracted with ethyl acetate twice. The combined organic layers were washed with water and brine, dried with $Na_2SO_4$, and concentrated to dryness. The residue was purified with silica gel column (eluted with petroleum ether:ethyl acetate=3:1 to 1:1) to afford compound 32-2 (0.5 g, 92.7% yield) as a white solid. LC/MS (ESI) m/z: 338 $(M+H)^+$.

Step 2: (2S,4R)-4-Methyl-2-(4-(methylsulfinyl)phenyl)piperidine hydrochloride (32-3)

To a solution of compound 32-2 (0.5 g, 1.48 mmol) in dioxane (5 mL) was added HCl-dioxane solution (5 mL, 4M). The resulting mixture was stirred at room temperature for 1 hour. The mixture was concentrated to dryness and washed with ether and dried under vacuum to afford compound 32-3 (220 mg, 62.8% yield) as a light yellow solid. LC/MS(ESI) m/z: 238 $(M+H)^+$.

Step 3: tert-Butyl 5-methoxy-7-methyl-4-(((2S,4R)-4-methyl-2-(4-(methylsulfinyl)phenyl)piperidin-1-yl)methyl)-1H-indole-1-carboxylate (32-4)

To a mixture of compound 32-3 (220 mg, 0.93 mmol) and tert-butyl 4-formyl-5-methoxy-7-methyl-1H-indole-1-carboxylate (296 mg, 1.02 mmol) in 1,2-DCE (5 mL) was added $NaBH(OAc)_3$ (589 mg, 2.78 mmol) in portions at 0° C. After addition, the reaction mixture was stirred at 50° C. overnight. The reaction was quenched with 5% aqueous $NaHCO_3$ solution and extracted with ethyl acetate twice. The combined organic layers were washed with brine, dried with $Na_2SO_4$ and concentrated to dryness. The residue was purified by silica gel column (eluted with petroleum ether:ethyl acetate=3:1 to 1:1) to afford compound 32-4 (133 mg, 27.8% yield) as a white solid. LC/MS(ESI) m/z: 511 $(M+H)^+$.

Step 4: tert-Butyl 4-(((2S,4R)-2-(4-(N-(tert-butoxycarbonyl)-S-methylsulfonimidoyl)phenyl)-4-methylpiperidin-1-yl)methyl)-5-methoxy-7-methyl-1H-indole-1-carboxylate (32-10)

To a mixture of 32-4 (30 mg, 0.058 mmol) and $BocNH_2$ (14 mg, 0.12 mmol) in DCM (2 mL) was added (diacetoxyiodo)benzene (21 mg, 0.065 mmol) and $Rh_2(OAc)_4$ (1 mg, catalytic) and $MgSO_4$ (50 mg) at 0° C. and the mixture was stirred at room temperature for 16 hours. The mixture was diluted with DCM and filtered. The filtrate was concentrated to dryness to afford a residue, which was purified by silica gel chromatography (eluted with petroleum ether:ethyl acetate=2:1 to 1:3) to afford compound 32-5 (22 mg, 60.6% yield) as a white solid. LC/MS(ESI) m/z: 626 $(M+H)^+$.

Step 5: 5-Methoxy-7-methyl-4-(((2S,4R)-4-methyl-2-(4-(S-methylsulfonimidoyl)phenyl)piperidin-1-yl)methyl)-1H-indole (Compound 22)

To a solution of compound 32-5 (22 mg, 0.035 mmol) in DCM (1 mL) was added TFA (1 mL). The reaction mixture was stirred at room temperature for 1 hour. The mixture was concentrated to dryness and the residue was purified by preparative HPLC to afford COMPOUND 22 (3.3 mg, 22% yield) as a white solid. $^1$H-NMR (400 MHz, DMSO-$d_6$) δ 8.99 (s, 2H), 10.81 (s, 1H), 7.93 (m, 2H), 7.75 (m, 2H), 7.25 (s, 1H), 6.65 (s, 1H), 6.49 (m, 1H), 4.16 (m, 1H), 3.70 (d, J=1.4 Hz, 3H), 3.55 (m, 1H), 3.23 (m, 1H), 3.18 (m, 1H), 3.07 (s, 3H), 2.76 (m, 1H), 2.41 (s, 3H), 1.99 (m, 1H), 1.67 (m, 1H), 1.51 (m, 1H), 1.24-1.17 (m, 1H), 1.04 (m, 1H), 0.86 (d, J=6.0 Hz, 3H). LC/MS(ESI) m/z: 426 $(M+H)^+$.

Synthesis of 5-Methoxy-7-methyl-4-(((2R,4S)-4-methyl-2-(4-(S-methylsulfonimidoyl)phenyl)piperidin-1-yl)methyl)-1H-indole (Compound 23)

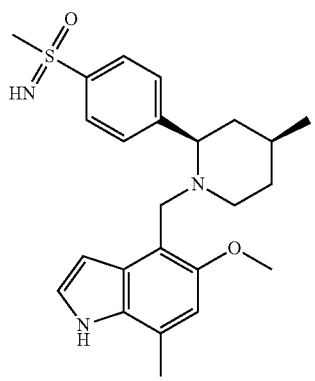

COMPOUND 23 was prepared according to the synthesis shown in Scheme 32 from appropriate starting materials. $^1$H NMR (400 MHz, DMSO-$d_6$) δ 10.83 (s, 1H), 7.94 (d, J=8.3

Hz, 2H), 7.75 (d, J=7.5 Hz, 2H), 7.26 (s, 1H), 6.65 (s, 1H), 6.50 (d, J=9.0 Hz, 1H), 4.18 (d, J=5.6 Hz, 1H), 3.71 (d, J=1.4 Hz, 3H), 3.56 (dd, J=12.0, 4.3 Hz, 1H), 3.25 (d, J=9.4 Hz, 2H), 3.08 (s, 3H), 2.77 (d, J=11.6 Hz, 1H), 2.42 (s, 3H), 1.99 (t, J=9.8 Hz, 1H), 1.67 (d, J=12.4 Hz, 1H), 1.51 (d, J=11.3 Hz, 2H), 1.03 (d, J=10.3 Hz, 1H), 0.86 (d, J=6.2 Hz, 3H). LC/MS (ESI) m/z: 426 (M+H)⁺.
Scheme 33: Synthesis of 4-((2S, 4R)-1-((5-Methoxy-2, 7-dimethyl-1H-indol-4-yl) methyl)-4-methylpiperidin-2-yl) benzoic acid (COMPOUND 24)
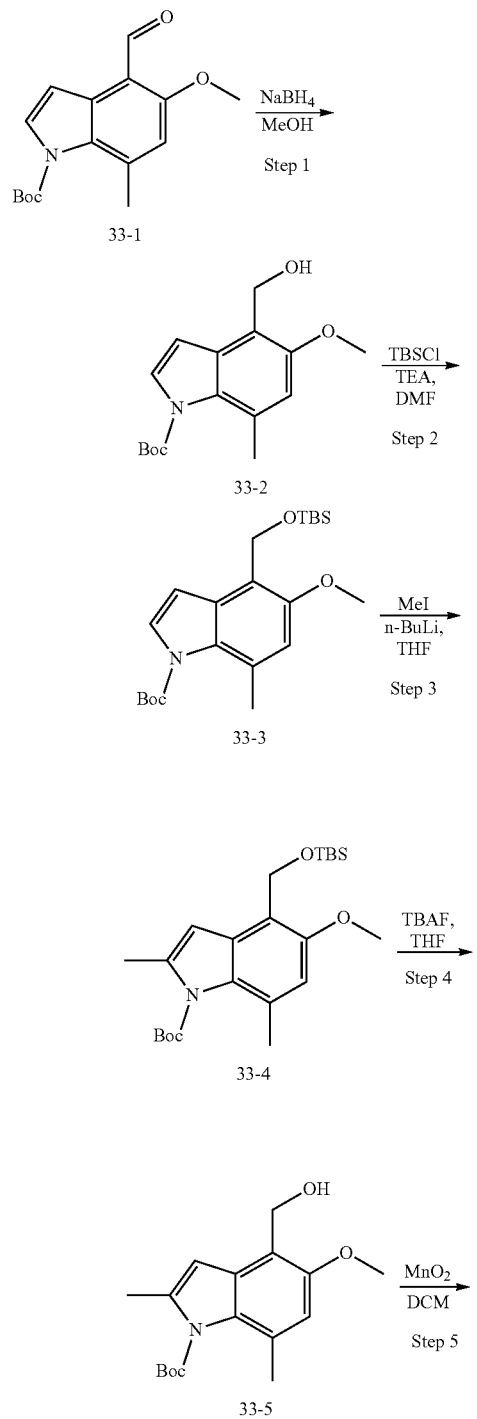
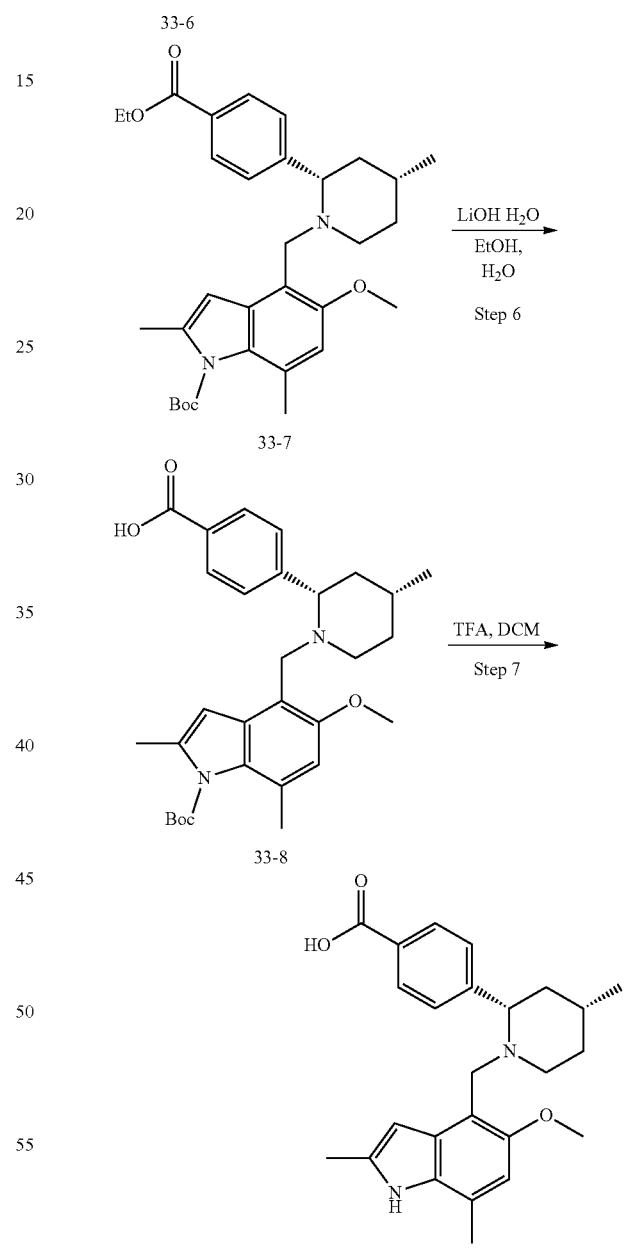
Step 1: tert-Butyl 4-(hydroxymethyl)-5-methoxy-7-methyl-1H-indole-1-carboxylate (33-2)
To a solution of compound 33-1 (0.8 g, 2.77 mmol) in MeOH (6 mL) was added NaBH₄ (230 mg, 6.09 mmol) at 0°

C. and the reaction mixture was stirred at room temperature for 30 minutes. The mixture was quenched by aqueous NH$_4$Cl solution and extracted with EtOAc twice. The combined organic layers were washed with brine, dried over anhydrous Na$_2$SO$_4$ and concentrated to afford compound 33-2 (0.8 g, 99.3% yield) as a light yellow solid, which was used directly in the next step without additional purification. LC/MS (ESI) m/z: 292 (M+H)$^+$.

Step 2: tert-Butyl 4-((tert-butyldimethylsilyloxy) methyl)-5-methoxy-7-methyl-1H-indole-1-carboxylate (33-3)

To a solution of compound 33-2 (400 mg, 1.38 mmol) in DCM (8 mL) was added imidazole (282 mg, 4.1 mmol) followed by portionwise addition of tert-butylchlorodimethylsilane (249 mg, 1.65 mmol) at 0° C. under N$_2$ atmosphere. The mixture was stirred at room temperature for 1 hour. The mixture was diluted with water and extracted with EtOAc twice. The combined organic layers were washed with brine, dried over anhydrous Na$_2$SO$_4$ and concentrated. The residue was purified by column chromatography on silica gel (eluted with petroleum ether/EtOAc=100:1 to 50:1) to afford compound 33-3 (480 mg, 86.2% yield) as a yellow solid. LC/MS (ESI) m/z: 406 (M+H)

Step 3: tert-Butyl 4-((tert-butyldimethylsilyloxy) methyl)-5-methoxy-2, 7-dimethyl-1H-indole-1-carboxylate (33-4)

To a solution of compound 33-3 (240 mg, 0.59 mmol) in anhydrous THF (6 mL) was added n-BuLi (0.28 mL, 0.71 mmol) dropwise at −70° C. The mixture was stirred at −70° C. for 1 hour and MeI (92 mg, 0.65 mmol) was added. The reaction mixture was stirred at −70° C. for 1 hour and then allowed to continue stirring overnight at room temperature. The mixture was quenched with aqueous NH$_4$Cl solution and extracted with EtOAc twice. The combined organic layers were washed with brine, dried over anhydrous Na$_2$SO$_4$ and concentrated. The residue was purified by preparative TLC (petroleum ether/EtOAc=80:1) to afford compound 33-4 (190 mg, 76.6% yield) as a white solid. LC/MS (ESI) m/z: 420 (M+H)

Step 4: tert-Butyl 4-(hydroxymethyl)-5-methoxy-2, 7-dimethyl-1H-indole-1-carboxylate (33-5)

To a solution of compound 33-4 (180 mg, 0.43 mmol) in THF (3 mL) was added TBAF/THF solution (0.43 mL, 0.43 mmol) and the reaction mixture was stirred at room temperature for 2 hours. The mixture was diluted with EtOAc and washed with saturated aqueous NH$_4$Cl solution and brine successively, dried over anhydrous Na$_2$SO$_4$ and concentrated. The residue was purified by column chromatography on silica gel (eluted with petroleum ether/EtOAc=30/1 to 5/1) to afford compound 33-5 (100 mg, 76.3% yield) as a yellow solid. LC/MS (ESI) m/z: 306 (M+H)

Step 5: tert-Butyl 4-formyl-5-methoxy-2, 7-dimethyl-1H-indole-1-carboxylate (33-6)

A round-bottom flask was charged with compound 33-5 (100 mg, 0.39 mmol), MnO$_2$ (342 mg, 3.93 mmol) and DCM (8 mL), and the resulting mixture was stirred at room temperature under a N$_2$ atmosphere overnight. The mixture was filtered and the filtrate was concentrated. The residue was purified by column chromatography on silica gel (eluted with petroleum ether/EtOAc=30:1 to 10:1) to afford compound 33-6 (65 mg, 65.6% yield) as a light yellow solid. LC/MS (ESI) m/z: 304 (M+H)$^+$.

Step 6: tert-Butyl 4-(((2S, 4R)-2-(4-(ethoxycarbonyl) phenyl)-4-methylpiperidin-1-yl) methyl)-5-methoxy-2, 7-dimethyl-1H-indole-1-carboxylate (33-7)

To a solution of compound 33-6 (65 mg, 0.21 mmol) and ethyl 4-((2S, 4R)-4-methylpiperidin-2-yl) benzoate (44 mg, 0.18 mmol) in 1,2-dichloroethane (5 mL) was added NaBH(OAc)$_3$ (114 mg, 0.54 mmol) at 0° C. and the reaction mixture was stirred at room temperature overnight. The mixture was concentrated to dryness and the residue was purified by column chromatography on silica gel (eluted with petroleum ether/EtOAc=30:1 to 5:1) to afford compound 33-7 (25 mg, 21.8% yield) as a white solid. LC/MS (ESI) m/z: 535 (M+H)$^+$.

Step 7: 4-((2S, 4R)-1((1-(tert-Butoxycarbonyl)-5-methoxy-2, 7-dimethyl-1H-indol-4-yl) methyl)-4-methylpiperidin-2-yl) benzoic Acid (33-8)

To a solution of compound 33-7 (25 mg, 0.047 mmol) in EtOH/H$_2$O (v/v=1:1, 2 mL) was added LiOH.H$_2$O (12 mg, 0.28 mmol) and the reaction mixture was stirred at room temperature for 4 hours. The mixture was acidified with 1M HCl to a pH of approximately 3 and extracted with DCM twice. The combined organic layers were concentrated to dryness to afford compound 33-7 (20 mg, 84.4% yield) as a white solid. LC/MS (ESI) m/z: 507 (M+H)$^+$.

Step 8: 4-((2S, 4R)-1-((5-Methoxy-2, 7-dimethyl-1H-indol-4-yl) methyl)-4-methylpiperidin-2-yl) benzoic Acid (Compound 24)

To a solution of compound 33-7 (20 mg, 0.039 mmol) in DCM (2 mL) was added TFA (1 mL) and the resulting mixture was stirred at room temperature for 2 hours. The mixture was concentrated to dryness and the residue was purified by preparative HPLC to afford COMPOUND 24 (5 mg, 25.0% yield) as a white solid. $^1$H-NMR (400 MHz, DMSO-d$_6$) δ 10.92 (s, 1H), 8.87 (s, 1H), 8.14 (d, J=8.4 Hz, 2H), 7.80 (s, 2H), 6.66 (s, 1H), 5.98 (s, 1H), 4.61 (t, J=9.2 Hz, 1H), 4.16-3.99 (m, 2H), 3.69 (s, 3H), 3.30 (s, 2H), 2.44 (S, 3H), 2.38 (S, 3H), 1.98-1.82 (m, 2H), 1.81-1.66 (m, 2H), 1.60-1.49 (m, 1H), 0.92 (d, J=6.0 Hz, 3H). LC/MS (ESI) m/z: 407 (M+H)$^+$.

Scheme 34: Synthesis of 5-Methoxy-7-methyl-4-((4-methyl-2-(4-(S-methylsulfonimidoyl)phenyl) piperidin-1-yl)methyl)-1H-indole (COMPOUND 25)

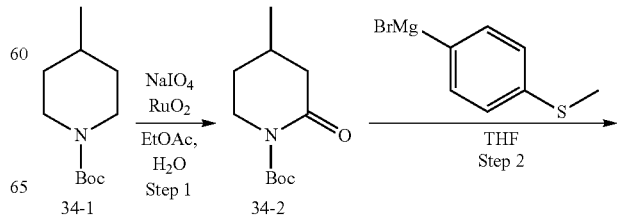

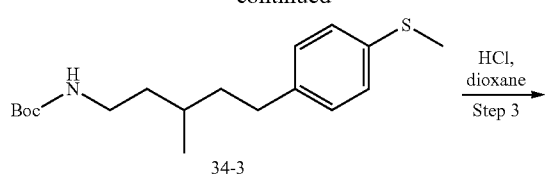

34-3

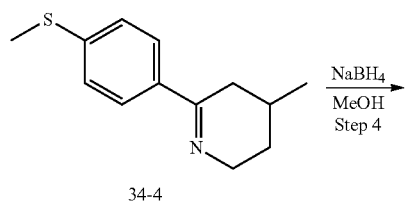

34-4

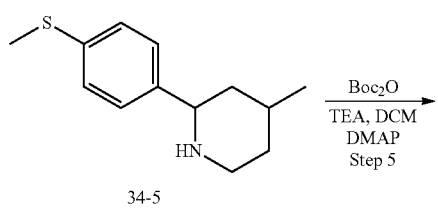

34-5

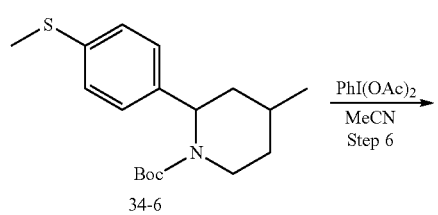

34-6

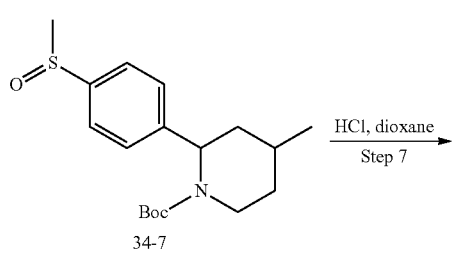

34-7

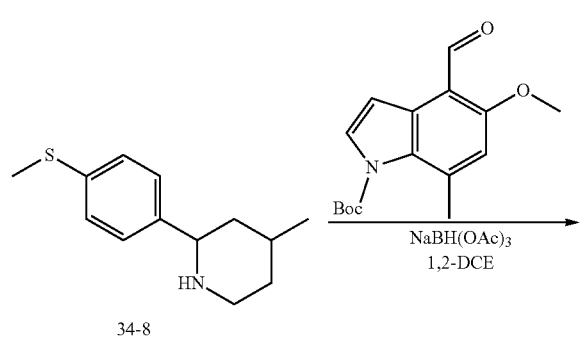

34-8

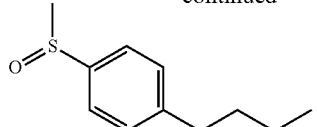

34-9

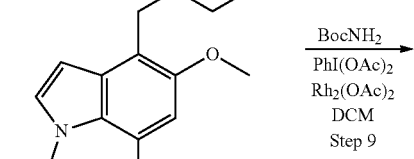

34-10

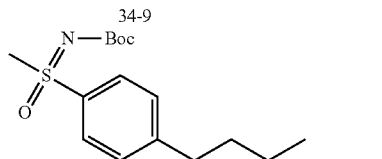

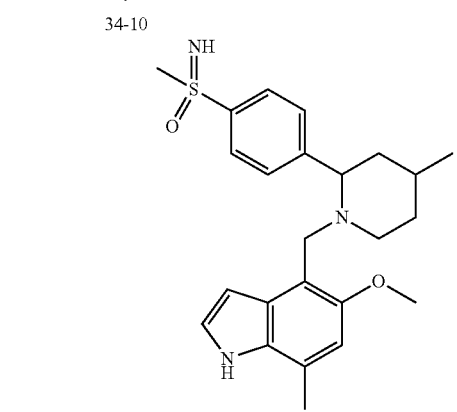

COMPOUND 25

Step 1: tert-Butyl 4-methyl-2-oxopiperidine-1-carboxylate (34-2)

To a mixture of compound 34-1 (20 g, 100.42 mmol) and RuO₂ (0.401 g, 3.02 mmol) in EtOAc (750 mL) and water (250 mL) was added NaIO₄ (75 g, 351.47 mmol). The reaction mixture was stirred at room temperature overnight. The reaction mixture was diluted with ethyl acetate, washed with water and brine, dried and concentrated to afford crude product that was purified by silica gel chromatography (PE:EtOAc=100:1 to 50:1) to afford compound 34-2 (12.9 g, 60.5% yield) as a yellow oil. LC/MS(ESI) m/z: 214 (M+H)⁺.

Step 2: tert-Butyl 3-methyl-5-(4-(methylthio)phenyl)pentylcarbamate (34-3)

To a solution of compound 34-2 (12.9 g, 60.5 mmol) in THF (150 mL) was added (4-(methylthio)phenyl)magnesium bromide (90.8 mL, 90.8 mmol) dropwise at 0° C. for 30 minutes. The mixture was stirred at room temperature for 2 hours before the reaction was quenched with saturated aqueous $NH_4Cl$ solution and extracted with ethyl acetate (200 mL). The organic phase was washed with brine, dried with $Na_2SO_4$ and concentrated to dryness. The residue was purified with silica gel chromatography (eluted with petroleum ether:ethyl acetate=50:1 to 10:1) to afford compound 34-3 (3.9 g, 20% yield) as a white solid. LC/MS(ESI) m/z: 324 $(M+H)^+$.

Step 3: 4-Methyl-6-(4-(methylthio)phenyl)-2,3,4,5-tetrahydropyridine (34-4)

To a solution of compound 34-3 (3.9 g, 12.07 mmol) in dioxane (10 mL) was added HCl-dioxane solution (10 mL, 4 M) and the resulting mixture was stirred at room temperature for 1 hour. The reaction solution was concentrated to dryness to afford compound 34-4 (1.6 g, 60.4% yield). The crude material was directly used in the next reaction without purification. LC/MS(ESI) m/z: 220 $(M+H)^+$.

Step 4: 4-Methyl-2-(4-(methylthio)phenyl)piperidine (34-5)

To a mixture of compound 34-4 (1.6 g, 7.29 mmol) in MeOH (20 mL) was added $NaBH_4$ (0.414 g, 10.94 mmol) and the mixture was stirred at room temperature for 1 hour. The mixture was quenched with water (50 mL) and extracted with ethyl acetate (100 mL). The organic phase was washed with brine, dried with $Na_2SO_4$, concentrated, and the residue was purified with silica gel chromatography (eluted with petroleum ether:ethyl acetate=10:1 to 3:1) to afford compound 34-5 (1 g, 62% yield) as a white solid. LC/MS(ESI) m/z: 222 $(M+H)^+$.

Step 5: tert-Butyl 4-methyl-2-(4-(methylthio)phenyl)piperidine-1-carboxylate 34-6)

Compound 34-5 (1 g, 4.52 mmol) was dissolved in 20 mL of DCM and treated sequentially with di-tert-butyldicarbonate (1.5 g, 6.78 mmol) and catalytic DMAP (0.1 g, 0.769 mmol) at ambient temperature before the reaction mixture was allowed to stir at room temperature for 16 hours. The mixture was diluted with DCM, washed with water and brine, dried over $Na_2SO_4$ and concentrated to dryness. The residue was purified by silica gel chromatography (eluted with petroleum ether:ethyl acetate=20:1 to 3:1) to afford compound 34-6 (1.3 g, 92.0% yield) as a yellow solid. LC/MS(ESI) m/z: 322 $(M+H)^+$.

Step 6: tert-Butyl 4-methyl-2-(4-(methylsulfinyl)phenyl)piperidine-1-carboxylate (34-7)

To a mixture of compound 34-6 (1.3 g, 4.16 mmol) in MeCN (10 mL) was added (diacetoxyiodo)benzene (1.47 g, 4.58 mmol). The reaction mixture was stirred at room temperature for 3 minutes. The mixture was quenched with aqueous $Na_2S_2O_3$ solution and extracted with ethyl acetate twice. The combined organic layers were washed with water and brine, dried with $Na_2SO_4$ and concentrated to dryness. The residue was purified by silica gel chromatography (eluted with petroleum ether:ethyl acetate=3:1 to 1:1) to afford compound 34-7 (1.3 g, 92.5% yield) as a white solid. LC/MS(ESI) m/z: 338 $(M+H)^+$.

Step 7: 4-Methyl-2-(4-(methylsulfinyl)phenyl)piperidine (34-8)

To a solution of compound 34-7 (1.3 g, 3.85 mmol) in dioxane (10 mL) was added HCl-dioxane solution (10 mL, 4M). The resulting mixture was stirred at room temperature for 1 hour. The mixture was concentrated to dryness, washed with ether, and dried under vacuum to afford compound 34-8 (0.8 g, 87.5% yield) as a light yellow solid. LC/MS(ESI) m/z: 238 $(M+H)^+$.

Step 8: tert-Butyl 5-methoxy-7-methyl-4-((4-methyl-2-(4-(methylsulfinyl)phenyl)piperidin-1-yl)methyl)-1H-indole-1-carboxylate (34-9)

To a mixture of compound 34-8 (0.8 g, 3.37 mmol) and tert-butyl 4-formyl-5-methoxy-7-methyl-1H-indole-1-carboxylate (1.07 g, 3.71 mmol) in 1,2-DCE (10 mL) was added $NaBH(OAc)_3$ (2.14 g, 10.11 mmol) in portions at 0° C. After addition, the reaction mixture was stirred at 50° C. overnight. The reaction was quenched with 5% aqueous $NaHCO_3$ solution and extracted with ethyl acetate twice. The combined organic layers were washed with brine, dried with $Na_2SO_4$ and concentrated to dryness. The residue was purified by silica gel chromatography (eluted with petroleum ether:ethyl acetate=3:1 to 1:1) to afford compound 34-9 (0.5 g, 29.1% yield) as a white solid. LC/MS(ESI) m/z: 511 $(M+H)^+$.

Step 9: tert-Butyl 4-((2-(4-(N-(tert-butoxycarbonyl)-S-methylsulfonimidoyl)phenyl)-4-methylpiperidin-1-yl)methyl)-5-methoxy-7-methyl-1H-indole-1-carboxylate (34-10)

To a mixture of 34-9 (0.5 g, 0.98 mmol) and $BocNH_2$ (235 mg, 2 mmol) in DCM (5 mL) was added (diacetoxyiodo)benzene (0.35 g, 1.08 mmol) and $Rh_2(OAc)_4$ (13 mg, 0.03 mmol) and $MgSO_4$ (300 mg) at 0° C. and the mixture was stirred at room temperature for 16 hours. The mixture was diluted with DCM and filtered. The filtrate was concentrated to dryness to afford a residue that was purified by silica gel chromatography (eluted with petroleum ether:ethyl acetate=2:1 to 1:3) to afford compound 34-10 (0.25 g, 40.8% yield) as a white solid. LC/MS(ESI) m/z: 626 $(M+H)^+$.

Step 10. 5-Methoxy-7-methyl-4-((4-methyl-2-(4-(S-methylsulfonimidoyl)phenyl)piperidin-1-yl)methyl)-1H-indole (Compound 25)

To a solution of compound 34-10 (0.25 g, 0.4 mmol) in DCM (3 mL) was added TFA (3 mL). The reaction mixture was stirred at room temperature for 1 hour. The mixture was concentrated to dryness and the residue was purified by preparative HPLC to afford COMPOUND 25 (19 mg, 11.7% yield) as a white solid. $^1$H-NMR (400 MHz, DMSO-$d_6$) δ 8.99 (s, 2H), 10.81 (s, 1H), 7.93 (m, 2H), 7.75 (m, 2H), 7.25 (s, 1H), 6.65 (s, 1H), 6.49 (m, 1H), 4.16 (m, 1H), 3.70 (d, J=1.4 Hz, 3H), 3.55 (m, 1H), 3.23 (m, 1H), 3.18 (m, 1H), 3.07 (s, 3H), 2.76 (m, 1H), 2.41 (s, 3H), 1.99 (m, 1H), 1.67 (m, 1H), 1.51 (m, 1H), 1.24-1.17 (m, 1H), 1.04 (m, 1H), 0.86 (d, J=6.0 Hz, 3H). LC/MS(ESI) m/z: 426 $(M+H)^+$.

Scheme 35: Synthesis of 4-(1-((5-Methoxy-7-methyl-1H-indol-4-yl)methyl)-4-methylpiperidin-2-yl)phenylphosphonic acid (COMPOUND 26)

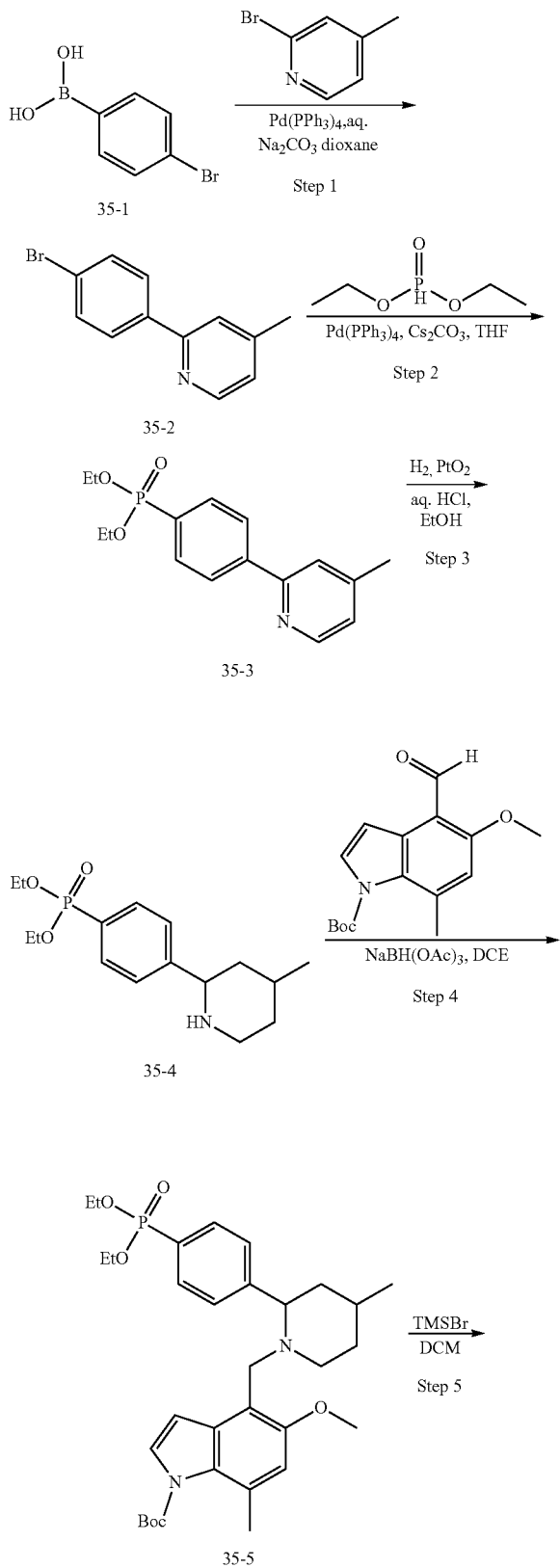

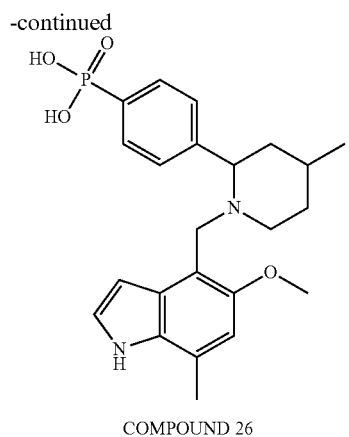

COMPOUND 26

Step 1: 2-(4-Bromophenyl)-4-methylpyridine (35-2)

To a mixture of compound 35-1 (2 g, 10 mmol) and 2-bromo-4-methylpyridine (1.72 g, 10 mmol) in 1,4-dioxane (42 mL) and $H_2O$ (7 mL) was added $Na_2CO_3$ (2.33 g, 22 mmol) followed by the addition of $Pd(PPh_3)_4$ (925 mg, 0.8 mmol). The reaction was stirred at 90° C. for 2 hours under a Na atmosphere. The mixture was cooled, diluted with EtOAc and filtered, and the filtrate was washed with water and brine, dried, and concentrated to afford crude product. The crude material was purified by silica gel column (eluted with petroleum ether:EtOAc=100:0 to 4:1) to afford compound 35-2 (1.2 g, 48.6% yield) as a white solid. LC/MS (ESI) m/z: 248(M+H)$^+$.

Step 2: Diethyl 4-(4-methylpyridin-2-yl)phenylphosphonate (35-3)

To a solution of compound 35-2 (940 mg, 3.8 mmol) in dry THF (12 mL) in a microwave reactor was added diethyl phosphonate (2.1 g, 15.2 mmol) and $Cs_2CO_3$ (2.6 g, 7.98 mmol) followed by the addition of $Pd(PPh_3)_4$ (440 mg, 0.38 mmol). The mixture was degassed under Na three times. The reaction mixture was stirred at 110° C. for 1.5 hours. The mixture was cooled, diluted with EtOAc and filtered, and the filtrate was washed with water and brine, dried, and concentrated to afford crude product. The crude material was purified by silica gel column (eluted with DCM:MeOH=100:0 to 40:1) to afford compound 35-3 (820 mg, 70.7% yield) as a white solid. LC/MS (ESI) m/z: 306(M+H)$^+$.

Step 3: Diethyl 4-(4-methylpiperidin-2-yl)phenylphosphonate (35-4)

To a solution of compound 35-3 (427 mg, 1.4 mmol) in EtOH (12 mL) was added $PtO_2$ (80 mg) and concentrated HCl (2.4 mL) and the mixture was stirred under 45 psi of H2 for 48 hours at room temperature. The mixture was filtered and the filter cake was washed with EtOAc twice. The combined filtrate was washed with water and brine, dried, and concentrated to afford crude product that was purified by silica gel column (eluted with DCM:MeOH=100:0 to 10:1) to afford compound 35-4 (82 mg, 18.8% yield) as a colorless oil. LC/MS (ESI) m/z: 312(M+H)$^+$.

Step 4: tert-Butyl 4-((2-(4-(diethoxyphosphoryl)phenyl)-4-methylpiperidin-1-yl)methyl)-5-methoxy-7-methyl-1H-indole-1-carboxylate (35-5)

To a mixture of compound 35-4 (82 mg, 0.26 mmol) in DCE (10 mL) was added tert-butyl 4-formyl-5-methoxy-7- methyl-1H-indole-1-carboxylate (136 mg, 0.47 mmol), NaBH(OAc)₃ (166 mg, 0.78 mmol) and 1 drop of AcOH. The mixture was stirred at 50° C. for 36 hours. The mixture was diluted with DCM and washed with water and brine, dried over anhydrous Na₂SO₄, filtered and concentrated to afford crude product, which was purified by preparative TLC (eluted with DCM:MeOH=20:1) to afford compound 35-5 (18 mg, 11.8% yield) as a colorless oil. LC/MS (ESI) m/z: 585(M+H)⁺.

Step 5: 4-(1-((5-Methoxy-7-methyl-1H-indol-4-yl)methyl)-4-methylpiperidin-2-yl)phenylphosphonic Acid (Compound 26)

To a solution of compound 35-5 (18 mg, 0.031 mmol) in dry DCM (2 mL) was added TMSBr (0.5 mL) at 0° C. The reaction mixture was stirred at room temperature for 16 hours. The reaction mixture was quenched with saturated NaHCO₃ solution and extracted with DCM/MeOH (20:1). The organic layer was washed with brine, dried over anhydrous Na₂SO₄, filtered and concentrated to dryness. The residue was purified by preparative HPLC to afford COMPOUND 26 (5 mg, 37.6% yield) as a white solid. ¹H-NMR (400 MHz, CD₃OD) δ 7.93-8.07 (m, 2H), 7.59 (d, J=6.0 Hz, 2H), 7.31 (d, J=3.1 Hz, 1H), 6.76 (s, 1H), 6.31 (d, J=3.1 Hz, 1H), 4.44 (d, J=9.8 Hz, 1H), 4.37 (d, J=12.6 Hz, 1H), 4.10 (d, J=12.7 Hz, 1H), 3.76 (s, 3H), 3.42-3.57 (m, 2H), 2.50 (s, 3H), 2.02-2.09 (m, 1H), 1.92-1.99 (m, 1H), 1.81-1.89 (m, 1H), 1.70-1.78 (m, 1H), 1.46-1.54 (m, 1H), 1.01 (d, J=6.4 Hz, 3H). LC/MS (ESI) m/z: 429 (M+H)⁺.

Scheme 36: Synthesis of N-Hydroxy-4-(1-((5-methoxy-7-methyl-1H-indol-4-yl)methyl)-4-methylpiperidin-2-yl)benzamide (COMPOUND 27)

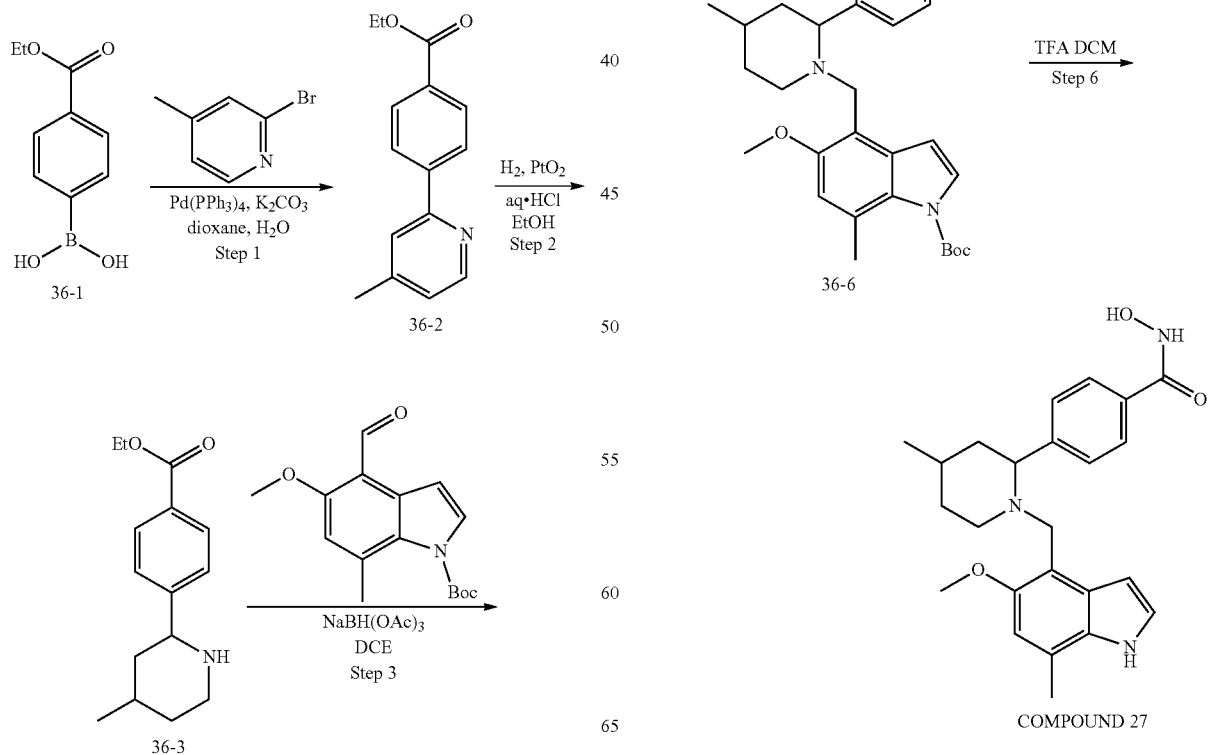

Step 1: Ethyl 4-(4-methylpyridin-2-yl)benzoate (36-2)

To a mixture of 36-1 (2 g, 10.31 mmol) and 2-bromo-4-methylpyridine (1.95 g, 11.34 mmol) in dioxane/H$_2$O (20 mL/5 mL) was added K$_2$CO$_3$ (3.56 g, 25.78 mmol) and the mixture was degassed under a N$_2$ atmosphere three times. Pd(PPh$_3$)$_4$ (0.95 g, 1.03 mmol) was added to the above mixture under a N$_2$ atmosphere and the resulting mixture was stirred at 90° C. for 16 hours under the N$_2$ atmosphere. The mixture was diluted with EtOAc, washed with water and brine, dried and concentrated to dryness. The residue was purified with silica gel chromatography (eluted with petroleum ether:etOAc=50:1 to 5:1) to afford compound 36-2 (880 mg, 35.4% yield) as a white solid. LC/MS(ESI) m/z: 242 (M+H)$^+$.

Step 2: Ethyl 4-(4-methylpiperidin-2-yl)benzoate (36-3)

To a solution of compound 36-2 (500 mg, 2.07 mmol) in EtOH (5 mL) was added PtO$_2$ (50 mg) and concentrated HCl (0.5 mL). The mixture was degassed under a N$_2$ atmosphere three times and the reaction was stirred under a H$_2$ balloon for 5 hours at room temperature. The mixture was filtered and the filtrate was concentrated to dryness. The residue was diluted with DCM, washed with 5% aqueous NaHCO$_3$ solution and brine, dried, and concentrated to dryness. The residue was purified by silica gel chromatography (eluted with petroleum ether:EtOAc=10:1 to 5:1) to afford compound 36-3 (140 mg, 27.8% yield) as a white solid. LC/MS(ESI) m/z: 248 (M+H)$^+$.

Step 3: tert-Butyl 4-((2-(4-(ethoxycarbonyl)phenyl)-4-methylpiperidin-1-yl)methyl)-5-methoxy-7-methyl-1H-indole-1-carboxylate (36-4)

To a mixture of compound 36-3 (140 mg, 0.57 mmol) and tert-butyl 4-formyl-5-methoxy-7-methyl-1H-indole-1-carboxylate (196 mg, 0.68 mmol) in 1,2-DCE (10 mL) was added NaBH(OAc)$_3$ (359 mg, 1.70 mmol). The reaction mixture was stirred at 50° C. overnight. The reaction was quenched with 5% aqueous NaHCO$_3$ solution and extracted with DCM. The organic phase was washed with brine, dried with Na$_2$SO$_4$, concentrated to dryness, and purified by silica gel chromatography (eluted with petroleum ether: EtOAc=3:1 to 1:1) to afford compound 36-4 (71 mg, 23.9% yield) as a white solid. LC/MS(ESI) m/z: 521 (M+H)$^+$.

Step 4: 4-(14(1-(tert-Butoxycarbonyl)-5-methoxy-7-methyl-1H-indol-4-yl)methyl)-4-methylpiperidin-2-yl)benzoic Acid (36-5)

To a solution of 36-4 (71 mg, 0.14 mmol) in methanol (1 mL) and water (1 mL) was added LiOH (29 mg, 1.21 mmol) and the mixture was stirred at room temperature for 16 hours. The reaction mixture was concentrated to dryness and the residue was dissolved in water. The mixture was washed with ether twice and acidified with 1N HCl to a pH of 3. The aqueous solution was extracted with DCM twice and the combined organic layers were dried over Na$_2$SO$_4$, filtered, and concentrated to dryness to afford 36-5 (67 mg, yield 99.8%) as a white solid. LC/MS(ESI) m/z: 493 (M+H)$^+$.

Step 5: tert-Butyl 4-((2-(4-(hydroxycarbamoyl)phenyl)-4-methylpiperidin-1-yl)methyl)-5-methoxy-7-methyl-1H-indole-1-carboxylate (36-6)

To a mixture of compound 36-5 (50 mg, 0.12 mmol), hydroxylamine hydrochloride (9 mg, 0.12 mmol) and DIPEA (49 mg, 0.36 mmol) in DMF (1 mL) was added HATU (96 g, 0.24 mmol). The resulting mixture was stirred at room temperature overnight. The mixture was diluted with EtOAc, washed with water and brine, dried and concentrated to dryness. The residue was purified by preparative HPLC (eluted with CH$_3$CN/water) to afford compound 36-6 (25 mg, 41.0% yield) as a white solid. LC/MS(ESI) m/z: 508 (M+H)$^+$.

Step 6: N-Hydroxy-4-(1-((5-methoxy-7-methyl-1H-indol-4-yl)methyl)-4-methylpiperidin-2-yl)benzamide (Compound 27)

To a mixture of compound 36-6 (25 mg, 0.049 mmol) in DCM (1 mL) was added TFA (1 mL). The resulting mixture was stirred at room temperature for 25 minutes. The reaction mixture was concentrated to dryness and the residue was purified by preparative HPLC to afford COMPOUND 27 (4 mg, 20.1% yield) as a white solid. $^1$HNMR (400 MHz, DMSO-d$_6$) δ 11.17 (s, 1H), 10.81 (s, 1H), 8.99 (m, 1H), 8.15 (s, 1H), 7.77 (d, J=8.3 Hz, 2H), 7.59 (d, J=7.6 Hz, 2H), 7.26-7.23 (m, 1H), 6.65 (s, 1H), 6.47 (s, 1H), 3.70 (s, 3H), 3.56 (m, 1H), 3.19-3.15 (m, 1H), 2.76 (m, 1H), 2.41 (s, 3H), 1.99 (s, 1H), 1.66 (m, 1H), 1.50 (m, 2H), 1.22 (m, 2H), 1.10-0.92 (m, 2H), 0.85 (d, J=6.2 Hz, 3H). LC/MS(ESI) m/z: 408 (M+H)$^+$.

Scheme 37: Synthesis of 4-(1-((5-Methoxy-7-methyl-1H-indol-4-yl)methyl)-4-methylpiperidin-2-yl)-5,6,7,8-tetrahydronaphthalene-1-carboxylic acid (COMPOUND 28)

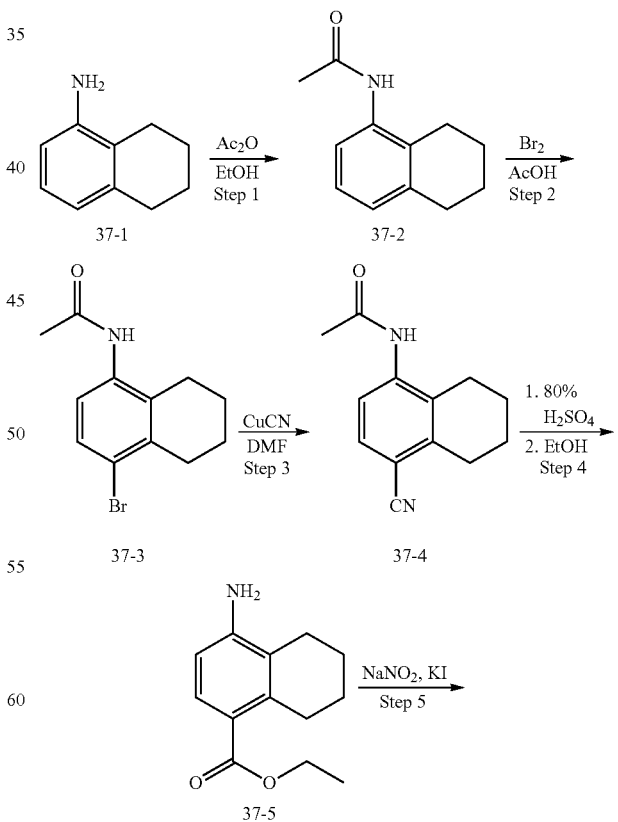

267

-continued

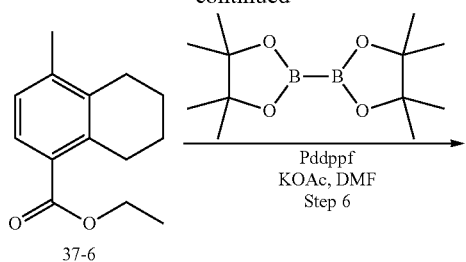

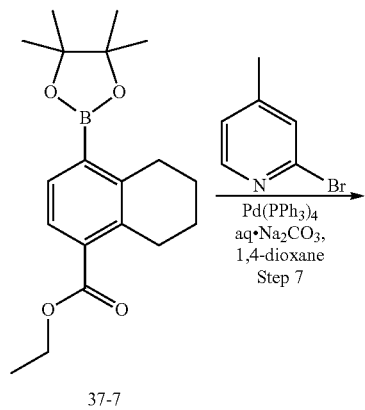

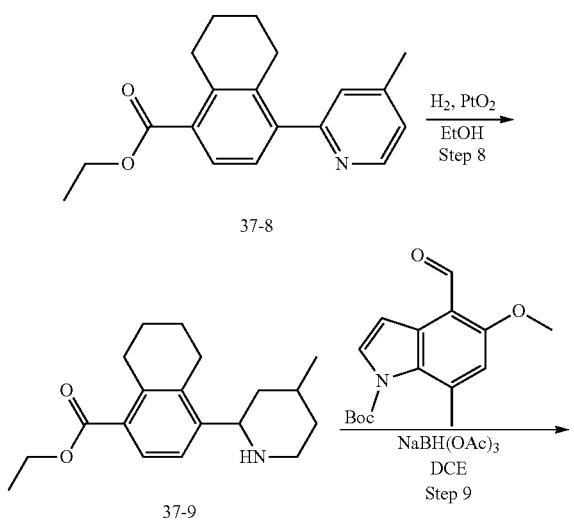

268

-continued

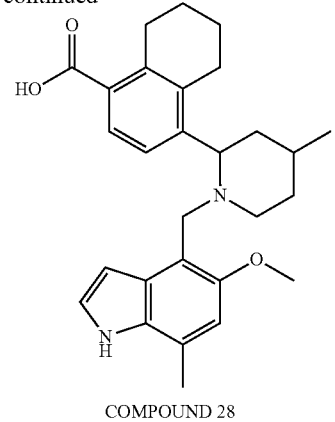

COMPOUND 28

Step 1:
N-(5,6,7,8-Tetrahydronaphthalen-1-yl)acetamide
(37-2)

To a solution of compound 37-1 (3.0 g, 0.02 mol) in EtOH (30 mL) was added Ac$_2$O (4.08 g, 0.04 mmol) and the mixture was stirred at room temperature overnight. The mixture was concentrated to dryness and the residue was re-crystallized from ether to afford compound 37-2 (3.7 g, yield 97.8%) as a white solid. LC/MS (ESI) m/z: 190 (M+H)$^+$.

Step 2: N-(4-Bromo-5,6,7,8-tetrahydronaphthalen-1-yl)acetamide (37-3)

To a solution of compound 37-2 (3.7 g, 19.6 mmol) in AcOH (40 mL) was added a solution of Br$_2$ (3.4 g, 21.6 mmol) in AcOH (4 mL) dropwise at a temperature below 10° C. The reaction mixture was stirred at room temperature for 3 hours. The mixture was poured into ice water and extracted with EtOAc twice. The organic layers were washed with 5% aqueous Na$_2$S$_2$O$_4$ solution and brine, dried over Na$_2$SO$_4$ and concentrated under reduced pressure to afford compound 37-3 (4.2 g, yield 80.3%) as a brown oil. LC/MS (ESI) m/z: 268 (M+H)$^+$.

Step 3: N-(4-Cyano-5,6,7,8-tetrahydronaphthalen-1-yl)acetamide (37-4)

To a solution of compound 37-3 (4.1 g, 15.4 mmol) in DMF (40 mL) was added CuCN (1.7 g, 18.5 mmol) and the reaction mixture was stirred at 150° C. for 16 hours. The mixture was poured into ice water and extracted with EtOAc twice. The organic layers were washed with 5% aqueous LiCl solution and brine, dried over Na$_2$SO$_4$ and concentrated under reduced pressure. The residue was purified by chromatography on silica gel (eluted with petroleum ether:ethyl acetate=10:1 to 6:1) to afford compound 37-4 (3.05 g, yield 92.4%) as a yellow solid. LC/MS (ESI) m/z: 215 (M+H)$^+$.

Step 4: Ethyl 4-amino-5,6,7,8-tetrahydronaphthalene-1-carboxylate (37-5)

A solution of compound 37-4 (700 mg) in 80% aqueous H2SO$_4$ solution (4 mL) was stirred at 150° C. for 5 hours. To the mixture was added EtOH (40 mL) and the mixture was stirred at 90° C. overnight. The mixture was poured into ice cooled saturated NaHCO$_3$ solution and the reaction was extracted with EtOAc twice. The combined organic layers were washed with brine, dried over Na$_2$SO$_4$ and concentrated under reduced pressure. The residue was purified by chromatography on silica gel (PE:EtOAc=20:1 to 10:1) to afford compound 37-5 (368 mg, yield 54.9%) as a brown oil. LC/MS (ESI) m/z: 220 (M+H)$^+$.

Step 5: Ethyl 4-iodo-5,6,7,8-tetrahydronaphthalene-1-carboxylate (37-6)

To a solution of compound 37-5 (368 mg, 1.80 mmol) in MeCN (2 mL) and 2 N aqueous HCl (2 mL) was added dropwise a solution of NaNO$_2$ (149 mg, 2.15 mmol) in water (0.5 mL) at a temperature below −5° C. and the reaction mixture was stirred at room temperature for 1 hour. A solution of KI (535 mg, 3.20 mmol) in water (1.5 mL) was added to the mixture dropwise and the resulting mixture was stirred at room temperature overnight. The mixture was partitioned between EtOAc and water. The organic layers was washed with brine, dried over Na$_2$SO$_4$ and concentrated under reduced pressure. The residue was purified by chromatography on silica gel (petroleum ether:ethyl acetate=1:0 to 500:1) to afford compound 37-6 (370 mg, 62.2% yield) as a brown oil.

Step 6: Ethyl 4-(4,4,5,5-tetramethyl-1,3,2-dioxaborolan-2-yl)-5,6,7,8-tetrahydronaphthalene-1-carboxylate (37-7)

To a mixture of compound 37-6 (280 mg, 0.89 mmol) and 4,4,4',4',5,5,5',5'-octamethyl-2,2'-bi(1,3,2-dioxaborolane) (338 mg, 1.32 mmol) in DMF (8 mL) was added AcOK (288 mg, 2.94 mmol), followed by Pd(dppf)Cl$_2$ (32.6 mg, 0.04 mmol) under N$_2$ atmosphere. The mixture was degassed under a N$_2$ atmosphere three times and the reaction mixture was stirred at 90° C. overnight under a N$_2$ atmosphere. The mixture was filtered and the filtrate was partitioned between EtOAc and water. The organic layer was washed with 5% aqueous LiCl solution and brine, dried over Na$_2$SO$_4$ and concentrated under reduced pressure. The residue was purified by chromatography on silica gel (petroleum ether:ethyl acetate=500:1 to 450:1) to afford compound 37-7 (200 mg, 68.1% yield) as a yellow oil.

Step 7: Ethyl 4-(4-methylpyridin-2-yl)-5,6,7,8-tetrahydronaphthalene-1-carboxylate (37-8)

To a mixture of compound 37-7 (200 mg, 0.61 mmol) and 2-bromo-4-methylpyridine (109 mg, 0.64 mmol) in 1,4-dioxane (4 mL) and water (1 mL) under a N$_2$ atmosphere was added Na$_2$CO$_3$ (77.6 mg, 0.73 mmol) followed by Pd(PPh$_3$)$_4$ (69 mg, 0.06 mmol). The mixture was degassed under N$_2$ atmosphere three times and the reaction mixture was stirred at 90° C. under the N$_2$ atmosphere overnight. The mixture was filtered and the filtrate was partitioned between EtOAc and water. The organic layer was washed with brine, dried over Na$_2$SO$_4$ and concentrated under reduced pressure. The residue was purified by chromatography on silica gel (petroleum ether:ethyl acetate=20:1 to 10:1) to afford compound 37-8 (110 mg, 61.2% yield) as a yellow oil. LC/MS (ESI) m/z: 296 (M+H)$^+$.

Step 8: Ethyl 4-(4-methylpiperidin-2-yl)-5,6,7,8-tetrahydronaphthalene-1-carboxylate (37-9)

To a solution of compound 37-8 (130 mg, 0.44 mmol) in EtOH (3 mL) was added concentrated HCl (0.3 mL) and PtO$_2$ (5.0 mg, 0.09 mmol). The mixture was hydrogenated under 50 Psi of H2 for 4 hours at room temperature. The mixture was then filtered and the filtrate was evaporated under reduced pressure. The residue was purified by chromatography on silica gel (DCM:MeOH=20:1) to afford compound 37-9 (68 mg, 51.3% yield) as a yellow oil. LC/MS (ESI) m/z: 302 (M+H)$^+$.

Step 9: tert-Butyl 4-((2-(4-(ethoxycarbonyl)-5,6,7,8-tetrahydronaphthalen-1-yl)-4-methylpiperidin-1-yl) methyl)-5-methoxy-7-methyl-1H-indole-1-carboxylate (37-10)

To a mixture of compound 37-9 (68 mg, 0.23 mmol) and tert-butyl 4-formyl-5-methoxy-7-methyl-1H-indole-1-carboxylate (78.6 mg, 0.27 mmol) in DCE (3 mL) was added NaBH(OAc)$_3$ (143.7 mg, 0.68 mmol) followed by AcOH (1 drop) in DCE at 0° C. under a N$_2$ atmosphere. The mixture was stirred at 50° C. for 24 hours. The mixture was partitioned between DCM and water. The organic layer was washed with brine, dried over Na$_2$SO$_4$ and concentrated under reduced pressure. The residue was purified by chromatography on silica gel (petroleum ether:ethyl acetate=20:1 to 5:1) to afford compound 37-10 (35 mg, 26.5% yield) as a yellow oil. LC/MS (ESI) m/z: 575 (M+H)$^+$.

Step 10: 4-(1-((5-Methoxy-7-methyl-1H-indol-4-yl) methyl)-4-methylpiperidin-2-yl)-5,6,7,8-tetrahydronaphthalene-1-carboxylic Acid (Compound 28)

To a solution of compound 37-10 (30 mg, 0.05 mmol) in EtOH (2 mL) was added 1 N aqueous NaOH solution (0.42, 0.42 mmol) and the reaction mixture was stirred at 50° C. for 1.5 days. The mixture was diluted with water and the solvent was evaporated under reduced pressure. The residue was washed with Et$_2$O twice and the aqueous layer was adjusted to a pH of approximately 3 by adding 1N aqueous HCl. The mixture was stirred at room temperature for 2 hours. The mixture was extracted with EtOAc/THF (10:1) twice. The combined organic layers were dried over Na$_2$SO$_4$ and concentrated under reduced pressure. The residue was purified by preparative HPLC to afford COMPOUND 28 (3.2 mg, 13.7% yield) as a light yellow solid. $^1$H-NMR (400 MHz, CD$_3$OD) δ 7.36 (m, 2H), 7.23 (d, J=3.2 Hz, 1H), 6.68 (s, 1H), 6.28 (d, J=3.1 Hz, 1H), 4.29 (d, J=12.4 Hz, 1H), 4.02 (d, J=12.6 Hz, 1H), 3.71 (s, 3H), 3.41-3.30 (m, 2H), 3.00-2.85 (m, 3H), 2.74 (m, 1H), 2.42 (s, 3H), 1.92-1.66 (m, 7H), 1.61-1.38 (m, 3H), 0.91 (d, J=6.3 Hz, 3H). LC/MS (ESI) m/z: 575 (M+H)$^+$.

Scheme 38: Synthesis of 4-((2S, 4R)-1-((5-Methoxy-7-methyl-1H-indol-4-yl) methyl)-4-methylpiperidin-2-yl) phenyl (methyl) phosphinic acid (COMPOUND 29)

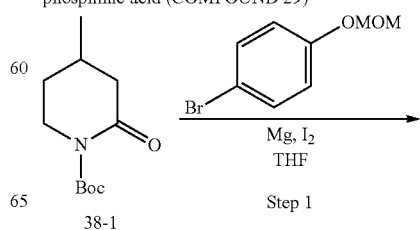

38-1

Step 1

-continued

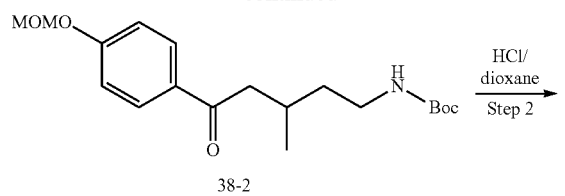
38-2

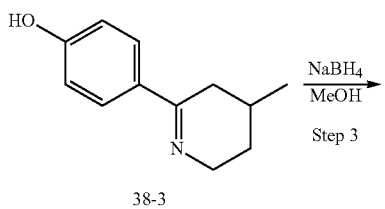
38-3

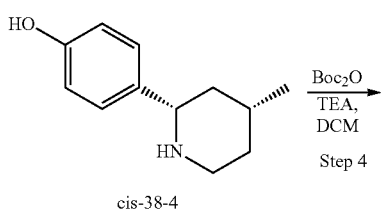
cis-38-4

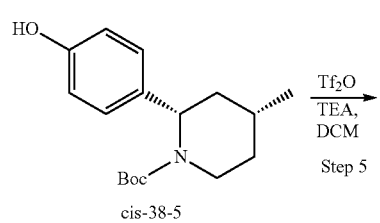
cis-38-5

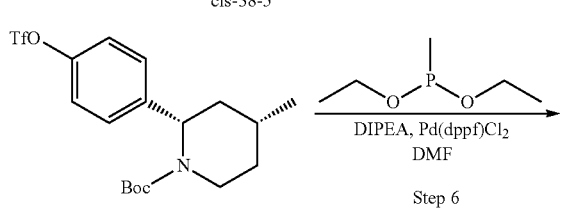
cis-38-6

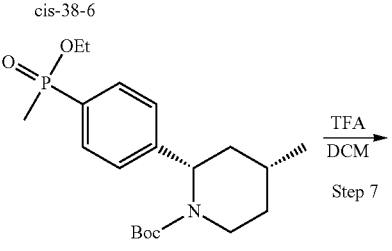
cis-38-7

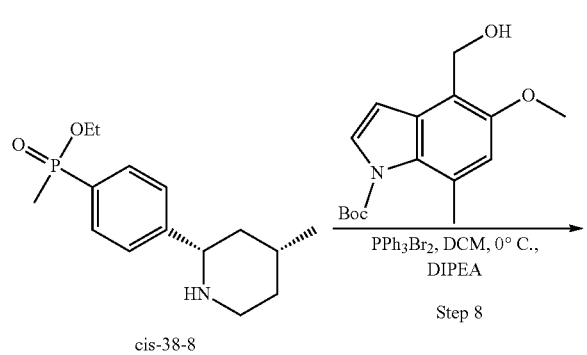
cis-38-8

-continued

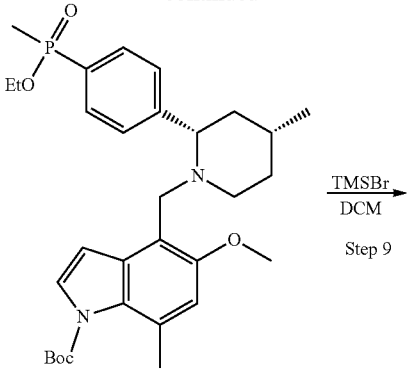
cis-38-9

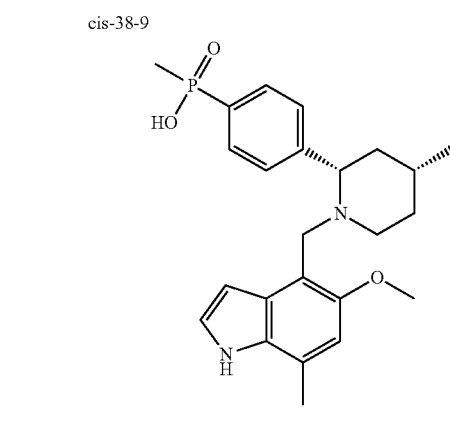
COMPOUND 29

Step 1: tert-Butyl (5-(4-(methoxymethoxy)phenyl)-3-methyl-5-oxopentyl)carbamate (38-2)

To a solution of magnesium (2.73 g, 112.3 mmol) in THF (50 mL) was added I2 (0.11 g, 0.432 mmol) followed by a solution of 1-bromo-4-(methoxymethoxy)benzene (2.4 g, 11.2 mmol) in THF (5 mL) under N₂ atmosphere. The mixture was heated to reflux until the color faded. Then the mixture was cooled to room temperature and a solution of 1-bromo-4-(methoxymethoxy)benzene (22 g, 101.1 mmol) in THF (78 mL) was added drop-wise to the mixture. The resulting mixture was stirred at room temperature for 1 hour. The mixture was added drop-wise to a solution of 4-methyl-2-oxopiperidine-1-carboxylate (18.4 g, 86.4 mmol) in THF (100 mL) under N₂ atmosphere at −78° C. and was stirred at this temperature for 1 hour. The reaction was quenched with saturated aqueous NH₄Cl solution and the mixture was diluted with EtOAc, washed with water and brine, dried over Na₂SO₄, filtered and concentrated to dryness. The residue was purified by silica gel chromatography (eluted with PE/EtOAc=10:1 to 2:1) to afford tert-butyl N-{5-[4-(methoxymethoxy)phenyl]-3-methyl-5-oxopentyl}carbamate (38-2, 9.9 g, yield 32.6%) as light yellow solid.

Step 2: 4-(4-Methyl-3, 4, 5, 6-tetrahydropyridin-2-yl) phenol (38-3)

A solution of tert-butyl compound 38-2 (8.06 g, 22.93 mmol) in HCl-dioxane (30 mL, 4M) was stirred at room temperature for 2 hours. The reaction was concentrated to dryness to afford compound 38-3 (4.30 g, yield 99.1%) as a light yellow solid, which was directly used in the next reaction without further purification. LC/MS (ESI) m/z: 190 (M+H)$^+$.

Step 3: 4-((2S, 4R)-4-Methylpiperidin-2-yl) phenol (cis-38-4)

To an ice-water cooled solution of compound 38-3 (4.30 g, 22.75 mmol) in methanol (50 mL) was added sodium borohydride (1.73 g, 45.50 mmol). The reaction mixture was stirred at room temperature for 3 hours. The reaction mixture was quenched with saturated aqueous NH$_4$Cl solution slowly and extracted with EtOAc twice. The combined organic layers were washed with brine, dried over anhydrous Na$_2$SO$_4$ and concentrated to afford compound cis-38-4 (3.45 g, yield 79.4%, a mixture of cis-enantiomers) as white solid, which was used directly in the next step. LC/MS (ESI) m/z: 192 (M+H)$^+$.

Step 4: (2S, 4R)-tert-Butyl 2-(4-hydroxyphenyl)-4-methylpiperidine-1-carboxylate (cis-38-5)

To a solution of cis-38-4 (3.45 g, 18.06 mmol) in dichloromethane (60 mL) was added triethylamine (5.47 g, 54.19 mmol) and di-tert-butyl dicarbonate (4.33 g, 19.87 mmol) and the mixture was stirred at room temperature overnight. The mixture was diluted with H$_2$O and extracted with EtOAc twice. The combined organic layers were washed with brine, dried with anhydrous Na$_2$SO$_4$, and concentrated. The residue was purified by chromatography on silica gel (PE/DCM/EtOAc=50:0:1 to 50:10:1) to afford cis-38-5 (2.66 g, yield 50.6%) as a white solid. LC/MS (ESI) m/z: 292 (M+H)$^+$.

Step 5: (2S, 4R)-tert-Butyl 4-methyl-2-(4-(trifluoromethylsulfonyloxy) phenyl) piperidine-1-carboxylate (cis-6)

To a mixture of compound cis-38-5 (2.66 g, 9.14 mmol) and pyridine (2.17 g, 27.42 mmol) in anhydrous dichloromethane (35 mL) was added triflic anhydride (5.15 g, 18.28 mmol) dropwise at 0° C. and the resulting mixture was stirred at room temperature for 2 hours under Na atmosphere. The reaction mixture was diluted with water and extracted with EtOAc twice. The combined organic layers were washed with brine, dried over anhydrous Na$_2$SO$_4$ and concentrated. The residue was purified by column chromatography on silica gel (eluted with PE/EtOAc=50:1) to afford compound cis-38-6 (2.86 g, yield 73.97%) as a light yellow liquid. LC/MS (ESI) m/z: 424 (M+H)

Step 6: (2S, 4R)-tert-Butyl 2-(4-(ethoxy (methyl) phosphoryl) phenyl)-4-methylpiperidine-1-carboxylate (cis-7)

To a mixture of compound cis-38-6 (0.50 g, 1.18 mmol) and N-ethyldiisopropylamine (0.76 g, 5.91 mmol) in dimethyl-formamide (8 mL) was added diethyl methylphosphonite (0.80 g, 5.91 mmol) and Pddppf (0.043 g, 0.059 mmol) under Na atmosphere and the mixture was stirred at 130° C. for 20 minutes in a microwave reactor. The mixture was diluted with H$_2$O and extracted with EtOAc twice. The combined organic layers were washed with brine, dried with anhydrous Na$_2$SO$_4$ and concentrated. The residue was purified by chromatography on silica gel (PE/EtOAc=100:1 to 3:1) to afford compound cis-38-7 (0.32 g, yield 71.1%) as a yellow oil. LC/MS (ESI) m/z: 382 (M+H)$^+$.

Step 7: Ethyl methyl (4-((2S, 4R)-4-methylpiperidin-2-yl) phenyl) phosphinate (cis-38-8)

To a solution of compound cis-38-7 (0.28 g, 0.73 mmol) in dichloromethane (6 mL) was added trifluoroacetic acid (1.5 mL) at 0° C. and the mixture was stirred at room temperature for 1.5 hours. The reaction mixture was concentrated and washed with ether and the residue was basified by aqueous NaHCO$_3$ solution and extracted with DCM twice. The combined organic layers were washed with brine, dried with anhydrous Na$_2$SO$_4$ and concentrated to afford compound cis-38-8 (0.20 g, yield 96.8%) as a yellow oil, which was used directly in the next step. LC/MS (ESI) m/z: 282 (M+H)$^+$.

Step 8: tert-Butyl 4-(((2S, 4R)-2-(4-(ethoxy (methyl) phosphoryl) phenyl)-4-methylpiperidin-1-yl) methyl)-5-methoxy-7-methyl-1H-indole-1-carboxylate (cis-38-9)

To a solution of tert-butyl 4-(hydroxymethyl)-5-methoxy-7-methyl-1H-indole-1-carboxylate (0.15 g, 0.50 mmol) in dichloromethane (8 mL) was added triphenyldibromophosphorane (0.27 g, 0.65 mmol) at 0° C. and the mixture was stirred at 0° C. for 1.5 hours under Na atmosphere. N-ethyldiisopropylamine (0.19 g, 1.49 mmol) was added followed by compound cis-38-8 (0.14 g, 0.50 mmol). The reaction was stirred at 0° C. for 1 hour under Na atmosphere. The reaction mixture was poured into ice-water and extracted with DCM twice. The combined organic layers were washed with brine, dried with anhydrous Na$_2$SO$_4$ and concentrated. The residue was purified by chromatography on silica gel (PE/EtOAc=60:1 to 4:1) to afford compound cis-38-9 (0.18 g, yield 65.4%) as a yellow oil. LC/MS (ESI) m/z: 555 (M+H)$^+$.

Step 9: 4-((2S, 4R)-1-((5-Methoxy-7-methyl-1H-indol-4-yl) methyl)-4-methylpiperidin-2-yl) phenyl (methyl) phosphinic Acid (Compound 29)

To a solution of cis-38-9 (0.15 g, 0.27 mmol) in dichloromethane (9 mL) was added bromo(trimethyl)silane (2 mL) at 0° C. and the resulting mixture was stirred at room temperature overnight under N$_2$ atmosphere. The solvent was removed and the residue was purified by pre-HPLC to afford COMPOUND 29 (0.015 g, yield 13.0%, a mixture of cis enantiomers) as a light purple solid. $^1$H-NMR (400 MHz, CD$_3$OD) δ 7.98 (dd, J=10.4, 8.0 Hz, 2H), 7.63 (d, J=6.8 Hz, 2H), 7.32 (d, J=3.2 Hz, 1H), 6.75 (s, 1H), 6.29 (d, J=3.2 Hz, 1H), 4.46 (dd, J=12.4, 2.8 Hz, 1H), 4.35 (d, J=12.4 Hz, 1H), 4.10 (d, J=12.4 Hz, 1H), 3.75 (s, 3H), 3.57-3.47 (m, 1H), 3.35-3.26 (m, 1H), 2.50 (s, 3H), 2.09-2.02 (m, 1H), 1.98-1.92 (m, 1H), 1.90-1.82 (m, 1H), 1.82-1.70 (m, 1H), 1.58-1.46 (m, 1H), 1.43 (d, J=13.6 Hz, 3H), 1.02 (d, J=6.4 Hz, 3H); LC/MS (ESI) m/z: 427 (M+H)$^+$.

Scheme 39:
Synthesis of 5-Methoxy-7-methyl-4-(((2S,4R)-4-methyl-2-(4-(S-methylsulfonimidoyl)phenyl)piperidin-1-yl)methyl)-1H-indole (COMPOUND 30) and 5-Methoxy-7-methyl-4-(((2S,4R)-4-methyl-2-(4-((R)-S-methylsulfonimidoyl)phenyl)piperidin-1-yl)methyl)-1H-indole (COMPOUND 31)

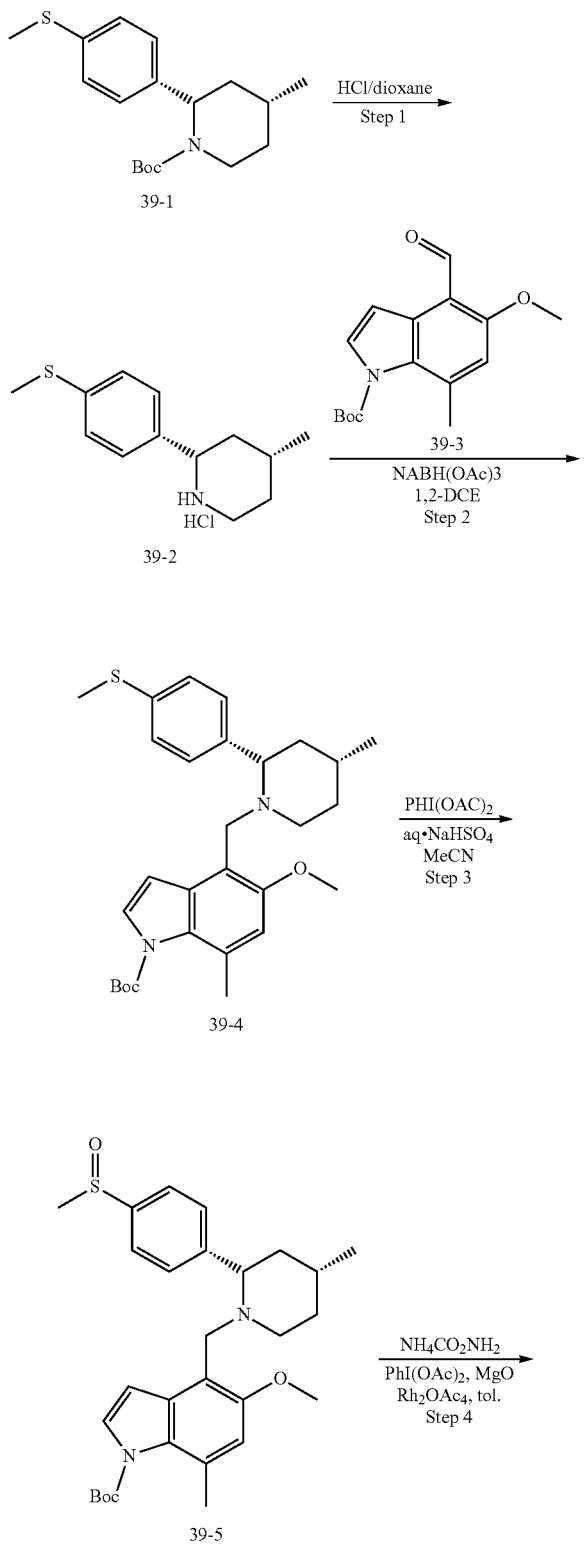

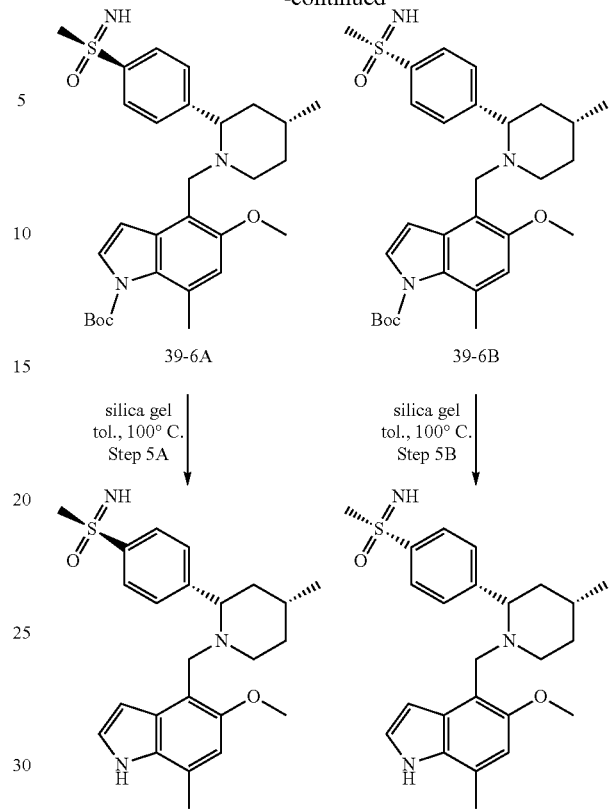

Step 1: (2S,4R)-4-Methyl-2-(4-(methylthio)phenyl)piperidine hydrochloride (39-2)

A solution of compound 39-1 (500 mg, 1.56 mmol) in HCl-dioxane solution (10 mL, 4M) was stirred at room temperature for 0.5 hour and the mixture was concentrated to dryness to afford compound 39-2 (400 mg, yield 99.6%) as a white solid. LC/MS (ESI) m/z: 222 (M+H)+.

Step 2: tert-Butyl 5-methoxy-7-methyl-4-(((2S,4R)-4-methyl-2-(4-(methylthio)phenyl)piperidin-1-yl)methyl)-1H-indole-1-carboxylate (39-4)

To a mixture of compound 39-2 (0.4 g, 1.56 mmol) and tert-butyl 4-formyl-5-methoxy-7-methyl-1H-indole-1-carboxylate (0.68 g, 2.34 mmol) in 1,2-DCE (10 mL) was added NaBH(OAc)₃ (0.99 g, 4.66 mmol) and the reaction mixture was stirred at 50° C. for 16 hrs. The reaction mixture was quenched with 5% aqueous NaHCO₃ solution and was extracted with EtOAc twice. The combined organic layers were washed with brine, dried with Na₂SO₄ and concentrated. The residue was purified by silica gel column (eluted with petroleum ether:ethyl acetate=20:1 to 5:1) to afford compound 39-4 (0.57 g, yield 73.9%) as a white solid. LC/MS (ESI) m/z: 495 (M+H)+.

Step 3: tert-Butyl 5-methoxy-7-methyl-4-(((2S,4R)-4-methyl-2-(4-(methylsulfinyl)phenyl)piperidin-1-yl)methyl)-1H-indole-1-carboxylate (39-5)

To a solution of compound 39-4 (570 mg, 1.15 mmol) in MeCN/water (10 mL, 5/1) was added (diacetoxyiodo)benzene (389 mg, 1.21 mmol) and NaHSO$_4$ (277 mg, 2.3 mmol) and the reaction mixture was stirred at room temperature for 10 minutes. The reaction mixture was quenched with aqueous NaHCO$_3$ (10 mL) and extracted with ethyl acetate (20 mL×3). The combined organic layers phases were washed with brine, dried with Na$_2$SO$_4$ and concentrated and the residue was purified with silica gel column (eluted with petroleum ether:ethyl acetate=5:1 so 1:1) to afford compound 39-5 (520 mg, yield 88.5%) as white solid. LC/MS (ESI) m/z: 511 (M+H)$^+$.

Step 4: tert-Butyl 5-methoxy-7-methyl-4-(((2S,4R)-4-methyl-2-(4-(S-methylsulfonimidoyl)phenyl)piperidin-1-yl)methyl)-1H-indole-1-carboxylate (39-6A) & tert-Butyl 5-methoxy-7-methyl-4-(((2S,4R)-4-methyl-2-(4-((R)—S-methylsulfonimidoyl)phenyl)piperidin-1-yl)methyl)-1H-indole-1-carboxylate (39-6B)

To a mixture of compound 39-5 (220 mg, 0.43 mmol), MgO (163 mg, 4.07 mmol), Rh$_2$(OAc)$_4$ (5 mg, 0.01 mmol), and ammonium carbamate (159 mg, 2.04 mmol) in toluene (10 mL) was added (diacetoxyiodo)benzene (677 mg, 2.03 mmol) and the reaction mixture was stirred at 40° C. for 16 hours. The mixture was quenched with 5% aqueous NaHCO$_3$ solution and extracted with DCM (20 mL×3). The combined organic layers were washed with brine, dried with Na$_2$SO$_4$, and concentrated. The residue was purified with silica gel column (eluted with petroleum ether:acetone=30:1 to 5:1) and further purified by preparatory Chiral SFC to afford compound 39-6A (25 mg, yield 11.0%) and 39-6B (29 mg, 12.8% yield) as white solids. LC/MS (ESI) m/z: 526 (M+H)$^+$. The absolute configurations of the sulfoximine diastereomers 39-6A and 39-6B were assigned arbitrarily.

Step 5A: 5-Methoxy-7-methyl-4-(((2S,4R)-4-methyl-2-(4-((S)—S-methylsulfonimidoyl)phenyl)piperidin-1-yl)methyl)-1H-indole (Compound 30)

To a solution of 39-6A (21 mg, 0.04 mmol) in toluene (12 mL) was added Sift (42 mg, 100-200 mesh) and the mixture was stirred at 100° C. for 16 hours. The mixture was concentrated to dryness and the residue was purified by preparative TLC (MeOH/DCM=15:1) to afford COMPOUND 30 (5.2 mg, yield 30.5%) as a white solid. $^1$H-NMR (400 MHz, CD$_3$OD) δ 8.03 (d, J=8.3 Hz, 2H), 7.79 (d, J=7.6 Hz, 2H), 7.21 (d, J=3.1 Hz, 1H), 6.68 (s, 1H), 6.43 (d, J=3.1 Hz, 1H), 3.90-3.78 (m, 1H), 3.76 (s, 3H), 3.52-3.37 (m, 1H), 3.17 (s, 3H), 3.10-3.01 (m, 1H), 2.46 (s, 3H), 2.36-2.21 (m, 1H), 2.22-1.96 (m, 1H), 1.79-1.69 (m, 1H), 1.60 (d, J=12.6 Hz, 2H), 1.37-1.30 (m, 2H), 0.92 (d, J=6.2 Hz, 3H). LC/MS (ESI) m/z: 426 (M+H)$^+$.

Step 5B: 5-Methoxy-7-methyl-4-(((2S,4R)-4-methyl-2-(4-((R)—S-methylsulfonimidoyl)phenyl)piperidin-1-yl)methyl)-1H-indole (Compound 31)

To a solution of 39-6B (21 mg, 0.04 mmol) in toluene (12 mL) was added SiO$_2$ (42 mg, 1.00-200 mesh) and the mixture was stirred at 100° C. for 16 hours. The mixture was concentrated to dryness and the residue was purified by preparative TLC (MeOH/DCM=15:1) to afford COMPOUND 31 (5 mg, yield 25.7%) as a white solid. $^1$H-NMR (400 MHz, CD$_3$OD) δ 8.06 (d, J=8.0 Hz, 2H), 7.80 (d, J=7.7 Hz, 2H), 7.23 (d, J=3.0 Hz, 1H), 6.69 (s, 1H), 6.41 (d, J=3.0 Hz, 1H), 3.97-3.83 (m, 1H), 3.75 (s, 3H), 3.56-3.39 (m, 1H), 3.18 (s, 3H), 3.15-3.03 (m, 1H), 2.47 (s, 3H), 2.22-2.00 (m, 1H), 1.89-1.77 (m, 1H), 1.77-1.49 (m, 3H), 1.36-1.30 (m, 2H), 0.94 (d, J=6.2 Hz, 3H); LC/MS (ESI) m/z: 426(M+H)$^+$.

Scheme 40:
Synthesis of (4-((2S,4R)-1-((5-methoxy-7-methyl-1H-indol-4-yl)methyl)-4-methylpiperidin-2-yl)phenyl)phosphonic acid (COMPOUND 32) and (4-((2R,4S)-1-((5-methoxy-7-methyl-1H-indol-4-yl)methyl)-4-methylpiperidin-2-yl)phenyl)phosphonic acid (COMPOUND 33)

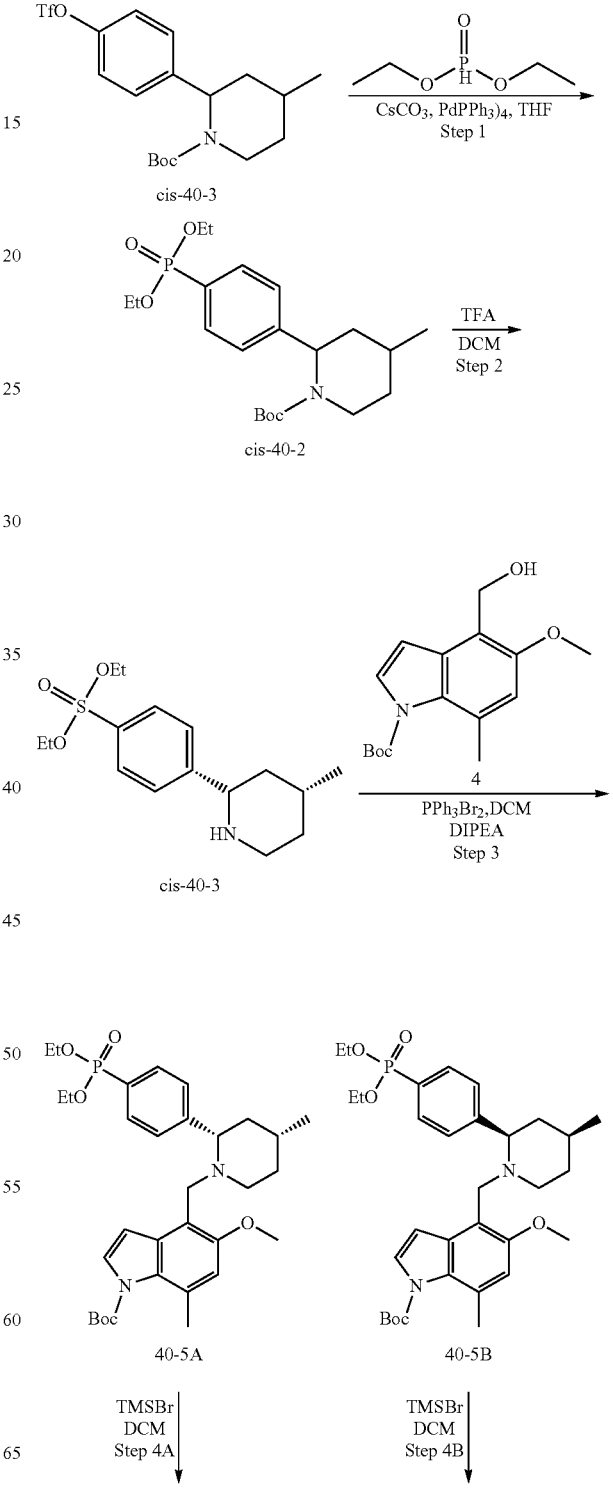

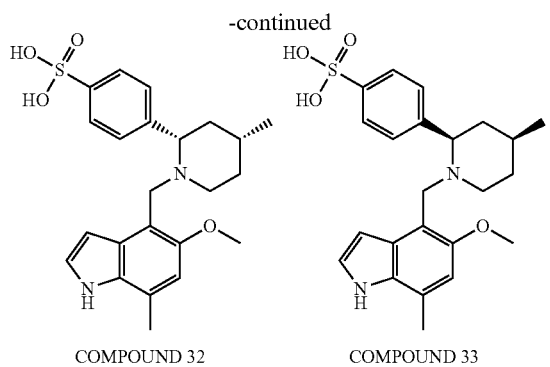

COMPOUND 32   COMPOUND 33

Step 1: tert-Butyl 2-(4-(diethoxyphosphoryl)phenyl)-4-methylpiperidine-1-carboxylate (cis-40-2)

To a mixture of compound cis-40-1 (1 g, 2.36 mmol) and cesium carbonate (1.62 g, 4.96 mmol) in tetrahydrofuran (15 mL) was added diethyl phosphite (1.31 g, 9.45 mmol) and tetrakis(triphenylphosphine)palladium (0.27 g, 0.24 mmol) under $N_2$ atmosphere and the mixture was stirred at 110° C. for 3 hours in a microwave reactor. The reaction mixture was diluted with water and extracted with EtOAc twice. The combined organic layers were washed with brine, dried over anhydrous $Na_2SO_4$ and concentrated. The residue was purified by column chromatography on silica gel (eluted with PE/EtOAc=50:1 to 4:1) to afford compound cis-40-2 (0.6 g, yield 61.7%) as a colorless oil. LC/MS (ESI) m/z: 412 $(M+H)^+$.

Step 2: Diethyl (4-(4-methylpiperidin-2-yl)phenyl) phosphonate (cis-40-3)

To a solution of compound cis-40-2 (0.6 g, 1.46 mmol) in dichloromethane (9 mL) was added trifluoroacetic acid (3 mL) at 0° C. and the mixture was stirred at room temperature for 1.5 hours. The reaction mixture was concentrated and washed with ether. The residue was basified with 10% aqueous NaOH solution and extracted with DCM/MeOH (20:1) twice. The combined organic layers were washed with brine, dried with anhydrous $Na_2SO_4$ and concentrated to afford compound cis-40-3 (0.45 g, yield 99.1%) as a yellow oil, which was used directly in the next step. LC/MS (ESI) m/z: 312 $(M+H)^+$.

Step 3: tert-Butyl 4-(((2R, 4S)-2-(4-(diethoxyphosphoryl) phenyl)-4-methylpiperidin-1-yl) methyl)-5-methoxy-7-methyl-1H-indole-1-carboxylate (40-5)

To a solution of compound 40-4 (0.34 g, 1.16 mmol) in dichloromethane (6 mL) was added triphenyldibromophosphorane (0.63 g, 1.50 mmol) at 0° C. and the mixture was stirred at 0° C. for 1.5 hours under $N_2$ atmosphere. Compound cis-40-3 (0.36 g, 1.16 mmol) was added followed by N-ethyldiisopropylamine (0.45 g, 3.47 mmol) and the resulting mixture was stirred at 0° C. for 1 hour under $N_2$ atmosphere. The reaction mixture was poured into ice water and extracted with DCM twice. The combined organic layers were washed with brine, dried with anhydrous $Na_2SO_4$ and concentrated. The residue was purified by chromatography on silica gel (PE/acetone=100:1 to 70:1) and further purified by preparatory Chiral SFC to afford compound 40-5A (0.11 g, yield 16.2%) and 40-5B (0.12 g, 17.7% yield) as a light yellow oil. LC/MS (ESI) m/z: 585 $(M+H)^+$.

Step 4A: (4-((2S,4R)-1-((5-Methoxy-7-methyl-1H-indol-4-yl)methyl)-4-methylpiperidin-2-yl)phenyl) phosphonic Acid (Compound 32)

To a solution of compound 40-5A (0.05 g, 0.086 mmol) in dichloromethane (4 mL) was added bromo(trimethyl) silane (1 mL) at 0° C. and the resulting mixture was stirred at room temperature overnight under $N_2$ atmosphere. The reaction mixture was quenched with MeOH at 0° C. and the mixture was concentrated to dryness to afford crude product, which was purified by preparative-HPLC to afford COMPOUND 32 (22 mg, yield 59.7%) as white solid. 1H-NMR (400 MHz, $CD_3OD$) δ 8.10 (s, 1H), 8.00 (dd, J=11.9, 7.9 Hz, 2H), 7.59 (d, J=5.7 Hz, 2H), 7.31 (d, J=3.1 Hz, 1H), 6.75 (s, 1H), 6.31 (d, J=3.1 Hz, 1H), 4.44 (dd, J=12.3, 2.6 Hz, 1H), 4.36 (d, J=12.7 Hz, 1H), 4.09 (d, J=12.7 Hz, 1H), 3.76 (s, 3H), 3.50 (d, J=12.7 Hz, 1H), 3.35-3.31 (m, 1H), 2.50 (s, 3H), 2.08-2.01 (m, 1H), 1.99-1.92 (m, 1H), 1.90-1.83 (m, 1H), 1.81-1.72 (m, 1H), 1.57-1.46 (m, 1H), 1.01 (d, J=6.4 Hz, 3H). LC/MS (ESI) m/z: 429 $(M+H)^+$.

Step 4B: 4-((2R, 4S)-1-((5-Methoxy-7-methyl-1H-indol-4-yl) methyl)-4-methylpiperidin-2-yl) phenylphosphonic Acid (Compound 33)

To a solution of compound 40-5B (0.05 g, 0.086 mmol) in dichloromethane (4 mL) was added bromo(trimethyl) silane (1 mL) at 0° C. and the resulting mixture was stirred at room temperature overnight under $N_2$ atmosphere. The reaction mixture was quenched with MeOH at 0° C. and the mixture was concentrated to dryness to afford crude product, which was purified by preparative-HPLC to afford COMPOUND 33 (0.02 g, yield 54.58%) as white solid. $^1$H-NMR (400 MHz, $CD_3OD$) δ 8.00 (dd, J=11.6, 8.0 Hz, 2H), 7.59 (d, J=6.0 Hz, 2H), 7.31 (d, J=3.2 Hz, 1H), 6.75 (s, 1H), 6.31 (d, J=3.2 Hz, 1H), 4.44 (dd, J=12.4, 2.4 Hz, 1H), 4.35 (d, J=12.8 Hz, 1H), 4.09 (d, J=12.8 Hz, 1H), 3.76 (s, 3H), 3.50 (d, J=12.0 Hz, 1H), 3.29-3.14 (m, 1H), 2.50 (s, 3H), 2.09-2.01 (m, 1H), 1.99-1.90 (m, 1H), 1.85 (d, J=14.4 Hz, 1H), 1.76 (dd, J=26.0, 12.4 Hz, 1H), 1.57-1.46 (m, 1H), 1.01 (d, J=6.4 Hz, 3H); LC/MS (ESI) m/z: 429 $(M+H)^+$.

Scheme 41:
Synthesis of 4-((2S,4R)-1-((5-Methoxy-7-methyl-1H-indol-4-yl)methyl)-4-methylpiperidin-2-yl)-5,6,7,8-tetrahydronaphthalene-1-carboxylic acid (COMPOUND 34) and 4-((2R,4R)-1-((5-Methoxy-7-methyl-1H-indol-4-yl)methyl)-4-methylpiperidin-2-yl)-5,6,7,8-tetrahydronaphthalene-1-carboxylic acid (COMPOUND 35)

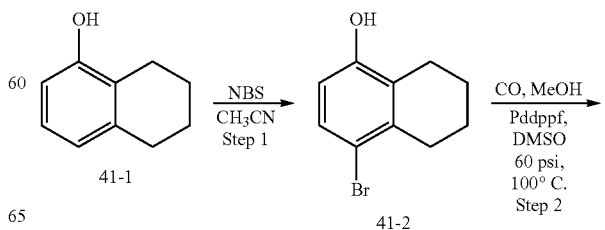

281
-continued

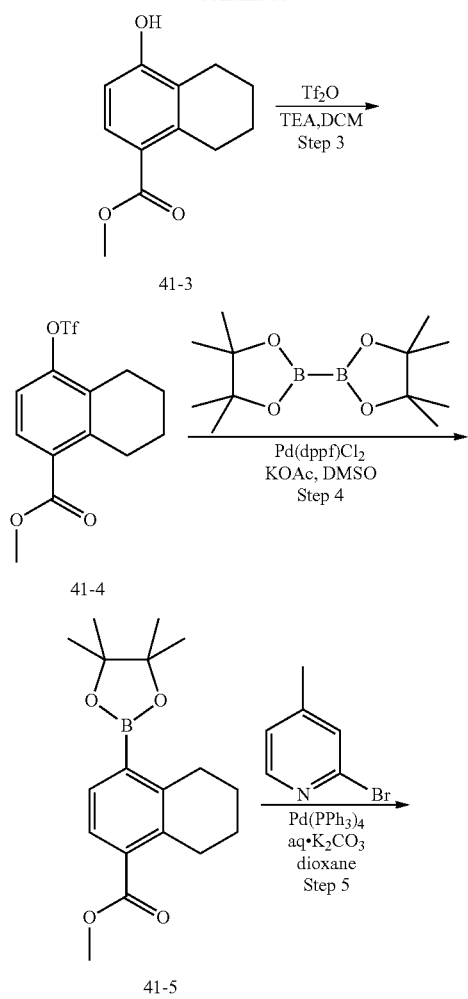

41-3

41-4

41-5

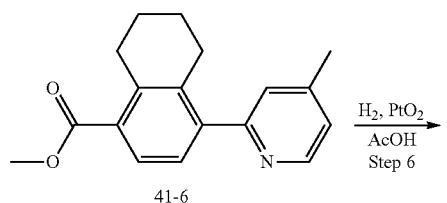

41-6

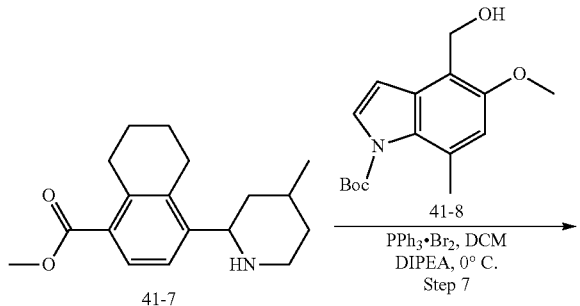

41-7    41-8

282
-continued

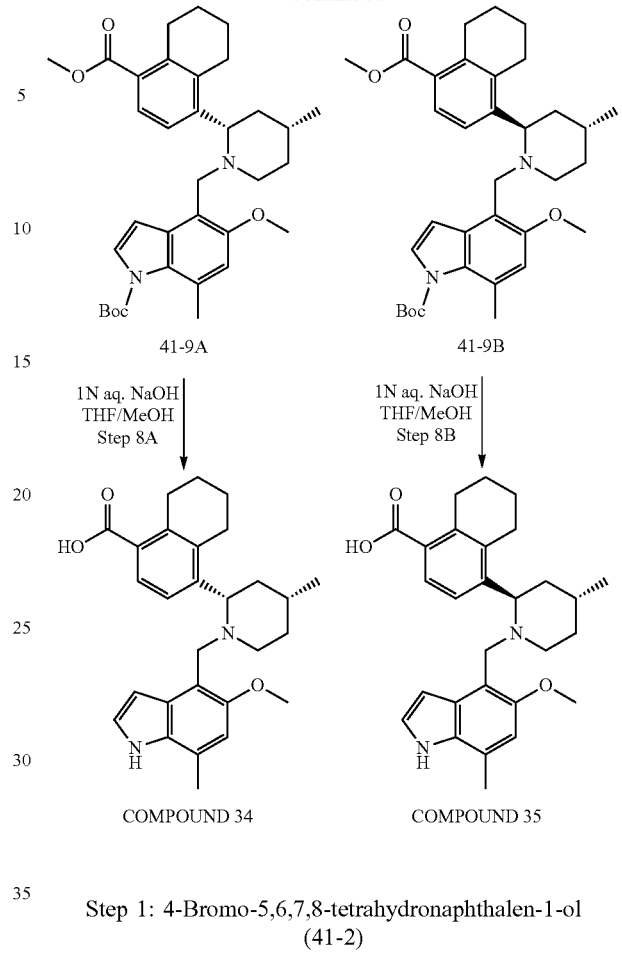

41-9A    41-9B

↓ 1N aq. NaOH THF/MeOH Step 8A     ↓ 1N aq. NaOH THF/MeOH Step 8B

COMPOUND 34    COMPOUND 35

Step 1: 4-Bromo-5,6,7,8-tetrahydronaphthalen-1-ol (41-2)

To a solution of compound 41-1 (5.0 g, 33.8 mmol) in MeCN (50 mL) was added NBS (7.2 g, 40.6 mmol) at 0° C. The reaction mixture was stirred at room temperature overnight. The mixture was evaporated under reduced pressure and the residue was purified by silica gel chromatography (petroleum ether:ethyl acetate=30:1 to 20:1) to afford compound 41-2 (6.8 g, 89.0% yield) as a white solid. LC/MS (ESI) m/z: 227 (M+H)$^+$.

Step 2: Methyl 4-hydroxy-5,6,7,8-tetrahydronaphthalene-1-carboxylate (41-3)

To a solution of compound 41-2 (6.5 g, 28.8 mmol) in MeOH (50 mL) was added Et$_3$N (12.8 mL, 86.4 mmol) followed by Pd(dppf)C12 (2.1 g, 2.88 mmol) in a pressure vessel. The reaction vessel was charged with CO (65 psi) and then heated to 100° C. for 16 hours. The reaction was cooled to ambient temperature and the mixture was filtered. The filtrate was concentrated under vacuum and the residue was purified by silica gel chromatography (petroleum ether: ethyl acetate=25:1 to 20:1) to afford compound 41-3 (4.4 g, 73.8% yield) as a white solid. LC/MS (ESI) m/z: 207 (M+H)$^+$.

Step 3: Methyl 4-(((trifluoromethyl)sulfonyl)oxy)-5,6,7,8-tetrahydronaphthalene-1-carboxylate (41-4)

To a mixture of compound 41-3 (4.4 g, 21.3 mmol) and pyridine (5.1 mL, 63.9 mmol) in dry DCM (50 mL) was added Tf$_2$O (7.2 mL, 42.6 mmol) dropwise at 0° C. The reaction mixture was stirred at 0° C. for 1.5 hours before the mixture was evaporated under reduced pressure. The residue was purified by chromatography on silica gel (petroleum ether:ethyl acetate=1:0 to 500:1) to afford compound 41-4 (5.4 g, 74.8% yield) as a white solid. LC/MS (ESI) m/z: 339 (M+H)$^+$.

Step 4: Methyl 4-(((trifluoromethyl)sulfonyl)oxy)-5, 6,7,8-tetrahydronaphthalene-1-carboxylate (41-5)

To a mixture of compound 41-4 (5.4 g, 16.0 mmol), 4,4,4',4',5,5,5',5'-octamethyl-2,2'-bi(1,3,2-dioxaborolane) (8.1 g, 32.0 mmol) in 1,4-dioxane (60 mL) was added AcOK (4.7 g, 48.0 mmol) followed by Pd(dppf)C12 (584 mg, 0.8 mmol). The mixture was degassed under N$_2$ atmosphere three times and the reaction mixture was stirred at 90° C. under N$_2$ atmosphere overnight. The mixture was filtered and the filtrate was evaporated under reduced pressure. The residue was purified by chromatography on silica gel (petroleum ether:ethyl acetate=1:0 to 500:1) to afford compound 41-5 (4.8 g, 94.1% yield) as a light oil.

Step 5: Methyl 4-(4-methylpyridin-2-yl)-5,6,7,8-tetrahydronaphthalene-1-carboxylate (41-6)

To a mixture of compound 41-5 (3.2 g, 10.1 mmol) and 2-bromo-4-methylpyridine (2.1 g, 12.1 mmol) in 1,4-dioxane (9 mL) and water (1 mL) was added K$_2$CO$_3$ (3.5 g, 25.3 mmol) followed by Pd(PPh$_3$)$_4$ (933.7 mg, 0.8 mmol). The mixture was degassed under N$_2$ atmosphere three times and the reaction mixture was stirred at 90° C. under N$_2$ atmosphere overnight. The mixture was filtered and the filtrate was partitioned with EtOAc and water. The organic layer was washed with brine, dried over Na$_2$SO$_4$ and concentrated under reduced pressure. The residue was purified by chromatography on silica gel (petroleum ether:ethyl acetate=20:1 to 10:1) to afford compound 41-6 (1.5 g, 53.0% yield) as a yellow oil. LC/MS (ESI) m/z: 282 (M+H)$^+$.

Step 6: Methyl 4-(4-methylpiperidin-2-yl)-5,6,7,8-tetrahydronaphthalene-1-carboxylate (41-7)

To a solution of compound 41-6 (1.8 g, 6.4 mmol) in AcOH (20 mL) was added PtO$_2$ (200 mg) in a pressure vessel. The reaction vessel was charged with H2 (65 psi) and stirred at room temperature for 16 hours. The mixture was filtered and the filtrate was concentrated under vacuum. The resulting residue was purified by silica gel chromatography (petroleum ether:ethyl acetate=25:1 to 20:1) to afford compound 41-7 (820 mg, 44.7% yield) as a white solid. LC/MS (ESI) m/z: 288 (M+H)$^+$.

Step 7: tert-Butyl 5-methoxy-4-(((2S,4R)-2-(4-(methoxycarbonyl)-5,6,7,8-tetrahydronaphthalen-1-yl)-4-methylpiperidin-1-yl)methyl)-7-methyl-1H-indole-1-carboxylate (41-9A) and tert-Butyl 5-methoxy-4-(((2R,4R)-2-(4-(methoxycarbonyl)-5,6,7,8-tetrahydronaphthalen-1-yl)-4-methylpiperidin-1-yl)methyl)-7-methyl-1H-indole-1-carboxylate (41-9B)

To a solution of compound 41-8 (320 mg, 1.1 mmol) in dry DCM (10 mL) was added triphenylphosphine dibromide (603.5 mg, 1.4 mmol) below 0° C. and the mixture was stirred at 0° C. for 1 hour. To the mixture was added DIPEA (0.54 mL, 3.3 mmol) followed by compound 41-7 (347.3 mg, 1.2 mmol) and the reaction mixture was stirred at 0° C. for another 1 hour. The mixture was poured into ice water and extracted with DCM twice. The combined organic layers were washed with brine, dried over Na$_2$SO$_4$ and concentrated under reduced pressure. The residue was purified by chromatography on silica gel (petroleum ether:ethyl acetate=30:1 to 20:1) and further purified by preparatory chiral SFC to afford compound 41-9A (200 mg, 32.5% yield, a mixture of two cis-enantiomers) and compound 41-9B (210 mg, 34.1% yield, a mixture of two trans-enantiomers) as white solids. LC/MS (ESI) m/z: 561 (M+H)$^+$.

Step 8A: 4-((2S,4R)-1-((5-Methoxy-7-methyl-1H-indol-4-yl)methyl)-4-methylpiperidin-2-yl)-5,6,7,8-tetrahydronaphthalene-1-carboxylic Acid (Compound 34)

To a solution of compound 41-9A (130 mg, 0.23 mmol) in THF/MeOH (3 mL/3 mL) was added 1 N aqueous NaOH solution (0.92 mL, 0.92 mmol) and the mixture was stirred at 55° C. for 16 hours. The mixture was diluted with water and washed with Et$_2$O twice. The aqueous layer was adjusted with 0.5 N aqueous HCl solution to a pH of approximately 5 and extracted with EtOAC/THF (2/1) twice. The combined organic layers were dried over Na$_2$SO$_4$ and concentrated under reduced pressure. The residue was purified by preparative HPLC to afford COMPOUND 34 (15 mg, 14.6% yield) as a white solid. $^1$H-NMR (400 MHz, CD$_3$OD) δ 7.47-7.39 (m, 2H), 7.31 (d, J=3.2 Hz, 1H), 6.76 (s, 1H), 6.37 (d, J=3.2 Hz, 1H), 4.71 (d, J=10.0 Hz, 1H), 4.37 (d, J=12.4 Hz, 1H), 4.09 (d, J=12.4 Hz, 1H), 3.50-3.43 (m, 1H), 3.41-3.33 (m, 1H), 3.08-2.92 (m, 3H), 2.85-2.76 (m, 1H), 2.00-1.86 (m, 4H), 1.86-1.75 (m, 3H), 1.68-1.58 (m, 1H), 1.56-1.46 (m, 1H), 1.00 (d, J=6.0 Hz, 3H); LC/MS (ESI) m/z: 447 (M+H)$^+$.

Step 8B: 4-((2R,4R)-1-((5-Methoxy-7-methyl-1H-indol-4-yl)methyl)-4-methylpiperidin-2-yl)-5,6,7,8-tetrahydronaphthalene-1-carboxylic Acid (Compound 35)

To a solution of compound 41-9B (130 mg, 0.23 mmol) in THF/MeOH (3 mL/3 mL) was added 1 N aqueous NaOH solution (0.92 mL, 0.92 mmol) and the mixture was stirred at 55° C. for 16 hours. The mixture was diluted with water and washed with Et$_2$O twice. The aqueous layer was adjust with 0.5 N aqueous HCl solution to a pH of approximately 5 and extracted with EtOAC/THF (2/1) twice. The combined organic layers were dried over Na$_2$SO$_4$ and concentrated under reduced pressure. The residue was purified by preparative HPLC to afford COMPOUND 35 (9 mg, 8.8% yield) as a white solid. $^1$H-NMR (400 MHz, CD$_3$OD) δ 7.57 (s, 1H), 7.46 (d, J=6.8 Hz, 1H), 7.33 (d, J=2.9 Hz, 1H), 6.77 (s, 1H), 6.37 (d, J=2.8 Hz, 1H), 4.75 (d, J=11.1 Hz, 1H), 4.37 (d, J=12.5 Hz, 1H), 4.13 (d, J=12.5 Hz, 1H), 3.80 (s, 3H), 3.53-3.46 (m, 1H), 3.43-3.36 (m, 1H), 3.11-2.97 (m, 3H), 2.87-2.80 (m, 1H), 2.51 (s, 3H), 2.01-1.79 (m, 7H), 1.69-1.61 (m, 1H), 1.58-1.50 (m, 1H), 1.01 (d, J=6.2 Hz, 3H); LC/MS (ESI) m/z: 447 (M+H)$^+$.

Example 9. Compounds of the Present Invention

TABLE 1

| Cmp No. | Structure | Name | IC$_{50}$ | RT min (Method A, C, or D) | MS M + 1 |
|---|---|---|---|---|---|
| 1 | 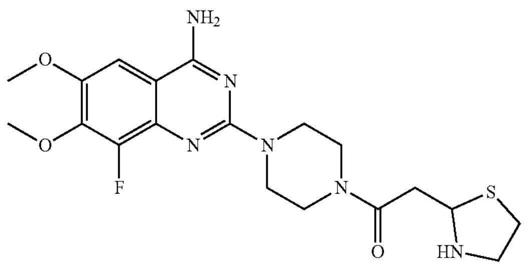 | 1-(4-(4-amino-8-fluoro-6,7-dimethoxyquinazolin-2-yl)piperazin-1-yl)-2-(thiazolidin-2-yl)ethan-1-one hydrochloride | * | 8.18 (D) | 437 |
| 2 | 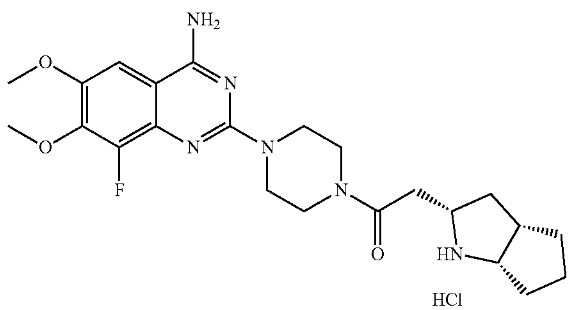 [SMILES: COc1cc2c(N)nc(N3CCN(C(=O)C[C@@H]4C[C@@H]5CCC[C@@H]5N4)CC3)nc2c(F)c1OC ; Cl] | 1-(4-(4-amino-8-fluoro-6,7-dimethoxyquinazolin-2-yl)piperazin-1-yl)-2-((2S,3aS,6aS)-octahydrocyclopenta[b]pyrrol-2-yl)ethan-1-one hydrochloride | *** | 7.59 (D) | 459 |
| 3 | 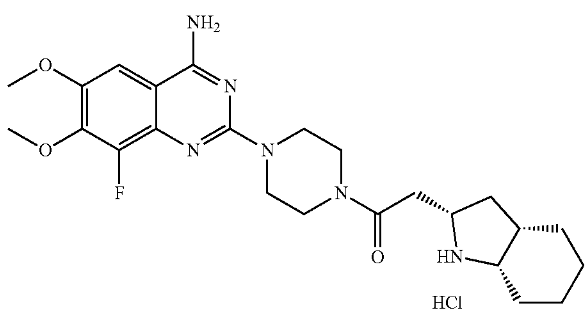 [SMILES: COc1cc2c(N)nc(N3CCN(C(=O)C[C@@H]4C[C@@H]5CCCC[C@@H]5N4)CC3)nc2c(F)c1OC ; Cl] | 1-(4-(4-amino-8-fluoro-6,7-dimethoxyquinazolin-2-yl)piperazin-1-yl)-2-((2S,3aS,7aS)-octahydro-1H-indol-2-yl)ethan-1-one hydrochloride | *** | 8.44 (C) | 473 |
| 4 | 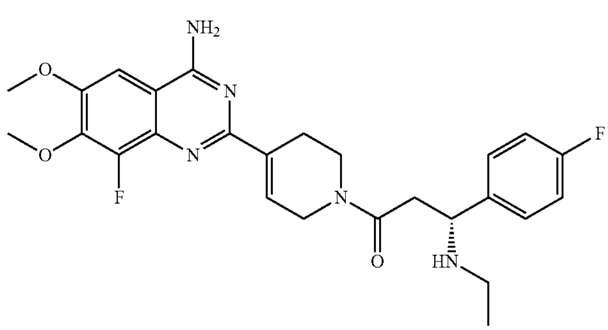 [SMILES: CCN[C@H](CC(=O)N1CC=C(c2nc(N)c3cc(OC)c(OC)c(F)c3n2)CC1)c1ccc(F)cc1] | (R)-1-(4-(4-amino-8-fluoro-6,7-dimethoxyquinazolin-2-yl)-3,6-dihydropyridin-1(2H)-yl)-3-(ethylamino)-3-(4-fluorophenyl)propan-1-one | *** | 8.97 (D) | 498 |

TABLE 1-continued

| Cmp No. | Structure | Name | IC$_{50}$ | RT min (Method A, C, or D) | MS M + 1 |
|---|---|---|---|---|---|
| 5 | 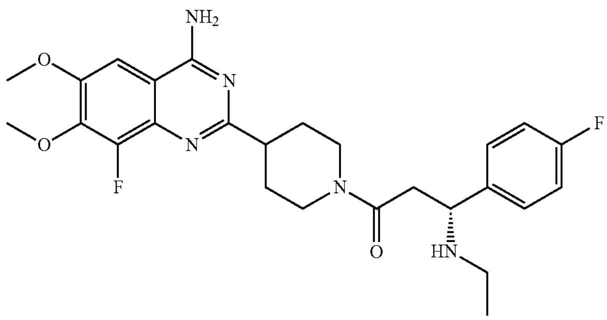 [SMILES: CCN[C@H](CC(=O)N1CCC(c2nc(N)c3cc(OC)c(OC)c(F)c3n2)CC1)c1ccc(F)cc1] | (R)-1-(4-(4-amino-8-fluoro-6,7-dimethoxyquinazolin-2-yl)piperidin-1-yl)-3-(ethylamino)-3-(4-fluorophenyl)propan-1-one | ** | 8.33 (D) | 500 |
| 6 | 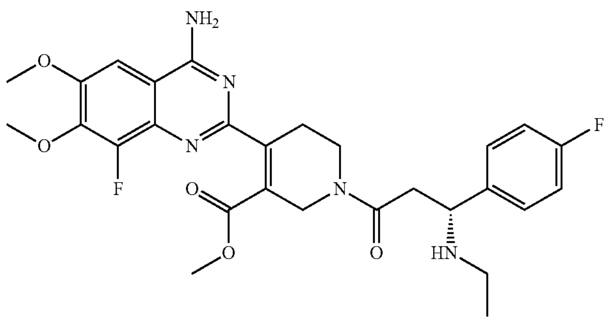 [SMILES: CCN[C@H](CC(=O)N1CCC(c2nc(N)c3cc(OC)c(OC)c(F)c3n2)=C(C(=O)OC)C1)c1ccc(F)cc1] | (R)-4-(4-amino-8-fluoro-6,7-dimethoxyquinazolin-2-yl)-1-(3-(ethylamino)-3-(4-fluorophenyl)propanoyl)-1,2,5,6-tetrahydropyridine-3-carboxylate | ** | 1.73 (A) | 556 |
| 7 | 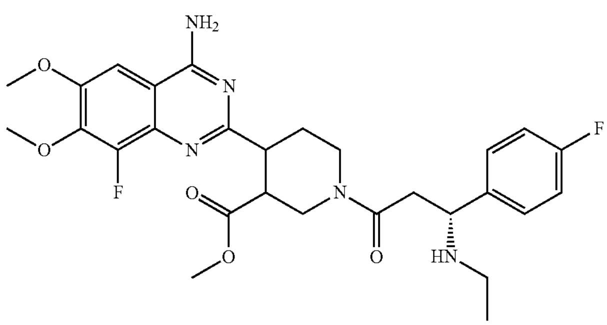 [SMILES: CCN[C@H](CC(=O)N1CCC(c2nc(N)c3cc(OC)c(OC)c(F)c3n2)C(C(=O)OC)C1)c1ccc(F)cc1] | 4-(4-amino-8-fluoro-6,7-dimethoxyquinazolin-2-yl)-1-((R)-3-(ethylamino)-3-(4-fluorophenyl)propanoyl)piperidine-3-carboxylate | * | 8.78 (D) | 558 |
| 8 | 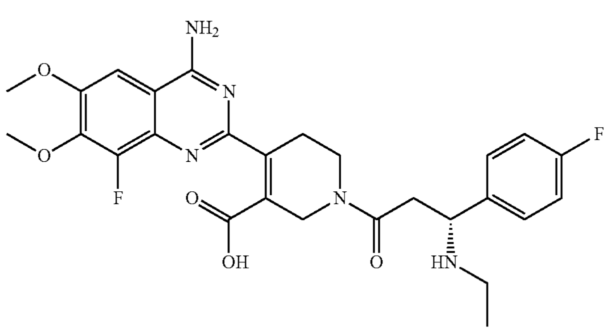 [SMILES: CCN[C@H](CC(=O)N1CCC(c2nc(N)c3cc(OC)c(OC)c(F)c3n2)=C(C(=O)O)C1)c1ccc(F)cc1] | (R)-4-(4-amino-8-fluoro-6,7-dimethoxyquinazolin-2-yl)-1-(3-(ethylamino)-3-(4-fluorophenyl)propanoyl)-1,2,5,6-tetrahydropyridine-3-carboxylic acid | * | 1.19 (A) | 542 |

TABLE 1-continued

| Cmp No. | Structure | Name | IC$_{50}$ | RT min (Method A, C, or D) | MS M + 1 |
|---|---|---|---|---|---|
| 9 | 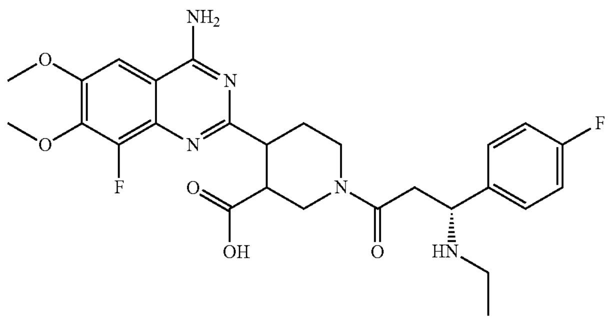 [SMILES: CCN[C@H](CC(=O)N1CCC(c2nc(N)c3cc(OC)c(OC)c(F)c3n2)C(C(=O)O)C1)c1ccc(F)cc1] | 4-(4-amino-8-fluoro-6,7-dimethoxyquinazolin-2-yl)-1-((R)-3-(ethylamino)-3-(4-fluorophenyl)propanoyl)piperidine-3-carboxylic acid | ** | 1.29 (A) | 544 |
| 10 | 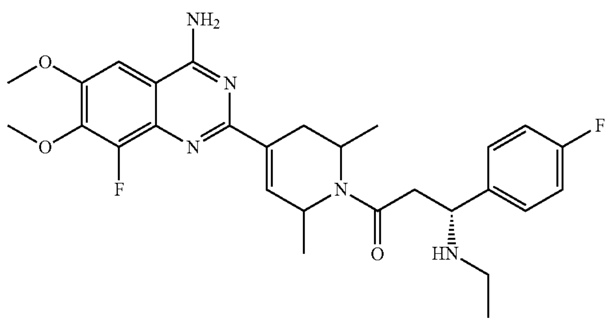 [SMILES: CCN[C@H](CC(=O)N1C(C)C=C(c2nc(N)c3cc(OC)c(OC)c(F)c3n2)CC1C)c1ccc(F)cc1] | (3R)-1-(4-(4-amino-8-fluoro-6,7-dimethoxyquinazolin-2-yl)-2,6-dimethyl-3,6-dihydropyridin-1(2H)-yl)-3-(ethylamino)-3-(4-fluorophenyl)propan-1-one | *** | Two isomers, 9.81/9.74 (C) | 526 |
| 11 | 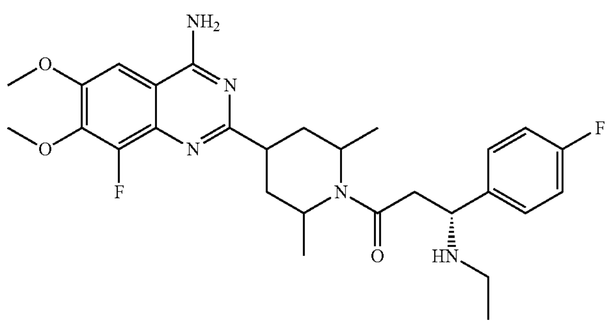 [SMILES: CCN[C@H](CC(=O)N1C(C)CC(c2nc(N)c3cc(OC)c(OC)c(F)c3n2)CC1C)c1ccc(F)cc1] | (3R)-1-(4-(4-amino-8-fluoro-6,7-dimethoxyquinazolin-2-yl)-2,6-dimethylpiperidin-1-yl)-3-(ethylamino)-3-(4-fluorophenyl)propan-1-one | ND | Two isomers, 9.34/9.45 (C) | 528 |
| 12 | 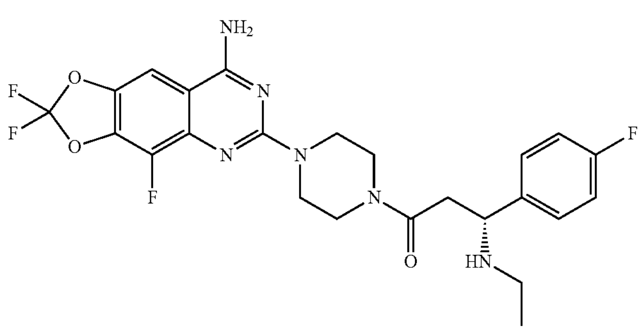 [SMILES: CCN[C@H](CC(=O)N1CCN(c2nc(N)c3cc4c(c(F)c3n2)OC(F)(F)O4)CC1)c1ccc(F)cc1] | (R)-1-(4-(8-amino-2,2,4-trifluoro-[1,3]dioxolo[4,5-g]quinazolin-6-yl)piperazin-1-yl)-3-(ethylamino)-3-(4-fluorophenyl)propan-1-one | ** | 11.11 (D) | 521 |

TABLE 1-continued

| Cmp No. | Structure | Name | IC$_{50}$ | RT min (Method A, C, or D) | MS M + 1 |
|---|---|---|---|---|---|
| 13 | 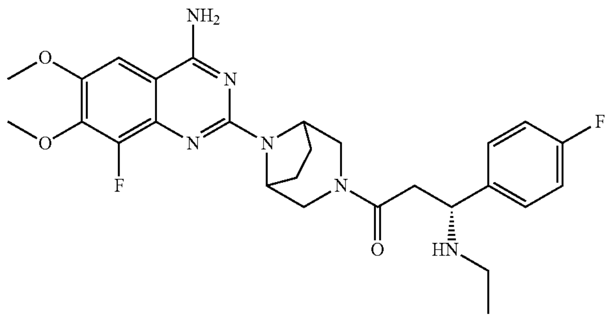 [SMILES: CCN[C@H](CC(=O)N1CC2CCC(C1)N2c1nc(N)c2cc(OC)c(OC)c(F)c2n1)c1ccc(F)cc1] | (3R)-1-(8-(4-amino-8-fluoro-6,7-dimethoxyquinazolin-2-yl)-3,8-diazabicyclo[3.2.1]octan-3-yl)-3-(ethylamino)-3-(4-fluorophenyl)propan-1-one | *** | 9.09 (D) | 527 |
| 14 | 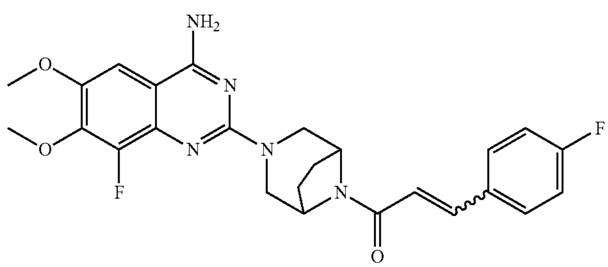 [SMILES: COc1cc2c(N)nc(N3CC4CCC(C3)N4C(=O)C=Cc3ccc(F)cc3)nc2c(F)c1OC] | 1-(3-(4-amino-8-fluoro-6,7-dimethoxyquinazolin-2-yl)-3,8-diazabicyclo[3.2.1]octan-8-yl)-3-(4-fluorophenyl)prop-2-en-1-one | * | Two isomers, 14.70/14.88 (D) | 482 |
| 15 | 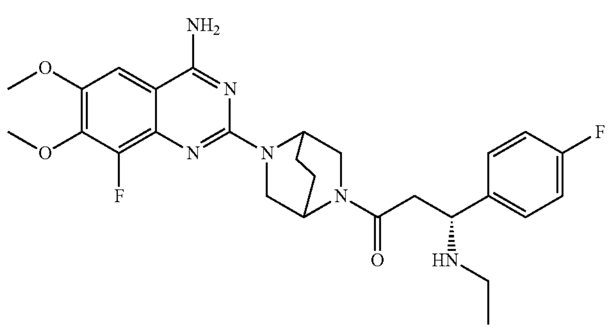 [SMILES: CCN[C@H](CC(=O)N1CC2CCC1CN2c1nc(N)c2cc(OC)c(OC)c(F)c2n1)c1ccc(F)cc1] | (3R)-1-(5-(4-amino-8-fluoro-6,7-dimethoxyquinazolin-2-yl)-2,5-diazabicyclo[2.2.2]octan-2-yl)-3-(ethylamino)-3-(4-fluorophenyl)propan-1-one | * | Two isomers, 8.62/8.77 (C) | 527 |

Table 1 shows illustrative compounds with characterizing data.

The assay of Example 12 was used to determine the IC$_{50}$'s of the compounds.

Three *s are used to denote compounds with an IC$_{50}$ less than 1 micromolar; two s indicate compound with an IC$_{50}$ between 1 micromolar and 10 micromolar, and one * denotes compounds with an IC$_{50}$ greater than 10 micromolar.

Example 10. Additional Compounds of the Present Invention

TABLE 2

| Cmp No. | Structure | Name | IC$_{50}$ (Stars) | RT min (Method A, C, or D) | MS (M + 1) |
|---|---|---|---|---|---|
| 16 | 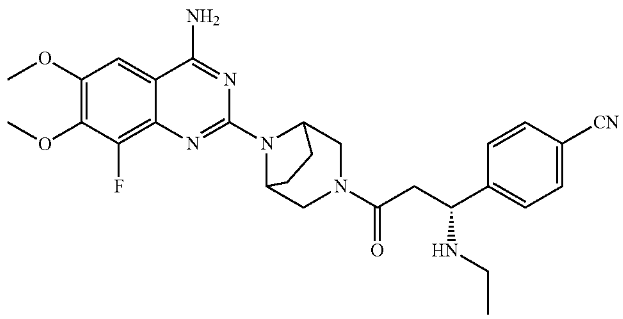 [SMILES: CCN[C@H](CC(=O)N1CC2CCC(C1)N2c1nc(N)c2cc(OC)c(OC)c(F)c2n1)c1ccc(C#N)cc1] | 4-((1R)-3-(8-(4-amino-8-fluoro-6,7-dimethoxyquinazolin-2-yl)-3,8-diazabicyclo[3.2.1]octan-3-yl)-1-(ethylamino)-3-oxopropyl)benzonitrile | *** | 9.46 (D) | 534 |
| 17 | 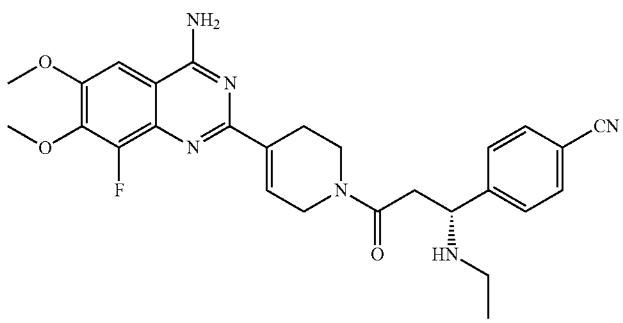 [SMILES: CCN[C@H](CC(=O)N1CC=C(c2nc(N)c3cc(OC)c(OC)c(F)c3n2)CC1)c1ccc(C#N)cc1] | (R)-4-(3-(4-(4-amino-8-fluoro-6,7-dimethoxyquinazolin-2-yl)-3,6-dihydropyridin-1(2H)-yl)-1-(ethylamino)-3-oxopropyl)benzonitrile | *** | 8.87 (C) | 505 |
| 18 | 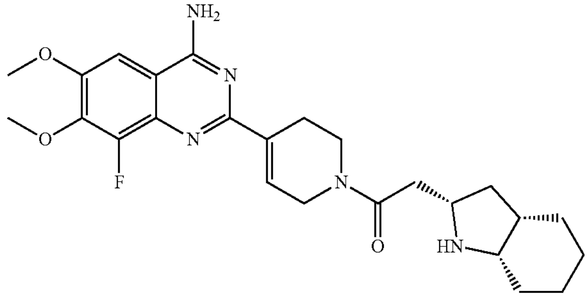 [SMILES: COc1cc2c(N)nc(C3=CCN(C(=O)C[C@@H]4C[C@@H]5CCCC[C@@H]5N4)CC3)nc2c(F)c1OC] | 1-(4-(4-amino-8-fluoro-6,7-dimethoxyquinazolin-2-yl)-3,6-dihydropyridin-1(2H)-yl)-2-((2S,3aS,7aS)-octahydro-1H-indol-2-yl)ethan-1-one | *** | 8.69 (D) | 470 |

Table 2 shows illustrative compounds with characterizing data.

The assay of Example 12 was used to determine the IC$_{50}$'s of the compounds.

Three *s are used to denote compounds with an IC$_{50}$ less than 1 micromolar; two s indicate compound with an IC$_{50}$ between 1 micromolar and 10 micromolar, and one * denotes compounds with an IC$_{50}$ greater than 10 micromolar.

Example 11. Additional Compounds of the Present Invention
TABLE 3
| Cmp No. | Structure | Name | IC$_{50}$ (Stars) | RT min (Method A, B, C, or D) | MS (M + 1) |
|---|---|---|---|---|---|
| 19 | 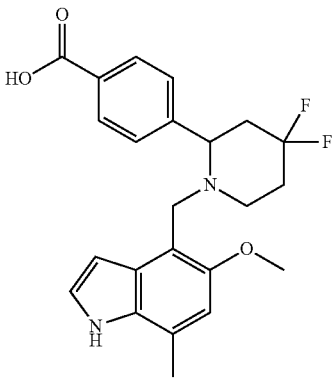 [SMILES: COc1cc(C)c2[nH]ccc2c1CN1CCC(F)(F)CC1c1ccc(C(=O)O)cc1] | 4-(4,4-difluoro-1-((5-methoxy-7-methyl-1H-indol-4-yl)methyl)piperidin-2-yl)benzoic acid | * | 1.76 (B) | 413 (M − 1) |
| 20 | 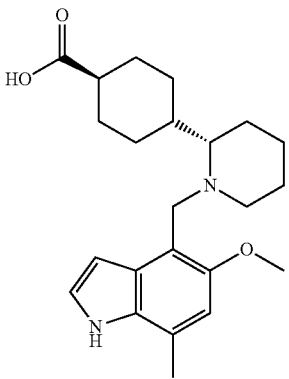 | (1R,4s)-4-((S)-1-((5-methoxy-7-methyl-1H-indol-4-yl)methyl)piperidin-2-yl)cyclohexane-1-carboxylic acid | * | 1.71 (B) | 385 |
| 21 | 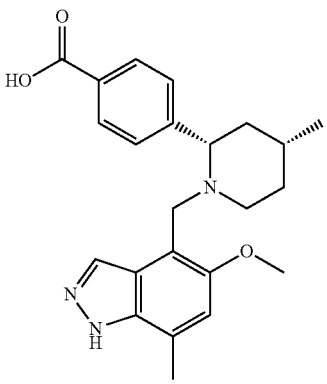 [SMILES: COc1cc(C)c2[nH]ncc2c1CN1CC[C@@H](C)C[C@H]1c1ccc(C(=O)O)cc1] | 4-((2S,4R)-1-((5-methoxy-7-methyl-1H-indazol-4-yl)methyl)-4-methylpiperidin-2-yl)benzoic acid | * | 0.39 (B) | 394 |

TABLE 3-continued

| Cmp No. | Structure | Name | IC$_{50}$ (Stars) | RT min (Method A, B, C, or D) | MS (M + 1) |
|---|---|---|---|---|---|
| 22 | 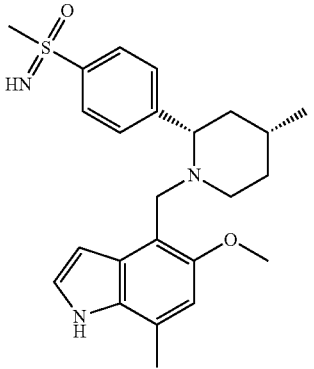 | imino(4-((2S,4R)-1-((5-methoxy-7-methyl-1H-indol-4-yl)methyl)-4-methylpiperidin-2-yl)phenyl)(methyl)-l6-sulfanone | *** | 0.33 (B) | 426 |
| 23 | 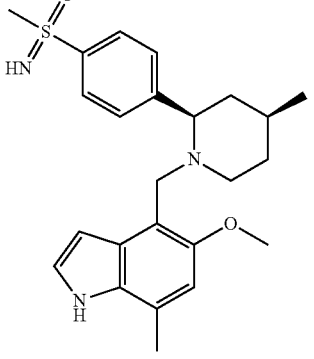 | imino(4-((2R,4S)-1-((5-methoxy-7-methyl-1H-indol-4-yl)methyl)-4-methylpiperidin-2-yl)phenyl)(methyl)-l6-sulfanone | * | 0.40 (B) | 426 |
| 24 | 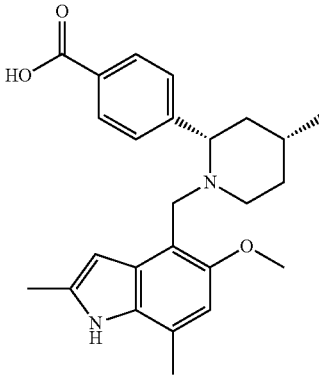 | 4-((2S,4R)-1-((5-methoxy-2,7-dimethyl-1H-indol-4-yl)methyl)-4-methylpiperidin-2-yl)benzoic acid | * | 2.32 (B) | 407 |
| 25 | 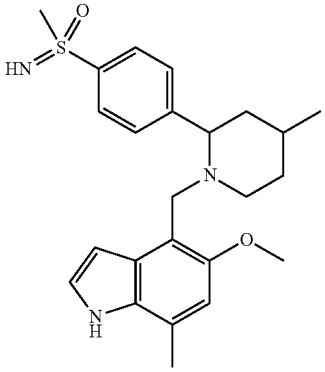 [SMILES: COc1cc(C)c2[nH]ccc2c1CN1CCC(C)CC1c1ccc(S(C)(=N)=O)cc1] | imino(4-(1-((5-methoxy-7-methyl-1H-indol-4-yl)methyl)-4-methylpiperidin-2-yl)phenyl)(methyl)-l6-sulfanone | *** | 1.54 (B) | 426 |

TABLE 3-continued

| Cmp No. | Structure | Name | IC$_{50}$ (Stars) | RT min (Method A, B, C, or D) | MS (M + 1) |
|---|---|---|---|---|---|
| 26 | 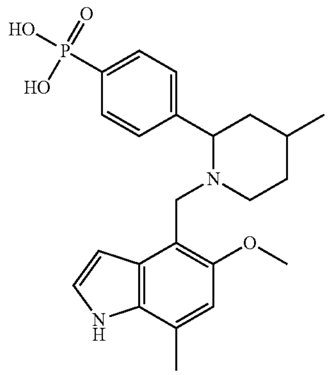 [SMILES: COc1cc(C)c2[nH]ccc2c1CN1CCC(C)CC1c1ccc(P(=O)(O)O)cc1] | (4-(1-((5-methoxy-7-methyl-1H-indol-4-yl)methyl)-4-methylpiperidin-2-yl)phenyl) phosphonic acid | *** | 3.55 (B) | 429 |
| 27 | 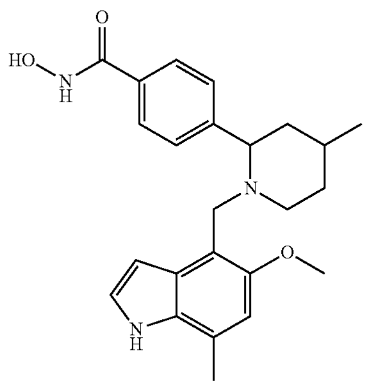 [SMILES: COc1cc(C)c2[nH]ccc2c1CN1CCC(C)CC1c1ccc(C(=O)NO)cc1] | N-hydroxy-4-(1-((5-methoxy-7-methyl-1H-indol-4-yl)methyl)-4-methylpiperidin-2-yl)benzamide | *** | 1.60 (B) | 408 |
| 28 | 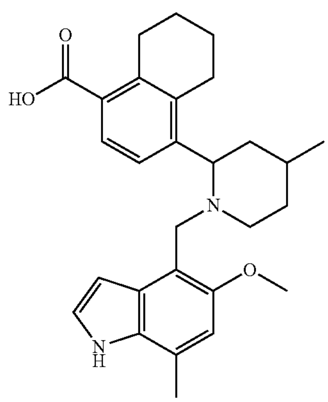 [SMILES: COc1cc(C)c2[nH]ccc2c1CN1CCC(C)CC1c1ccc(C(=O)O)c2c1CCCC2] | 4-(1-((5-methoxy-7-methyl-1H-indol-4-yl)methyl)-4-methylpiperidin-2-yl)-5,6,7,8-tetrahydro-naphthalene-1-carboxylic acid | *** | 2.72 (B) | 447 |
| 29 | 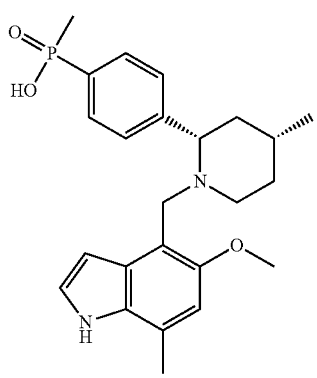 [SMILES: COc1cc(C)c2[nH]ccc2c1CN1CC[C@@H](C)C[C@H]1c1ccc(P(C)(=O)O)cc1] | (4-((2S,4R)-1-((5-methoxy-7-methyl-1H-indol-4-yl)methyl)-4-methylpiperidin-2-yl)phenyl)(methyl) phosphinic acid | *** | 1.86 (B) | 427 |

TABLE 3-continued

| Cmp No. | Structure | Name | IC$_{50}$ (Stars) | RT min (Method A, B, C, or D) | MS (M + 1) |
|---|---|---|---|---|---|
| 30 | 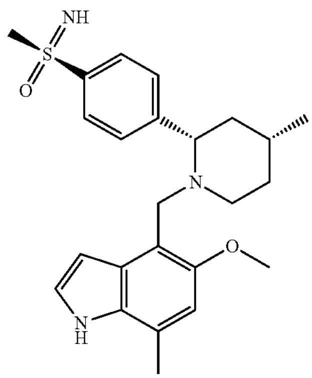 | (S)-imino(4-((2S,4R)-1-((5-methoxy-7-methyl-1H-indol-4-yl)methyl)-4-methylpiperidin-2-yl)phenyl)(methyl)-$\lambda^6$-sulfanone | *** | 1.53 (B) | 426 |
| 31 | 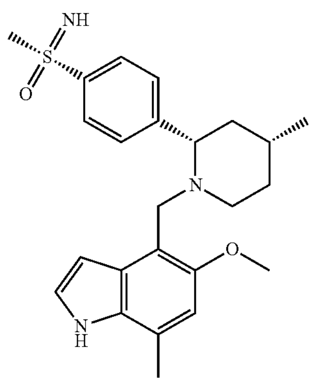 | (R)-imino(4-((2S,4R)-1-((5-methoxy-7-methyl-1H-indol-4-yl)methyl)-4-methylpiperidin-2-yl)phenyl)(methyl)-$\lambda^6$-sulfanone | *** | 1.61 (B) | 426 |
| 32 | 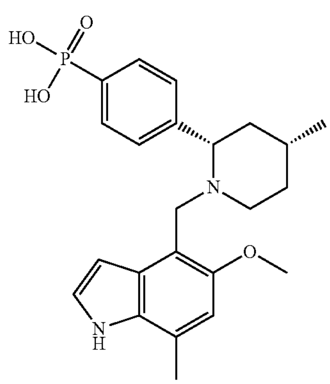 [SMILES: COc1cc(C)c2[nH]ccc2c1CN1CC[C@@H](C)C[C@H]1c1ccc(P(=O)(O)O)cc1] | (4-((2S,4R)-1-((5-methoxy-7-methyl-1H-indol-4-yl)methyl)-4-methylpiperidin-2-yl)phenyl)phosphonic acid | *** | 3.18 (E) | 429 |
| 33 | 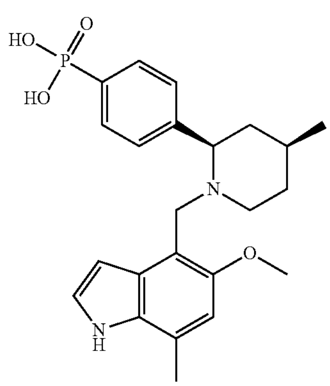 [SMILES: COc1cc(C)c2[nH]ccc2c1CN1CC[C@H](C)C[C@@H]1c1ccc(P(=O)(O)O)cc1] | (4-((2R,4S)-1-((5-methoxy-7-methyl-1H-indol-4-yl)methyl)-4-methylpiperidin-2-yl)phenyl)phosphonic acid | ** | 3.15 (E) | 429 |

TABLE 3-continued

| Cmp No. | Structure | Name | IC$_{50}$ (Stars) | RT min (Method A, B, C, or D) | MS (M + 1) |
|---|---|---|---|---|---|
| 34 | 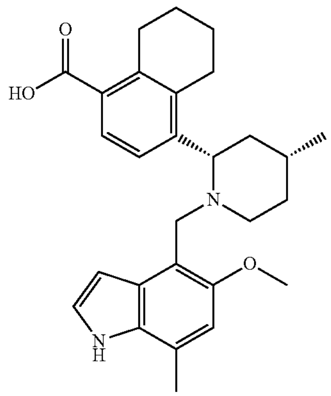 [SMILES: COc1cc(C)c2[nH]ccc2c1CN1CC[C@@H](C)C[C@H]1c1ccc(C(=O)O)c2c1CCCC2] | 4-((2S,4R)-1-((5-methoxy-7-methyl-1H-indol-4-yl)methyl)-4-methylpiperidin-2-yl)-5,6,7,8-tetrahydronaphthalene-1-carboxylic acid | *** | 2.69 (B) | 447 |
| 35 | 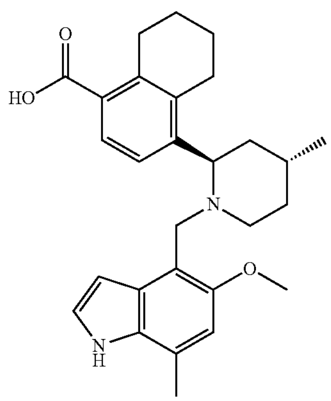 [SMILES: COc1cc(C)c2[nH]ccc2c1CN1CC[C@@H](C)C[C@@H]1c1ccc(C(=O)O)c2c1CCCC2] | 4-((2R,4R)-1-((5-methoxy-7-methyl-1H-indol-4-yl)methyl)-4-methylpiperidin-2-yl)-5,6,7,8-tetrahydronaphthalene-1-carboxylic acid | * | 2.63 (B) | 447 |

Table 3 shows illustrative compounds with characterizing data.
The assay of Example 12 was used to determine the IC$_{50}$'s of the compounds.
Three *s are used to denote compounds with an IC$_{50}$ less than 1 micromolar; two s indicate compound with an IC$_{50}$ between 1 micromolar and 10 micromolar, and one * denotes compounds with an IC$_{50}$ greater than 10 micromolar.

Example 12. Hemolysis Assay

The hemolysis assay was previously described by G. Ruiz-Gomez, et al., J. Med. Chem. (2009) 52: 6042-6052. Prior to the assay, the optimum concentration of Normal Human Serum (NHS) needed to achieve 100% lysis of rabbit erythrocytes (RE) is determined by titration. In the assay, NHS (Complement Technology) is diluted in GVB$^0$ Buffer (0.1% gelatin, 5 mM Veronal, 145 mM NaCl, 0.025% NaN$_3$, pH 7.3, Complement Technology) plus 10 mM Mg-EGTA and incubated with test compound at various concentrations for 15 minutes at 37° C. RE (Complement Technology) freshly suspended in GVB$^0$ plus 10 mM Mg-EGTA are added to a final concentration of 1×10$^8$ cells/mL and reactions are incubated for 30 minutes at 37° C. Positive control reactions (100% lysis) consist of GVB$^0$ plus 10 mM Mg-EGTA with NHS and RE but without test compound; negative control reactions (0% lysis) consist of GVB$^0$ plus 10 mM Mg-EGTA with RE only. Samples are centrifuged at 2000 g for 3 minutes and supernatants collected. Absorbance at 405 nm (A405) is recorded using a microplate spectrophotometer. IC$_{50}$ values are calculated by nonlinear regression from the percentage of hemolysis as a function of test compound concentration.

Example 13. Liquid Chromatography (LC) Methods

The LC methods referenced in the above tables are provided below:
LC Method A
Instrument: Waters Acquity Ultra Performance LC
Column: ACQUITY UPLC BEH C18 2.1×50 mm, 1.7
Column Temperature: 40° C.
Mobile Phase: Solvent A: H$_2$O+0.05% FA; Solvent B: CH$_3$CN+0.05% FA
Flow Rate: 0.8 mL/min
Gradient: 0.24 min @ 15% B, 3.26 min gradient (15-85% B), then 0.5 min @ 85% B.
Detection: UV (PDA), ELS, and MS (SQ in EI mode)
LC Method B
Instrument: Shimadzu LC-2010A HT
Column: Athena, C18-WP, 50×4.6 mm, 5
Column Temperature: 40° C.
Mobile Phase: Solvent A: H$_2$O/CH$_3$OH/FA=90/10/0.1; Solvent B: H$_2$O/CH$_3$OH/FA=10/90/0.1
Flow Rate: 3 mL/min
Gradient: 0.4 min @ 30% B, 3.4 min gradient (30-100% B), then 0.8 min @ 100% B
Detection: UV (220/254 nm)

HPLC Method C:
Instrument: Agilent 1100/1200 series LC system with DAD detector
Column: Atlantis dC18 (250×4.6) mm, 5 μm
Column Temperature: Ambient
Mobile Phase A: 0.1% TFA in water, Mobile Phase B: Acetonitrile
Flow Rate: 1.0 mL/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)
HPLC Method D:
Instrument: Shimadzu LC 20AD system with PDA detector
Column: Phenomenex Gemini NX C18 (150×4.6) mm, 5 μm
Column Temperature: Ambient
Mobile Phase A: 10 mM NH4OAC in water, Mobile Phase B: Acetonitrile
Flow Rate: 1.0 mL/min
Gradient:

| Time (min) | 0.0 | 15 | 20 | 23 | 30 |
|---|---|---|---|---|---|
| % B | 10 | 100 | 100 | 10 | 10 |

Detection: (210-400 nm)
HPLC Method E
Instrument: Shimadzu LC-2010A HT
Column: YMC Pack, ODS-A, 50×4.6 mm, 5 μm
Column Temperature: 40° C.
Mobile Phase: Solvent A: $H_2O/CH_3OH/FA=90/10/0.1$; Solvent B: $H_2O/CH_3OH/FA=10/90/0.1$
Flow Rate: 3 mL/min
Gradient: 0.7 min @ 0% B, 3.4 min gradient (0-50% B), then 0.8 min @ 50% B
Detection: UV (220/254 nm)

Example 14. Human Factor B Assay

CVF-Bb complex is prepared from purified cobra venom factor (1 μM); human Complement factor B and human Complement factor D are available from a commercial source (Complement Technology, Tyler, Tex.). CVF-Bb complex at 3 nM concentration is incubated with test compound at various concentrations for 10 minutes at room temperature in PBS pH 7.4 containing 10 mM MgCl2 and 0.05% (w/v) CHAPS. Human Complement C3 substrate (Complement Technology, Tyler, Tex.) is added to a final concentration of 1 μM. After 1 hour incubation at room temperature, the enzyme reaction is stopped by addition of a cocktail of concentrated pan-protease inhibitors. The product of the reaction, C3a, is quantified by means of an enzyme-linked-immunosorbent assay (Quidel, San Diego, Calif.) and/or denaturing gel electrophoresis (SDS-PAGE). $IC_{50}$ values are calculated from percentage of inhibition of CVF-Bb activity as a function of test compound concentration.

Example 15. Effect of Combination Therapy

The combinatorial efficacy of two compounds on the Complement alternative pathway (CAP) is assessed by determining the effect of two compounds mixed together at various concentrations with Normal Human Serum (NETS) on the hemolysis of rabbit erythrocytes (RE) or the production of terminal Complement complex (TCC). In both assays the two test compounds are prepared individually in seven-point dilution series, with an eighth sample for each containing solvent alone, and each of the 64 possible combinations is tested in duplicate or triplicate wells.

In the hemolysis assay, NETS (Complement Technology) diluted to 10% in $GVB^0$ Buffer (0.1% gelatin, 5 mM Veronal, 145 mM NaCl, 0.025% $NaN_3$, pH 7.3, Complement Technology) plus 10 mM Mg-EGTA is incubated with the compounds at various concentrations for 15 minutes at 37° C. RE (Complement Technology) freshly suspended in $GVB^0$ plus 10 mM Mg-EGTA are added to a final concentration of $1\times10^8$ cells/mL and reactions are incubated for 30 minutes at 37° C. Positive control reactions consist of $GVB^0$ plus Mg-EGTA with NHS and RE but without test compounds; negative control reactions consist of $GVB^0$ plus Mg-EGTA with RE only. Samples are centrifuged at 2000 g for 3 minutes and supernatants collected. Absorbance at 405 nM (A405) is recorded using a microplate spectrophotometer.

The assay for TCC production is conducted using the Complement system Alternative Pathway Wieslab assay kit (Euro Diagnostica). NETS diluted to 5.56% in the provided diluent is incubated with each compound in the wells of the provided assay plates for 60 minutes at 37° C. The wells are emptied and washed with the provided wash solution, incubated with 100 enzyme-linked detection antibody at 37° C. for 30 minutes, emptied and washed again, and incubated with 100 μL substrate at room temperature for 30 minutes. The provided quantitation standards are used as described by the manufacturer. Positive control reactions consist of diluent with NETS but without test compounds; negative control reactions consist of diluent only. After the 30-minute incubation, the $A_{405}$ of each well is recorded using a microplate spectrophotometer. TCC production is quantitated from $A_{405}$ by reference to the quantitation standards.

Combinatorial effect in both assays are analyzed using the three-dimensional surface-graphing method of Prichard, M. N. and C. Shipman, Jr., Antiviral Research 1990, 14:181-205, wherein the X-axis and Y-axis indicate test compound concentrations and the Z-axis indicates the difference between measured inhibition and a theoretically determined additive inhibition. For an additive combinatorial relationship the surface graph will resemble a horizontal plane of zero height, whereas positive surface peaks indicate greater inhibition than expected and therefore synergy, and negative surface peaks indicate less inhibition than expected and therefore antagonism.

Combinatorial efficacy on the hemolysis of rabbit erythrocytes (RE) can be examined using a compound described herein and a wide variety of second active agents. One non-limiting example is the peptidic Complement C3 inhibitor Compstatin (Tocris Bioscience). In another example, the combinatorial efficacy of a compound as described herein and a Complement Factor B inhibitor can be assessed. Alternatively, the combinatorial efficacy of a compound of the present invention and a monoclonal antibody directed against Complement CS protein (anti-CS, Quidel A217, murine monoclonal antibody to human Complement CS, isotype IgG1K) on the production of terminal Complement complex (TCC) can be assessed. In another non-limiting example, the combinatorial efficacy of an active compound of the invention and the broad spectrum inhibitor FUT-175 (BD Biosciences) on the hemolysis of rabbit erythrocytes (RE) is assessed.

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. A compound selected from:

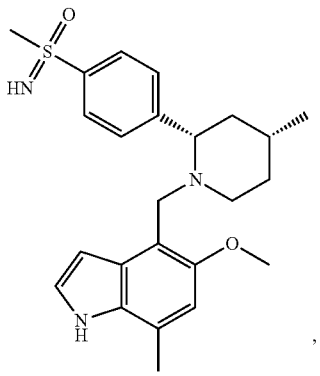

,

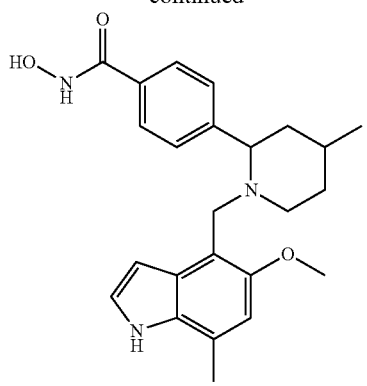

,

-continued

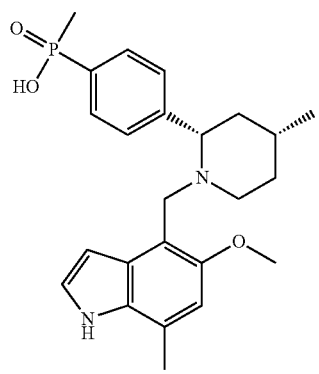

,

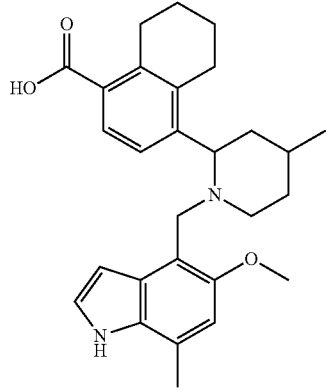

,

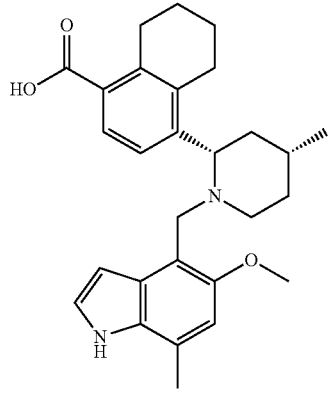

,

-continued
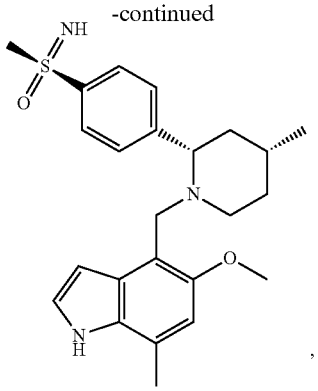
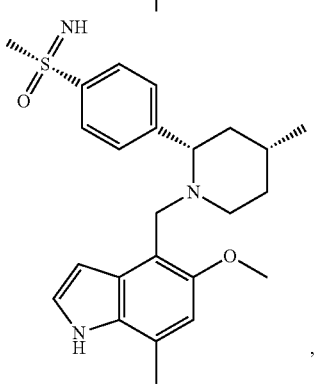
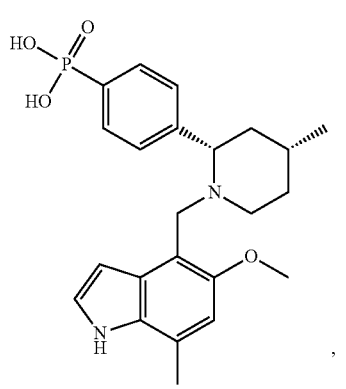
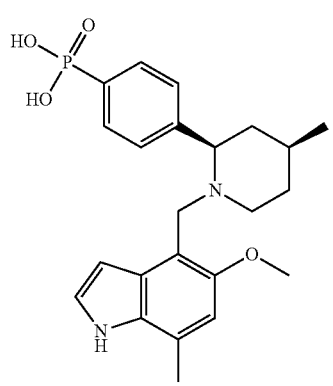
or a pharmaceutically acceptable salt thereof.
2. The compound of claim 1 selected from:
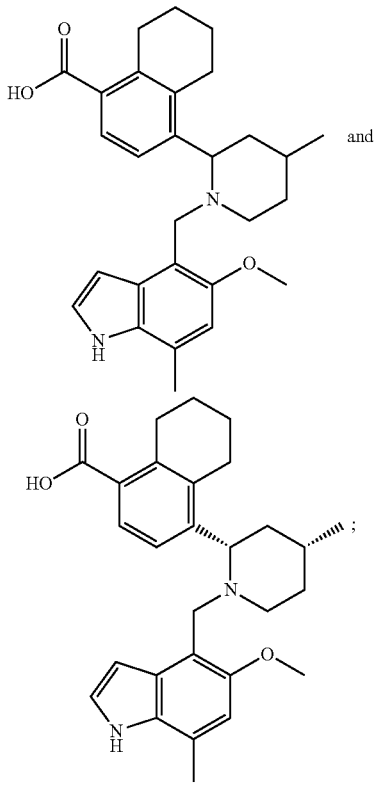
or a pharmaceutically acceptable salt thereof.
3. The compound of claim 1 selected from:
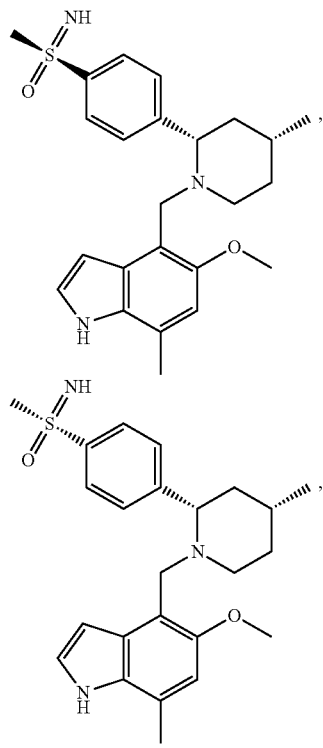

-continued

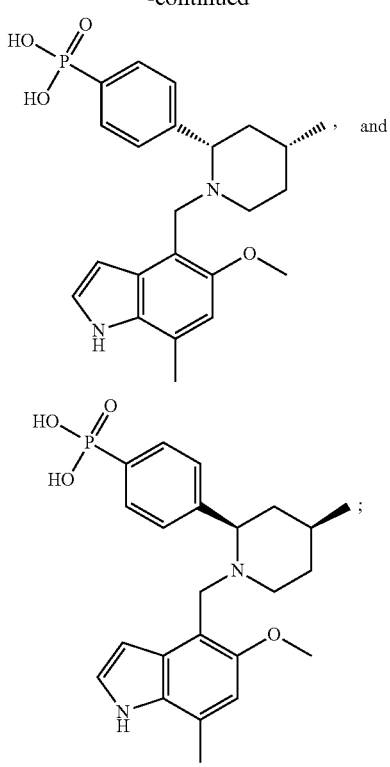

or a pharmaceutically acceptable salt thereof.

4. The compound of claim 1 selected from:

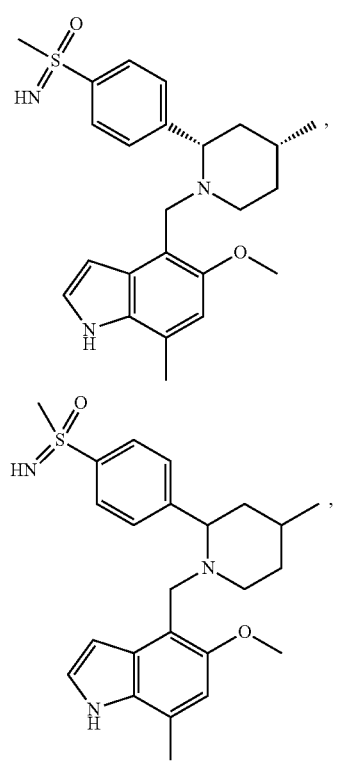

-continued

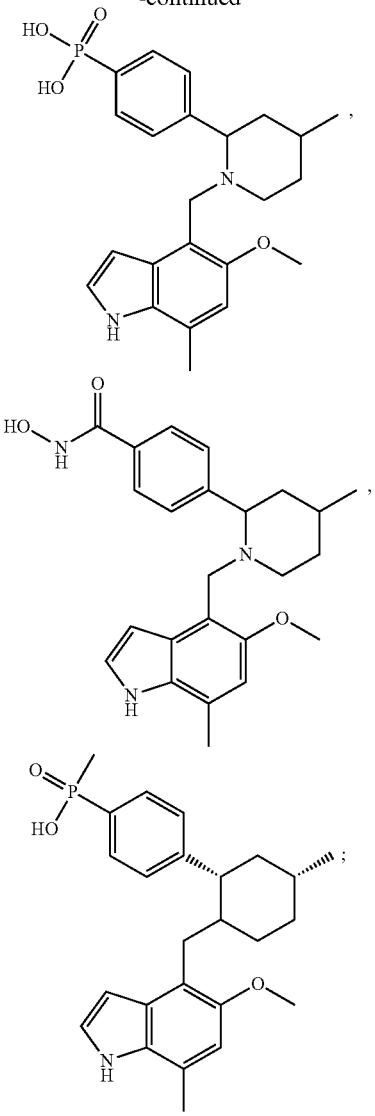

or a pharmaceutically acceptable salt thereof.

5. A pharmaceutical composition comprising an effective amount of a compound of claim 1 and a pharmaceutically acceptable excipient.

6. A method for the treatment of a disorder mediated by Complement Factor B, comprising administering an effective amount of a compound of claim 1 to a host in need thereof or its pharmaceutically acceptable salt, optionally in a pharmaceutically acceptable carrier.

7. The method of claim 6, wherein the host is a human.

8. The method of claim 7, wherein the disorder is age-related macular degeneration (AMD).

9. The method of claim 7, wherein the disorder is retinal degeneration, ophthalmic disease, multiple sclerosis, arthritis, or COPD.

10. The method of claim 7, wherein the disorder is an ophthalmic disease.

11. The method of claim 7, wherein the disorder is paroxysmal nocturnal hemoglobinuria (PNH).

12. The method of claim 7, wherein the disorder is a respiratory disease.

13. The method of claim 7, wherein the disorder is a cardiovascular disease.

14. The method of claim 7, wherein the disorder is atypical or typical hemolytic uremic syndrome.

15. The method of claim 7, wherein the disorder is rheumatoid arthritis.

16. The method of claim 7, wherein the disorder is C3 glomerulonephritis.

* * * * *